United States Patent
Gilmore et al.

(10) Patent No.: US 8,399,451 B2
(45) Date of Patent: Mar. 19, 2013

(54) HETEROCYCLIC COMPOUNDS

(75) Inventors: John L. Gilmore, Yardley, PA (US); James E. Sheppeck, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 194 days.

(21) Appl. No.: 12/850,892

(22) Filed: Aug. 5, 2010

(65) Prior Publication Data

US 2011/0190255 A1  Aug. 4, 2011

Related U.S. Application Data

(60) Provisional application No. 61/232,054, filed on Aug. 7, 2009.

(51) Int. Cl.
| | |
|---|---|
| A61K 31/4245 | (2006.01) |
| A61K 31/454 | (2006.01) |
| A61K 31/4439 | (2006.01) |
| A61K 31/506 | (2006.01) |
| A61K 31/4545 | (2006.01) |
| A61K 31/5377 | (2006.01) |
| A61K 31/497 | (2006.01) |
| C07D 413/14 | (2006.01) |
| C07D 413/04 | (2006.01) |
| C07D 417/14 | (2006.01) |

(52) U.S. Cl. ............ 514/210.2; 514/326; 514/364; 514/342; 514/256; 514/318; 514/236.2; 514/254.03; 544/138; 544/333; 544/369; 546/194; 546/271.1; 546/209; 548/131; 548/950

(58) Field of Classification Search ........... 514/210.2, 514/364; 544/138, 333; 546/209, 194; 548/131, 548/950
See application file for complete search history.

(56) References Cited

U.S. PATENT DOCUMENTS

| | | | |
|---|---|---|---|
| 5,597,825 | A | 1/1997 | Himmelsbach et al. |
| 6,069,143 | A | 5/2000 | Ali et al. |
| 7,160,883 | B2 | 1/2007 | Dyckman et al. |
| 7,199,142 | B2 | 4/2007 | Chen et al. |
| 7,309,721 | B2 | 12/2007 | Budhu et al. |
| 7,351,725 | B2 | 4/2008 | Doherty et al. |
| 7,479,504 | B2 | 1/2009 | Bugianesi et al. |
| 7,572,811 | B2 | 8/2009 | Pan et al. |
| 7,790,707 | B2 | 9/2010 | Saha et al. |
| 2005/0070506 | A1 | 3/2005 | Doherty et al. |
| 2007/0173487 | A1 | 7/2007 | Saha et al. |
| 2008/0200535 | A1 | 8/2008 | Ohmori et al. |
| 2010/0113528 | A1 | 5/2010 | Ahmed et al. |
| 2010/0160369 | A1 | 6/2010 | Canne Bannen et al. |

FOREIGN PATENT DOCUMENTS

| | | |
|---|---|---|
| WO | WO9605193 | 2/1996 |
| WO | WO9806694 | 2/1998 |
| WO | WO2004/035538 | 4/2004 |
| WO | WO2004/058149 | 7/2004 |
| WO | WO2004/071442 | 8/2004 |
| WO | WO2004/103279 | 12/2004 |
| WO | WO2004/103306 | 12/2004 |
| WO | WO2004/103309 | 12/2004 |
| WO | WO2004/113330 | 12/2004 |
| WO | WO2005/000833 | 1/2005 |
| WO | WO2005/032465 | 4/2005 |
| WO | WO2005/058848 | 6/2005 |
| WO | WO2006/047195 | 5/2006 |
| WO | WO2006/088944 | 8/2006 |
| WO | WO2006/100631 | 9/2006 |
| WO | WO2006/100633 | 9/2006 |
| WO | WO2006/115188 | 11/2006 |
| WO | WO2006/131336 | 12/2006 |
| WO | WO2006/137019 | 12/2006 |
| WO | WO2007/024922 | 3/2007 |
| WO | WO2007/080542 | 7/2007 |
| WO | WO2007/085451 | 8/2007 |
| WO | WO2007/091396 | 8/2007 |
| WO | WO2007/116866 | 10/2007 |
| WO | WO2008/016674 | 2/2008 |
| WO | WO2008/023783 | 2/2008 |

(Continued)

OTHER PUBLICATIONS

Hale et al., *Bioorg. Med. Chem. Lett.*, 14:3501 (2004).

(Continued)

*Primary Examiner* — Yong Chu
(74) *Attorney, Agent, or Firm* — Gary D. Greenblatt

(57) ABSTRACT

Disclosed are compounds of Formula (I)

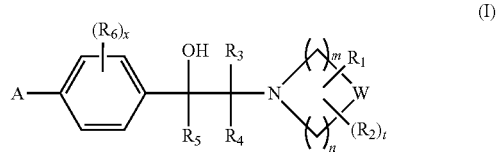

(I)

or a stereoisomer or a pharmaceutically acceptable salt thereof, wherein:
A is

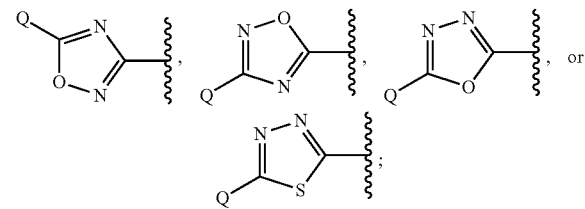

Q is a substituted 5-membered monocyclic heteroaryl group; W is $CH_2$, O, or NH; and $R_1$, $R_2$, $R_3$, $R_4$, $R_5$, $R_6$, m, n, t, and x are defined herein. Also disclosed are methods of using such compounds as selective agonists for G protein-coupled receptor $S1P_1$, and pharmaceutical compositions comprising such compounds. These compounds are useful in treating, preventing, or slowing the progression of diseases or disorders in a variety of therapeutic areas, such as autoimmune diseases and vascular disease.

11 Claims, No Drawings

FOREIGN PATENT DOCUMENTS

| | | |
|---|---|---|
| WO | WO2008/028937 | 3/2008 |
| WO | WO2008/029306 | 3/2008 |
| WO | WO2008/029370 | 3/2008 |
| WO | WO2008/029371 | 3/2008 |
| WO | WO2008/030843 | 3/2008 |
| WO | WO2008/035239 | 3/2008 |
| WO | WO 2008029370 A1 * | 3/2008 |
| WO | WO2008/037476 | 4/2008 |
| WO | WO2008/064315 | 5/2008 |
| WO | WO2008/074820 | 6/2008 |
| WO | WO2008/074821 | 6/2008 |
| WO | WO2008/076356 | 6/2008 |
| WO | WO2008/079382 | 7/2008 |
| WO | WO2008/091967 | 7/2008 |
| WO | WO2008/114157 | 9/2008 |
| WO | WO2009/011850 | 1/2009 |
| WO | WO2009/043889 | 4/2009 |
| WO | WO2009/043890 | 4/2009 |
| WO | WO2009/057079 | 5/2009 |
| WO | WO 2009/080663 | 7/2009 |
| WO | WO2009/151529 | 12/2009 |
| WO | WO2010/041655 | 4/2010 |
| WO | WO2010/064707 | 6/2010 |
| WO | WO2010/069949 | 6/2010 |
| WO | WO2010/072352 | 7/2010 |
| WO | WO2010/072712 | 7/2010 |
| WO | WO2010/081692 | 7/2010 |
| WO | WO2010/085581 | 7/2010 |
| WO | WO2010/085582 | 7/2010 |
| WO | WO2010/085584 | 7/2010 |
| WO | WO2010/113528 | 10/2010 |
| WO | WO2010/113796 | 10/2010 |

OTHER PUBLICATIONS

Sanna et al., *J. Biol. Chem.*, 279:13839 (2004).
Anliker et al., *J. Biol. Chem.*, 279:20555 (2004).
Mandala et al., *J. Pharmacol. Exp. Ther.*, 309:758 (2004).
Brinkman et al., *J. Biol. Chem.*, 277:21453 (2002).
Mandala et al., *Science*, 296:346 (2002).
Fujino et al., *J. Pharmacol. Exp. Ther.*, 305:70 (2003).
Brinkmann et al., *Am. J. Transplant.*, 4:1019 (2004).
Webb et al., *J. Neuroimmunol.*, 153:108 (2004).
Morris et al., *Eur. J. Immunol.*, 35:3570 (2005).
Chiba, *Pharmacology & Therapeutics*, 108:308 (2005).
Kahan et al., *Transplantation*, 76:1079 (2003).
Kappos et al., *N. Engl. J. Med.*, 355:1124 (2006).
Koyrakh et al., *Am. J. Transplant.*, 5:529 (2005).
Hale et al., *J. Med. Chem.*, 47:6662 (2004).
Rosen et al., *Trends Immunol.*, 28:102 (2007).
International Search Report dated Nov. 24, 2010.

* cited by examiner

HETEROCYCLIC COMPOUNDS

The present invention generally relates to heterocyclic compounds useful as $S1P_1$ agonists. Provided herein are heterocyclic compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Down-regulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant.*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Patent Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Patent Publication No. 2007/0203100), WO 06/047195, WO 06/100633, WO 06/115188, WO 06/131336, WO 2007/024922, WO 07/109330, WO 07/116866, WO 08/023783 (U.S. Patent Publication No. 2008/0200535), WO 08/029370, WO 08/114157, WO 08/074820, WO 09/043889, WO 09/057079, and U.S. Pat. No. 6,069,143. Also see Hale et al., *J. Med. Chem.*, 47:6662 (2004).

There still remains a need for compounds useful as $S1P_1$ agonists and yet having selectivity over $S1P_3$.

Applicants have found potent compounds that have activity as $S1P_1$ agonists. Further, applicants have found compounds that have activity as $S1P_1$ agonists and are selective over $S1P_3$. These compounds are provided to be useful as pharmaceuticals with desirable stability, bioavailability, therapeutic index, and toxicity values that are important to their drugability.

SUMMARY OF THE INVENTION

The present invention provides heterocyclic compounds, which are useful as modulators of $S1P_1$ activity, including stereoisomers, salts, solvates, and prodrugs thereof.

The present invention also provides processes and intermediates for making the compounds of the present invention or stereoisomers, salts, or prodrugs thereof.

The present invention also provides pharmaceutical compositions comprising a compound of Formula (I), or stereoisomers, pharmaceutically acceptable salts, or prodrugs thereof; and a pharmaceutically acceptable carrier.

The present invention also provides a method of treating a disease or disorder associated with the activity of G protein-coupled receptor S1P$_1$, the method comprising administering to a mammalian patient a compound of Formula (I) or stereoisomers, pharmaceutically acceptable salts, or prodrugs thereof.

The present invention also provides the compounds of the present invention or stereoisomers, pharmaceutically acceptable salts, or prodrugs thereof, for use in therapy.

The present invention also provides the use of the compounds of the present invention or stereoisomers, pharmaceutically acceptable salts, or prodrugs thereof, for the manufacture of a medicament for the treatment or prophylaxis of S1P$_1$ receptor-related conditions, such as autoimmune and vascular diseases.

The compounds of Formula (I) and compositions comprising the compounds are S1P$_1$ agonists, which are selective for S1P$_1$ activity over S1P$_3$ activity. The compounds of Formula (I) and compositions comprising said compounds may be used in treating, preventing or curing various S1P$_1$ receptor-related conditions while reducing or minimizing the side effects due to S1P$_3$ activity. Pharmaceutical compositions comprising these compounds are useful in treating, preventing, or slowing the progression of diseases or disorders in a variety of therapeutic areas, such as autoimmune and vascular diseases.

DETAILED DESCRIPTION

In a first aspect, the present invention provides a compound of Formula (I):

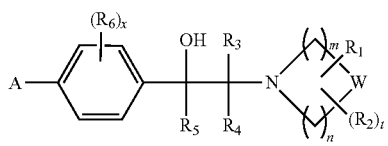

(I)

or a stereoisomer or a pharmaceutically acceptable salt thereof, wherein:
m is 1 or 2;
n is 1 or 2;
wherein:
W is CH$_2$ when (m+n) is 2 or 3; or
W is CH$_2$, O, or NH when (m+n) is 4;
R$_1$ is —(CR$_d$R$_d$)$_a$OH, —(CR$_d$R$_d$)$_a$COOH, —(CR$_d$R$_d$)$_a$C(O)NR$_c$R$_c$, —(CR$_d$R$_d$)$_a$C(O)NHS(O)$_2$(C$_{1-3}$alkyl), —(CR$_d$R$_d$)$_a$C(O)NHS(O)$_2$(aryl), or —(CR$_d$R$_d$)$_a$tetrazolyl;
each R$_2$ is independently halo, C$_{1-4}$alkyl, C$_{1-2}$haloalkyl, —OH, C$_{1-3}$alkoxy, and/or —NR$_c$R$_c$;
R$_3$ and R$_4$ are independently H and/or C$_{1-6}$alkyl, or R$_3$ and R$_4$ together with the carbon atom to which they are attached, form a 3- to 6-membered ring containing zero or 1 heteroatom selected from O and N;
R$_5$ is H or C$_{1-4}$alkyl;
each R$_6$ is independently C$_{1-3}$alkyl, halo, C$_{1-3}$haloalkyl, —CN, —OH, C$_{1-3}$alkoxy, and/or C$_{1-3}$haloalkoxy;
A is

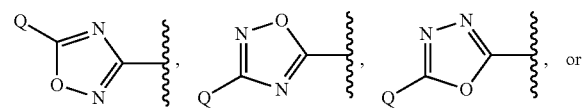

or

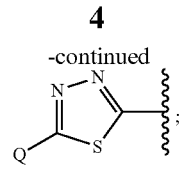

Q is a 5-membered monocyclic heteroaryl group having 1 to 3 heteroatoms independently selected from N, O, and/or S, wherein said heteroaryl group is substituted with R$_a$ and zero or 1 R$_b$, provided that when A is

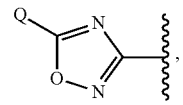

Q is not 2-furanyl, 4-thiazolyl, 4-oxazolyl, or 1,2,3-triazolyl;
R$_a$ is C$_{2-6}$alkyl, C$_{2-4}$haloalkyl, C$_{3-6}$cycloalkyl, tetrahydropyranyl, or a cyclic group selected from phenyl, benzyl, and 5- to 6-membered monocyclic heteroaryl groups having 1 to 3 heteroatoms independently selected from N, O, and/or S, wherein said cyclic group is substituted with zero, 1, 2, or 3 substituents independently selected from halo, —CN, —OH, C$_{1-4}$alkyl, C$_{1-4}$alkoxy, C$_{1-3}$haloalkyl, and/or C$_{1-2}$haloalkoxy;
R$_b$ is C$_{1-3}$alkyl or C$_{1-3}$haloalkyl, provided that if R$_a$ is alkyl then R$_b$ is C$_{1-3}$haloalkyl;
each R$_c$ is independently H and/or C$_{1-4}$alkyl;
each R$_d$ is independently H, —OH, C$_{1-4}$alkyl, C$_{1-4}$haloalkyl, and/or C$_{1-4}$alkoxy;
a is zero, 1, 2, or 3;
t is zero, 1, 2, 3, or 4; and
x is zero, 1, or 2;
with the proviso that the following compounds are excluded:

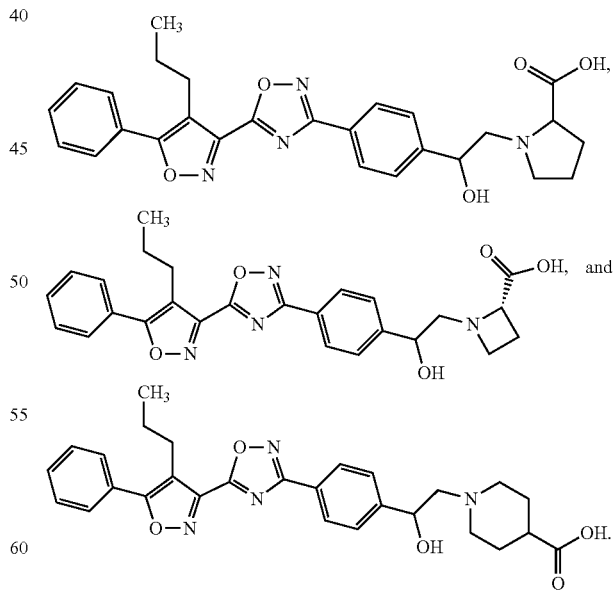

One embodiment provides a compound of Formula (I) or stereoisomers, salts, or prodrugs thereof, wherein m is 1, n is 1, and W is CH$_2$. A compound of this embodiment has the structure represented by Formula (II):

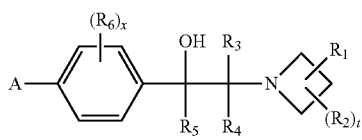
(II)

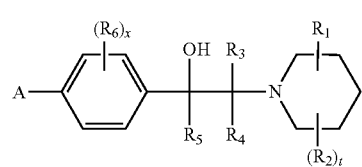
(IVa)

or stereoisomers, salts, or prodrugs thereof, wherein $R_1$, $R_2$, $R_3$, $R_4$, $R_5$, $R_6$, A, t, and x are defined in the first aspect. Preferably, $R_1$ is —$(CR_dR_d)_aOH$ or —$(CR_dR_d)_aCOOH$, wherein a is zero, 1, 2, or 3. Preferably, each $R_d$ is independently H or —$CH_3$. Preferably, $R_5$ is H or —$CH_3$.

One embodiment provides a compound of Formula (I) or stereoisomers, salts, or prodrugs thereof, wherein one of m and n is 1 and the other of m and n is 2, and W is $CH_2$. A compound of this embodiment has the structure represented by Formula (III):

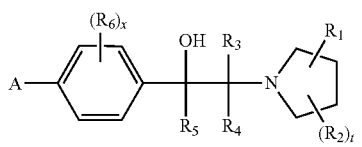
(III)

or a stereoisomer or a pharmaceutically acceptable salt thereof, wherein $R_1$, $R_2$, $R_3$, $R_4$, $R_5$, $R_6$, A, t, and x are defined in the first aspect. Preferably, $R_1$ is —$(CR_dR_d)_aOH$ or —$(CR_dR_d)_aCOOH$, wherein a is zero, 1, 2, or 3. Preferably, each $R_d$ is independently H or —$CH_3$. Preferably, $R_5$ is H or —$CH_3$.

One embodiment provides a compound of Formula (I) or stereoisomers, salts, or prodrugs thereof, wherein m is 2 and n is 2. A compound of this embodiment has the structure represented by Formula (IV):

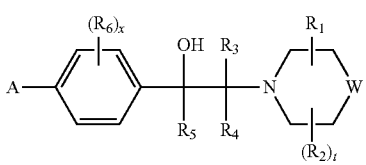
(IV)

or a stereoisomer or a pharmaceutically acceptable salt thereof, wherein $R_1$, $R_2$, $R_3$, $R_4$, $R_5$, $R_6$, A, W, t, and x are defined in the first aspect. Preferably, $R_1$ is —$(CR_dR_d)_aOH$ or —$(CR_dR_d)_aCOOH$, wherein a is zero, 1, 2, or 3. Preferably, each $R_d$ is independently H or —$CH_3$. Preferably, $R_5$ is H or —$CH_3$.

One embodiment provides a compound of Formula (I) or stereoisomers, salts, or prodrugs thereof, wherein m is 2, n is 2, and W is $CH_2$. A compound of this embodiment has the structure represented by Formula (IVa):

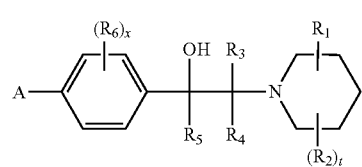

or a stereoisomer or a pharmaceutically acceptable salt thereof, wherein $R_1$, $R_2$, $R_3$, $R_4$, $R_5$, $R_6$, A, t, and x are defined in the first aspect. Preferably, $R_1$ is —$(CR_dR_d)_aOH$ or —$(CR_dR_d)_aCOOH$, wherein a is zero, 1, 2, or 3. Preferably, each $R_d$ is independently H or —$CH_3$. Preferably, $R_5$ is H or —$CH_3$.

One embodiment provides a compound of Formula (I) or stereoisomers, salts, or prodrugs thereof, wherein m is 2, n is 2, and W is O. A compound of this embodiment has the structure represented by Formula (IVb):

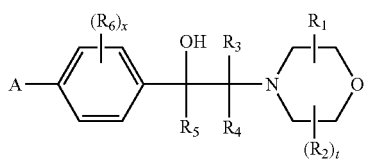
(IVb)

or a stereoisomer or a pharmaceutically acceptable salt thereof, wherein $R_1$, $R_2$, $R_3$, $R_4$, $R_5$, $R_6$, A, t, and x are defined in the first aspect. Preferably, $R_1$ is —$(CR_dR_d)_aOH$ or —$(CR_dR_d)_aCOOH$, wherein a is zero, 1, 2, or 3. Preferably, each $R_d$ is independently H or —$CH_3$. Preferably, $R_5$ is H or —$CH_3$.

One embodiment provides a compound of Formula (I) or stereoisomers, salts, or prodrugs thereof, wherein m is 2, n is 2, and W is NH. A compound of this embodiment has the structure represented by Formula (IVc):

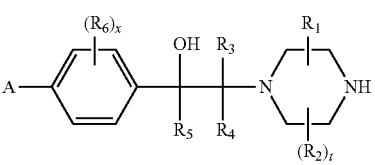
(IVc)

or a stereoisomer or a pharmaceutically acceptable salt thereof, wherein $R_1$, $R_2$, $R_3$, $R_4$, $R_5$, $R_6$, A, t, and x are defined in the first aspect. Preferably, $R_1$ is —$(CR_dR_d)_aOH$ or —$(CR_dR_d)_aCOOH$, wherein a is zero, 1, 2, or 3. Preferably, each $R_d$ is independently H or —$CH_3$. Preferably, $R_5$ is H or —$CH_3$.

One embodiment provides a compound of Formula (I) or stereoisomers, salts, or prodrugs thereof, wherein:
A is

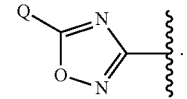

A compound of this embodiment has the structure represented by Formula (Ia):

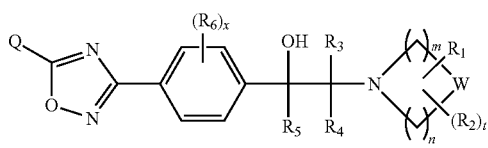

(Ia)

or a stereoisomer or a pharmaceutically acceptable salt thereof, wherein Q is a 5-membered monocyclic heteroaryl group having 1 to 3 heteroatoms independently selected from N, O, and/or S, wherein said heteroaryl group is substituted with $R_a$ and zero or 1 $R_b$, provided that A is not

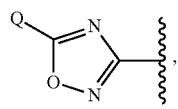

then Q is not 2-furanyl, 4-thiazolyl, 4-oxazolyl, or 1,2,3-triazolyl; and $R_1$, $R_2$, $R_3$, $R_4$, $R_5$, $R_6$, W, m, n, t, and x are defined in the first aspect. In this embodiment, examples of suitable groups for Q include, thiophenyl, pyrrolyl, 3-furanyl, pyrazolyl, imidazolyl, isoxazolyl, 2-oxazolyl, 5-oxazolyl, isothiazolyl, 2-thiazolyl, 5-thiazolyl, 1,2,4-triazolyl, oxadiazolyl, and thiadiazolyl. Preferably, Q is thiophenyl, pyrazolyl, isoxazolyl, and 5-thiazolyl.

One embodiment provides a compound of Formula (I) or stereoisomers, salts, or prodrugs thereof, wherein:
A is

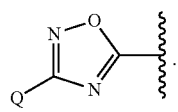

A compound of this embodiment has the structure represented by Formula (Ib):

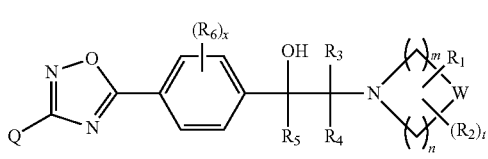

(Ib)

or a stereoisomer or a pharmaceutically acceptable salt thereof, wherein $R_1$, $R_2$, $R_3$, $R_4$, $R_5$, $R_6$, W, Q, m, n, t, and x are defined in the first aspect. In this embodiment, examples of suitable groups for Q include, thiophenyl, pyrrolyl, furanyl, pyrazolyl, imidazolyl, isoxazolyl, oxazolyl, isothiazolyl, thiazolyl, triazolyl, oxadiazolyl, and thiadiazolyl. Preferably, Q is thiophenyl, pyrazolyl, isoxazolyl, and 5-thiazolyl.

One embodiment provides a compound of Formula (I) or stereoisomers, salts, or prodrugs thereof, wherein:
A is

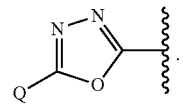

A compound of this embodiment has the structure represented by Formula (Ic):

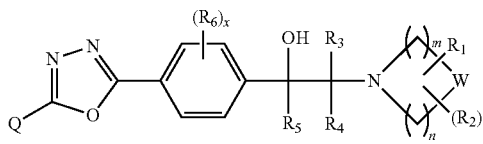

(Ic)

or a stereoisomer or a pharmaceutically acceptable salt thereof, wherein $R_1$, $R_2$, $R_3$, $R_4$, $R_5$, $R_6$, W, Q, m, n, t, and x are defined in the first aspect. In this embodiment, examples of suitable groups for Q include, thiophenyl, pyrrolyl, furanyl, pyrazolyl, imidazolyl, isoxazolyl, oxazolyl, isothiazolyl, thiazolyl, triazolyl, oxadiazolyl, and thiadiazolyl. Preferably, Q is thiophenyl, pyrazolyl, isoxazolyl, and 5-thiazolyl.

One embodiment provides a compound of Formula (I) or stereoisomers, salts, or prodrugs thereof, wherein:
A is

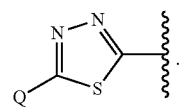

A compound of this embodiment has the structure represented by Formula (Id):

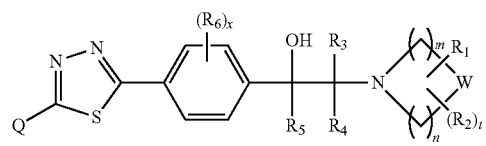

(Id)

or a stereoisomer or a pharmaceutically acceptable salt thereof, wherein $R_1$, $R_2$, $R_3$, $R_4$, $R_5$, $R_6$, W, Q, m, n, t, and x are defined in the first aspect. In this embodiment, examples of suitable groups for Q include, thiophenyl, pyrrolyl, furanyl, pyrazolyl, imidazolyl, isoxazolyl, oxazolyl, isothiazolyl, thiazolyl, triazolyl, oxadiazolyl, and thiadiazolyl. Preferably, Q is thiophenyl, pyrazolyl, isoxazolyl, and 5-thiazolyl.

One embodiment provides a compound of Formula (I) or stereoisomers, salts, or prodrugs thereof, wherein $R_1$ is —$(CR_dR_d)_a$OH, —$(CR_dR_d)_a$COOH, or —$(CR_dR_d)_a$NR$_c$R$_c$ wherein a is zero, 1, 2, or 3; and $R_2$, $R_3$, $R_4$, $R_5$, $R_6$, $R_c$, $R_d$, W, A, m, n, t, and x are defined in the first aspect. Preferably, $R_1$ is —$(CR_dR_d)_a$OH or —$(CR_dR_d)_a$COOH. Preferably, a is zero, 1, or 2. Preferably, each $R_d$ is independently H and/or $C_{1-4}$alkyl, and more preferably, each $R_d$ is independently H and/or $C_{1-2}$alkyl. Preferably, each $R_d$ is independently H and/or —$CH_3$. For example, $R_1$ may be selected from —$(CH_2)_a$OH, —$(CH_2)_a$COOH, —$C(CH_3)_2$COOH, and —$(CH_2)_a$NR$_c$R$_c$.

One embodiment provides a compound of Formula (I) or stereoisomers, salts, or prodrugs thereof, wherein $R_1$ is —$(CR_dR_d)_aC(O)NHS(O)_2(C_{1-3}alkyl)$; a is zero, 1, 2, or 3; and $R_2$, $R_3$, $R_4$, $R_5$, $R_6$, $R_d$, W, A, m, n, t, and x are defined in the first aspect. Preferably, each $R_d$ is independently H and/or —$CH_3$, and more preferably, each $R_d$ is H.

One embodiment provides a compound of Formula (I) or stereoisomers, salts, or prodrugs thereof, wherein $R_1$ is —$(CR_dR_d)_aC(O)NHS(O)_2(aryl)$; a is zero, 1, 2, or 3; and $R_2$, $R_3$, $R_4$, $R_5$, $R_6$, $R_d$, W, A, m, n, t, and x are defined in the first aspect. Preferably, each $R_d$ is independently H and/or —$CH_3$, and more preferably, each $R_d$ is H.

One embodiment provides a compound of Formula (I) or stereoisomers, salts, or prodrugs thereof, wherein $R_1$ is —$(CR_dR_d)_a$tetrazolyl; a is zero, 1, 2, or 3; and $R_2$, $R_3$, $R_4$, $R_5$, $R_6$, $R_d$, W, A, m, n, t, and x are defined in the first aspect. Preferably, each $R_d$ is independently H and/or —$CH_3$, and more preferably, each $R_d$ is H.

One embodiment provides a compound of Formula (I) or stereoisomers, salts, or prodrugs thereof, wherein $R_1$ is —$(CR_dR_d)_aOH$, —$(CR_dR_d)_aCOOH$, —$(CR_dR_d)_aC(O)NR_cR_c$, —$(CR_dR_d)_aC(O)NHS(O)_2(C_{1-3}alkyl)$, or —$(CR_dR_d)_a$tetrazolyl; and each $R_d$ is independently H, —OH, $C_{1-2}$alkyl, $C_{1-3}$fluoroalkyl, and/or $C_{1-2}$alkoxy. Preferably, each $R_d$ is independently, H, —OH, —$CH_3$, —$CF_3$, and/or —$OCH_3$; more preferably, each $R_d$ is H, —OH, and/or —$CH_3$; and still more preferably, each $R_d$ is H and/or —$CH_3$.

One embodiment provides a compound of Formula (I) or stereoisomers, salts, or prodrugs thereof, wherein each $R_2$ is independently halo, $C_{1-4}$alkyl, —$CF_3$, —OH, and/or —$OCH_3$; and t is zero, 1, 2, or 3. Preferably, each $R_2$ is independently F, Cl, —OH, and/or $C_{1-4}$alkyl, and more preferably, each $R_2$ is independently F, —OH, and/or —$CH_3$. Preferably t is zero, 1, or 2; and more preferably, t is zero or 1.

One embodiment provides a compound of Formula (I) or stereoisomers, salts, or prodrugs thereof, wherein $R_3$ and $R_4$ are independently H and/or $C_{1-6}$alkyl. Preferably, $R_3$ and $R_4$ are independently H and/or $C_{1-4}$alkyl, more preferably, $R_3$ and $R_4$ are independently H and/or —$CH_3$, and still more preferably, $R_3$ is H and $R_4$ is H.

One embodiment provides a compound of Formula (I) or stereoisomers, salts, or prodrugs thereof, wherein $R_3$ and $R_4$ together with the carbon atom to which they are attached form a 3- to 6-membered ring containing zero or 1 heteroatom selected from O and N. Examples of 3- to 6-membered rings with zero heteroatoms include cyclopropane, cyclobutane, cyclopentane, and cyclohexane. Examples of 3- to 6-membered rings with 1 heteroatom include oxetane, tetrahydrofuran, tetrahydropyran, azetidine, pyrrolidine, and piperidine.

One embodiment provides a compound of Formula (I) or stereoisomers, salts, or prodrugs thereof, wherein $R_5$ is H or $C_{1-2}$alkyl. Preferably, $R_5$ is H or —$CH_3$, and more preferably, $R_5$ is H.

One embodiment provides a compound of Formula (I) or stereoisomers, salts, or prodrugs thereof, wherein $R_3$, $R_4$, and $R_5$ are independently H and/or $C_{1-2}$alkyl, preferably H and/or —$CH_3$; and still more preferably, $R_3$, $R_4$, and $R_5$ are each H.

One embodiment provides a compound of Formula (I) or stereoisomers, salts, or prodrugs thereof, wherein each $R_6$ is independently $C_{1-3}$alkyl, halo, $C_{1-2}$haloalkyl, —CN, —OH, and/or $C_{1-2}$alkoxy. Preferably, each $R_6$ is independently $C_{1-2}$alkyl, F, $C_{1-2}$haloalkyl, and/or —CN; and more preferably H, —$CH_3$, and/or —$CF_3$.

One embodiment provides a compound of Formula (I) or stereoisomers, salts, or prodrugs thereof, wherein x is zero or 1. In this embodiment, preferably $R_6$ is $C_{1-2}$alkyl, F, $C_{1-2}$haloalkyl, or —CN; and more preferably H, —$CH_3$, or —$CF_3$.

One embodiment provides a compound of Formula (I) or stereoisomers, salts, or prodrugs thereof, wherein Q is a 5-membered heteroaryl group having 1 to 3 heteroatoms independently selected from N, O, and/or S, wherein said heteroaryl group is substituted with $R_a$ and zero or 1 $R_b$, and provided that when A is

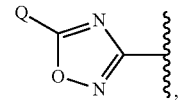

Q is not 2-furanyl, 4-thiazolyl, 4-oxazolyl, or 1,2,3-triazolyl. Examples of suitable 5-membered heteroaryl groups include furanyl, thiophenyl, pyrazolyl, imidazolyl, isoxazolyl, oxazole, isothiazolyl, thiazolyl, triazolyl, oxadiazolyl, and thiadiazolyl. Preferably, Q is a heteroaryl group selected from thiophenyl, pyrazolyl, and isoxazolyl, wherein said heteroaryl group is substituted with $R_a$ and zero or 1 $R_b$. Preferably, $R_b$ is propyl or —$CF_3$ provided that if $R_a$ is alkyl, then $R_b$ is —$CF_3$. Preferably, $R_a$ is phenyl or pyridinyl. Preferably, $R_a$ is phenyl and $R_b$ is propyl or —$CF_3$.

One embodiment provides a compound of Formula (I) or stereoisomers, salts, or prodrugs thereof, wherein $R_a$ is $C_{2-4}$alkyl, $C_{2-3}$fluoroalkyl, $C_{4-6}$cycloalkyl, tetrahydropyranyl, or a cyclic group selected from phenyl, benzyl, and 5- to 6-membered monocyclic heteroaryl groups having 1 to 3 heteroatoms independently selected from N, O, and/or S, wherein said cyclic group is substituted with zero to 3 substituents independently selected from halo, —CN, —OH, $C_{1-4}$alkyl, $C_{1-4}$alkoxy, $C_{1-3}$haloalkyl, and/or $C_{1-2}$haloalkoxy; provided that if $R_a$ is $C_{2-4}$alkyl, then $R_b$ is $C_{1-3}$haloalkyl. Examples of suitable monocyclic heteroaryl groups include furanyl, thiophenyl, pyrazolyl, imidazolyl, isoxazolyl, oxazole, isothiazolyl, thiazolyl, triazolyl, oxadiazolyl, and thiadiazolyl. Preferably, $R_a$ is $C_{2-4}$alkyl, $C_{2-3}$fluoroalkyl, cyclohexyl, tetrahydropyranyl, or a cyclic group selected from phenyl, benzyl, and 5- to 6-membered monocyclic heteroaryl groups having 1 to 2 heteroatoms independently selected from N, O, and/or S, wherein said cyclic group is substituted with zero to 3 substituents independently selected from halo, —CN, —OH, $C_{1-4}$alkyl, $C_{1-2}$alkoxy, —$CF_3$, and/or —$OCF_3$. More preferably, $R_a$ is $C_{3-4}$alkyl, cyclohexyl, —$CH_2CF_3$, tetrahydropyranyl, or a cyclic group selected from phenyl, pyridinyl, and pyrimidinyl, wherein said cyclic group is substituted with zero to 2 substituents independently selected from F, Cl, Br, $C_{1-3}$alkyl, —$CF_3$, and/or —$OCH_3$.

One embodiment provides a compound of Formula (I) or stereoisomers, salts, or prodrugs thereof, wherein $R_b$ is $C_{1-3}$alkyl or $C_{1-2}$fluoroalkyl, provided that if $R_a$ is $C_{1-3}$alkyl then $R_b$ is $C_{1-2}$fluoroalkyl. Preferably, $R_b$ is $C_{1-3}$alkyl or —$CF_3$.

One embodiment provides a compound of Formula (I) or stereoisomers, salts, or prodrugs thereof, wherein: $R_3$ and $R_4$ are independently H and/or $C_{1-4}$alkyl; Q is a 5-membered monocyclic heteroaryl group having 1 to 3 heteroatoms independently selected from N, O, and/or S, wherein said heteroaryl group is substituted with $R_a$ and zero or 1 $R_b$; $R_a$ is $C_{2-4}$alkyl or a cyclic group selected from phenyl, benzyl, and 5-membered monocyclic heteroaryl groups having 1 to 3 heteroatoms independently selected from N, O, and/or S, wherein said cyclic group is substituted with zero, 1, 2, or 3 substituents independently selected from halo, —CN, $C_{1-4}$alkyl, $C_{1-3}$alkoxy, —$CF_3$, and/or —$OCF_3$; and $R_b$ is $C_{1-3}$alkyl or —$CF_3$; provided that if $R_a$ is $C_{2-4}$alkyl, then $R_b$ is —$CF_3$.

One embodiment provides a compound of Formula (I) or stereoisomers, salts, or prodrugs thereof, wherein: $R_1$ is —$(CH_2)_a$OH, —$(CH_2)_a$COOH, —$C(CH_3)_2$COOH, or —$C(O)NR_cR_c$; each $R_2$ is independently F, Cl, —OH, and/or $C_{1-4}$alkyl; each $R_6$ is independently $C_{1-2}$alkyl, F, Cl, $C_{1-2}$haloalkyl, —CN, —OH, $C_{1-2}$alkoxy, and/or $C_{1-2}$haloalkoxy; $R_a$ is $C_{2-4}$alkyl or a cyclic group selected from phenyl, benzyl, and 5-membered monocyclic heteroaryl groups having 1 to 2 heteroatoms independently selected from N, O, and/or S, wherein said cyclic group is substituted with zero, 1, 2, or 3 substituents independently selected from halo, —CN, $C_{1-4}$alkyl, $C_{1-2}$alkoxy, —$CF_3$, and/or —$OCF_3$; and t is zero, 1, 2, or 3.

One embodiment provides a compound of Formula (I) or stereoisomers, salts, or prodrugs thereof, having formula (Ie):

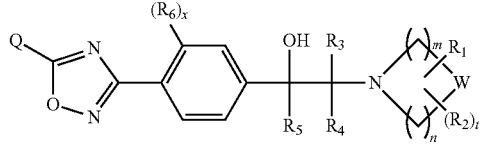

(Ie)

or a stereoisomer or a pharmaceutically acceptable salt thereof, wherein:

m is 1 or 2;

n is 1 or 2;

wherein:

W is $CH_2$ when (m+n) is 2 or 3; or

W is $CH_2$, O, or NH when (m+n) is 4;

$R_1$ is —$CH_2OH$, —$CH_2CH_2OH$, —$(CH_2)_a$COOH, —$C(CH_3)_2$COOH, or —$C(O)N(ethyl)_2$;

$R_2$ is F, —OH, or —$CH_3$;

$R_3$ and $R_4$ are independently H and/or —$CH_3$;

$R_5$ is H or —$CH_3$ $R_6$ is —$CF_3$;

Q is a heteroaryl group selected from thiophenyl, pyrazolyl, isoxazolyl, 5-thiazolyl, imidazolyl, and isothiazolyl, wherein said heteroaryl group is substituted with $R_a$ and zero or 1 $R_b$;

$R_a$ is $C_{3-4}$alkyl, —$CH_2CF_3$, cyclohexyl, tetrahydropyranyl, or a cyclic group selected from phenyl, pyridinyl, and pyrimidinyl, wherein said cyclic group is substituted with zero to 2 substituents independently selected from F, Cl, Br, $C_{1-3}$alkyl, —$CF_3$, and/or —$OCH_3$;

$R_b$ is $C_{1-3}$alkyl or —$CF_3$, provided that if $R_a$ is $C_{3-4}$alkyl then $R_b$ is —$CF_3$;

a is zero, 1, or 2;

t is zero or 1; and x is zero or 1.

One embodiment provides a compound of Formula (I) or stereoisomers, salts, or prodrugs thereof, wherein W is $CH_2$, one of m and n is 1, and the other of m and n is 1 or 2. Compounds of this embodiment include compounds having formula (If):

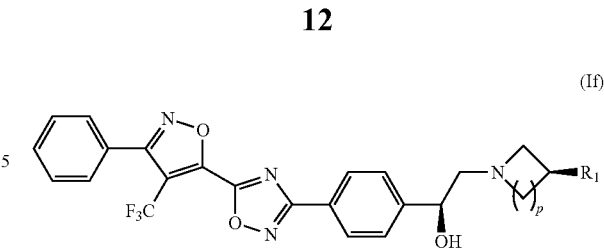

(If)

or a pharmaceutically acceptable salt thereof, wherein p is 1, 2, or 3; and $R_1$ is defined in the first aspect of the invention. Preferably, $R_1$ is —$(CH_2)_a$COOH or $(CH_2)_a$OH; and more preferably, $R_1$ is —$(CH_2)_a$COOH.

One embodiment provides a compound of Formula (I) or stereoisomers, salts, or prodrugs thereof, having formula (Ig):

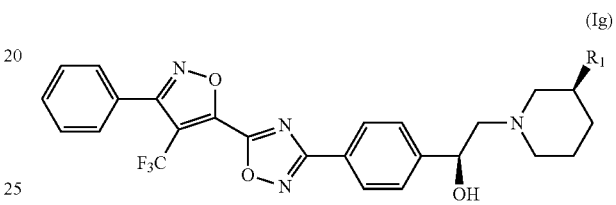

(Ig)

or a pharmaceutically acceptable salt thereof; and $R_1$ is defined in the first aspect of the invention. Preferably, $R_1$ is —$(CH_2)_a$COOH, —$C(CH_3)_2$COOH, or $(CH_2)_a$OH; and more preferably, $R_1$ is —$(CH_2)_a$COOH.

One embodiment provides a compound of Formula (I) or stereoisomers, salts, or prodrugs thereof, $R_1$ is —$(CH_2)_a$OH, —$(CH_2)_a$COOH, —$C(CH_3)_2$COOH, or —$C(O)N(ethyl)_2$; $R_2$ is F, —OH, or —$CH_3$; $R_3$ is H; $R_4$ is H; $R_5$ is H or —$CH_3$; $R_6$ is —$CF_3$; $R_a$ is butyl, phenyl, chlorophenyl, benzyl, pyridinyl, methyl pyridinyl, or thiophenyl; t is zero or 1; and x is zero or 1.

One embodiment provides a compound of Formula (I) or stereoisomers, salts, or prodrugs thereof, wherein:

A is

and Q is 3-isoxazolyl substituted with $R_a$ and zero or 1 $R_b$. A compound of this embodiment has the structure represented by Formula (Ia-1):

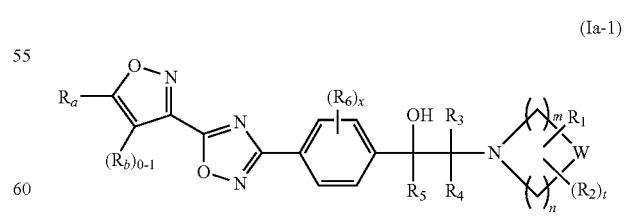

(Ia-1)

or a stereoisomer or a pharmaceutically acceptable salt thereof, wherein $R_1$, $R_2$, $R_3$, $R_4$, $R_5$, $R_6$, W, m, n, t, x, $R_a$ and $R_b$ are defined in the first aspect. Included in this embodiment are compounds in which $R_a$ is $C_{3-4}$alkyl, $C_{2-3}$fluoroalkyl, cyclohexyl, tetrahydropyran, or a cyclic group selected from phenyl, pyridinyl, and pyrimidinyl, wherein said cyclic group is substituted with zero, 1, 2, or 3 substituents independently selected from halo, $C_{1-4}$alkyl, $C_{1-2}$alkoxy, $C_{1-3}$haloalkyl, and/or $C_{1-2}$haloalkoxy. Also included in this embodiment are compounds in which $R_b$ is $C_{1-3}$alkyl or $C_{1-2}$fluoroalkyl, provided that if $R_a$ is alkyl then $R_b$ is $C_{1-2}$fluoroalkyl. Preferably, $R_b$ is $C_{1-3}$alkyl or —$CF_3$.

One embodiment provides a compound of Formula (I) or stereoisomers, salts, or prodrugs thereof, wherein:
A is

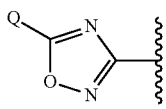

and Q is 5-isoxazolyl substituted with $R_a$ and zero or 1 $R_b$. A compound of this embodiment has the structure represented by Formula (Ia-2):

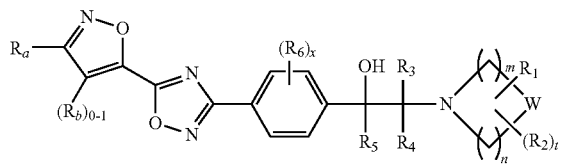

(Ia-2)

or a stereoisomer or a pharmaceutically acceptable salt thereof, wherein $R_1$, $R_2$, $R_3$, $R_4$, $R_5$, $R_6$, W, m, n, t, x, $R_a$ and $R_b$ are defined in the first aspect. Included in this embodiment are compounds in which $R_a$ is $C_{3-4}$alkyl, $C_{2-3}$fluoroalkyl, cyclohexyl, tetrahydropyran, or a cyclic group selected from phenyl, pyridinyl, and pyrimidinyl, wherein said cyclic group is substituted with zero, 1, 2, or 3 substituents independently selected from halo, $C_{1-4}$alkyl, $C_{1-2}$alkoxy, $C_{1-3}$haloalkyl, and/or $C_{1-2}$haloalkoxy. Also included in this embodiment are compounds in which $R_b$ is $C_{1-3}$alkyl or $C_{1-2}$fluoroalkyl, provided that if $R_a$ is alkyl then $R_b$ is $C_{1-2}$fluoroalkyl. Preferably, $R_b$ is $C_{1-3}$alkyl or —$CF_3$.

One embodiment provides a compound of Formula (I) or stereoisomers, salts, or prodrugs thereof, wherein:
A is

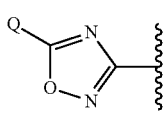

and Q is 2-thiophenyl substituted with $R_a$. A compound of this embodiment has the structure represented by Formula (Ia-3):

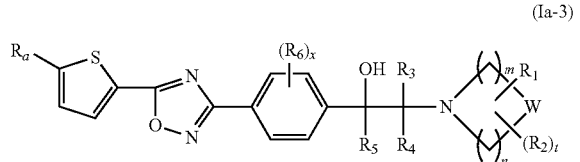

(Ia-3)

or a stereoisomer or a pharmaceutically acceptable salt thereof, wherein $R_1$, $R_2$, $R_3$, $R_4$, $R_5$, $R_6$, W, m, n, t, x, and $R_a$ are defined in the first aspect. Included in this embodiment are compounds in which $R_a$ is $C_{3-4}$alkyl, $C_{2-3}$fluoroalkyl, cyclohexyl, tetrahydropyran, or a cyclic group selected from phenyl, pyridinyl, and pyrimidinyl, wherein said cyclic group is substituted with zero, 1, 2, or 3 substituents independently selected from halo, $C_{1-4}$alkyl, $C_{1-2}$alkoxy, $C_{1-3}$haloalkyl, and/or $C_{1-2}$haloalkoxy. Also included in this embodiment are compounds in which $R_a$ is pyridinyl or phenyl, each substituted with zero, 1, or 2 substituents independently selected from F, Cl, Br, $C_{1-3}$alkyl, —$CF_3$, and/or —$OCH_3$.

One embodiment provides compounds of Formula (I) or stereoisomers, salts, or prodrugs thereof, wherein:
A is

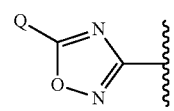

and Q is pyrazolyl substituted with $R_a$ and zero or 1 $R_b$. Compounds of this embodiment have structures represented by Formula (Ia-4), Formula (Ia-5), and Formula (Ia-6):

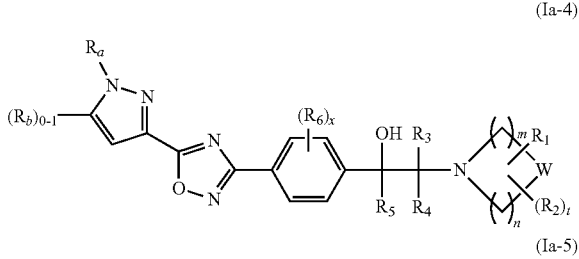

(Ia-4)

(Ia-5)

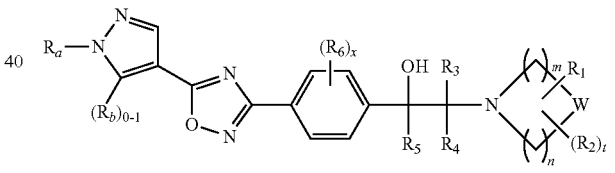

(Ia-6)

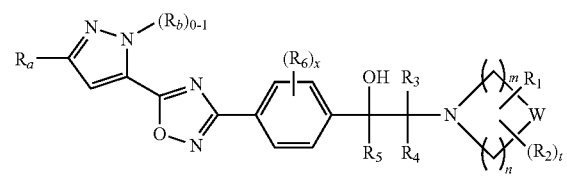

or a stereoisomer or a pharmaceutically acceptable salt thereof, wherein $R_1$, $R_2$, $R_3$, $R_4$, $R_5$, $R_6$, W, m, n, t, x, $R_a$ and $R_b$ are defined in the first aspect. Included in this embodiment are compounds in which $R_a$ is $C_{3-4}$alkyl, $C_{2-3}$fluoroalkyl, cyclohexyl, tetrahydropyran, or a cyclic group selected from phenyl, pyridinyl, and pyrimidinyl, wherein said cyclic group is substituted with zero, 1, 2, or 3 substituents independently selected from halo, $C_{1-4}$alkyl, $C_{1-2}$alkoxy, $C_{1-3}$haloalkyl, and/or $C_{1-2}$haloalkoxy. Also included in this embodiment are compounds in which $R_b$ is $C_{1-3}$alkyl or $C_{1-2}$fluoroalkyl, provided that if $R_a$ is alkyl then $R_b$ is $C_{1-2}$fluroalkyl. Preferably, $R_b$ is $C_{1-3}$alkyl or —$CF_3$.

One embodiment provides a compound of Formula (I) or stereoisomers, salts, or prodrugs thereof, wherein:

A is

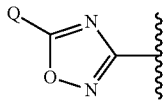

and Q is 5-thiazolyl substituted with $R_a$ and zero or 1 $R_b$. A compound of this embodiment has the structure represented by Formula (Ia-7):

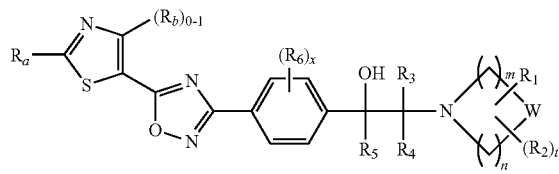

(Ia-7)

or a stereoisomer or a pharmaceutically acceptable salt thereof, wherein $R_1$, $R_2$, $R_3$, $R_4$, $R_5$, $R_6$, W, m, n, t, x, $R_a$ and $R_b$ are defined in the first aspect. Included in this embodiment are compounds in which $R_a$ is $C_{3-4}$alkyl, $C_{2-3}$fluoroalkyl, cyclohexyl, tetrahydropyran, or a cyclic group selected from phenyl, pyridinyl, and pyrimidinyl, wherein said cyclic group is substituted with zero, 1, 2, or 3 substituents independently selected from halo, $C_{1-4}$alkyl, $C_{1-2}$alkoxy, $C_{1-3}$haloalkyl, and/or $C_{1-2}$haloalkoxy. Also included in this embodiment are compounds in which $R_b$ is $C_{1-3}$alkyl or $C_{1-2}$fluoroalkyl, provided that if $R_a$ is alkyl then $R_b$ is $C_{1-2}$fluoroalkyl. Preferably, $R_b$ is —$CH_3$ or —$CF_3$.

One embodiment provides a compound of Formula (I) or stereoisomers, salts, or prodrugs thereof, wherein:
A is

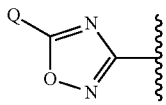

and Q is

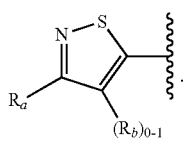

A compound of this embodiment has the structure represented by Formula (Ia-8):

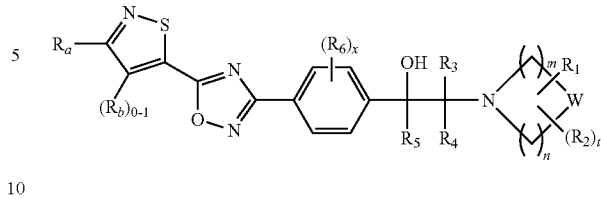

(Ia-8)

or a stereoisomer or a pharmaceutically acceptable salt thereof, wherein $R_1$, $R_2$, $R_3$, $R_4$, $R_5$, $R_6$, W, m, n, t, x, $R_a$ and $R_b$ are defined in the first aspect. Included in this embodiment are compounds in which $R_a$ is $C_{3-4}$alkyl, $C_{2-3}$fluoroalkyl, cyclohexyl, tetrahydropyran, or a cyclic group selected from phenyl, pyridinyl, and pyrimidinyl, wherein said cyclic group is substituted with zero, 1, 2, or 3 substituents independently selected from halo, $C_{1-4}$alkyl, $C_{1-2}$alkoxy, $C_{1-3}$haloalkyl, and/or $C_{1-2}$haloalkoxy. Also included in this embodiment are compounds in which $R_b$ is $C_{1-3}$alkyl or $C_{1-2}$fluoroalkyl, provided that if $R_a$ is alkyl then $R_b$ is $C_{1-2}$fluoroalkyl. Preferably, $R_b$ is $C_{1-3}$alkyl or —$CF_3$.

One embodiment provides a compound of Formula (I) or stereoisomers, salts, or prodrugs thereof, wherein:
A is

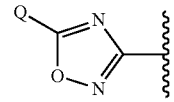

and Q is

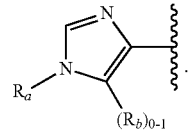

A compound of this embodiment has the structure represented by Formula (Ia-9):

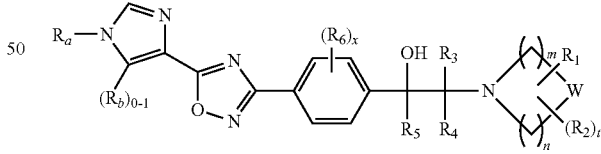

(Ia-9)

or a stereoisomer or a pharmaceutically acceptable salt thereof, wherein $R_1$, $R_2$, $R_3$, $R_4$, $R_5$, $R_6$, W, m, n, t, x, $R_a$ and $R_b$ are defined in the first aspect. Included in this embodiment are compounds in which $R_a$ is $C_{3-4}$alkyl, $C_{2-3}$fluoroalkyl, cyclohexyl, tetrahydropyran, or a cyclic group selected from phenyl, pyridinyl, and pyrimidinyl, wherein said cyclic group is substituted with zero, 1, 2, or 3 substituents independently selected from halo, $C_{1-4}$alkyl, $C_{1-2}$alkoxy, $C_{1-3}$haloalkyl, and/or $C_{1-2}$haloalkoxy. Also included in this embodiment are compounds in which $R_b$ is $C_{1-3}$alkyl or $C_{1-2}$fluoroalkyl, provided that if $R_a$ is alkyl then $R_b$ is $C_{1-2}$fluoroalkyl. Preferably, $R_b$ is $C_{1-3}$alkyl or —$CF_3$.

One embodiment provides a compound of Formula (I) or stereoisomers, salts, or prodrugs thereof, wherein said compound is selected from: 1-(2-hydroxy-2-(4-(5-(5-phenyl-4-propylisoxazol-3-yl)-1,2,4-oxadiazol-3-yl)phenyl)ethyl) azetidine-3-carboxylic acid (1); 1-(2-hydroxy-2-(4-(5-(5-phenyl-4-propylisoxazol-3-yl)-1,2,4-oxadiazol-3-yl)phenyl) ethyl)piperidine-2-carboxylic acid (2); 1-(2-hydroxy-2-(4-(5-(5-phenyl-4-propylisoxazol-3-yl)-1,2,4-oxadiazol-3-yl) phenyl)ethyl)piperidine-3-carboxylic acid (3); (3S)-1-(2-hydroxy-2-(4-(5-(5-phenyl-4-propylisoxazol-3-yl)-1,2,4-oxadiazol-3-yl)phenyl)ethyl)piperidine-3-carboxylic acid (4); (3R)-1-(2-hydroxy-2-(4-(5-(5-phenyl-4-propylisoxazol-3-yl)-1,2,4-oxadiazol-3-yl)phenyl)ethyl)piperidine-3-carboxylic acid (5); 1-(2-hydroxy-2-(4-(5-(5-phenyl-4-propylisoxazol-3-yl)-1,2,4-oxadiazol-3-yl)phenyl)ethyl) pyrrolidine-3-carboxylic acid (6); (2R)-1-(2-hydroxy-2-(4-(5-(5-phenyl-4-propylisoxazol-3-yl)-1,2,4-oxadiazol-3-yl) phenyl)ethyl)azetidine-2-carboxylic acid (7); 2-(1-(2-hydroxy-2-(4-(5-(5-phenyl-4-propylisoxazol-3-yl)-1,2,4-oxadiazol-3-yl)phenyl)ethyl)piperidin-2-yl)acetic acid (8 and 9); 2-((2S)-1-(2-hydroxy-2-(4-(5-phenyl-4-propylisoxazol-3-yl)-1,2,4-oxadiazol-3-yl)phenyl)ethyl)pyrrolidin-2-yl)acetic acid (10); 4-(2-hydroxy-2-(4-(5-(5-phenyl-4-propylisoxazol-3-yl)-1,2,4-oxadiazol-3-yl)phenyl)ethyl) morpholine-2-carboxylic acid (11); 2-((3S)-1-(2-hydroxy-2-(4-(5-(5-phenyl-4-propylisoxazol-3-yl)-1,2,4-oxadiazol-3-yl)phenyl)ethyl)piperidin-3-yl)acetic acid (12); 2-((3R)-1-(2-hydroxy-2-(4-(5-(5-phenyl-4-propylisoxazol-3-yl)-1,2,4-oxadiazol-3-yl)phenyl)ethyl)piperidin-3-yl)acetic acid (13); (3S)-1-(2-hydroxy-2-(4-(5-(5-isobutyl-4-(trifluoromethyl) isoxazol-3-yl)-1,2,4-oxadiazol-3-yl)phenyl)ethyl)piperidine-3-carboxylic acid (20); 4-(2-hydroxy-2-(4-(5-(5-phenyl-4-propylisoxazol-3-yl)-1,2,4-oxadiazol-3-yl)phenyl) ethyl)piperazine-2-carboxylic acid (21); 2-(1-(2-hydroxy-2-(4-(5-(5-phenyl-4-propylisoxazol-3-yl)-1,2,4-oxadiazol-3-yl)phenyl)ethyl)piperidin-3-yl)acetic acid (22); 1-(2-hydroxy-2-(4-(5-(5-phenyl-4-propylisoxazol-3-yl)-1,2,4-oxadiazol-3-yl)phenyl)ethyl)piperidin-3-ol (23); N,N-diethyl-1-(2-hydroxy-2-(4-(5-(5-phenyl-4-propylisoxazol-3-yl)-1,2,4-oxadiazol-3-yl)phenyl)ethyl)piperidine-3-carboxamide (24); 2-((3R)-1-(2-hydroxy-2-(4-(5-(5-phenyl-4-(trifluoromethyl)isoxazol-3-yl)-1,2,4-oxadiazol-3-yl) phenyl)ethyl)piperidin-3-yl)acetic acid (35); (3S)-1-(2-hydroxy-2-(4-(5-(5-phenyl-4-(trifluoromethyl)isoxazol-3-yl)-1,2,4-oxadiazol-3-yl)phenyl)ethyl)piperidine-3-carboxylic acid (36); (3S)-1-(2-hydroxy-2-(4-(5-(3-(6-methylpyridin-2-yl)-4-(trifluoromethyl)isoxazol-5-yl)-1,2, 4-oxadiazol-3-yl)phenyl)ethyl)piperidine-3-carboxylic acid (37); (3S)-1-(2-(4-(5-(5-(4-chlorophenyl)isoxazol-3-yl)-1,2, 4-oxadiazol-3-yl)phenyl)-2-hydroxyethyl)piperidine-3-carboxylic acid (53); 2-((R)-1-((S)-2-hydroxy-2-(4-(5-(5-isobutyl-4-(trifluoromethyl)isoxazol-3-yl)-1,2,4-oxadiazol-3-yl) phenyl)ethyl)piperidin-3-yl)acetic acid, TFA (108); 2-((R)-1-((S)-2-(4-(5-(5-tert-butyl-4-(trifluoromethyl)isoxazol-3-yl)-1,2,4-oxadiazol-3-yl)phenyl)-2-hydroxyethyl)piperidin-3-yl)acetic acid, TFA (109); 2-((R)-1-((S)-2-hydroxy-2-(4-(5-(5-isopropyl-4-(trifluoromethyl)isoxazol-3-yl)-1,2,4-oxadiazol-3-yl)phenyl)ethyl)piperidin-3-yl)acetic acid, HCl (110); 2-((R)-1-((S)-2-(4-(5-(5-cyclohexyl-4-(trifluoromethyl)isoxazol-3-yl)-1,2,4-oxadiazol-3-yl)phenyl)-2-hydroxyethyl)piperidin-3-yl)acetic acid, HCl (111); 2-((R)-1-((S)-2-(4-(5-(5-(3-chlorophenyl)-4-(trifluoromethyl) isoxazol-3-yl)-1,2,4-oxadiazol-3-yl)phenyl)-2-hydroxyethyl)piperidin-3-yl)acetic acid (112); and 2-((3R)-1-((2S)-2-(4-(5-(5-(2-chlorophenyl)-4-(trifluoromethyl) isoxazol-3-yl)-1,2,4-oxadiazol-3-yl)phenyl)-2-hydroxyethyl)piperidin-3-yl)acetic acid, HCl (113).

One embodiment provides a compound of Formula (I) or stereoisomers, salts, or prodrugs thereof, wherein said compound is selected from: (S)-1-((S)-2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (13); (S)-1-((R)-2-hydroxy-2-(4-(5-(3-phenyl-4-(trifluoromethyl) isoxazol-5-yl)-1,2,4-oxadiazol-3-yl)phenyl)ethyl) piperidine-3-carboxylic acid (15); (3S)-1-(2-hydroxy-2-(4-(5-(3-(pyridin-2-yl)-4-(trifluoromethyl)isoxazol-5-yl)-1,2, 4-oxadiazol-3-yl)phenyl)ethyl)piperidine-3-carboxylic acid (16); (3S)-1-(2-hydroxy-2-(4-(5-(3-phenyl-4-(trifluoromethyl)isoxazol-5-yl)-1,2,4-oxadiazol-3-yl)phenyl)propyl)piperidine-3-carboxylic acid (17); 2-((3R)-1-(2-hydroxy-2-(4-(5-(3-phenyl-4-(trifluoromethyl)isoxazol-5-yl)-1,2,4-oxadiazol-3-yl)phenyl)ethyl)piperidin-3-yl)acetic acid (18 and 19); 1-(2-hydroxy-2-(4-(5-(3-phenyl-4-(trifluoromethyl)isoxazol-5-yl)-1,2,4-oxadiazol-3-yl)phenyl)ethyl)azetidine-3-carboxylic acid (25); (3S)-1-(2-hydroxy-2-(4-(5-(3-phenyl-4-(trifluoromethyl)isoxazol-5-yl)-1,2,4-oxadiazol-3-yl)-3-(trifluoromethyl)phenyl)ethyl)piperidine-3-carboxylic acid (26); 2-(1-(2-hydroxy-2-(4-(5-(3-phenyl-4-(trifluoromethyl)isoxazol-5-yl)-1,2,4-oxadiazol-3-yl)phenyl)ethyl)azetidin-3-yl)acetic acid (27); 4-(2-hydroxy-2-(4-(5-(3-phenyl-4-(trifluoromethyl)isoxazol-5-yl)-1,2,4-oxadiazol-3-yl) phenyl)ethyl)morpholine-2-carboxylic acid (28); 2-(4-(2-hydroxy-2-(4-(5-(3-phenyl-4-(trifluoromethyl)isoxazol-5-yl)-1,2,4-oxadiazol-3-yl)phenyl)ethyl)morpholin-3-yl) acetic acid (29); 2-(3-(hydroxymethyl)piperidin-1-yl)-1-(4-(5-(3-phenyl-4-(trifluoromethyl)isoxazol-5-yl)-1,2,4-oxadiazol-3-yl)phenyl)ethanol (30); 2-(3-(2-hydroxyethyl) piperidin-1-yl)-1-(4-(5-(3-phenyl-4-(trifluoromethyl) isoxazol-5-yl)-1,2,4-oxadiazol-3-yl)phenyl)ethanol (31); 5-hydroxy-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (32); 2-(4-(2-hydroxy-2-(4-(5-(3-phenyl-4-(trifluoromethyl)isoxazol-5-yl)-1,2,4-oxadiazol-3-yl)phenyl)ethyl)morpholin-2-yl)acetic acid (33); 3-fluoro-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (34); 1-(2-hydroxy-2-(4-(5-(3-phenyl-4-(trifluoromethyl)isoxazol-5-yl)-1,2,4-oxadiazol-3-yl) phenyl)ethyl)-3-methylpiperidine-3-carboxylic acid (38); 3-hydroxy-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (39); 3-(1-(2-hydroxy-2-(4-(5-(3-phenyl-4-(trifluoromethyl)isoxazol-5-yl)-1,2,4-oxadiazol-3-yl)phenyl)ethyl)piperidin-3-yl)propanoic acid (40); (2R)-1-(2-hydroxy-2-(4-(5-(3-phenyl-4-(trifluoromethyl)isoxazol-5-yl)-1,2,4-oxadiazol-3-yl)phenyl)ethyl)piperidine-2-carboxylic acid (41); 1-(2-hydroxy-2-(4-(5-(3-phenyl-4-(trifluoromethyl)isoxazol-5-yl)-1,2,4-oxadiazol-3-yl) phenyl)ethyl)-6-methylpiperidine-2-carboxylic acid (42); 2-((3R)-1-(2-hydroxy-2-(4-(5-(3-(pyridin-2-yl)-4-(trifluoromethyl)isoxazol-5-yl)-1,2,4-oxadiazol-3-yl)phenyl)ethyl) piperidin-3-yl)acetic acid (54); (3S)-1-(1-hydroxy-2-methyl-1-(4-(5-(3-phenyl-4-(trifluoromethyl)isoxazol-5-yl)-1,2,4-oxadiazol-3-yl)phenyl)propan-2-yl)piperidine-3-carboxylic acid, TFA (55); and 2-((3R)-1-(2-hydroxy-2-(4-(5-(3-(pyridin-2-yl)-4-(trifluoromethyl)isoxazol-5-yl)-1,2,4-oxadiazol-3-yl)phenyl)ethyl)piperidin-3-yl)acetic acid (56).

One embodiment provides a compound of Formula (I) or stereoisomers, salts, or prodrugs thereof, wherein said compound is selected from: (3S)-1-(2-hydroxy-2-(4-(5-(5-(pyridin-2-yl)thiophen-2-yl)-1,2,4-oxadiazol-3-yl)phenyl)ethyl) piperidine-3-carboxylic acid (43); and 2-((R)-1-((S)-2- hydroxy-2-(4-(5-(4-phenyl-5-(trifluoromethyl)thiophen-2-yl)-1,2,4-oxadiazol-3-yl)phenyl)ethyl)piperidin-3-yl)acetic acid (115).

One embodiment provides a compound of Formula (I) or stereoisomers, salts, or prodrugs thereof, wherein said compound is selected from: (3S)-1-(2-hydroxy-2-(4-(5-(1-phenyl-5-propyl-1H-pyrazol-4-yl)-1,2,4-oxadiazol-3-yl)phenyl)ethyl)piperidine-3-carboxylic acid (44); (3S)-1-(2-hydroxy-2-(4-(5-(5-methyl-1-phenyl-1H-pyrazol-3-yl)-1,2,4-oxadiazol-3-yl)phenyl)ethyl)piperidine-3-carboxylic acid (45); (3S)-1-(2-hydroxy-2-(4-(5-(1-phenyl-1H-pyrazol-4-yl)-1,2,4-oxadiazol-3-yl)phenyl)ethyl)piperidine-3-carboxylic acid (47); (3S)-1-(2-(4-(5-(3-(4-chlorophenyl)-1H-pyrazol-5-yl)-1,2,4-oxadiazol-3-yl)phenyl)-2-hydroxyethyl)piperidine-3-carboxylic acid (48); (3S)-1-(2-(4-(5-(3-(2-chlorophenyl)-1H-pyrazol-5-yl)-1,2,4-oxadiazol-3-yl)phenyl)-2-hydroxyethyl)piperidine-3-carboxylic acid (49); (3S)-1-(2-hydroxy-2-(4-(5-(1-methyl-3-phenyl-1H-pyrazol-5-yl)-1,2,4-oxadiazol-3-yl)phenyl)ethyl)piperidine-3-carboxylic acid (50); (3S)-1-(2-(4-(5-(5-ethyl-1-(pyridin-2-yl)-1H-pyrazol-4-yl)-1,2,4-oxaziazol-3-yl)phenyl)-2-hydroxyethyl)piperidine-3-carboxylic acid (51); (3S)-1-(2-hydroxy-2-(4-(5-(5-methyl-1-phenyl-1H-pyrazol-4-yl)-1,2,4-oxadiazol-3-yl)phenyl)ethyl)piperidine-3-carboxylic acid (52); (S)-1-((S)-2-hydroxy-2-(4-(5-(1-phenyl-5-(trifluoromethyl)-1H-pyrazol-4-yl)-1,2,4-oxadiazol-3-yl)phenyl)ethyl)piperidine-3-carboxylic acid (57); 2-((R)-1-((S)-2-hydroxy-2-(4-(5-(1-phenyl-5-(trifluoromethyl)-1H-pyrazol-4-yl)-1,2,4-oxadiazol-3-yl)phenyl)ethyl)piperidin-3-yl)acetic acid, HCl (59); 2-((R)-1-((S)-2-(4-(5-(1-cyclohexyl-5-(trifluoromethyl)-1H-pyrazol-4-yl)-1,2,4-oxadiazol-3-yl)phenyl)-2-hydroxyethyl)piperidin-3-yl)acetic acid, HCl (60); 2-((3R)-1-((2S)-2-(4-(5-(1-(3-chloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, TFA (61); 2-((R)-1-((S)-2-(4-(5-(1-(6-chloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl (61); 2-((R)-1-((S)-2-(4-(5-(1-(4-fluorophenyl)-5-(trifluoromethyl)-1H-pyrazol-4-yl)-1,2,4-oxadiazol-3-yl)phenyl)-2-hydroxyethyl)piperidin-3-yl)acetic acid, HCl (62); 2-((R)-1-((S)-2-(4-(5-(1-(3-chlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl (63); 2-((R)-1-((S)-2-hydroxy-2-(4-(5-(1-(pyridin-2-yl)-5-(trifluoromethyl)-1H-pyrazol-4-yl)-1,2,4-oxadiazol-3-yl)phenyl)ethyl)piperidin-3-yl)acetic acid, tetrabutylammonium salt (64); 2-((R)-1-((S)-2-(4-(5-(1-(4-chlorophenyl)-5-(trifluoromethyl)-1H-pyrazol-4-yl)-1,2,4-oxadiazol-3-yl)phenyl)-2-hydroxyethyl)piperidin-3-yl)acetic acid (65); 2-((R)-1-((S)-2-(4-(5-(1-(4-bromophenyl)-5-(trifluoromethyl)-1H-pyrazol-4-yl)-1,2,4-oxadiazol-3-yl)phenyl)-2-hydroxyethyl)piperidin-3-yl)acetic acid (66); 2-((R)-1-((S)-2-hydroxy-2-(4-(5-(1-m-tolyl-5-(trifluoromethyl)-1H-pyrazol-4-yl)-1,2,4-oxadiazol-3-yl)phenyl)ethyl)piperidin-3-yl)acetic acid, HCl (67); 2-((3R)-1-((2S)-2-hydroxy-2-(4-(5-(1-(2-methoxyphenyl)-5-(trifluoromethyl)-1H-pyrazol-4-yl)-1,2,4-oxadiazol-3-yl)phenyl)ethyl)piperidin-3-yl)acetic acid (68); 2-((R)-1-((S)-2-hydroxy-2-(4-(5-(1-(tetrahydro-2H-pyran-4-yl)-5-(trifluoromethyl)-1H-pyrazol-4-yl)-1,2,4-oxadiazol-3-yl)phenyl)ethyl)piperidin-3-yl)acetic acid (69); 2-((R)-1-((S)-2-(4-(5-(1-(5-chloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl (70); 2-((R)-1-((S)-2-hydroxy-2-(4-(5-(1-(2,2,2-trifluoroethyl)-5-(trifluoromethyl)-1H-pyrazol-4-yl)-1,2,4-oxadiazol-3-yl)phenyl)ethyl)piperidin-3-yl)acetic acid, HCl (71); 2-((3R)-1-((2S)-2-(4-(5-(1-(2-chlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl (72); 2-((3R)-1-((2S)-2-(4-(5-(1-(2,4-difluorophenyl)-5-(trifluoromethyl)-1H-pyrazol-4-yl)-1,2,4-oxadiazol-3-yl)phenyl)-2-hydroxyethyl)piperidin-3-yl)acetic acid, HCl (73); 2-((3R)-1-((2S)-2-hydroxy-2-(4-(5-(5-(trifluoromethyl)-1-(2-(trifluoromethyl)phenyl)-1H-pyrazol-4-yl)-1,2,4-oxadiazol-3-yl)phenyl)ethyl)piperidin-3-yl)acetic acid, HCl (74); 2-((R)-1-((S)-2-hydroxy-2-(4-(5-(5-(trifluoromethyl)-1-(3-(trifluoromethyl)phenyl)-1H-pyrazol-4-yl)-1,2,4-oxadiazol-3-yl)phenyl)ethyl)piperidin-3-yl)acetic acid, HCl (75); 2-((R)-1-((S)-2-hydroxy-2-(4-(5-(5-(trifluoromethyl)-1-(4-(trifluoromethyl)phenyl)-1H-pyrazol-4-yl)-1,2,4-oxadiazol-3-yl)phenyl)ethyl)piperidin-3-yl)acetic acid (76); 2-((3R)-1-((2S)-2-hydroxy-2-(4-(5-(1-o-tolyl-5-(trifluoromethyl)-1H-pyrazol-4-yl)-1,2,4-oxadiazol-3-yl)phenyl)ethyl)piperidin-3-yl)acetic acid (77); 2-((R)-1-((S)-2-hydroxy-2-(4-(5-(1-p-tolyl-5-(trifluoromethyl)-1H-pyrazol-4-yl)-1,2,4-oxadiazol-3-yl)phenyl)ethyl)piperidin-3-yl)acetic acid (78); 2-((R)-1-((S)-2-hydroxy-2-(4-(5-(1-(4-isopropylphenyl)-5-(trifluoromethyl)-1H-pyrazol-4-yl)-1,2,4-oxadiazol-3-yl)phenyl)ethyl)piperidin-3-yl)acetic acid (79); 2-((R)-1-((S)-2-hydroxy-2-(4-(5-(1-(4-methoxyphenyl)-5-(trifluoromethyl)-1H-pyrazol-4-yl)-1,2,4-oxadiazol-3-yl)phenyl)ethyl)piperidin-3-yl)acetic acid (80); 2-((R)-1-((S)-2-hydroxy-2-(4-(5-(1-isobutyl-5-(trifluoromethyl)-1H-pyrazol-4-yl)-1,2,4-oxadiazol-3-yl)phenyl)ethyl)piperidin-3-yl)acetic acid, HCl (81); 2-((R)-1-((S)-2-(4-(5-(1-(5-fluoropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl (82); 2-((3R)-1-((2S)-2-(4-(5-(1-(5-chloro-3-fluoropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl (83); 2-((3R)-1-((2S)-2-(4-(5-(1-(5-ethoxy-3-fluoropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl (84); 2-((R)-1-((S)-2-hydroxy-2-(4-(5-(1-(pyrimidin-2-yl)-5-(trifluoromethyl)-1H-pyrazol-4-yl)-1,2,4-oxadiazol-3-yl)phenyl)ethyl)piperidin-3-yl)acetic acid (85); 2-((R)-1-((S)-2-hydroxy-2-(4-(5-(1-(pyridin-3-yl)-5-(trifluoromethyl)-1H-pyrazol-4-yl)-1,2,4-oxadiazol-3-yl)phenyl)ethyl)piperidin-3-yl)acetic acid (86); 2-((R)-1-((S)-2-hydroxy-2-(4-(5-(5-(trifluoromethyl)-1-(5-(trifluoromethyl)pyridin-2-yl)-1H-pyrazol-4-yl)-1,2,4-oxadiazol-3-yl)phenyl)ethyl)piperidin-3-yl)acetic acid, HCl (87); 2-((3R)-1-((S)-2-(4-(5-(1-(3,5-dichloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl (88); 2-((3R)-1-((2S)-2-(4-(5-(1-(2,4-dichlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl (89); 2-((3R)-1-((2S)-2-(4-(5-(1-(4-chloro-2-methylphenyl)-5-(trifluoromethyl)-1H-pyrazol-4-yl)-1,2,4-oxadiazol-3-yl)phenyl)-2-hydroxyethyl)piperidin-3-yl)acetic acid, HCl (90); 2-((R)-1-((S)-2-(4-(5-(1-(4-chloro-3-methylphenyl)-5-(trifluoromethyl)-1H-pyrazol-4-yl)-1,2,4-oxadiazol-3-yl)phenyl)-2-hydroxyethyl)piperidin-3-yl)acetic acid, HCl (91); 2-((R)-1-((S)-2-(4-(5-(1-(3,4-dichlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl (92); 2-((R)-1-((S)-2-hydroxy-2-(4-(5-(1-(4-methylpyridin-2-yl)-5-(trifluoromethyl)-1H-pyrazol-4-yl)-1,2,4-oxadiazol-3-yl)phenyl)ethyl)piperidin-3-yl)acetic acid, HCl (93); 2-((R)-1-((S)-2-hydroxy-2-(4-(5-(1-(5-methylpyridin-2-yl)-5-(trifluoromethyl)-1H-pyrazol-4-yl)-1,2,4-oxadiazol-3-yl)phenyl)ethyl)piperidin-3-yl)acetic acid (94); 2-((3R)-1-((2S)-2-(4-(5-(1-(5-chloro-3-(trifluoromethyl)pyridin-2-yl)-

5-(trifluoromethyl)-1H-pyrazol-4-yl)-1,2,4-oxadiazol-3-yl) phenyl)-2-hydroxyethyl)piperidin-3-yl)acetic acid (95); 2-((R)-1-((S)-2-hydroxy-2-(4-(5-(1-(6-methyl-4-(trifluoromethyl)pyridin-2-yl)-5-(trifluoromethyl)-1H-pyrazol-4-yl)-1,2,4-oxadiazol-3-yl)phenyl)ethyl)piperidin-3-yl)acetic acid, HCl (96); (S)-1-((S)-2-(4-(5-(1-(4-chlorophenyl)-5-(trifluoromethyl)-1H-pyrazol-4-yl)-1,2,4-oxadiazol-3-yl) phenyl)-2-hydroxyethyl)piperidine-3-carboxylic acid, HCl (97); (S)-1-((S)-2-hydroxy-2-(4-(5-(5-(trifluoromethyl)-1-(5-(trifluoromethyl)pyridin-2-yl)-1H-pyrazol-4-yl)-1,2,4-oxadiazol-3-yl)phenyl)ethyl)piperidine-3-carboxylic acid, HCl (98); (S)-1-((S)-2-hydroxy-2-(4-(5-(1-(4-methoxyphenyl)-5-(trifluoromethyl)-1H-pyrazol-4-yl)-1,2,4-oxadiazol-3-yl)phenyl)ethyl)piperidine-3-carboxylic acid, HCl (99); (S)-1-((S)-2-(4-(5-(1-(3,5-dichloropyridin-2-yl)-5-(trifluoromethyl)-1H-pyrazol-4-yl)-1,2,4-oxadiazol-3-yl)phenyl)-2-hydroxyethyl)piperidine-3-carboxylic acid, HCl (100); (S)-1-((S)-2-(4-(5-(1-(5-fluoropyridin-2-yl)-5-(trifluoromethyl)-1H-pyrazol-4-yl)-1,2,4-oxadiazol-3-yl)phenyl)-2-hydroxyethyl)piperidine-3-carboxylic acid, HCl (101); (S)-1-((S)-2-hydroxy-2-(4-(5-(1-m-tolyl-5-(trifluoromethyl)-1H-pyrazol-4-yl)-1,2,4-oxadiazol-3-yl)phenyl)ethyl)piperidine-3-carboxylic acid (102); (S)-1-((S)-2-hydroxy-2-(4-(5-(1-(5-methylpyridin-2-yl)-5-(trifluoromethyl)-1H-pyrazol-4-yl)-1,2,4-oxadiazol-3-yl)phenyl)ethyl)piperidine-3-carboxylic acid (103); (S)-1-((S)-2-hydroxy-2-(4-(5-(1-(pyridin-2-yl)-5-(trifluoromethyl)-1H-pyrazol-4-yl)-1,2,4-oxadiazol-3-yl) phenyl)ethyl)piperidine-3-carboxylic acid (104); (S)-1-((S)-2-(4-(5-(1-(5-chloropyridin-2-yl)-5-(trifluoromethyl)-1H-pyrazol-4-yl)-1,2,4-oxadiazol-3-yl)phenyl)-2-hydroxyethyl) piperidine-3-carboxylic acid (105); (S)-1-((S)-2-(4-(5-(1-cyclohexyl-5-(trifluoromethyl)-1H-pyrazol-4-yl)-1,2,4-oxadiazol-3-yl)phenyl)-2-hydroxyethyl)piperidine-3-carboxylic acid (106); (S)-1-((S)-2-(4-(5-(1-(2,4-difluorophenyl)-5-(trifluoromethyl)-1H-pyrazol-4-yl)-1,2,4-oxadiazol-3-yl)phenyl)-2-hydroxyethyl)piperidine-3-carboxylic acid, HCl (107); and 2-((R)-1-((S)-2-(4-(5-(1-(4-fluorophenyl)-3-(trifluoromethyl)-1H-pyrazol-4-yl)-1,2,4-oxadiazol-3-yl)phenyl)-2-hydroxyethyl)piperidin-3-yl) acetic acid (116).

One embodiment provides a compound of Formula (I) or stereoisomers, salts, or prodrugs thereof, wherein said compound is (3S)-1-(2-hydroxy-2-(4-(5-(4-methyl-2-phenylthiazol-5-yl)-1,2,4-oxadiazol-3-yl)phenyl)ethyl)piperidine-3-carboxylic acid (46).

One embodiment provides a compound of Formula (I) or stereoisomers, salts, or prodrugs thereof, wherein said compound is selected from: 2-((R)-1-((S)-2-(4-(5-(1-(4-chlorophenyl)-5-(trifluoromethyl)-1H-imidazol-4-yl)-1,2,4-oxadiazol-3-yl)phenyl)-2-hydroxyethyl)piperidin-3-yl)acetic acid (117); and 2-((R)-1-((S)-2-hydroxy-2-(4-(5-(1-(pyridin-2-yl)-5-(trifluoromethyl)-1H-imidazol-4-yl)-1,2,4-oxadiazol-3-yl)phenyl)ethyl)piperidin-3-yl)acetic acid (118).

One embodiment provides a compound of Formula (I) or stereoisomers, salts, or prodrugs thereof, wherein said compound is (S)-1-((S)-2-hydroxy-2-(4-(5-(3-phenyl-4-(trifluoromethyl)isothiazol-5-yl)-1,2,4-oxadiazol-3-yl)phenyl) ethyl)piperidine-3-carboxylic acid, HCl (114).

The compounds of Formula (I) have GTPγS $S1P_1$ $EC_{50}$ values of 5 μM or less as measured by the $S1P_1$ Receptor GTPγS Binding Assay described herein below. Preferably, the compounds of Formula (I) have GTPγS $S1P_1$ $EC_{50}$ values in the range of 0.01 nM to 2 μM, and more preferably, in the range of from 0.01 nM to 1 μM. Other preferred compounds of Formula (I) have GTPγS $S1P_1$ $EC_{50}$ values in the range of from 0.01 nM to 100 nM.

The compounds of Formula (I) are selective for $S1P_1$ activity over $S1P_3$ activity as measured by the selectivity ratio of the GTPγS $S1P_3$ $EC_{50}$ value to the GTPγS $S1P_1$ $EC_{50}$ value. The $S1P_1$ Receptor GTPγS Binding Assay and the $S1P_3$ Binding Assay are described herein below. The compounds of Formula (I) have selectivity ratios (GTPγS $S1P_3/S1P_1$) of at least 3.5 or greater, preferably at least 50 or greater, and more preferably at least 100 or greater. For example, suitable compounds of Formula (I) can have selectivity ratios in the range of from 50 to 50,000. Other suitable compounds of Formula (I) can have selectivity ratios in the range of from 100 to 50,000.

In one embodiment, the compounds of Formula (I) are provided having GTPγS $S1P_1$ $EC_{50}$ values in the range of from 0.01 nM to 100 nM and selectivity ratios (GTPγS $S1P_3/S1P_1$) of at least 50, and more preferably, at least 100.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, or I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_1$-$C_6$ alkyl" denotes straight and branched chain alkyl groups with one to six carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$—), and 2,2,2-trfluoroethyl (—$CH_2CF_3$). When numbers appear in a subscript after the symbol "C", the subscript defines with more specificity the number of carbon atoms that a particular haloalkyl group may contain. For example, "$C_1$-$C_4$ haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$).

The term "haloalkoxy" refers to a haloalkyl group bonded through an oxygen linkage (—O—), wherein the haloalkyl group has one or more halo substituents. For example, "$C_{1-6}$haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy.

"Fluoroalkoxy" and "—O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "heteroatom" refers to oxygen (O), sulfur (S), and nitrogen (N).

The term "thiophenyl" as used herein, refers to a group having the structure:

The term "heteroaryl" refers to substituted and unsubstituted aromatic 5- or 6-membered monocyclic groups which have at least one heteroatom (O, S or N), preferably having 1, 2, or 3 heteroatoms independently selected from O, S, and/or N. The ring of the heteroaryl group can contain one or two oxygen or sulfur atoms and/or from one to four nitrogen atoms provided that the total number of heteroatoms in the ring is four or less and the ring has at least one carbon atom. The nitrogen and sulfur atoms may optionally be oxidized and the nitrogen atoms may optionally be quaternized. The heteroaryl group may be attached at any available nitrogen or carbon atom of any ring. The heteroaryl ring system may contain zero, one, two, or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

The term "heterocyclo" or "heterocyclyl" may be used interchangeably and refer to non-aromatic 3- to 7-membered monocyclic groups, in which the ring has 1 to 3 heteroatoms independently selected from O, S, and/or N. The heterocyclyl ring can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom.

The group in which A is

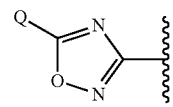

and Q is 2-furanyl has the structure:

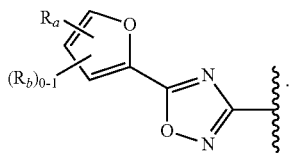

The group in which A is

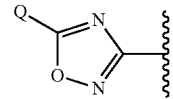

and Q is 4-thiazolyl has the structure:

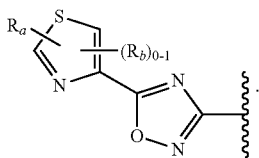

The group in which A is

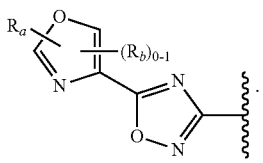

and Q is 4-oxazolyl has the structure:

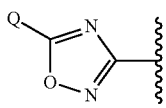

The group in which A is

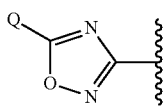

and Q is 1,2,3-triazolyl has the structure:

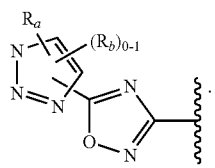

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 90%, preferably 95%, and more preferably 99%, of a compound of Formula (I) ("substantially pure"), which is then used or formulated as described herein.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, Bundgaard, H. ed., Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent vascular disease or autoimmune diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends Immunol.*, 28:102 (2007)).

By virtue of their $S1P_1$ activity as agonists, the compounds of the present invention are immuno-regulatory agents useful for treating or preventing autoimmune or chronic inflammatory diseases. The compounds of the present invention are useful to suppress the immune system in instances where immuno-suppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also embodied within the present invention is a method of preventing or treating resistance to transplantation or transplantation rejection of organs or tissues in a mammalian patient in need thereof, which comprises administering a compound of Formula (I) or a pharmaceutically acceptable salt thereof. A therapeutically effective amount for preventing or treating resistance to transplantation or transplantation rejection may be administered.

A method of suppressing the immune system in a mammalian patient in need thereof, which comprises administering to the patient a compound of Formula (I) or a pharmaceutically acceptable salt thereof, is yet another embodiment. A therapeutically effective amount for suppressing the immune system may be administered.

Most particularly, the method described herein encompasses a method of treating or preventing bone marrow or organ transplant rejection which is comprised of administering to a mammalian patient in need of such treatment or prevention a compound of Formula (I) or a pharmaceutically acceptable salt thereof. A therapeutically effective amount for treating or preventing bone marrow or organ transplant rejection may be administered.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. Examples of compounds suitable for use in the method of this embodiment include compounds of Formula (I) or pharmaceutically acceptable salts thereof, wherein: A is

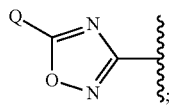

$R_1$ is —$(CH_2)_a$OH or —$(CH_2)_a$COOH; $R_2$ is F, —OH, or —$CH_3$; $R_3$ is H; $R_4$ is H; $R_5$ is H or —$CH_3$; $R_6$ is —$CF_3$; t is zero or 1; x is zero or 1; and Q, W, m, and n are defined in the first aspect. Preferably, Q is thiophenyl, pyrazolyl, isoxazolyl, imidazolyl, isothiazolyl, and 5-thiazolyl. Preferably, $R_a$ is $C_{3-4}$alkyl, —$CH_2CF_3$, cyclohexyl, tetrahydropyranyl, or a cyclic group selected from phenyl, pyridinyl, and pyrimidinyl, wherein said cyclic group is substituted with zero to 2 substituents independently selected from F, Cl, Br, $C_{1-3}$alkyl, —$CF_3$, and/or —$OCH_3$. Preferably, Q is substituted with zero or 1 $R_b$, wherein $R_b$ is $C_{1-3}$alkyl or —$CF_3$, provided that if $R_a$ is alkyl, then $R_b$ is —$CF_3$. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

One embodiment provides a method of treating a disease or disorder associated with the activity of G protein-coupled receptor $S1P_1$, the method comprising administering to a mammalian patient of a compound of Formula (I) or a pharmaceutically acceptable salt thereof, wherein: A is

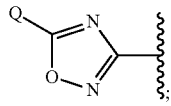

$R_1$ is —$(CH_2)_a$OH or —$(CH_2)_a$COOH; $R_2$ is F, —OH, or —$CH_3$; $R_3$ is H; $R_4$ is H; $R_5$ is H or —$CH_3$; $R_6$ is —$CF_3$; t is zero or 1; x is zero or 1; and Q, W, m, and n are defined in the first aspect. Preferably, Q is thiophenyl, pyrazolyl, isoxazolyl, imidazolyl, isothiazolyl, and 5-thiazolyl. Preferably, $R_a$ is $C_{3-4}$alkyl, —$CH_2CF_3$, cyclohexyl, tetrahydropyranyl, or a cyclic group selected from phenyl, pyridinyl, and pyrimidinyl, wherein said cyclic group is substituted with zero to 2 substituents independently selected from F, Cl, Br, $C_{1-3}$alkyl, —$CF_3$, and/or —$OCH_3$. Preferably, Q is substituted with zero or 1 $R_b$, wherein $R_b$ is $C_{1-3}$alkyl or —$CF_3$, provided that if $R_a$ is alkyl, then $R_b$ is —$CF_3$. The method of the present embodiment includes administration of a therapeutically effect amount of a compound of Formula (I) or a pharmaceutically effective salt thereof.

The methods of treating $S1P_1$-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the $S1P_1$ receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo [1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), or their ligands including CD154 (GP39, or CD40L); antibodies to, fusion proteins, or soluble receptors of human cytokines or growth factors, for example, TNF such as, infliximab (REMICADE®), etanercept (ENBREL®), adalimumab (HUMIRA®), LT, Il-1 such as anakinra (KINERET®) (an IL-1 receptor antagonist), IL-2, IL-4, IL-5, Il-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis,* Third Edition, Wiley & Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, the oxadiazole compounds of the present invention (1.7) may be prepared through the reaction of carboxylic acids (1.1) with N'-hydroxybenzimidamides (1.5) (prepared from the corresponding benzonitriles (1.4)) using a variety of coupling reagents (e.g., EDC, HOBt, BOP, BOP-Cl). Alternatively, the N'-hydroxybenzimidamides may be reacted with acid fluoride (1.2) or acid chloride compounds (1.3). In each case, the initially formed N'-acyloxybenzimidamides (1.6) may spontaneously convert to the oxadiazoles under the reaction conditions. In cases where the N'-acyloxybenzimidamide (1.6) does not cyclize spontaneously, it may be isolated and subjected to reaction conditions to effect the cyclodehydration to (1.7). Such conditions include heating (either conventional or microwave), or treatment with a fluoride source (such as tetrabutylammonium fluoride) or with a base such as potassium t-butoxide.

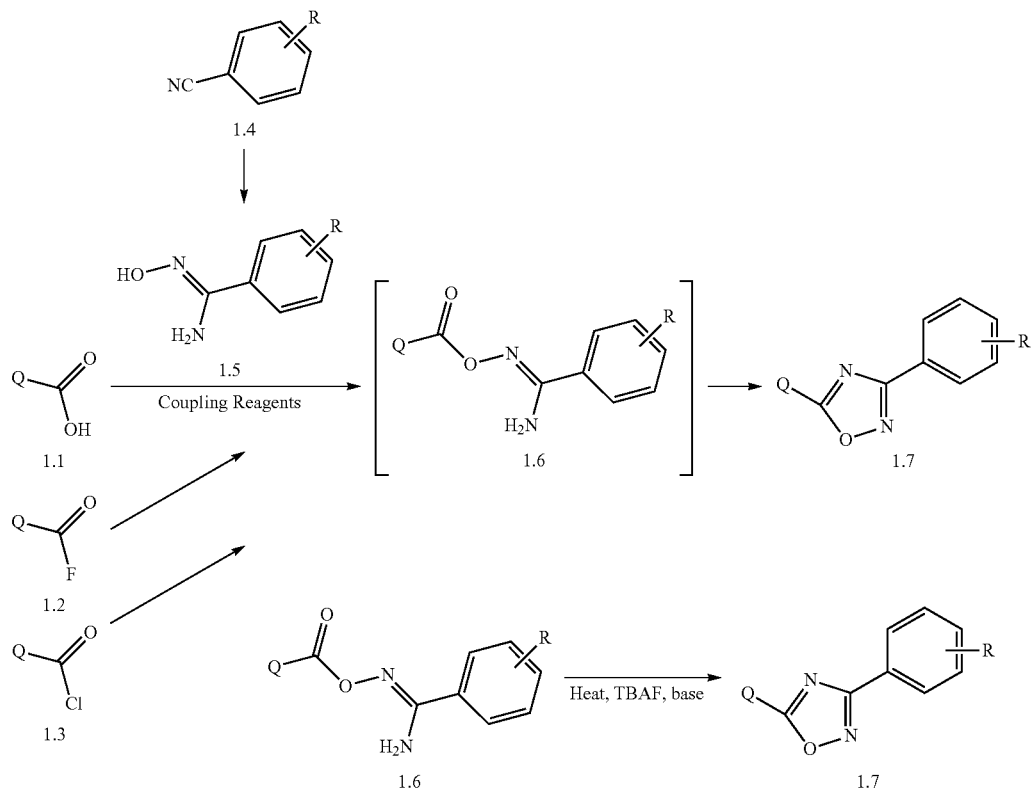

Scheme 1

As shown in Scheme 2, compounds of Formula (I) may be prepared through the reaction of acids (1.1), acid fluorides (1.2) or acid chlorides (1.3) with a fully functionalized N'-acyloxybenzimidamides (2.1) and (4.5) via means described above to produce compounds of structure (2.2). Removal of protecting groups from heterocyclic compound (2.2) is meant to convey use of deprotecting reaction conditions to provide compounds of Formula (I). For example, when $R_1$ is an ester, treatment with a strong acid in water (e.g., HCl) or hydrolysis with base (e.g., NaOH) will provide the corresponding carboxylic acid. When $R_1$ is a SEM-protected tetrazole (SEM=$Me_3SiCH_2CH_2OCH_2$—), it can be deprotected using strong aqueous acid or tetrabutylammonium fluoride. When X is a trialkylsilyl protecting group, it may also be deprotected using strong aqueous acid or tetrabutylammonium fluoride to provide compounds of Formula (I).

Alternatively, the aryl bromide (3.1) may also undergo a Stille coupling with a vinyl 1-alkoxy-1-trialkylstannane to form vinyl ether (3.6) which can then be treated with an electrophilic bromide source (such as but not limited to N-bromosuccinimide) to give bromomethylketone (3.7). Compound (3.7) may also be synthesized directly by electrophilic bromination of the appropriately functionalized acetophenone (not shown) which in turn may be synthesized using methods familiar to one skilled in the art. Reaction of bromomethylketone (3.7) with amine (3.9) can provide the aminomethylketone (3.8). This material may then be reduced using sodium borohydride for example or using asymmetric methods such as enzymatic reduction or chiral reducing agents to produce chiral amino alcohol (3.4). The addition of nucleophilic carbon sources (e.g., $R_5MgBr$; $R_5$—Li; and

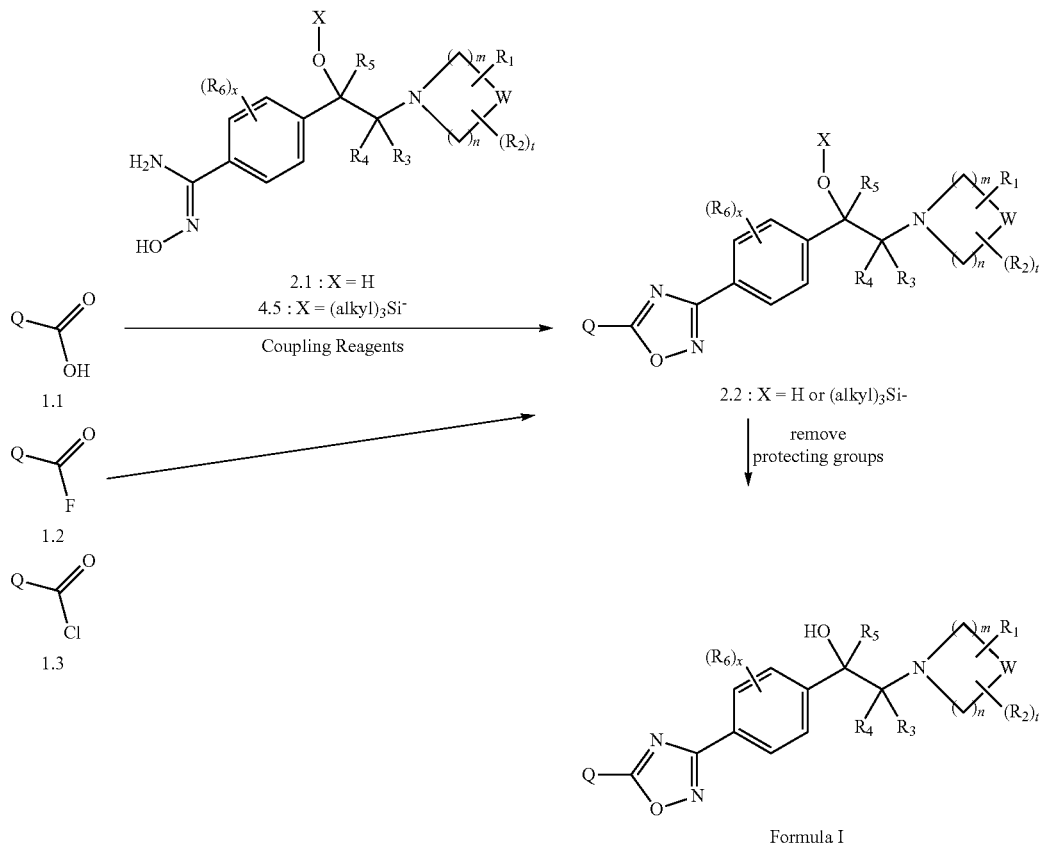

TMS—$R_5$ in the presence of TBAF) can provide intermediate (3.4) wherein R5 is other than H.

Intermediate epoxide (3.3) may also be opened regioselectively using trialkylsilyl bromides (such as bromotriethylsilane) to give either the silyl protected bromo alcohol or the hydroxy bromo alcohol (3.5) depending on the reaction conditions and workup. Reaction of the hydroxyl bromo alcohol (3.5) with amine (3.9) provides the desired amino alcohol (3.4). Amino alcohol (3.4) can then be converted to the desired N'-hydroxybenzimidamide (2.1) by treatment with hydroxylamine as illustrated in Scheme 3.

Alternatively, advanced intermediate (2.1) may also be produced as described in Scheme 3. The reaction of aryl bromides (3.1), iodides, or triflates with optionally substituted vinyl stannane reagents in the presence of Pd(0) in a Stille reaction or a Suzuki reaction in the case of vinyl boronic acids (see *Chem. Rev.*, 107:133-173 (2007)) and can provide styrene (3.2). This olefin may be epoxidized (using reagents such as m-chloroperbenzoic acid) to form epoxide (3.3). This epoxide can then be reacted with appropriately substituted heterocyclic amines (3.9) under thermal conditions or in the presence of a Lewis acid to provide the amino alcohol (3.4). This compound can be treated with hydroxylamine or its salts in the presence of base and heated to form the N'-hydroxybenzimidamide (2.1).

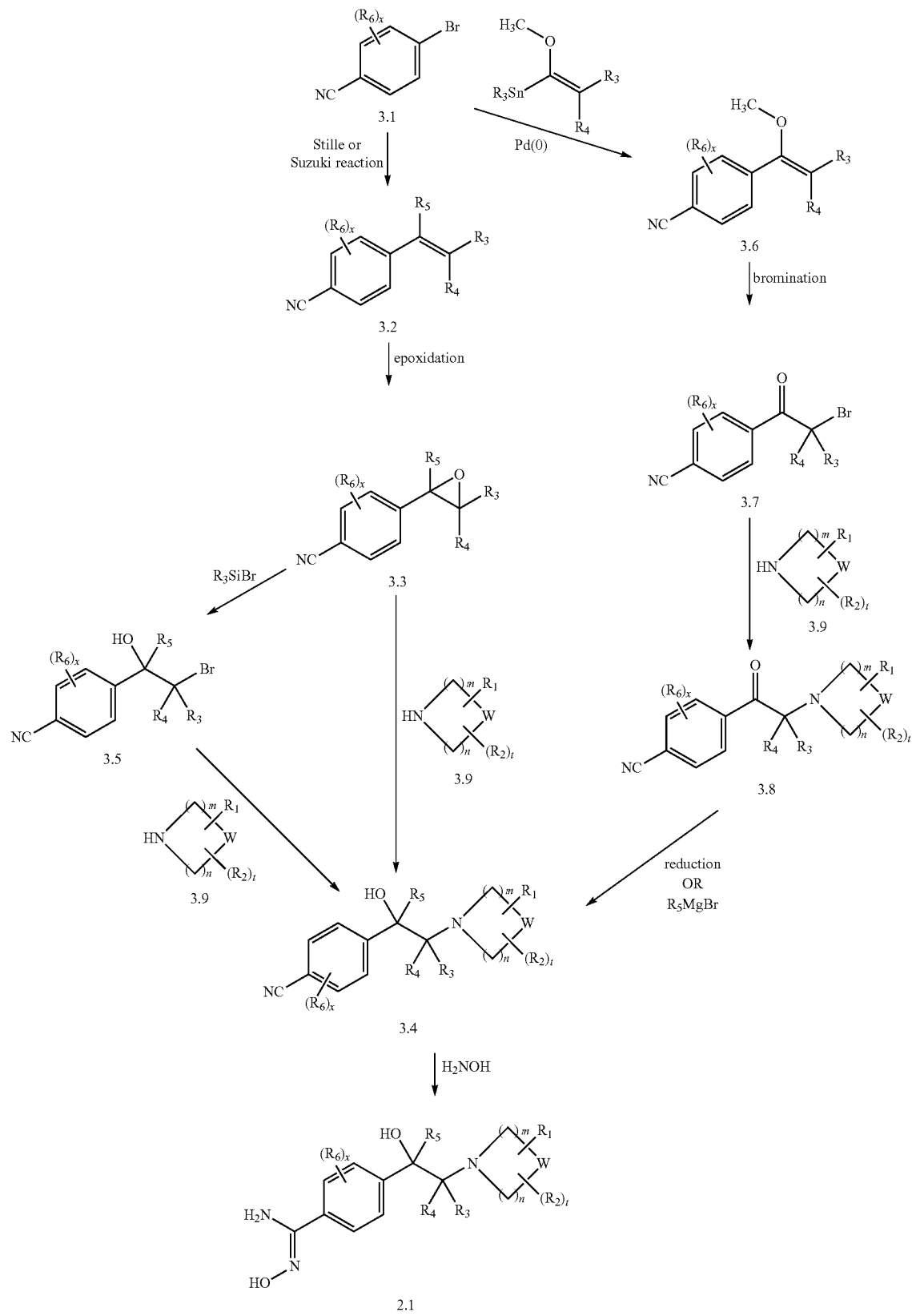

A versatile means of making specific enantiomers and diastereomers of compounds of Formula (I) is described in Scheme 4. Bromoketone (3.7) (available commercially or synthesized as described in Scheme 3) can be reduced using a number of asymmetric chiral reducing agents (e.g., enzymatic reduction found in *Tetrahedron: Asymmetry*, 17:1769-1774 (2006) or chemical reduction found in *Angew. Chem. Int. Ed.*, 37:1986-2012 (1998)) to provide the desired chiral alcohol (4.1). Protection of the hydroxyl group with a trialkylsilyl protecting group will yield compound (4.2) that can be reacted with secondary amines of diverse structure (3.9) in an SN2 reaction to give compound (4.3). Treatment of this compound with hydroxylamine can provide amidoxime (4.4). Alternatively, the order of operations above (chiral reduction, amine SN2 reaction, and hydroxyl protection) may be rearranged to ultimately arrive at the same intermediate (4.4). Thus, SN2 reaction of (3.7) with amine (3.9) to make (3.8) followed by reduction to form (4.6) and silyl protection to from (4.3) can likewise yield (4.4) after treatment with hydroxylamine. Alternatively, intermediate (4.1) can be directly converted to (4.6) via SN2 displacement of a leaving group (such as Br) by amine (3.9) or (4.1) can be cyclized to an intermediate epoxide (4.5) that can undergo epoxide opening by amine (3.9) to form amino alcohol (4.6). Note: the epoxide opening of (4.5) to (4.6) would result in an inversion of the R3/R4 stereochemistry to that shown in (4.6) (and ultimately (4.4)) but is meant to illustrate that either diastereomer of (4.6) may be prepared depending on the R3/R4 group and conditions used.

Scheme 4

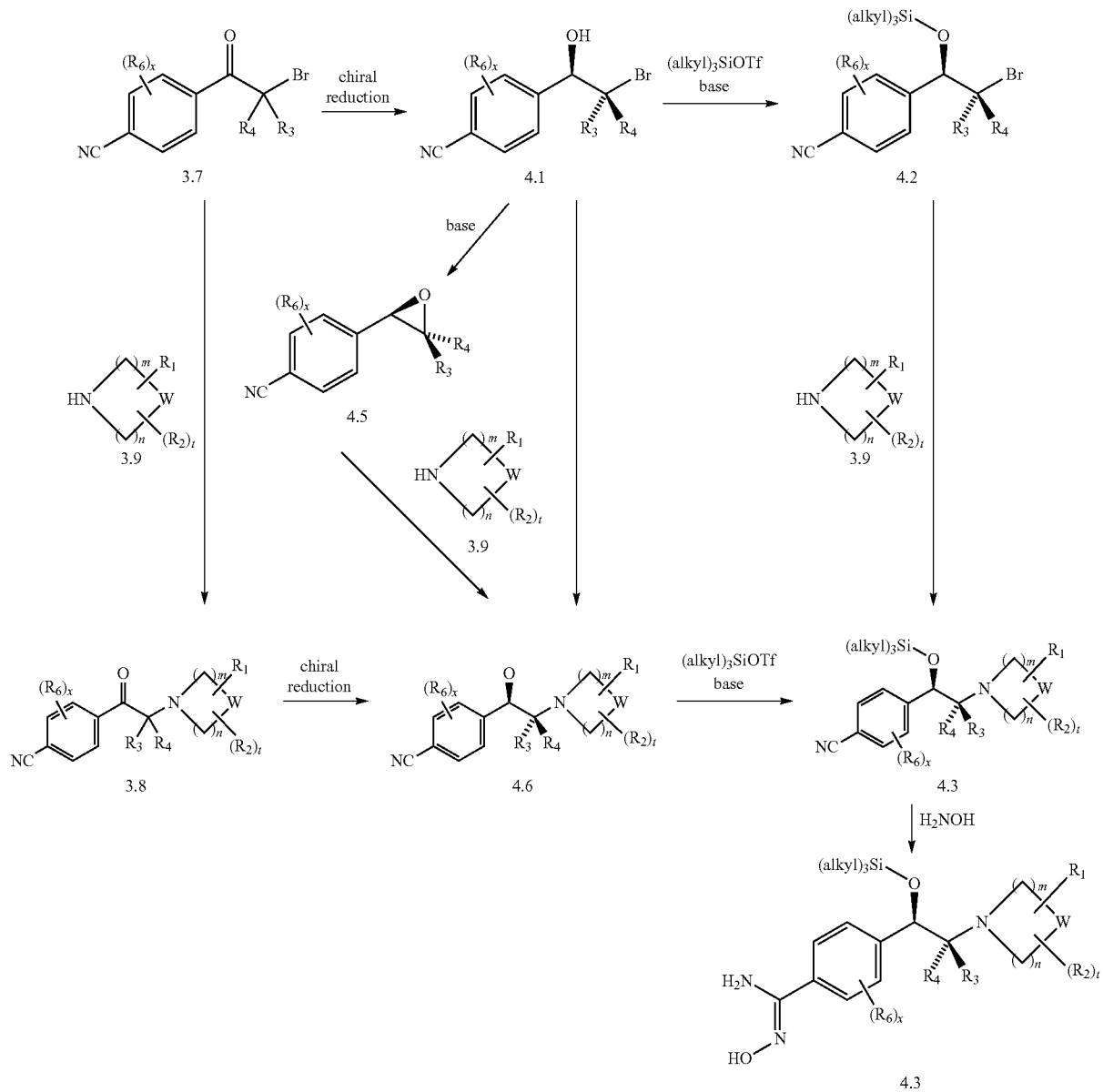

An alternate method for making intermediate amino alcohol (2.1) is shown in Scheme 5. Secondary amines (3.9) (available commercially, synthesized using literature procedures, or using methods described herein) may be reacted with substituted tert-butyl bromoacetates (5.1) under basic conditions in an SN2 reaction to provide amino ester (5.2). This intermediate may be selectively reduced to the amino aldehyde (5.3) using conditions such as diisobutylaluminum hydride in a non-polar solvent such as toluene or using a 3-step procedure of 1) deprotection of the t-butyl ester under acidic conditions, 2) reduction of the resulting acid with a borane reagent (e.g., borane-dimethylsulfide complex) to an alcohol, and 3) oxidation of the alcohol to an aldehyde using a number of methods (Swern as found in *Synlett*, 13:2295-2298 (2004), $SO_3$-pyridine, Dess-Martin periodinane) familiar to one skilled in the art of organic synthesis. Intermediate amino aldehyde (5.3) can then be reacted with a metalated 4-cyanoarene (e.g., 4-cyano-1-lithiobenzene) to provide the desired amino alcohol (3.4). This compound can then be transformed into N'-hydroxybenzimidamide (2.1) as mentioned above and taken through the procedures in Scheme 2 to provide compounds of Formula (I).

reaction). Olefin (6.2) may be epoxidized (using reagents such as m-chloroperbenzoic acid) to form epoxide (6.3). This epoxide can then be reacted with heterocyclic amines (3.9) under thermal conditions or in the presence of a Lewis acid to provide the amino alcohol (6.4). This compound can be treated with the appropriate reagents for removing any protecting groups to provide compounds of Formula (I).

Alternatively, the aryl bromide (6.1) may also undergo a Stille coupling with a vinyl 1-alkoxy-1-trialkylstannane to form vinyl ether (6.6) which can then be treated with an electrophilic bromide source (such as but not limited to N-bromosuccinimide) to give bromomethylketone (6.7). Compound (6.7) may also be synthesized directly by electrophilic bromination of the appropriately functionalized acetophenone (not shown) which in turn may be synthesized using methods familiar to one skilled in the art. Reaction of this intermediate with amine (3.9) can provide the aminomethylketone (6.8). This material may then be reduced (e.g., using sodium borohydride) to make racemic amino alcohol (6.4) or using methods in Scheme 4 to make specific stereoisomers. Alternatively, treatment of (6.8) with nucleophilic carbon sources (e.g., $R_5MgBr$; $R_5$—Li; and TMS-$R_5$ in the Scheme 5

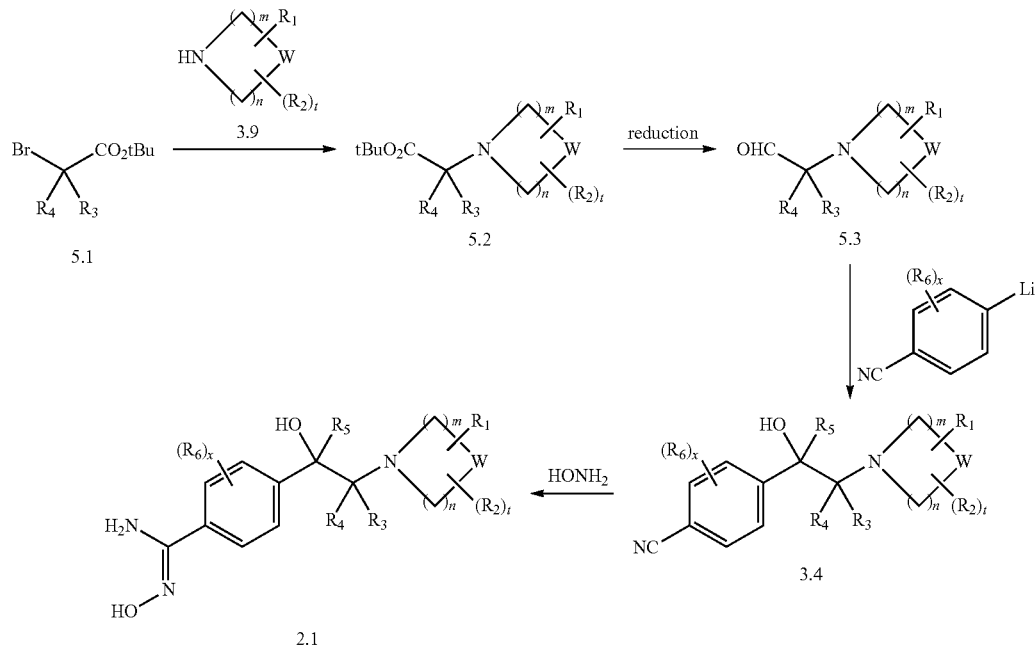

Another means of synthesizing compounds of Formula (I) is to use the chemical transformation detailed in Scheme 3 wherein the heterocyclic side chain is not installed at the end of the synthesis but at the beginning. As shown in Scheme 6, this is accomplished by using the synthetic methods described in Scheme 1 to prepare functionalized intermediate bromide (6.1) or styrene (6.2) (which can also be prepared from (6.1) using an optionally substituted vinyl stannane reagent in a Stille reaction or a vinylboronic acid in a Suzuki presence of TBAF) can provide intermediate (6.4) wherein $R_5$ is other than H.

Intermediate epoxide (6.3) may also be opened regioselectively using trialkylsilyl bromides (such as bromotriethylsilane) to give either the silyl protected bromo alcohol or the hydroxy bromo alcohol (6.5) depending on the reaction conditions and workup. Reaction of the hydroxyl bromo alcohol (6.5) with amine (3.9) provides the desired amino alcohol (6.4). Amino alcohol (6.4) is converted directly to compounds of Formula (I) by deprotection as mentioned above.

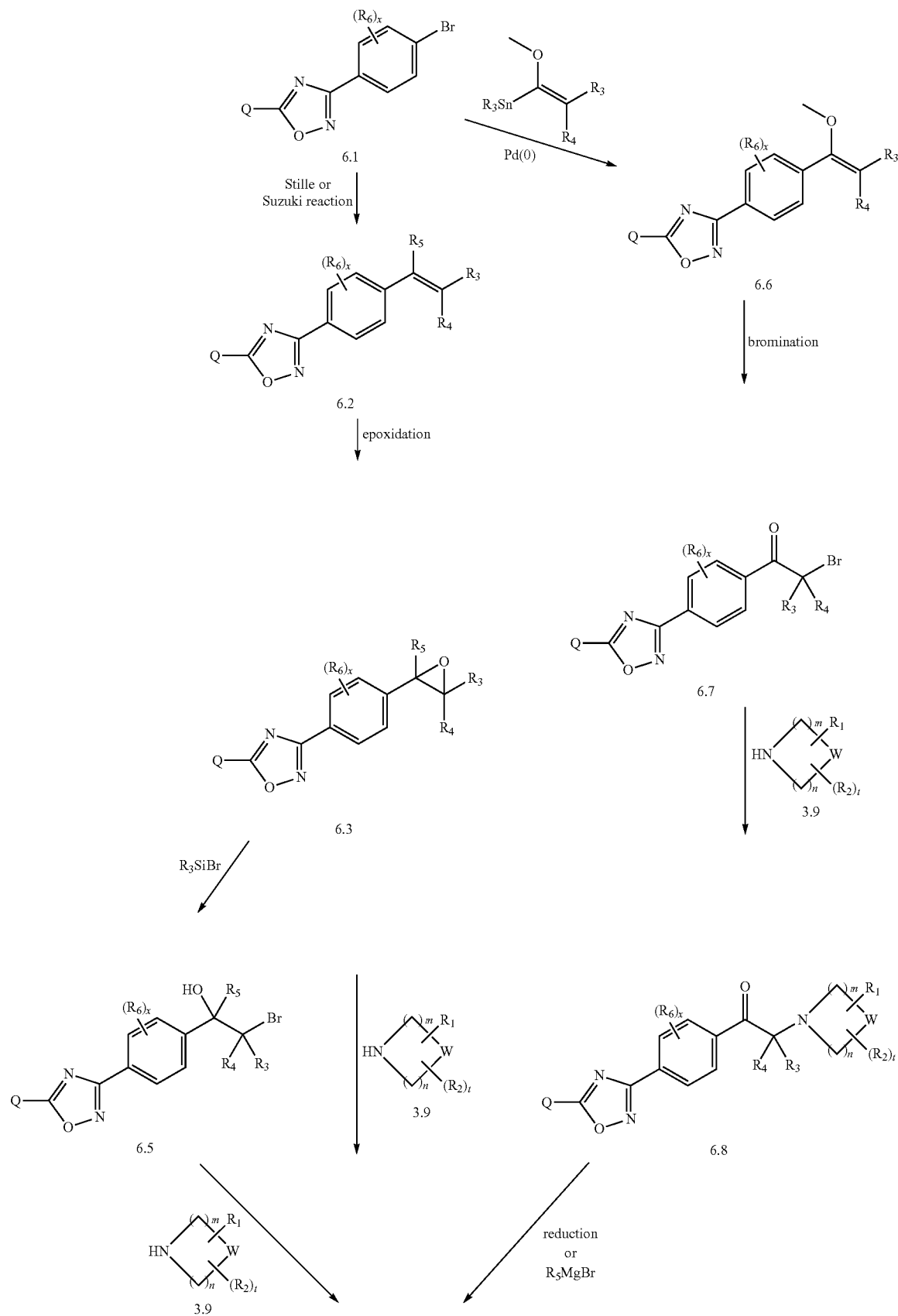

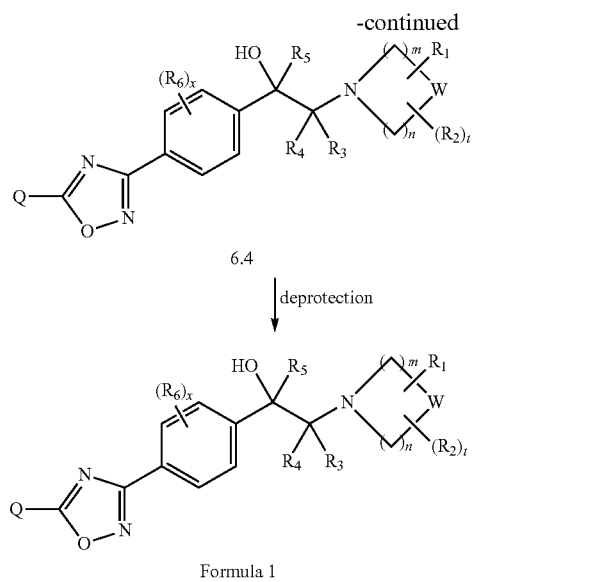

6.4

↓ deprotection

Formula 1

The carboxylic acid fragments (1.1) may be prepared by a variety of methods, including those illustrated in Scheme 7 for the isoxazoles bearing the carboxylic acid group at the 5-position. Reaction of chloro-oxime (7.1) with substituted propiolates (7.2) under basic conditions provides a mixture of isoxazole carboxylates (7.3/7.4) generally in favor of regioisomer (7.3). After separation of the isomers (such as by silica gel chromatography or reverse phase preparative HPLC), (7.4) may be hydrolyzed to give the required isoxazole carboxylic acid (7.5). Reaction of chloro-oxime (7.1) with substituted propargylic alcohols (7.6) under basic conditions provides a mixture of isoxazole carboxylates (7.7/7.8) generally in favor of isomer (7.8). After separation of the isomers (such as by silica gel chromatography or reverse phase preparative HPLC), (7.8) may be oxidized to give acid (7.5). Esters (7.4) may also be obtained regioselectively through the reaction of (7.1) with substituted 2-bromo-acrylates (7.9). When chloro-oximes (7.1) are reacted with unsubstituted propiolates (7.10), isoxazoles (7.11) are produced regioselectively. The unsubstituted isoxazole position may then be converted to a halogenated derivative (7.12) which may then be used for further transformations including but not limited to transition metal cross coupling reactions or insertion reactions.

Scheme 7

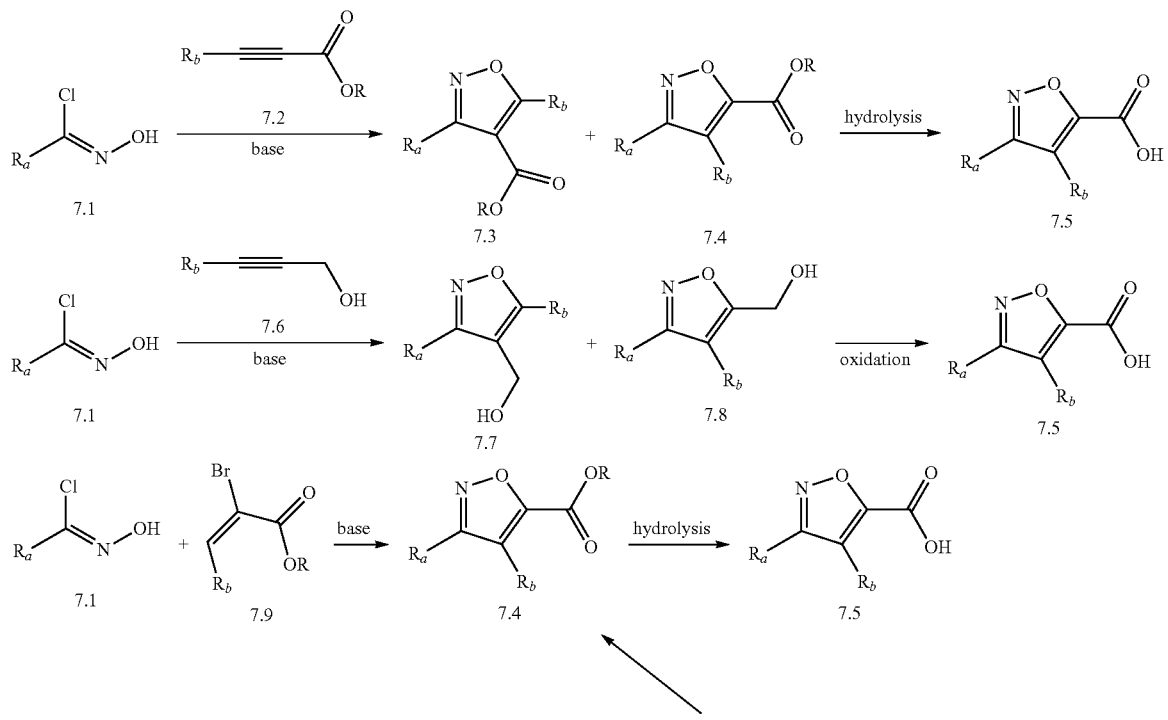

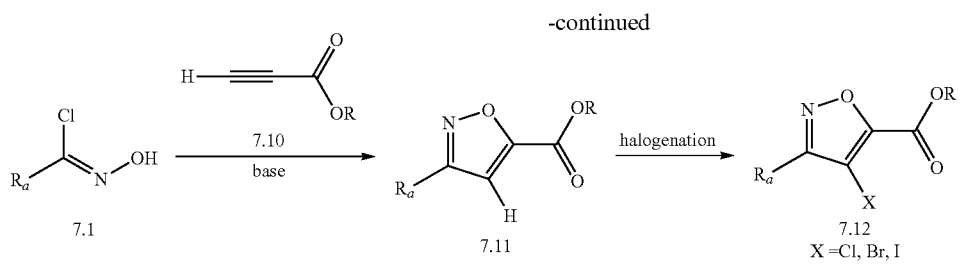

Illustrated in Scheme 8 are synthetic routes for preparing the isoxazoles bearing the carboxylic acid group at the 3-position. Isoxazole-3-carboxylic esters (8.3) may be prepared from the reaction of internal alkynes (8.1) with dimethyl 2-nitromalonate (8.2) under thermal decomposition conditions (heating in an inert solvent or neat) or reaction with chloro-oximes (8.5) under basic conditions. Hydrolysis of the esters (8.3) then provides the acids (8.4). The reaction of terminal alkynes (8.6) with chloro-oximes (8.7) leads to isoxazole esters lacking substitution at the 4-position. The unsubstituted isoxazole position may then be converted to a halogenated derivative (8.9) which may then be used for further transformations including but not limited to transition metal cross coupling reactions or insertion reactions.

aprotic) in the presence or absence of additional base as required to afford pyrazole esters (9.4). Compounds (9.4) can be isolated, or directly hydrolyzed to the corresponding pyrazole acids (9.5). Pyrazoles bearing a different substitution pattern may be synthesized using the literature procedures (*Zh. Organischeskoi Khim.*, 30:1225-1229 (1994)) by treating diketoester (9.7) with mono-substituted hydrazines in a variety of solvents (e.g., ethanol) to give the pyrazole ester (9.8) that can be hydrolyzed to pyrazole acid (9.9). Yet another pyrazole substitution pattern can be synthesized using a procedure described in WO 2007/045868 which involves the [3+2] cycloaddition of TMS-diazomethane with

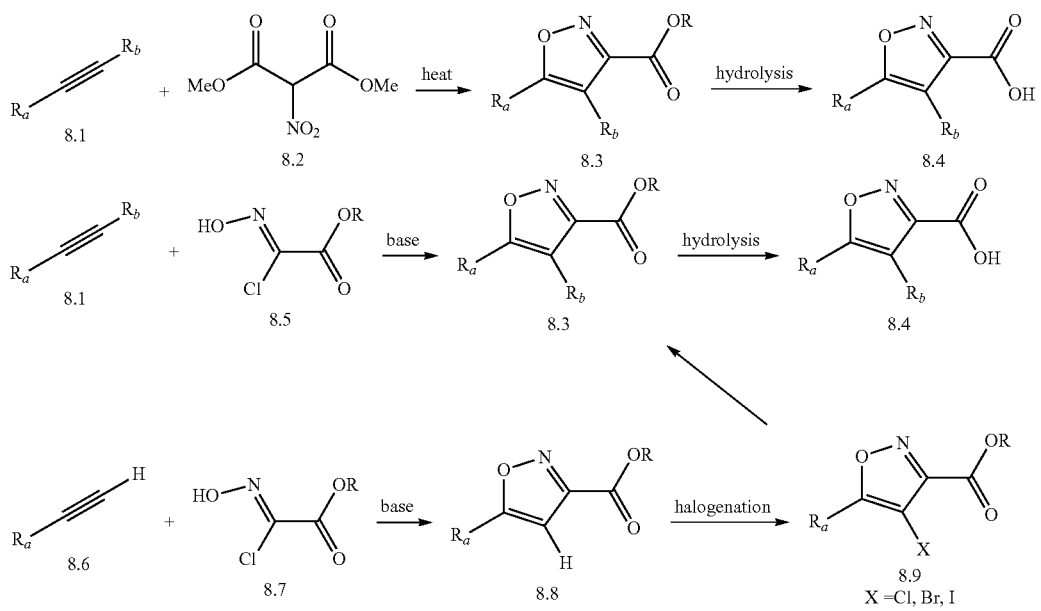

The carboxylic acid fragments (1.1) may be prepared by a variety of synthetic methods, including those illustrated in Scheme 9, which describes the synthesis of pyrazole and imidazole carboxylic acids. Acetoacetate ester compounds (9.1) can be converted to activated methylene derivatives (9.2 or 9.6), for example, through reaction with triethyl orthoformate or N,N-dimethylformamide-dimethylacetal (DMF-DMA) respectively in the presence of a catalytic amount of acid (such as para-toluenesulfonic acid). Compounds (9.2 or 9.6) can then be reacted with hydrazine or mono-substituted hydrazines in a variety of solvents (polar, non-polar, protic, a propargylic ester (9.10) in non-polar solvent to give unsubstituted pyrazole (9.11) which can be hydrolyzed to the desired pyrazole acid (9.12) as described before. One method to prepare substituted imidazole acids is using the procedure of Tamura et al. (*J. Org. Chem.*, 58:32-35 (1993)) and Huang et al. (*J. Fluorine Chem.*, 74, 279 (1995)). Amine (9.13) is reacted with an activated acid $R_b$—$CO_2H$ to give an intermediate amide that is activated in situ with $PPh_3$ and $CCl_4$. This reactive intermediate can be intercepted by the anion of an isocyanide to give imidazole ester (9.14) which can then be deprotected using aqueous acid or base to provide imidazole acid (9.15).

Scheme 9

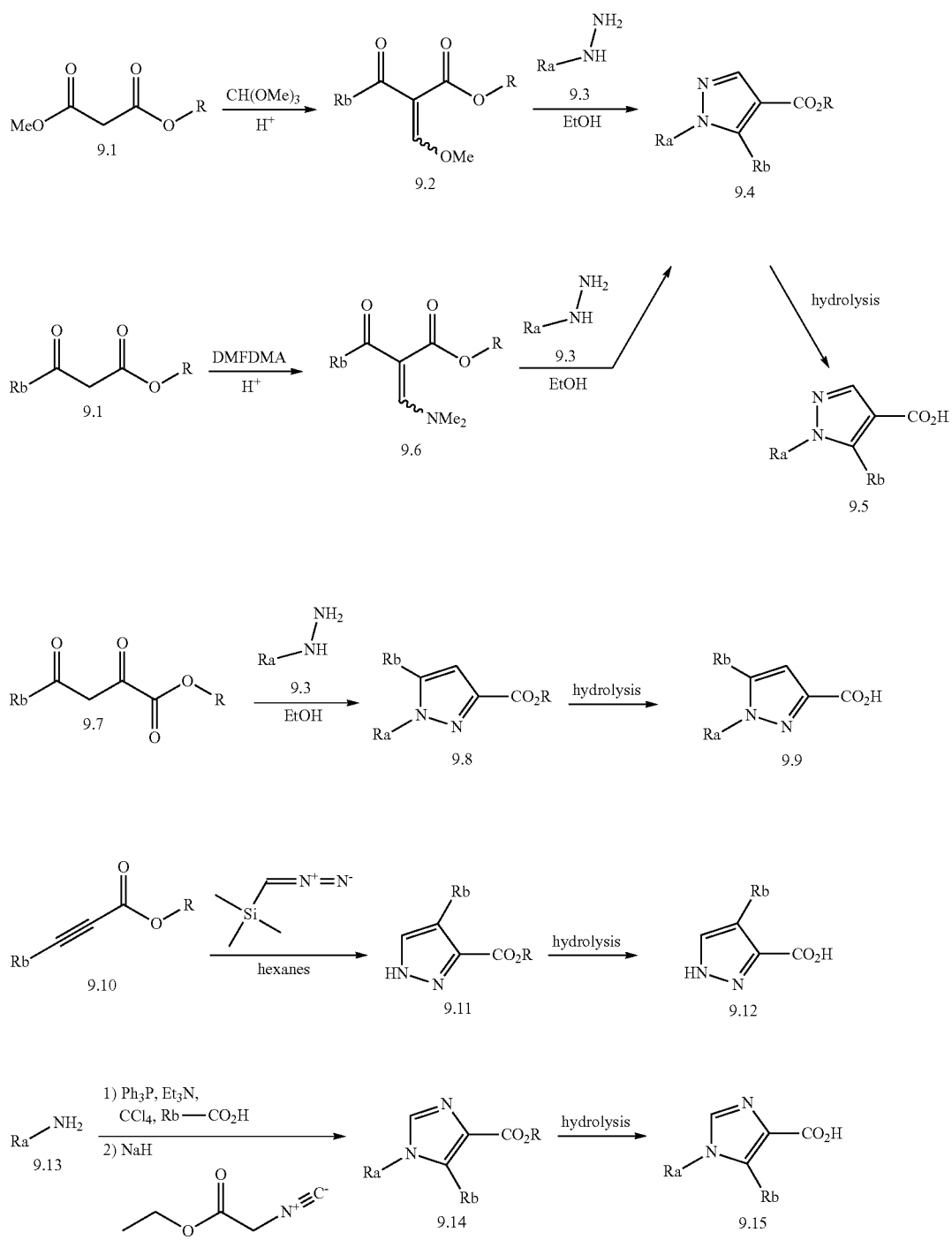

A complementary approach to the synthesis of the substituted pyrazoles illustrated in Scheme 9 is to prepare the unsubstituted pyrazoles and functionalize the pyrazole nitrogen afterwards using methods shown in Scheme 10. Starting from either intermediates (10.4, 10.8, or 10.11) where $R_a$=hydrogen, several chemical transformations can be used to introduce, alkyl, aryl, or heteroaryl $R_a$ substituents. Shown are three transformations: a copper-diamine mediated Buchwald coupling using an aryl or heteroaryl halide (Buchwald et al., *J. Org. Chem.*, 69:5578 (2004)), a copper-mediated boronic acid coupling to a pyrazole (*Bioorg. Med. Chem. Lett.*, 13:561-566 (2003)), and a simple alkylation using base and an alkyl halide in a variety of solvents to give intermediates (10.4, 10.8, or 10.11) where $R_a$=alkyl, substituted alkyl, aryl, or heteroaryl. The esters of these compounds can be deprotected by hydrolysis to give the desired substituted pyrazole acids (10.5, 10.9, and 10.12).

Scheme 10

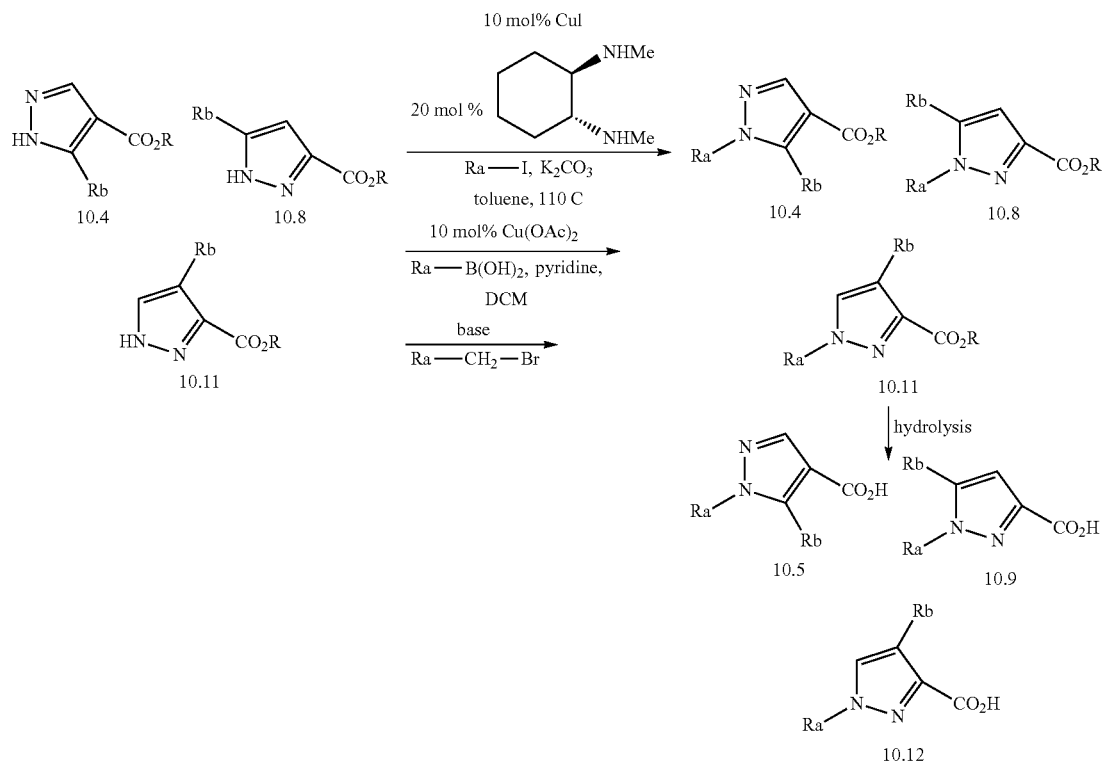

Illustrated in Schemes 11 and 12 are methods that may be followed to prepare replacements of the central 1,2,4-oxadiazole ring described above. Scheme 11 shows how to prepare 1,2,4-oxadiazoles, having different connectivity from those shown above, starting from chloro-oxime (11.1). This material can be reacted with a bromo-olefin (11.2 or 11.3) in a [3+2] cycloaddition followed by loss of HBr to directly form cyano-substituted isoxazole (11.4). Alternatively, the same cycloaddition may be performed using a disubstituted acrylonitrile (11.9) to give an intermediate isoxazolidine (11.10) that will aromatize to isoxazole (11.4) upon oxidation (*J. Chem. Soc., Perkin Trans. 1*, 10:1168-1174 (2001)). Nitrile (11.4) may then be converted to the hydroxyamidine (9.5) by treatment with hydroxylamine. Coupling this compound with epoxide-containing benzoic acids (11.6) (prepared using procedures such as *J. Amer. Chem. Soc.*, 122:3220-3221 (2000) and *Tetrahedron Lett.*, 36, 5457-5460 (1995)) using methods described in Scheme 1 can provide 1,2,4-oxadiazole (11.7). Reaction of this epoxide with amine (3.9) in an alcoholic solvent with heat to give compound (11.8) which, after deprotection, provides compounds of Formula (I).

Scheme 11

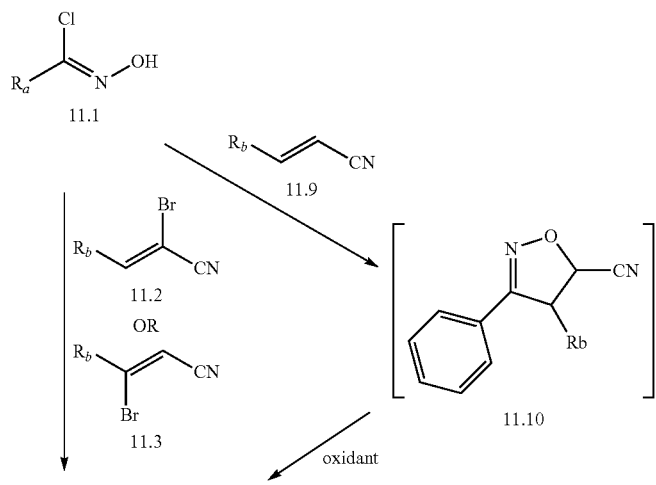

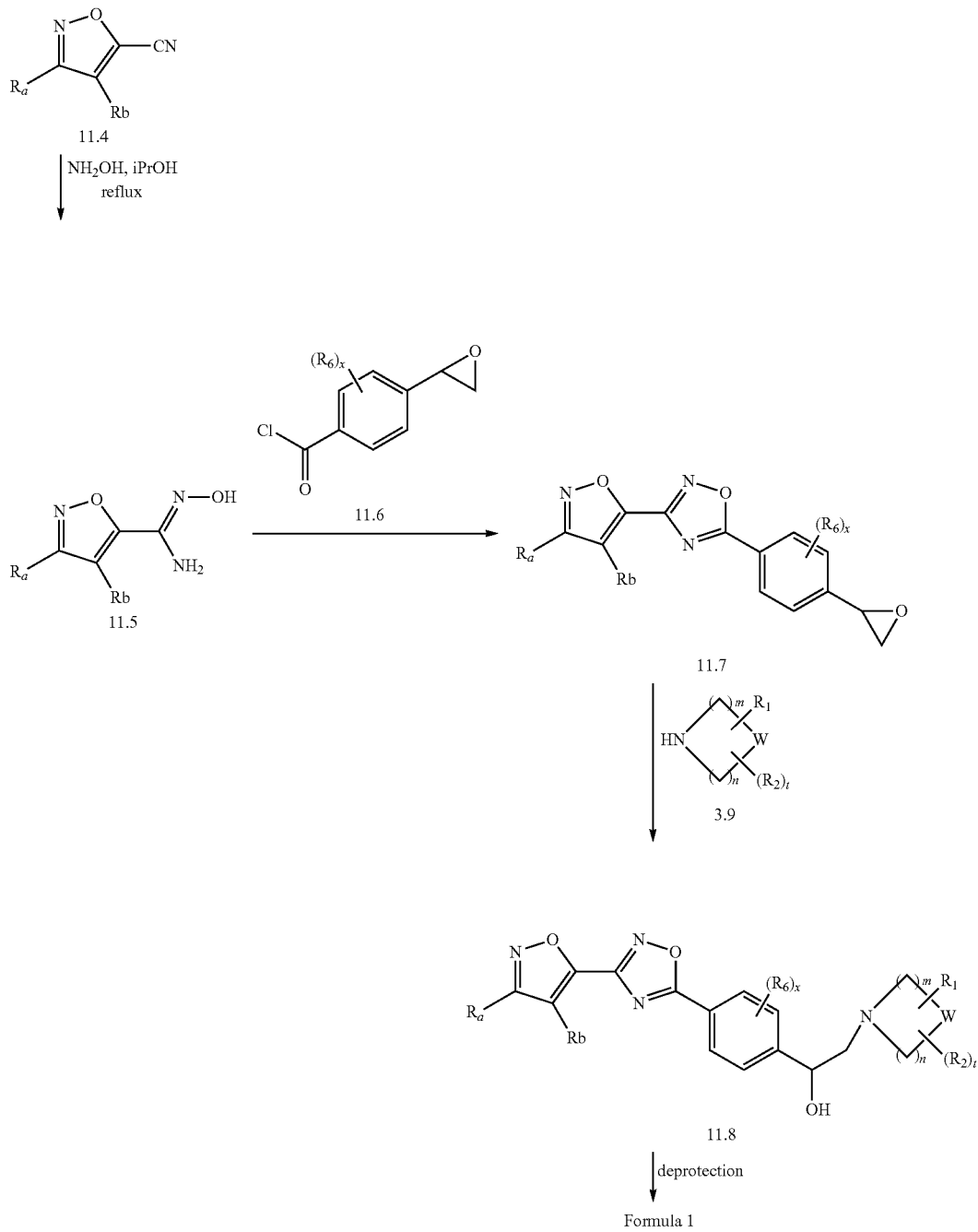

Scheme 12 illustrates a route to synthesize compounds of Formula (I) wherein the central 1,2,4-oxadiazole ring described above has been transposed to other heterocyclic ring systems. Ester-substituted isoxazoles (12.1) (prepared as described above) can be activated with coupling reagents such as BOP reagent and then treatment with hydrazine to give hydrazide (12.2). Coupling of the hydrazide to styrenyl-carboxylic acid (12.3) under EDC, HOBt conditions (or methods similar to those described in Scheme 1) can provide carbazides of structure (12.4). Treatment of compound (12.4) under dehydrating conditions (such as phosphorus oxychloride) provides 1,3,4-oxadiazoles (12.5) that can be transposed into compounds of Formula (I) using the methods already described in Scheme 6. Alternatively, treatment of carbazide (12.4) with Lawesson's reagent or by refluxing in P2S5 and pyridine (see *Bioorg. Med. Chem. Lett.,* 142-145 (2009) and *Tetrahedron,* 63:2437-2445 (2007)) provides the corresponding 1,3,4-thiadiazole (12.6) that can also be converted to compounds of Formula (I) using the methods described in Scheme 6.

Scheme 12

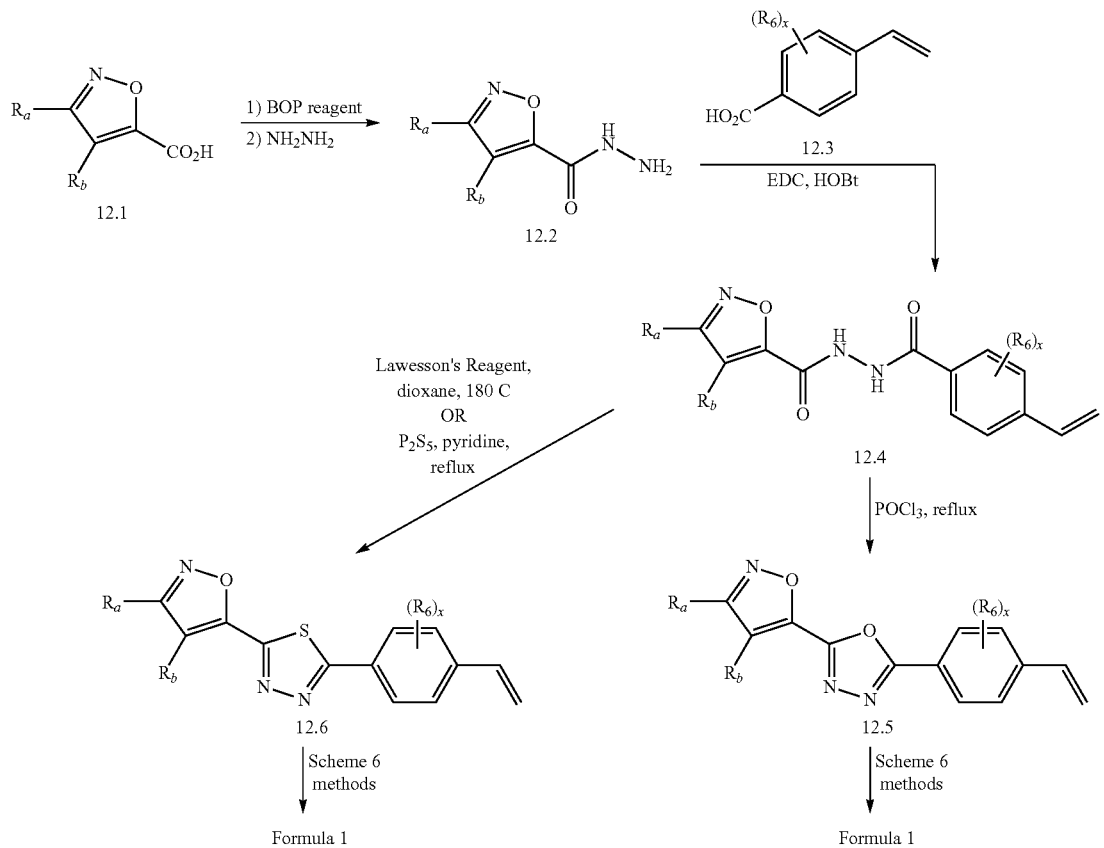

Abbreviations

| | |
|---|---|
| ACN | acetonitrile |
| AcOH | acetic acid |
| BOC | t-butyl carbamate |
| BOP | benzotriazol-1-yloxytris(trimethylamino)phosphonium hexafluorophosphate |
| BOP-Cl | bis-(2-oxo-3-oxazolidinyl)phosphinic chloride |
| Bu | butyl |
| DBU | 1,8-diazabicyclo[5.4.0]undec-7-ene |
| DCE | dichloroethane |
| DCM | dichloromethane |
| DIEA | diisopropylethylamine |
| DMF | dimethylformamide |
| DMSO | dimethyl sulfoxide |
| EDC | 1-(3-dimethylaminopropyl)-3-ethylcarbodiimide hydrochloride |
| Et | ethyl |
| EtOAc | ethyl acetate |
| h | hour(s) |
| HCl | hydrochloric acid |
| HOBt | hydroxybenzotriazole |
| HPLC | high pressure liquid chromatography |
| HMPA | hexamethylphosphorus triamide |
| hr | hour(s) |
| IPA | isopropyl alcohol |
| i-PrOH | isopropyl alcohol |
| LC/MS | liquid chromatography/mass spectroscopy |
| m-CPBA | 3-chloroperbenzoic acid |
| Me | methyl |
| MeCN | acetonitrile |
| MeOH | methanol |
| min | minute(s) |

-continued

| | |
|---|---|
| MPLC | medium pressure liquid chromatography |
| MS | mass spectroscopy |
| NaOH | sodium hydroxide |
| NaOtBu | sodium butoxide |
| NMR | nuclear magnetic resonance |
| $Pd_2(dba)_3$ | tris-(dibenzylideneacetone)dipalladium |
| rt | room temperature |
| SEM | trimethylsilyloxyethoxymethyl |
| TBAF | tetrabutylammonium fluoride |
| TEA | triethylamine |
| TEMPO | 2,2,6,6-tetramethylpiperidine 1-oxyl |
| TFA | trifluoroacetic acid |
| THF | tetrahydrofuran |
| TMS-Cl | chlorotrimethylsilane |

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein, but rather is defined by the claims appended hereto.

Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially using Roman numerals (e.g., Intermediate I, Intermediate II, etc.) and are abbreviated as Int-I, Int-II, etc. In some instances the preparation of common intermediates may require multiple steps to be prepared. Each step is identified by the common intermediate and the step, e.g., Int-I-A, Int-I-B, and so forth. Compounds of the Examples are identified by the example and step in which they were prepared (e.g., "1-A" or "Preparation 1A" denotes the Example 1, step A) or by the example only where the compound is the title compound of the example (for example, "1" denotes the title compound of Example 1). In some instances alternate preparations of intermediates or Examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and/or decreased number of linear steps. The intent of describing alternative preparations is to further enable the preparation of the Examples of this invention.

Those experiments which specify that they were performed in a microwave were conducted in a SmithSynthesizer manufactured by Personal Chemistry or a Discover microwave manufactured by CEM corporation. The microwave ovens generate a temperature which can be selected to be between 60-250° C. The microwaves automatically monitor the pressure which is between 0-300 PSI. Reaction hold times and temperature set points are reported.

Silica gel purification was performed on an Isco Companion medium pressure liquid chromatography instrument using prepacked silica gel cartridges Redi-Sep) from Isco (12 g, 24 g, 40 g, 80 g, 120 g, 220, 330 g appropriate to the scale of the purification) using solvent gradients described for each Example but in most cases, 0-100% EtOAc in hexanes (or 25-100%) over 25 minutes.

Retention time data reported for each example uses one of the three following General Analytical HPLC methods. All products were run using Method A unless otherwise indicated:

Method A: Column: Waters Sunfire C18, 2.5 μm particles (2.1×30 mm); 0-100% B gradient. Mobile Phase A=0.1% TFA in MeOH:Water (10:90), Mobile Phase B=0.1% TFA in MeOH:Water (90:10); Gradient Time=4 min; Flow Rate=1 ml/min; uv detection 220 nM.

Method B: Identical to Method A using a 2 min gradient

Method C: Column: SUPELCO® Ascentis Express C18, 4.6×50 mm, 2.7-μm particles; Mobile Phase A: 5:95 acetonitrile:water with 10 mM ammonium acetate; Mobile Phase B: 95:5acetonitrile:water with 10 mM ammonium acetate; Temperature 45° C.; Gradient: 0-100% B over 4 minutes, then a 1-minute hold at 100% B; Flow: 4 mL/min. Injection 2 conditions: Column: SUPELCO® Ascentis Express C18, 4.6×50 mm, 2.7-μm particles; Mobile Phase A: 5:95 acetonitrile:water with 0.05% TFA; Mobile Phase B: 95:5 acetonitrile:water with 0.05% TFA; Temperature 45° C.; Gradient: 0-100% B over 4 minutes, then a 1-minute hold at 100% B; Flow: 4 mL/min.

Preparative HPLC methods use one of the following methods unless otherwise noted in the specific example. Method 1: Column: PHENOMENEX® Luna C18, 5-μm particles (30× 250 mm), Guard Column: none; Mobile Phase A: water with 0.05% TFA; Mobile Phase B: acetonitrile with 0.05% TFA; Gradient: 25-100% B over 25 minutes, then a 5-minute hold at 100% B; Flow rate: 30 mL/min. Method 2: Column: Waters XBridge C18, 19×100 mm, 5-μm particles; Guard Column: none; Mobile Phase A: 5:95 acetonitrile:water with 0.05% TFA; Mobile Phase B: 95:5 acetonitrile:water with 0.05% TFA; Gradient: 25-100% B over 10 minutes, then a 5-minute hold at 100% B; Flow: 20 mL/min.

Final purity was determined using two different analytical LC/MS methods and determining area-under-the curve of product and impurities with uv detection at 220 nM and 254 nM. The lesser purity of the two runs is reported as % purity for the Examples described herein. Column 1 conditions: Column: Sunfire C18, 3.0×150 mm, 3.5-μm particles; Mobile Phase A: 5:95 acetonitrile:water with 0.05% TFA; Mobile Phase B: 95:5 acetonitrile:water with 0.05% TFA; Gradient: 0-100% B over 15 minutes, then a 1-minute hold at 100% B; Flow: 1 mL/min. Column 2 conditions: Column: Xbridge Phenyl, 3.0×150 mm, 3.5-μm particles; Mobile Phase A: 5:95 acetonitrile:water with 0.05% TFA; Mobile Phase B: 95:5 acetonitrile:water with 0.05% TFA; Gradient: 0-100% B over 4 minutes, then a 1-minute hold at 100% B; Flow: 1 mL/min.

Intermediate I (Int-I)

(3-Phenyl-4-(trifluoromethyl)isoxazole-5-carboxylic acid)

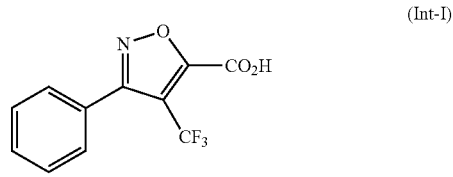 [SMILES: O=C(O)c1onc(-c2ccccc2)c1C(F)(F)F]

(Int-I)

Preparation of Int-I-A:. 4,4,4-Trifluorobut-2-yn-1-ol

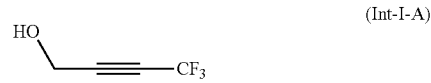

(Int-I-A)

To a solution of diisopropylamine (24.7 mL, 176 mmol) in ether (100 mL) at −78° C. was added a 10M solution of butyllithium in ether (17.6 mL, 176 mmol) over 5 min. After 10 min. at −78° C., 2-bromo-3,3,3-trifluoroprop-1-ene (14.0 g, 80 mmol) was added to the pale yellow solution. After an additional 10 min., paraformaldehyde (2.40 g, 80 mmol) was added, the dry-ice bath was removed, and the reaction mixture was stirred at room temperature overnight. As the reaction mixture approached room temperature, it became dark in color. The reaction was quenched with a 1N aqueous solution of hydrochloric acid (100 mL), diluted with ether (500 mL), washed with a 1N aqueous solution of hydrochloric acid (2×100 mL), washed with brine 100 mL, and dried over anhydrous sodium sulfate. Concentration under reduced pressure afforded a dark liquid which was distilled under Low-Vacuum (~50 Torr, ~50° C.) to give 4,4,4-trifluorobut-2-yn-1-ol (7.1 g, 57.2 mmol, 72% yield) as a pale yellow liquid. $^1$H NMR (500 MHz, CDCl$_3$) δ ppm 2.31 (br. s., 1H) and 4.38-4.42 (m, 2H).

An Alternate Preparation of Int-I-A: 4,4,4-Trifluorobut-2-yn-1-ol

To an ether (pre-dried over magnesium sulfate) solution of phenanthroline (2.16 mg, 0.012 mmol) (indicator) at −278°

C. under nitrogen was added a 2M solution of n-butyl lithium in pentane. An orange color immediately appeared. Trifluoromethylacetylene gas was bubbled through the solution at −78° C. After ~4 min. of gas introduction, the orange color almost completely disappeared, the reaction solution became cloudy (due to some precipitation), and a pale light orange color persisted. Paraformaldehyde was added, and the dry ice/isopropanol bath was removed after 5 min. and replaced with a 0° C. ice-bath. Stirring was continued for 45 min., the ice bath was removed, and stirring was continued for an additional 1.25 h. The reaction flask was immersed in a 0° C. ice bath, and a saturated aqueous solution of ammonium chloride (20.0 mL) was added. The layers were separated, and the organic layer was washed with water (2×), washed with brine, and dried over anhydrous sodium sulfate. Concentration under low-vacuum (~50 Torr) without heat afforded a dark brown liquid which was purified by vacuum distillation (~50 Torr, ~50° C.) to give 4,4,4-trifluorobut-2-yn-1-ol (7.1 g, 57.2 mmol, 72% yield) as a colorless liquid.

Preparation of Int-1-B: N-Hydroxybenzimidoyl chloride

(Int-I-B)

This compound was prepared according to the method of Liu, K C. et al., *J. Org. Chem.*, 45:3916-1918 (1980).

To a colorless, homogeneous solution of (E)-benzaldehyde oxime (24.4 g, 201 mmol) in N,N-dimethylformamide (60 mL) at room temperature was added N-chlorosuccinimide (26.9 g, 201 mmol) portion-wise over 30 min. During each addition, the reaction mixture became yellow and then gradually returned to near colorlessness. Additionally, an exotherm was noted with each portion added. (It is extremely important to make sure the reaction initiates after the addition of the first ~⅕ of the NCS; an ice-bath was readily available.). After the addition was complete, the homogeneous reaction mixture was stirred overnight at room temperature. The reaction mixture was diluted with 250 mL of water and extracted with ether (3×100 mL). The organic layers were combined, washed with water (2×100 mL), washed with a 10% aqueous solution of lithium chloride (2×100 mL), and washed with brine (100 mL). The aqueous layers were back extracted with ether (100 mL), and the combined organic layers (400 mL) were dried over anhydrous sodium sulfate. Concentration under reduced pressure afforded (Z)-N-hydroxybenzimidoyl chloride (30.84 g, 198 mmol, 98% yield) as a fluffy, pale yellow solid. The product had an HPLC ret. time=1.57 min.- Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M+1=155.8. ¹H NMR (500 MHz, DMSO-d₆) δ ppm 7.30-7.64 (m, 3H), 7.73-7.87 (m, 2H), and 12.42 (s, 1H).

Preparation of Int-I-C: 3-Phenyl-4-(trifluoromethyl)isoxazol-5-yl)methanol

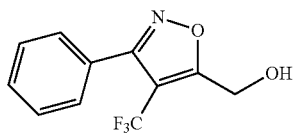

(Int-I-C)

To a pale yellow, homogeneous mixture of N-hydroxybenzimidoyl chloride (5.50 g, 35.4 mmol) and 4,4,4-trifluorobut-2-yn-1-ol (5.46 g, 39 6 mmol) in dichloroethane (85 mL) in a 250 mL round bottom flask at 70° C. was added triethylamine (9.85 mL, 70.7 mmol) in 22 mL of dichloroethane over 2.5 h via an addition funnel (the first ~50% over 2 h and the remaining 50% over 0.5 h). After the addition was complete, the reaction mixture was complete by HPLC (total time at 70° C. was 3 h). The reaction mixture was stirred at room temperature overnight.

The reaction mixture was diluted with dichloromethane (100 mL), washed with water (100 mL), and the organic layer was collected. The aqueous layer was extracted with dichloromethane (2×50 mL), and the combined organic layers were dried over anhydrous sodium sulfate. The solvent was removed under reduced pressure. Analysis indicated that the product mixture was composed of a 86:14 mixture of the desired regioisomer (Int-I-C), (3-phenyl-4-(trifluoromethyl) isoxazol-5-yl)methanol, and the undesired regioisomer, (3-phenyl-5-(trifluoromethyl)isoxazol-4-yl)methanol. The mixture was purified by silica gel chromatography using a mixture of ethyl acetate and hexane (1% to pack and load-5%-9%-12%) to afford (3-phenyl-4-(trifluoromethyl)isoxazol-5-yl)methanol (5.34 g, 21.96 mmol, 62.1% yield) as a pale yellow oil. The compound had an HPLC ret. time=1.91 min.-Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M+1=244.2. ¹H NMR (500 MHz, CDCl₃) δ ppm 2.21 (br. s., 1H), 4.97 (s, 2H), 7.47-7.56 (m, 3H), and 7.65 (d, J=6.60 Hz, 2H).

Alternate Preparation of Int-I: 3-Phenyl-4-(trifluoromethyl)isoxazole-5-carboxylic acid

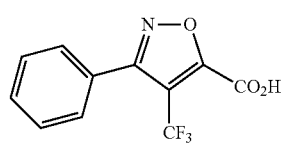

(Int-I)

Preparation of Jones' Reagent

To an orange, homogeneous solution of chromium trioxide (12.4 g, 0.123 mol) in water (88.4 mL) at 0° C. was added sulfuric acid (10.8 mL) dropwise via addition funnel over 30 min. with stirring. The addition funnel was rinsed with water (1 mL) to give 1.23 M solution of Jones' Reagent (0.123 mol of reagent in 100 mL of solvent).

To a solution of (3-phenyl-4-(trifluoromethyl)isoxazol-5-yl)methanol (5.24 g, 21.6 mmol) in acetone (75 mL) at room temperature (immersed in a water bath) was added Jones' Reagent (43.8 mL, 53.9 mmol) via addition funnel slowly over 1.5 h. The dark reaction mixture was stirred at room temperature overnight. By HPLC, the reaction was 93% complete. An additional 0.5 equivalents (9 mL) of the Jones' Reagent was added. After 1 h, the reaction was 95% complete. After an additional 3 h, the reaction was 96% complete. An additional 0.5 equivalents (9 mL) of the Jones' Reagent was added. The reaction mixture was stirred for an additional 2.5 h. By HPLC, the reaction was 97% complete. Isopropyl alcohol (6 mL) was added, and the mixture was stirred for 90 min, resulting in a dark green precipitate. The mixture was diluted with ether (600 mL), washed with a 2% aqueous solution of sodium hydrogen sulfite (5×100 mL), and the organic layer was collected. The aqueous layer was back-extracted with ether (2×100 mL). By HPLC, there was no additional product in the aqueous layer. The combined organic layers were washed with water (100 mL), washed with a saturated aqueous solution of brine (100 mL), and dried over anhydrous sodium sulfate. The aqueous layer was back-extracted with ether (100 mL), and the organic layer was added to the previous organic layers. The solution was concentration under reduced pressure to give 3-phenyl-4-(trifluoromethyl) isoxazole-5-carboxylic acid as an off-white solid. The solid was diluted with dichloromethane (200 mL), washed with a 2% aqueous solution of sodium hydrogen sulfite, washed with brine, and dried over anhydrous sodium sulfate. Concentration under reduced pressure afforded 3-phenyl-4-(trifluoromethyl)isoxazole-5-carboxylic acid (3.84 g, 14.93 mmol, 69.3% yield) as a pale yellow solid. The product was 96% pure by HPLC with a ret. time=1.60 min.-Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=258.2.

The sodium hydrogen sulfite aqueous layer still contained a significant amount of product. The brine layer contained no additional product and was discarded. The aqueous layer was saturated with sodium chloride, the pH was adjusted to ~3.5, and the solution was extracted with ether (3×100 mL). The organic layer was dried over anhydrous sodium sulfate and concentrated to afford additional 3-phenyl-4-(trifluoromethyl)isoxazole-5-carboxylic acid (1.12 g, 4.36 mmol, 20.21% yield) as a white solid. The product was >99% pure by HPLC with a ret. time=1.60 min.-Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=258.1. $^1$H NMR (500 MHz, DMSO-$d_6$) δ ppm 7.55-7.63 (m, 5H).

The products were combined to give 4.96 g (90% yield) of 3-phenyl-4-(trifluoromethyl)isoxazole-5-carboxylic acid or Int-1.

Alternate Preparation of Int-I: 3-Phenyl-4-(trifluoromethyl)isoxazole-5-carboxylic acid starting with (3-phenyl-4-(trifluoromethyl)isoxazol-5-yl)methanol

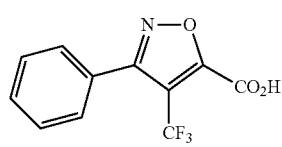

(Int-I)

A mixture of (3-phenyl-4-(trifluoromethyl)isoxazol-5-yl)methanol (2.1 g, 8.64 mmol), TEMPO (0.094 g, 0.604 mmol), and a sodium phosphate buffer (0.67M) (32.2 mL, 21.59 mmol) in acetonitrile (30 mL) was heated to 35° C. A fresh solution of sodium phosphate buffer (40 mL, pH ~6.5) consisting of a 1:1 solution of $NaH_2PO_4$ (20 mL, 0.67M) and $Na_2HPO_4$ (20 mL, 0.67M) was prepared and used. Solutions of sodium chlorite (3.91 g, 34.5 mmol) in water (4.5 mL) and bleach (4.3 mL, 6% wt.) were added simultaneously over 40 min. The reaction was monitored by HPLC, and after 2 h, ~30% of the starting material remained. After 6 h, 10% remained. Additional bleach (100 µL) was added, and the reaction mixture was left at room temperature overnight. Additional bleach (100 µL) was added. The resulting mixture was allowed to stir at 35° C. for additional 2 h. HPLC indicated complete conversion. The reaction was quenched by the slow addition of a solution of sodium sulfite (2.07 mL, 43.2 mmol) in water (90 mL) at 0° C., resulting in the disappearance of the brown reaction color. The solvent was removed under reduced pressure, and the remaining aqueous residue was extracted with ethyl acetate (3×40 mL). The organic layers were combined, washed with water (8 mL), washed with brine (8 mL), and dried over anhydrous sodium sulfate. Concentration under reduced pressure afforded 3-phenyl-4-(trifluoromethyl)isoxazole-5-carboxylic acid (2.2 g, 8.55 mmol, 99% yield) as a pale yellow solid.

Alternate Preparation of 3-Phenyl-4-(trifluoromethyl)isoxazole-5-carboxylic acid starting with 4,4,4-trifluorobut-2-ynoate (Int-I)

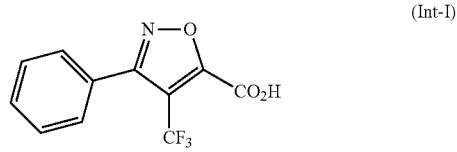 [SMILES: O=C(O)c1onc(-c2ccccc2)c1C(F)(F)F]

(Int-I)

Preparation of Int-I-D: Ethyl 3-phenyl-4-(trifluoromethyl)isoxazole-5-carboxylate

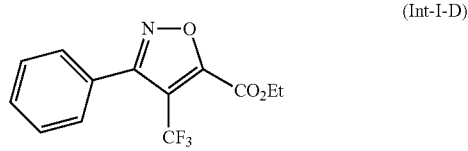 [SMILES: CCOC(=O)c1onc(-c2ccccc2)c1C(F)(F)F]

(Int-I-D)

To a pale yellow mixture of (Z)-N-hydroxybenzimidoyl chloride (1.04 g, 6.68 mmol) and ethyl 4,4,4-trifluorobut-2-ynoate (1.238 g, 7.45 mmol) in diethyl ether (20 mL) at room temperature was added triethylamine (1.86 mL, 13.4 mmol) over 15 min., resulting in a precipitant. After the addition was complete, the pale yellow slurry was stirred at room temperature over the weekend. The heterogeneous reaction mixture was filtered under reduced pressure to remove the triethylamine hydrochloride salt, and the filtrate was concentrated to give the product mixture as a dark yellow, viscous oil (2.03 g). By HPLC, the reaction mixture was composed of a mixture of the desired regioisomer, ethyl 3-phenyl-4-(trifluoromethyl) isoxazole-5-carboxylate, and the undesired regioisomer, ethyl 3-phenyl-5-(trifluoromethyl)isoxazole-4-carboxylate, in an approximately 15:85 ratio. The compound mixture was dissolved in hexane and sonicated for 5 min. The hexane was decanted off, and the dark red, oily residue was found to have only trace product by HPLC. The hexane was removed under reduced pressure, and the residue (1.89 g) was purified by preparative HPLC. The desired fractions containing ethyl 3-phenyl-4-(trifluoromethyl)isoxazole-5-carboxylate were concentrated, and the residue was diluted with dichloromethane, washed with a saturated aqueous solution of sodium bicarbonate, and dried over anhydrous sodium sulfate. Concentration under reduced pressure afforded ethyl 3-phenyl-4-(trifluoromethyl)isoxazole-5-carboxylate (0.087 g, 0.305 mmol, 4.6% yield) as a pale yellow solid. The compound had an HPLC ret. time=2.88 min.-Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. $^1$H NMR (400 MHz, $CDCl_3$) δ ppm 1.46 (t, J=7.15 Hz, 3H), 4.53 (q, J=7.03 Hz, 2H), 7.48-7.55 (m, 3H), and 7.58 (d, J=7.53 Hz, 2H).

An Alternate Preparation of Int-I-D: Ethyl 3-phenyl-4-(trifluoromethyl)isoxazole-5-carboxylic acid starting with ethyl 4,4,4-trifluorobut-2-enoate Preparation of Int-I-E: Ethyl 2,3-dibromo-4,4,4-trifluorobutanoate

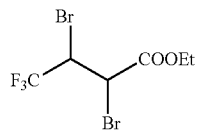
(Int-I-E)

Bromine (18.4 mL, 357 mmol) was added dropwise over 30 minutes to a solution of commercially available (E)-ethyl 4,4,4-trifluorobut-2-enoate (50 g, 297 mmol) in carbon tetrachloride (50 mL) at room temperature under nitrogen. The resulting dark red solution was refluxed for 4 hours. Additional bromine (2 ml) was added and heating was continued until the HPLC analysis showed that the starting material had been consumed. The reaction mixture was concentrated under reduced pressure to give light brown oil which used in the next step without purification. HPLC (XBridge 5µ C18 4.6×50 mm, 4 mL/min, solvent A: 10% MeOH/water with 0.2% $H_3PO_4$, solvent B: 90% MeOH/water with 0.2% $H_3PO_4$, gradient with 0-100% B over 4 minutes): 2.96 and 3.19 minutes.

Preparation of Int-I-F (Z/E): Ethyl 2-bromo-4,4,4-trifluorobut-2-enoate

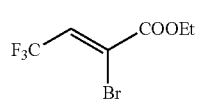
(Int-I-F)

To a solution of ethyl 2,3-dibromo-4,4,4-trifluorobutanoate (Int-1-E) in hexane (200 mL) cooled to 0° C. was added triethylamine (49.7 ml, 357mmol) drop-wise over 35 minutes, during which time a white precipitate formed. The reaction mixture was stirred for an additional 2 hours until LC indicated complete conversion. The solid was filtered and rinsed with hexane (3×50mL), and the filtrate was concentrated and passed through a short silica gel pad eluting with 10% ethyl acetate/hexane to give (Z/E)-ethyl 2-bromo-4,4,4-trifluorobut-2-enoate (65.5 g, 265mmol, 89% yield for two steps) as a colorless oil. Alternatively, the crude product can be purified by distillation (85° C./~60 mmHg). $^1$H NMR ($CDCl_3$, 400 MHz) δ 7.41 (q, 1H, J=7.28 Hz), 4.35 (q, 2H, J=7.11 Hz), 1.38 (t, 3H, J=7.15 Hz); HPLC (XBridge 5µ C18 4.6×50 mm, 4 mL/min, solvent A: 10% MeOH/water with 0.2% $H_3PO_4$, solvent B: 90% MeOH/water with 0.2% $H_3PO_4$, gradient with 0-100% B over 4 minutes): 3.09 minutes.

Alternate Preparation of Int-I-D: Ethyl 3-phenyl-4-(trifluoromethyl)isoxazole-5-carboxylate

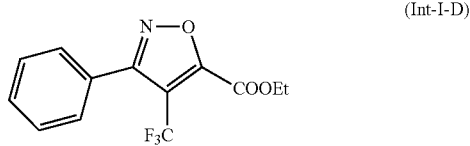 [SMILES: CCOC(=O)c1onc(-c2ccccc2)c1C(F)(F)F]
(Int-I-D)

(Z/E)-Ethyl 2-bromo-4,4,4-trifluorobut-2-enoate, Int-I-F, (39.7 g, 161mmol) and N-hydroxybenzimidoyl chloride (30 g, 193mmol) were dissolved in ethyl acetate (150 mL). Indium (III) chloride (8.89 g, 40.2 mmol) was added and the resulting mixture stirred for 60 minutes at RT under $N_2$. Potassium hydrogen carbonate (32.2 g, 321 mmol) was added to the reaction mixture which was allowed to stir overnight for 14 hours at RT. The solvent was removed in vacuo. The residue was re-suspended in 300 mL hexane and stirred for 10 minutes then filtered. The filter cake was washed with hexane (3×30 mL) and the combined filtrate was concentrated in vacuo to give crude product, which was further purified with flash chromatography to generate 33 g product (72%) as light yellowish oil as a mixture of the desired isomer Int-I-D and undesired isomer ethyl 3-phenyl-5-(trifluoromethyl)isoxazole-4-carboxylate in a ratio of ~30/1. MS m/e 286.06 (M+H$^+$); $^1$H NMR ($CDCl_3$, 400 MHz) δ 7.56 (m, 5H), 4.53 (q, 2H, J=7.3 Hz), 1.46 (t, 3H, J=7.2 Hz); HPLC (XBridge 5µ C18 4.6×50 mm, 4 mL/min, Solvent A: 10% MeOH/water with 0.2% $H_3PO_4$, Solvent B: 90% MeOH/water with 0.2% $H_3PO_4$, gradient with 0-100% B over 4 minutes): 3.57 minutes.

Preparation of Int-I Li salt: 3-Phenyl-4-(trifluoromethyl)isoxazole-5-carboxylic acid, lithium salt

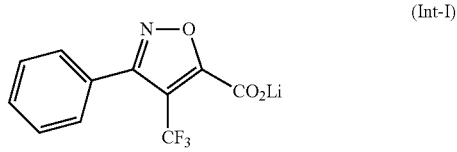
(Int-I)

A mixture of ethyl 3-phenyl-4-(trifluoromethyl)isoxazole-5-carboxylate, Int-I-D, (0.085 g, 0.298 mmol) and lithium hydroxide hydrate (0.013 g, 0.298 mmol) in methanol (2.0 mL) and water (1.0 mL) was stirred at room temperature overnight. The reaction mixture was concentrated to dryness to give 3-phenyl-4-(trifluoromethyl)isoxazole-5-carboxylic acid, lithium salt (0.079 g, 0.299 mmol, 100% yield) as a pale yellow solid. The compound had an HPLC ret. time=1.72 min.-Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=258.0. $^1$H NMR (400 MHz, $CDCl_3$) δ ppm 7.49-7.57 (m, 3H) and 7.58-7.62 (m, 2H).

Preparation of Int-I-G:
3-Phenyl-4-(trifluoromethyl)isoxazole-5-carbonyl fluoride

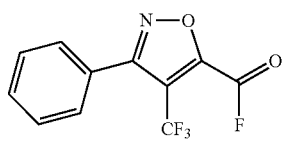

(Int-I-G)

To a mixture of 3-phenyl-4-(trifluoromethyl)isoxazole-5-carboxylic acid (3.00 g, 11.7 mmol) and pyridine (1.132 mL, 14 0 mmol) in dichloromethane (100 mL) at room temperature was added 2,4,6-trifluoro-1,3,5-triazine (cyanuric fluoride) (1.18 mL, 14.0 mmol). The reaction mixture was stirred at room temperature overnight, diluted with dichloromethane (300 mL), washed with an ice-cold solution of 0.5N aqueous hydrochloric acid (2×100 mL), and the organic layer was collected. The aqueous layer was back-extracted with dichloromethane (200 mL), and the combined organic layers were dried anhydrous sodium sulfate and concentrated to afford 3-phenyl-4-(trifluoromethyl)isoxazole-5-carbonyl fluoride (2.91 g, 11.2 mmol, 96% yield) as a yellow, viscous oil. The product was found to react readily with methanol and on analysis was characterized as the methyl ester, which had an HPLC ret. time=2.56 min.-Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=272.3 (methyl ester).

Intermediate II (Int-II)

Ethyl 5-phenylis oxazole-3-carboxylate

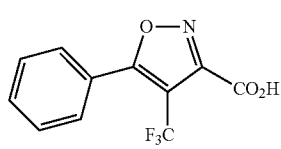

(Int-II)

Preparation of Int-II-A: Ethyl 5-phenylisoxazole-3-carboxylate

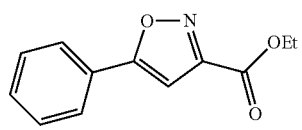

(Int-II-A)

To a mixture of (Z)-ethyl 2-chloro-2-(hydroxyimino)acetate (3.03 g, 20 mmol) and ethynylbenzene (4.39 mL, 40 mmol) in ether (80 mL) at room temperature was added a solution of triethylamine (5.58 mL, 40 0 mmol) in ether (20 mL) dropwise over 60 minutes. The reaction mixture was stirred for 2 h at room temperature. The reaction mixture was filtered, and the filtrate was concentrated to a yellow oil which was purified by flash silica gel chromatography using a mixture of ethyl acetate in hexane (0-12%) to afford ethyl 5-phenylisoxazole-3-carboxylate (3.06 g, 14.09 mmol, 70% yield) as a white solid. The compound had an HPLC retention time=2.99 minutes (YMC-Combi 4.6×50 mm S-5 ODS column) eluting with 10-90% aqueous methanol +0.2% phosphoric acid over a 4 minute gradient. MS:(M+H)=218.12. $^1$H NMR (400 MHz, $CDCl_3$) δ ppm 1.45 (t, J=7.3 Hz, 3H), 4.48 (q, J=7.3, 2H), 6.93 (s, 1H), 7.45-7.53 (m, 3H), and 7.77-7.85 (m, 2H).

Preparation of Int-II-B: Ethyl 4-iodo-5-phenylisoxazole-3-carboxylate

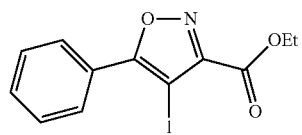

(Int-II-B)

A mixture of ethyl 5-phenylisoxazole-3-carboxylate (406 mg, 1.87 mmol) and N-iodosuccinimide (505 mg, 2.24 mmol) in trifluoroacetic acid (10 mL) was stirred at room temperature for 1.5 h. The volatiles were removed under reduced pressure, and the residue was partitioned between ethyl acetate (50 mL) and water (50 mL). The organic layer was washed with a 1N aqueous solution of sodium hydroxide (50 mL), washed with a 2.5% aqueous solution of sodium bisulfate (50 mL), washed with brine (50 mL), and dried over anhydrous magnesium sulfate. Concentration under reduced pressure afforded ethyl 4-iodo-5-phenylisoxazole-3-carboxylate (641 mg, 1.87 mmol, 100% yield) as a light yellow oil. The compound had an HPLC retention time=3.36 minutes (YMC-Combi 4.6×50 mm S-5 ODS column) eluting with 10-90% aqueous methanol+0.2% phosphoric acid over a 4 minute gradient. MS:(M+H)=343.97. $^1$H NMR (400 MHz, $CDCl_3$) δ ppm 1.47 (t, J=7.1 Hz, 3H), 4.50 (q, J=7.0 Hz, 2H), 7.52-7.56 (m, 3H), and 8.05 (m, 2H).

Large Scale: A mixture of ethyl 5-phenylisoxazole-3-carboxylate (3.05 g, 14.0 mmol) and N-iodosuccinimide (3.79 g, 16 9 mmol) in trifluoroacetic acid (78 mL) was stirred at room temperature for 3.5 h. The volatiles were removed under reduced pressure, and the residue was partitioned between ethyl acetate (150 mL) and water (150 mL). The organic layer was washed with a 1N aqueous solution of sodium hydroxide (150 mL), washed with a 3% aqueous solution of sodium bisulfate (2×150 mL), washed with brine (150 mL), and dried over anhydrous magnesium sulfate. Concentration under reduced pressure afforded ethyl 4-iodo-5-phenylisoxazole-3-carboxylate (4.69 g, 13.7 mmol, 97% yield) as a light yellow oil.

Preparation of Int-II-C: Ethyl 5-phenyl-4-(trifluoromethyl)isoxazole-3-carboxylate

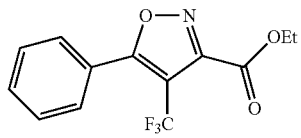

(Int-II-C)

To a solution of ethyl 4-iodo-5-phenylisoxazole-3-carboxylate (638 mg, 1.86 mmol) and copper(I) iodide (70.8 mg, 0.372 mmol) in N,N-dimethylformamide (9 mL) and HMPA (1.2 mL) at room temperature was added methyl 2,2-difluoro-2-(fluorosulfonyl)acetate (0.947 mL, 7.44 mmol) in one portion. The reaction mixture was immediately immersed in an oil bath at 75-80° C. and was stirred for 6 hrs. The reaction mixture was then allowed to cool to room temperature and was stirred overnight. The reaction mixture was partitioned between ethyl ether (125 mL) and a saturated aqueous solution of ammonium chloride (125 mL). The organic layer was washed with a saturated aqueous solution of ammonium chloride (125 mL), washed with water (2×125 mL), washed with brine (50 mL), and dried over anhydrous magnesium sulfate. Concentration under reduced pressure followed by purification by silica gel chromatography using a mixture of ethyl acetate in hexane (0-10%) afforded ethyl 5-phenyl-4-(trifluoromethyl)isoxazole-3-carboxylate (454 mg, 1.59 mmol, 86% yield) as a colorless oil. The compound had an HPLC retention time=3.44 minutes (YMC-Combi 4.6×50 mm S-5 ODS column) eluting with 10-90% aqueous methanol+0.2% phosphoric acid over a 4 minute gradient. MS:(M+H)=286.01. $^1$H NMR (400 MHz, CDCl$_3$) δ ppm 1.45 (t, J=7.2 Hz, 3H), 4.51 (q, J=7.3 Hz, 2H), 7.52-7.62 (m, 3H), and 7.69 (d, J=7.5 Hz, 2H).

Large Scale: To a solution of ethyl 4-iodo-5-phenylisoxazole-3-carboxylate (4.62 g, 13.5 mmol) and copper(I) iodide (0.513 g, 2.69 mmol) in N,N-dimethylformamide (59.8 mL) and HMPA (7.48 mL) at room temperature was added methyl 2,2-difluoro-2-(fluorosulfonyl)acetate (6.86 mL, 53.9 mmol) at once. The reaction mixture was immediately immersed in an oil bath at 75-80° C. Stirring was continued at this temperature for 3.5 h. After cooling to room temperature, the reaction mixture was cooled in an ice bath. A saturated aqueous solution of ammonium chloride (~50 mL) was added slowly to quench the reaction. The mixture was partitioned between ethyl ether (400 mL) and a saturated aqueous solution of ammonium chloride (400 mL). The organic layer was washed with a saturated aqueous solution of ammonium chloride (200 mL), washed with water (2×200 mL), washed with brine (50 mL), and dried over anhydrous magnesium sulfate. Concentration under reduced pressure followed by purification by silica gel chromatography using a mixture of ethyl acetate in hexane (0-10%) afforded ethyl 5-phenyl-4-(trifluoromethyl)isoxazole-3-carboxylate (3.6 g, 12.6 mmol, 94% yield) as a colorless oil.

Int-II: 5-Phenyl-4-(trifluoromethyl)isoxazole-3-carboxylic acid

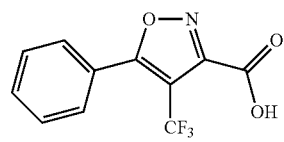

(Int-II)

To a solution of ethyl 5-phenyl-4-(trifluoromethyl)isoxazole-3-carboxylate (3.6 g, 12 6 mmol) in methanol (100 mL) and water (20 mL) at room temperature was added lithium hydroxide, monohydrate (0.583 g, 13.9 mmol). The reaction mixture was stirred at room temperature for 30 minutes. The methanol was removed under reduce pressure, and the residue was diluted with water (~100 mL). Ethyl ether (200 mL) was added, and the pH of the aqueous layer was adjusted to <1 with a 1N aqueous solution of hydrochloric acid. The mixture was transferred to a separatory funnel, and after agitation, the layers were separated. The organic layer was washed with brine (100 mL), dried over anhydrous magnesium sulfate, and concentrated to afford 5-phenyl-4-(trifluoromethyl)isoxazole-3-carboxylic acid (3.12 g, 12.13 mmol, 96% yield) as a white, crystalline solid. The compound had an HPLC retention time=2.58 minutes (YMC-Combi 4.6×50 mm S-5 ODS column) eluting with 10-90% aqueous methanol+0.2% phosphoric acid over a 4 minute gradient. MS:(M+Na)=279.95. $^1$H NMR (400 MHz, CDCl$_3$) δ ppm 7.53-7.64 (m, 3H), and 7.70 (d, J=7.5 Hz, 2H).

Preparation of Int-II-D. 5-Phenyl-4-(trifluoromethyl)isoxazole-3-carbonyl fluoride

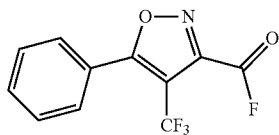

(Int-II-D)

To a mixture of 5-phenyl-4-(trifluoromethyl)isoxazole-3-carboxylic acid (197 mg, 0.766 mmol) and pyridine (0.074 mL, 0.919 mmol) in dichloromethane (5 mL) at room temperature was added cyanuric fluoride (0.078 mL, 0.919 mmol). The reaction mixture was stirred at room temperature for 18 h. The mixture was diluted with dichloromethane (40 mL) and washed with an ice-cold 0.5N aqueous solution of hydrochloric acid (20 mL). The aqueous layer was extracted with dichloromethane (20 mL), and the combined organic layers were washed with ice-cold water (20 mL) and dried over anhydrous magnesium sulfate. Concentration under reduced pressure afforded 5-phenyl-4-(trifluoromethyl)isoxazole-3-carbonyl fluoride (199 mg, 0.768 mmol, 100% yield) as a pale yellow oil. The compound had an HPLC retention time=2.53 min. (methyl ester)-Column: CHROMOLITH®

SpeedROD 4.6×50 mm (4 min.); Solvent A=10% MeOH, 90% H₂O, 0.1% TFA; Solvent B=90% MeOH, 10% H₂O, 0.1% TFA.

Intermediate III (Int-III)

5-Phenyl-4-propylisoxazole-3-carboxylic acid

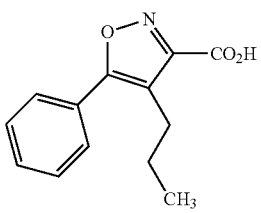
(Int-III)

Pent-1-ynylbenzene (17 mL, 106 mmol) and diethyl 2-nitromalonate (30 mL, 172 mmol) were placed in a stainless steel pressure bomb and heated to 160° C. for 18 hours. Cooled in ice bath then slowly released remaining pressure. The reaction mixture was diluted with ethyl acetate and washed with 1N NaOH. The aqueous layer was back extracted once. The organic layer was dried over MgSO₄, filtered, and concentrated. The crude material was treated with 1N NaOH/EtOH at 75° C. for two hours. Diluted with water and washed with EtOAc. The aqueous layer was separated, acidified with concentrated HCl, and extracted with EtOAc. The organic layer was dried with MgSO₄, filtered and concentrated to afford 20 g of 5-phenyl-4-propylisoxazole-3-carboxylic acid.

Intermediate IV (Int-IV)

3-(Pyridin-2-yl)-4-(trifluoromethyl)isoxazole-5-carboxylic acid

(Int-IV)

Preparation of Int-IV-A:
(E,Z)-N-Hydroxypicolinimidoyl chloride

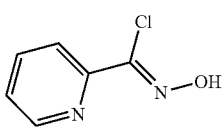
(Int-IV-A)

To a colorless, homogeneous solution of commercially available (E)-picolinaldehyde oxime (6.75 g, 55 3 mmol) in N,N-dimethylformamide (55 mL) at room temperature was added N-chlorosuccinimide (7.38 g, 55.3 mmol) portion-wise. After the addition of ~⅓ of the NCS, the reaction mixture was immersed in an oil bath at 60° C., and the remaining NCS was added portion-wise over 1.5 h. After the addition was complete, the homogeneous reaction mixture was stirred for 60 min. at 60° C. and was then cooled to room temperature. Water (400 mL) was added, and the aqueous mixture was extracted with ether (3×200 mL). The organic layer was collected, washed with water (2×200 mL), washed with a saturated aqueous solution of brine (100 mL), and dried over anhydrous magnesium sulfate. Concentration under reduced pressure afforded (E,Z)-N-hydroxypicolinimidoyl chloride (6.45 g, 41.2 mmol, 75% yield) as a tan solid. The compound had an HPLC retention time=0.515 min.-Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M+1=156.8. ¹H NMR (400 MHz, CDCl₃) δ ppm 7.37-7.43 (m, 1H), 7.80 (td, J=7.78, 1.76 Hz, 1H), 7.91-7.97 (m, 1H), 8.72 (d, J=4.02 Hz, 1H), and 9.85 (br. s., 1H).

Preparation of Int-IV-B: Ethyl 3-(pyridin-2-yl)-4-(trifluoromethyl)isoxazole-5-carboxylate

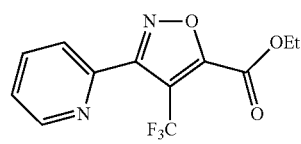
(Int-IV-B)

To a yellow, homogeneous mixture of (E,Z)-N-hydroxypicolinimidoyl chloride (4.67 g, 29.8 mmol) and ethyl 4,4,4-trifluorobut-2-ynoate (4.50 g, 27 1 mmol) in dichloromethane (90 mL) at room temperature was added triethylamine (7.93 mL, 56.9 mmol) slowly over 30 min. During the addition, the reaction mixture slowly became dark in color. The reaction was stirred overnight at room temperature. The solvent was removed under reduced pressure, and the residue was diluted with ether (100 mL) and washed with water (100 mL). The organic layer was collected, and the aqueous layer was extracted with ether (2×100 mL). The combined organic layers were dried over anhydrous magnesium sulfate and concentrated under reduced pressure. By HPLC, the product mixture contained a ~15:85 mixture of the desired isomer and its regioisomer. The mixture was purified by preparative HPLC, and the desired fractions were concentrated under reduced pressure. The residue was diluted with ethyl acetate (100 mL), washed with a saturated aqueous solution of sodium bicarbonate (100 mL), washed with brine (50 mL), and dried over anhydrous magnesium sulfate. Concentration under reduced pressure afforded ethyl 3-(pyridin-2-yl)-4-(trifluoromethyl)isoxazole-5-carboxylate (0.518 g, 1.81 mmol, 6.7% yield) as a pale yellow, viscous oil. The compound had an HPLC ret. time=2.18 min.-Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M+1=286.9. ¹H NMR (400 MHz, CDCl₃) δ ppm 1.46 (t, J=7.15 Hz, 3H), 4.54 (q, J=7.03 Hz, 2H), 7.46

(ddd, J=7.53, 4.77, 1.25 Hz, 1H), 7.76-7.81 (m, 1H), 7.83-7.89 (m, 1H), and 8.78 (d, J=4.77 Hz, 1H).

Alternate Preparation of Ethyl 3-(pyridin-2-yl)-4-(trifluoromethyl)isoxazole-5-carboxylate (Int-IV-B)

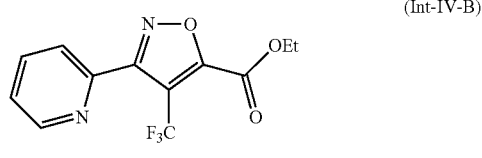 [SMILES: CCOC(=O)c1onc(-c2ccccn2)c1C(F)(F)F]
(Int-IV-B)

To a solution of (Z)-ethyl 2-bromo-4,4,4-trifluorobut-2-enoate (1.58 g, 6.39 mmol) and (E,Z)-N-hydroxypicolinimidoyl chloride (2.0 g, 12.8 mmol) in ethyl acetate (10 mL) was added indium (III) chloride (0.283 g, 1.28 mmol). The resulting mixture was stirred for 30 minutes under nitrogen, and then potassium hydrogen carbonate (0.959 g, 9.58 mmol) was added. The reaction mixture was stirred for 14 h. The mixture was filtered, and the solid was rinsed with ethyl acetate (10 ml). The filtrate was washed with a saturated aqueous solution of ammonium chloride (10 mL), washed with brine (10 mL), and concentrated. The residue was purified by flash silica gel chromatography using EtOAc/Hexane as the solvent. The fractions containing the product were pooled and concentrated to give the product as an oil (1.15 g, 63% yield) as a mixture of the desired isomer, ethyl 3-(pyridin-2-yl)-4-(trifluoromethyl)isoxazole-5-carboxylate and the undesired isomer, ethyl 3-(pyridine-2-yl)-5-(trifluoromethyl)isoxazole-4-carboxylate in a ratio of approximately 30:1. MS m/e 287.02 (M+H$^+$); $^1$H NMR (DMSO, 400 MHz) δ 8.73 (d, J=4.0 Hz, 1H), 8.01(m, 1H), 7.87(d, J=8.0 Hz, 1H), 7.65(m, 1H), 4.53 (q, J=8.0 Hz, 2H,), 1.46 (t, J=8.0 Hz, 3H); HPLC (XBridge 5μ C18 4.6×50 mm, 4 mL/min; solvent A: 10% MeOH/water with 0.2% H$_3$PO$_4$; solvent B: 90% MeOH/water with 0.2% H$_3$PO$_4$, gradient with 0-100% B over 4 minutes): 3.57 minutes.

Preparation of Int-IV. 3-(Pyridin-2-yl)-4-(trifluoromethyl)isoxazole-5-carboxylic acid

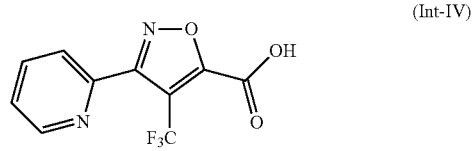 [SMILES: O=C(O)c1onc(-c2ccccn2)c1C(F)(F)F]
(Int-IV)

To a solution of ethyl 3-(pyridin-2-yl)-4-(trifluoromethyl) isoxazole-5-carboxylate (511 mg, 1.79 mmol) in methanol (12 mL) and water (3 mL) at room temperature was added lithium hydroxide, hydrate (74.9 mg, 1.79 mmol). The reaction mixture was stirred for 1 hr. A 1N aqueous solution of hydrochloric acid (1.8 mL) was added, and the solvent were removed under reduced pressure to afford 3-(pyridin-2-yl)-4-(trifluoromethyl)isoxazole-5-carboxylic acid+1LiCl (531 mg, 1.767 mmol, 99% yield) as a white solid. The compound had an HPLC ret. time=0.725 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=258.8. $^1$H NMR (400 MHz, CD$_3$OD) δ ppm 7.59 (dd, J=7.03, 5.02 Hz, 1H), 7.82 (d, J=7.78 Hz, 1H), 8.01 (td, J=7.78, 1.76 Hz, 1H), and 8.73 (d, 1H).

Intermediate V (Int-V)

5-Isobutyl-4-(trifluoromethyl)isoxazole-3-carboxylic acid

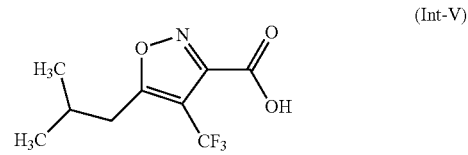 [SMILES: CC(C)Cc1onc(C(=O)O)c1C(F)(F)F]
(Int-V)

Preparation of Int-V-A: Methyl 4-Iodo-5-isobutylisoxazole-3-carboxylate

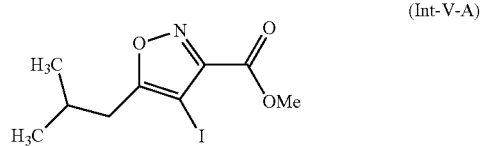
(Int-V-A)

A mixture of methyl 5-isobutylisoxazole-3-carboxylate (0.923 g, 5.04 mmol) and N-iodosuccinimide (1.247 g, 5.54 mmol) in trifluoroacetic acid (25 mL) was stirred at room temperature overnight. By HPLC, the reaction was complete. The trifluoroacetic acid was removed under reduced pressure, and the residue was diluted with dichloromethane (100 mL), washed with a saturated aqueous solution of sodium bicarbonate (2×25 mL), washed with a 2.5% aqueous solution of sodium bisulfate (25 mL), and dried over anhydrous sodium sulfate. Concentration under reduced pressure followed by purification by flash silica gel chromatography using a 5% mixture of ethyl acetate in hexane afforded methyl 4-iodo-5-isobutylisoxazole-3-carboxylate (1.21 g, 3.91 mmol, 78% yield) as a pale yellow oil. The product had an HPLC ret. time=2.40 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=310.1.

Preparation of Int-V-B: Methyl 5-Isobutyl-4-(trifluoromethyl)isoxazole-3-carboxylate

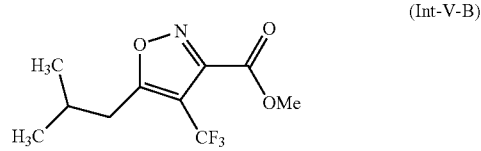
(Int-V-B)

To a solution of methyl 4-iodo-5-isobutylisoxazole-3-carboxylate (1.21 g, 3.91 mmol), copper(I) iodide (0.149 g, 0.783 mmol), and HMPA (2.59 mL) in N,N-dimethylformamide (19 mL) was added methyl 2,2-difluoro-2-(fluorosulfonyl)acetate (1.993 mL, 15.66 mmol) over 1 min. The reaction mixture was immediately immersed in an oil bath at 75° C. and was stirred overnight. The clear, orange reaction mixture was cooled to room temperature and diluted with ether (100 mL), washed with a saturated aqueous solution of ammonium chloride (2×100 mL), washed with a 10% aqueous solution of lithium chloride (2×50 mL), and washed with brine (50 mL). The aqueous layer was back-extracted with ether (100 mL +50 mL), and the combined organic layers were dried over anhydrous sodium sulfate. Concentration under reduced pressure followed by purification by flash silica gel chromatography using a 5% mixture of ethyl acetate in hexane provided methyl 5-isobutyl-4-(trifluoromethyl)isoxazole-3-carboxylate (0.819 g, 3.26 mmol, 83% yield) as a clear, colorless oil. The product had an HPLC ret. time=2.52 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. $^1$H NMR (500 MHz, CDCl$_3$) δ ppm 0.99 (s, 3H), 1.00 (s, 3H), 2.09-2.20 (m, 1H), 2.86 (dd, J=7.21, 1.11 Hz, 2H), and 4.01 (s, 3H).

Preparation of Int-V-C: 5-Isobutyl-4-(trifluoromethyl)isoxazole-3-carboxylic acid

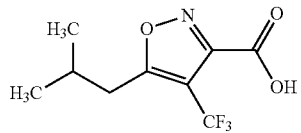
(Int-V-C)

A mixture of methyl 5-isobutyl-4-(trifluoromethyl)isoxazole-3-carboxylate (0.816 g, 3.25 mmol) and lithium hydroxide hydrate (0.136 g, 3.25 mmol) in methanol (18 mL) and water (9.00 mL) was stirred at room temperature overnight. By HPLC and LCMS, the hydrolysis was complete. The reaction mixture was concentrated under reduced pressure, and the residue dissolved in 1N aqueous hydrochloric acid and extracted with ether. The organic layer was collected and dried over anhydrous sodium sulfate. Concentration under reduced pressure afforded 5-isobutyl-4-(trifluoromethyl)isoxazole-3-carboxylic acid (0.746 g, 3.15 mmol, 97% yield) as an off-white solid. The product had an HPLC ret. time=2.00 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. $^1$H NMR (400 MHz, DMSO-d$_6$) δ ppm 0.91 (s, 3H), 0.93 (s, 3H), 1.97-2.09 (m, 1H), and 2.89 (d, J=7.28 Hz, 2H).

Preparation of Int-V-D: 3-Isobutyl-4-(trifluoromethyl)isoxazole-5-carbonyl fluoride

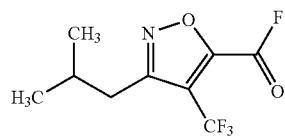
(Int-V-D)

To a mixture of 3-isobutyl-4-(trifluoromethyl)isoxazole-5-carboxylic acid (0.070 g, 0.295 mmol) and pyridine (0.029 mL, 0.354 mmol) in dichloromethane (2.5 mL) at room temperature was added 2,4,6-trifluoro-1,3,5-triazine (cyanuric fluoride) (0.030 mL, 0.354 mmol). The reaction mixture was stirred at room temperature for 5.5 h. The heterogeneous reaction was complete by HPLC and was diluted with dichloromethane, washed with an ice-cold solution of 0.5N aqueous hydrochloric acid (2×), and the organic layer was collected. The aqueous layer was back-extracted with dichloromethane, and the combined organic layers were dried with anhydrous sodium sulfate and concentrated to afford 3-isobutyl-4-(trifluoromethyl)isoxazole-5-carbonyl fluoride (0.050 g, 0.209 mmol, 70.8% yield) as a yellow solid. The product had an HPLC ret. time=2.52 min (methyl ester)-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA.

Example 1

1-(2-Hydroxy-2-(4-(5-(5-phenyl-4-propylisoxazol-3-yl)-1,2,4-oxadiazol-3-yl)phenyl)ethyl)azetidine-3-carboxylic acid

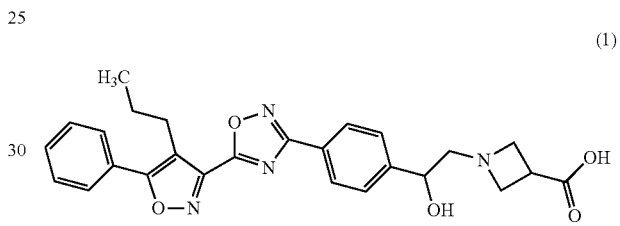
(1)

Preparation 1A: 5-(5-Phenyl-4-propylisoxazol-3-yl)-3-(4-vinylphenyl)-1,2,4-oxadiazole

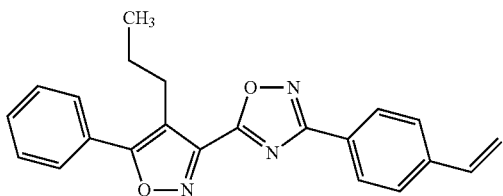
(1A)

To a mixture of 5-phenyl-4-propylisoxazole-3-carboxylic acid, Int-III (3 g, 12.97 mmol) and pyridine (1.049 mL, 12.97 mmol) in DCM (50 mL) was added cyanuric fluoride (1.095 mL, 12.97 mmol). The reaction mixture was stirred 1 hour at room temperature. The reaction mixture was diluted with DCM (50 mL) and washed with 1M HCl. The organic layer was dried over MgSO$_4$, filtered, and concentrated. The residue was dissolved in acetonitrile (50.0 mL). (Z)-N'-hydroxy-4-vinylbenzimidamide (2.104 g, 12.97 mmol) and DIEA (3.40 mL, 19.46 mmol) were added. [Note: N'-hydroxy-4-vinylbenzimidamide was prepared by 4-vinylbenzonitrile (4.36 g, 33 8 mmol) and hydroxylamine hydrochloride (4.69 g, 67 5 mmol) in 2-propanol (50 mL) was added sodium bicarbonate (11.34 g, 135 mmol). Heated at 80° C. for 2 hours. The reaction mixture was diluted with ethyl acetate and washed with water. The organic layer was dried with MgSO$_4$, filtered, and concentrated to afford 5.3 g of N'-hydroxy-4- vinylbenzimidamide.] The mixture was heated at 70° C. overnight. The reaction mixture was diluted with ethyl acetate and washed with saturated KH$_2$PO$_4$. The organic layer was dried with MgSO$_4$, filtered, and concentrated to yield Preparation 1A. MS (m+1)=358. HPLC Peak RT=2.34 minutes. (Analytical Method B).

Preparation 1B: 3-(4-(Oxiran-2-yl)phenyl)-5-(5-phenyl-4-propylisoxazol-3-yl)-1,2,4-oxadiazole

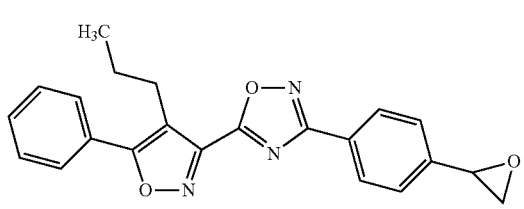

(1B)

To a mixture of 5-(5-phenyl-4-propylisoxazol-3-yl)-3-(4-vinylphenyl)-1,2,4-oxadiazole (4.64 g, 12.97 mmol) in DCM (500 mL) was added m-CPBA (9 g, 52.2 mmol). The reaction mixture was stirred overnight at room temperature. Next, the reaction mixture was washed with 1N NaOH. The organic layer was dried with MgSO$_4$, filtered, and concentrated to yield Preparation 1B. MS (m+1)=374. HPLC Peak RT=4.36 minutes (Analytical Method A).

Preparation 1C: 2-Bromo-1-(4-(5-(5-phenyl-4-propylisoxazol-3-yl)-1,2,4-oxadiazol-3-yl)phenyl)ethanol

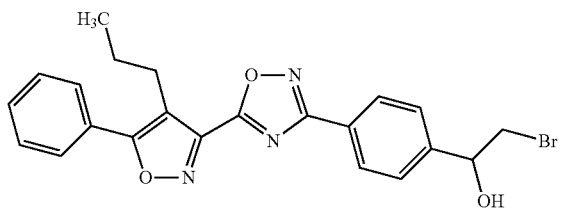

(1C)

To a mixture of 3-(4-(oxiran-2-yl)phenyl)-5-(5-phenyl-4-propylisoxazol-3-yl)-1,2,4-oxadiazole (205 mg, 0.549 mmol) in THF (5 mL) at −78° C. was slowly added bromotriethylsilane (100 μL, 0.582 mmol). The reaction mixture was stirred for 1 hour at −78° C. LC/MS was employed to determine extent of reaction. An aliquot was removed and concentrated in vacuo. Crude NMR indicated mostly desired regioisomer. The reaction was quenched with water and extracted with EtOAc. The organic layer was dried with MgSO$_4$, filtered, and concentrated. The solids were purified on a silica cartridge using an EtOAc/hexanes gradient to yield 130 mg of Preparation 1C as a white solid. $^1$H NMR (400 MHz, chloroform-d) δ ppm 8.16-8.24 (2H, m), 7.72-7.81 (2H, m), 7.61 (2H, m, J=8.13 Hz), 7.49-7.58 (3H, m), 5.12 (1H, dd, J=7.47, 5.93 Hz), 4.09-4.17 (1H, m), 4.01-4.08 (1H, m), 2.97-3.05 (2H, m), 1.70-1.83 (2H, m), 1.06 (3H, t=7.36 Hz).

Preparation 1D: tert-Butyl 1-(2-hydroxy-2-(4-(5-(5-phenyl-4-propylisoxazol-3-yl)-1,2,4-oxadiazol-3-yl)phenyl)ethyl)azetidine-3-carboxylate

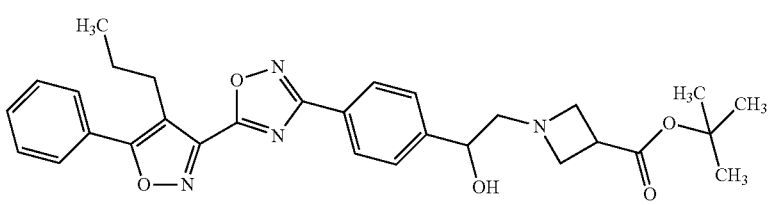

(1D)

To a mixture of 2-bromo-1-(4-(5-(5-phenyl-4-propylisoxazol-3-yl)-1,2,4-oxadiazol-3-yl)phenyl)ethanol (30 mg, 0.066 mmol) and tert-butyl azetidine-3-carboxylate (21.52 mg, 0.099 mmol) in DMSO (2 mL) was added TEA (0.028 mL, 0.198 mmol). The reaction mixture was heated at 80° C. for 2 hours. The reaction mixture was filtered and purified by HPLC. HPLC conditions: PHENOMENEX® Luna C18 5 micron column (250×30mm); 30-100% CH$_3$CN/water (0.1% TFA); 25 minute gradient; 30 mL/min. Isolated fractions were obtained with the correct mass were freeze-dried overnight to yield 10 mg of Preparation 1D. MS (m+1) =531. HPLC Peak RT=3.67 minutes (Analytical Method A). Purity=92%.

Example 1

1-(2-Hydroxy-2-(4-(5-(5-phenyl-4-propylisoxazol-3-yl)-1,2,4-oxadiazol-3-yl)phenyl)ethyl)azetidine-3-carboxylic acid To tert-butyl 1-(2-hydroxy-2-(4-(5-(5-phenyl-4-propylisoxazol-3-yl)-1,2,4-oxadiazol-3-yl)phenyl)ethyl)azetidine-3-carboxylate (8 mg, 0.015 mmol) was added DCM (2 mL) and TFA (2.000 mL). The reaction mixture was stirred 2 hours. Next, the solvent was removed and the remaining contents were freeze dried from MeCN to yield 8 mg of 1-(2-hydroxy-2-(4-(5-(5-phenyl-4-propylisoxazol-3-yl)-1,2,4-oxadiazol-3-yl)phenyl)ethyl)azetidine-3-carboxylic acid as a TFA salt. $^1$H NMR (400 MHz, DMSO-d$_6$) δ ppm 8.19 (2H, d, J=8.35 Hz), 7.83 (2H, dd, J=8.02, 1.65 Hz), 7.58-7.73 (5H, m), 4.32-4.83 (3H, m), 3.43-4.20 (6H, m), 2.95-3.05

(2H, m), 1.65-1.75 (2H, m), 0.97 (3H, t, J=7.36 Hz). MS (m+1)=475. HPLC Peak RT=3.38 minutes (Analytical Method A). Purity=90%.

Example 2

1-(2-Hydroxy-2-(4-(5-(5-phenyl-4-propylisoxazol-3-yl)-1,2,4-oxadiazol-3-yl)phenyl)ethyl)piperidine-2-carboxylic acid

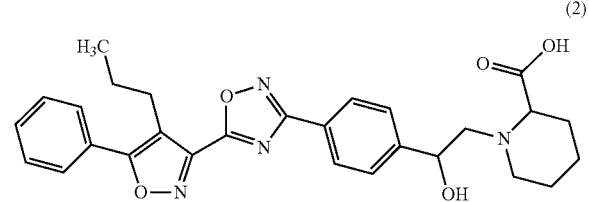 [SMILES: CCCc1c(-c2nc(-c3ccc(C(O)CN4CCCCC4C(=O)O)cc3)no2)noc1-c1ccccc1]

(2)

To a mixture of 2-bromo-1-(4-(5-(5-phenyl-4-propylisoxazol-3-yl)-1,2,4-oxadiazol-3-yl)phenyl)ethanol, Preparation 1C (30 mg, 0.066 mmol) and piperidine-2-carboxylic acid (25.6 mg, 0.198 mmol) in DMSO (2 mL) was added DBU (0.030 mL, 0.198 mmol). The reaction mixture was heated at 80° C. for 2 hours. The reaction mixture was filtered and purified by HPLC. HPLC conditions: PHENOMENEX® Luna C18 5 micron column (250×30mm); 25-100% CH₃CN/water (0.1% TFA); 25 minute gradient; 30 mL/min. Isolated fractions with correct mass were freeze-dried overnight to yield 19 mg of 1-(2-hydroxy-2-(4-(5-(5-phenyl-4-propylisoxazol-3-yl)-1,2,4-oxadiazol-3-yl)phenyl)ethyl)piperidine-2-carboxylic acid as a TFA salt. $^1$H NMR (400 MHz, DMSO-d$_6$) δ ppm 8.10 (2H, dd, J=8.35, 2.20 Hz), 7.77 (2H, dd, J=7.91, 1.54 Hz), 7.52-7.64 (5H, m), 5.20 (1H, d, J=18.24 Hz), 3.67 (2H, br. s.), 2.87-3.01 (2H, m), 1.99-2.21 (2H, m), 1.69-1.88 (4H, m), 1.64 (2H, dq, J=15.24, 7.59 Hz), 1.39-1.56 (3H, m), 0.92 (3H, t, J=7.36 Hz). MS (m+1)=503. HPLC Peak RT=3.47 minutes (Analytical Method A). Purity=88%.

Example 3

1-(2-Hydroxy-2-(4-(5-(5-phenyl-4-propylisoxazol-3-yl)-1,2,4-oxadiazol-3-yl)phenyl)ethyl)piperidine-3-carboxylic acid

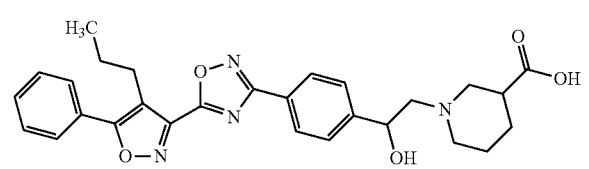

(3)

To a mixture of 2-bromo-1-(4-(5-(5-phenyl-4-propylisoxazol-3-yl)-1,2,4-oxadiazol-3-yl)phenyl)ethanol, Preparation 1C (30 mg, 0.066 mmol) and piperidine-3-carboxylic acid (25.6 mg, 0.198 mmol) in DMSO (2 mL) was added DBU (0.030 mL, 0.198 mmol). The reaction mixture was heated at 80° C. for 2 hours. The reaction mixture was filtered and purified by HPLC. HPLC conditions: PHENOMENEX® Luna C18 5 micron column (250×30mm); 25-100% CH₃CN/water (0.1% TFA); 25 minute gradient; 30 mL/min. Isolated fractions with correct mass were freeze-dried overnight to yield 18 mg 1-(2-hydroxy-2-(4-(5-(5-phenyl-4-propylisoxazol-3-yl)-1,2,4-oxadiazol-3-yl)phenyl)ethyl)piperidine-3-carboxylic acid as a TFA salt. $^1$H NMR (400 MHz, DMSO-d$_6$) δ ppm 8.16 (2H, dd, J=8.35, 1.98 Hz), 7.83 (2H, dd, J=7.91, 1.54 Hz), 7.56-7.75 (5H, m), 5.13-5.39 (1H, m), 4.11-4.31 (2H, m), 3.21-3.41 (3H, m), 2.96-3.05 (2H, m), 2.70-2.85 (1H, m), 1.75-2.14 (4H, m), 1.62-1.77 (2H, m), 1.36-1.56 (1H, m), 0.98 (3H, t, J=7.36 Hz). MS (m+1)=503. HPLC Peak RT=3.35 minutes (Analytical Method A). Purity=90%.

Example 4

(3S)-1-(2-Hydroxy-2-(4-(5-(5-phenyl-4-propylisoxazol-3-yl)-1,2,4-oxadiazol-3-yl)phenyl)ethyl)piperidine-3-carboxylic acid

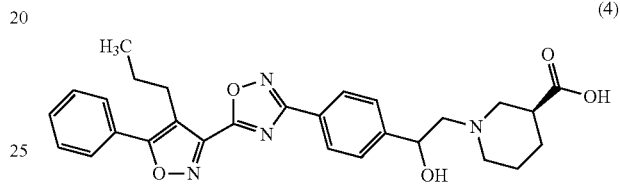

(4)

To a mixture of (S)-piperidine-3-carboxylic acid, HCl (32.8 mg, 0.198 mmol) in DMSO (2 mL) was added DBU (0.060 mL, 0.396 mmol). After 5 minutes, 2-bromo-1-(4-(5-(5-phenyl-4-propylisoxazol-3-yl)-1,2,4-oxadiazol-3-yl)phenyl)ethanol, Preparation 1C (30 mg, 0.066 mmol) was added. The reaction mixture was heated at 80° C. for 2 hours. The reaction mixture was filtered and purified by HPLC. HPLC conditions: PHENOMENEX® Luna C18 5 micron column (250×30mm); 30-100% CH₃CN/water (0.1% TFA); 25 minute gradient; 30 mL/min. Isolated fractions with correct mass were freeze-dried overnight to yield 6 mg of (3S)-1-(2-hydroxy-2-(4-(5-(5-phenyl-4-propylisoxazol-3-yl)-1,2,4-oxadiazol-3-yl)phenyl)ethyl)piperidine-3-carboxylic acid as a TFA salt. $^1$H NMR (400 MHz, DMSO-d$_6$) δ ppm 8.12 (2H, dd, J=8.24, 1.87 Hz), 7.79 (2H, dd, J=8.02, 1.65 Hz), 7.67 (2H, d, J=8.35 Hz), 7.56-7.64 (3H, m), 5.13-5.28 (1H, m), 3.81 (1H, d, J=11.86 Hz), 3.67 (2H, t, J=14.17 Hz), 3.21-3.33 (3H, m), 2.92-3.01 (2H, m), 1.77-2.14 (2H, m), 1.61-1.73 (2H, m), 1.33-1.51 (1H, m), 0.94 (1H, s), 0.94 (3H, t, J=7.36 Hz). MS (m+1)=503. HPLC Peak RT=3.37 minutes (Analytical Method A). Purity=85%.

Example 5

(3R)-1-(2-Hydroxy-2-(4-(5-(5-phenyl-4-propylisoxazol-3-yl)-1,2,4-oxadiazol-3-yl)phenyl)ethyl)piperidine-3-carboxylic acid

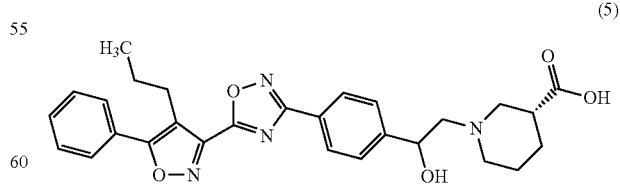

(5)

To (R)-1-(tert-butoxycarbonyl)piperidine-3-carboxylic acid (45.4 mg, 0.198 mmol) was added TFA/DCM (1:1). The mixture was stirred for 1 hour and solvent was removed solvent in vacuo, followed by chasing once with DCM. The resulting mixture was dried in vacuo. This crude residue was dissolved in DMSO (2 mL) and DBU (0.060 mL, 0.396 mmol) was added. After 5 minutes, 2-bromo-1-(4-(5-(5-phenyl-4-propylisoxazol-3-yl)-1,2,4-oxadiazol-3-yl)phenyl)ethanol, Preparation 1C (30 mg, 0.066 mmol) was added. The reaction mixture was heated at 80° C. for 2 hours. The reaction mixture was filtered and purified by HPLC. HPLC conditions: PHENOMENEX® Luna C18 5 micron column (250×30mm); 20-100% CH₃CN/water (0.1% TFA); 25 minute gradient; 30 mL/min. Isolated fractions with correct mass were freeze-dried overnight to yield 6 mg of (3R)-1-(2-hydroxy-2-(4-(5-(5-phenyl-4-propylisoxazol-3-yl)-1,2,4-oxadiazol-3-yl)phenyl)ethyl)piperidine-3-carboxylic acid as a TFA salt. $^1$H NMR (400 MHz, MeOH-d₃) δ ppm 8.21 (2H, d, J=7.91 Hz), 7.71 (2H, dd, J=8.02, 1.65 Hz), 7.47-7.56 (5H, m), 4.46 (1H, br. s.), 4.10 (2H, d, J=6.37 Hz), 3.25-3.61 (2H, m), 2.92-3.03 (3H, m), 2.91 (2H, br. s.), 2.01-2.27 (1H, m), 1.81-2.00 (3H, m), 1.60-1.76 (2H, m, J=7.61, 7.61, 7.61, 7.61, 7.36 Hz), 1.20-1.59 (1H, m), 0.95 (3H, t, J=7.36 Hz). MS (m+1)=503. HPLC Peak RT=3.32 minutes (Analytical Method A). Purity=96%.

Example 6

1-(2-Hydroxy-2-(4-(5-(5-phenyl-4-propylisoxazol-3-yl)-1,2,4-oxadiazol-3-yl)phenyl)ethyl)pyrrolidine-3-carboxylic acid (6)

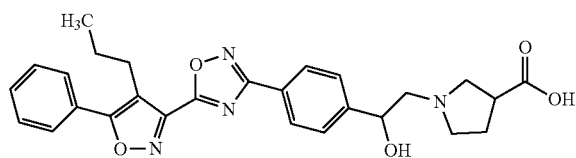

To a mixture of 2-bromo-1-(4-(5-(5-phenyl-4-propylisoxazol-3-yl)-1,2,4-oxadiazol-3-yl)phenyl)ethanol, Preparation 1C (30 mg, 0.066 mmol) and pyrrolidine-3-carboxylic acid (22.81 mg, 0.198 mmol) in DMSO (2 mL) was added DBU (0.030 mL, 0.198 mmol). The reaction mixture was heated at 80° C. for 2 hours. The crude material was purified via preparative LC/MS with the following conditions: Column: Waters XBridge C18, 19×100 mm, 5-μm particles; Guard Column: none; Mobile Phase A: 5:95 acetonitrile:water with 0.05% TFA; Mobile Phase B: 95:5, acetonitrile:water with 0.05% TFA; Gradient: 25-100% B over 10 minutes, then a 5-minute hold at 100% B; Flow: 20 mL/min. Fractions containing the product were combined and dried via centrifugal evaporation. The yield of 1-(2-hydroxy-2-(4-(5-(5-phenyl-4-propylisoxazol-3-yl)-1,2,4-oxadiazol-3-yl)phenyl)ethyl)pyrrolidine-3-carboxylic acid was 16.3 mg, and its purity was 96%. $^1$H NMR (400 MHz, MeOH-d₃) δ ppm 8.21 (2H, d, J=8.35 Hz), 7.81 (2H, dd, J=8.02, 1.65 Hz), 7.69 (2H, d, J=8.35 Hz), 7.54-7.66 (3H, m), 5.10-5.22 (1H, m), 3.39-3.54 (4H, m), 3.24-3.27 (3H, m), 3.00-3.10 (2H, m), 2.23-2.57 (2H, m), 1.70-1.83 (2H, m), 1.05 (3H, t, J=7.36 Hz). MS (m+1)=489. HPLC Peak RT=2.08 minutes. (Analytical Method C). Purity=96%.

Example 7

(2R)-1-(2-Hydroxy-2-(4-(5-(5-phenyl-4-propylisoxazol-3-yl)-1,2,4-oxadiazol-3-yl)phenyl)ethyl)azetidine-2-carboxylic acid (7)

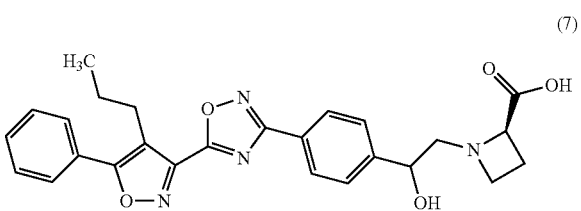 [SMILES: CCCc1c(-c2nc(-c3ccc(C(O)CN4CC[C@@H]4C(=O)O)cc3)no2)noc1-c1ccccc1]

To a mixture of 2-bromo-1-(4-(5-(5-phenyl-4-propylisoxazol-3-yl)-1,2,4-oxadiazol-3-yl)phenyl)ethanol, Preparation 1C (30 mg, 0.066 mmol) and D-Azetidine-2-carboxylic acid (20.03 mg, 0.198 mmol) in DMSO (2 mL) was added DBU (0.030 mL, 0.198 mmol). The reaction mixture was heated at 80° C. for 2 hours. The reaction mixture was filtered and purified by HPLC. HPLC conditions: PHENOMENEX® Luna C18 5 micron column (250×30mm); 25-100% CH₃CN/water (0.1% TFA); 25 minute gradient; 30 mL/min. Isolated fractions with correct mass were freeze-dried overnight to yield 16 mg of (2R)-1-(2-hydroxy-2-(4-(5-(5-phenyl-4-propylisoxazol-3-yl)-1,2,4-oxadiazol-3-yl)phenyl)ethyl) azetidine-2-carboxylic acid as a TFA salt. $^1$H NMR (400 MHz, DMSO-d₆) δ ppm 8.14 (2H, dd, J=8.57, 2.86 Hz), 7.82 (2H, dd, J=8.02, 1.65 Hz), 7.58-7.70 (5H, m), 5.16-5.29 (1H, m), 4.89-5.10 (1H, m), 3.84-4.05 (2H, m), 3.18-3.41 (2H, m), 2.96-3.03 (2H, m), 2.51-2.61 (1H, m), 1.63-1.76 (2H, m), 0.97 (3H, t, K=7.25 Hz). MS (m+1)=475. HPLC Peak RT=3.5 minutes (Analytical Method A). Purity=90%.

Examples 8 and 9

2-(1-(2-Hydroxy-2-(4-(5-(5-phenyl-4-propylisoxazol-3-yl)-1,2,4-oxadiazol-3-yl)phenyl)ethyl)piperidin-2-yl)acetic acid (8)

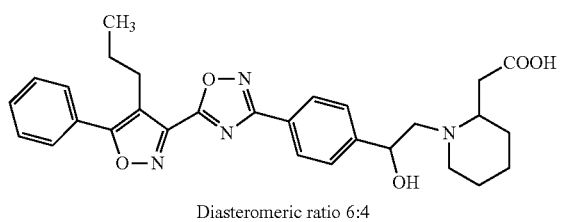

Diasteromeric ratio 6:4

83
-continued

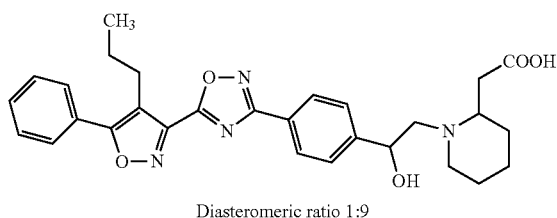

(9)

Diasteromeric ratio 1:9

To a mixture of 2-bromo-1-(4-(5-(5-phenyl-4-propylisoxazol-3-yl)-1,2,4-oxadiazol-3-yl)phenyl)ethanol, Preparation 1C (30 mg, 0.066 mmol) and 2-(piperidin-2-yl)acetic acid, $H_2O$ (31.9 mg, 0.198 mmol) in DMSO (2 mL) was added DBU (0.030 mL, 0.198 mmol). The reaction mixture was heated at 80° C. for 2 hours. The reaction mixture was filtered and purified by HPLC. HPLC conditions: PHENOMENEX® Luna C18 5 micron column (250×30mm); 30-100% $CH_3CN$/water (0.1% TFA); 25 minute gradient; 30 mL/min. Isolated two fractions with correct mass were freeze-dried overnight. The two fractions isolated had differing ratios of the diastereomeric mixture of 2-(1-(2-hydroxy-2-(4-(5-(5-phenyl-4-propylisoxazol-3-yl)-1,2,4-oxadiazol-3-yl)phenyl)ethyl)piperidin-2-yl)acetic acid.

Example 8: $^1$H NMR (400 MHz, MeOH-$d_3$) δ ppm 8.14-8.25 (2H, m), 7.80 (3H, dd, J=8.02, 1.65 Hz), 7.66-7.74 (1H, m), 7.53-7.66 (4H, m), 5.04 (1H, t, J=5.82 Hz), 5.00-5.35 (1H, m), 4.35 (2H, d, J=5.49 Hz), 3.80-4.02 (1H, m), 3.70 (1H, br. s.), 3.33-3.54 (4H, m), 2.99-3.10 (2H, m), 2.68-2.96 (1H, m), 1.82-2.09 (2H, m), 1.70-1.81 (2H, m, J=15.27, 7.58, 7.47, 7.47 Hz), 1.40-1.70 (1H, m), 1.04 (2H, t, J=7.36 Hz). MS (m+1)=517. HPLC Peak RT=3.38 and 3.53 minutes are product (Analytical Method A). Purity=95%. LCMS shows a 6 to 4 ratio of diastereomers (with respect to above LC retention times).

Example 9: $^1$H NMR (400 MHz, MeOH-$d_3$) δ ppm 8.18 (2H, d, J=8.13 Hz), 7.81 (2H, dd, J=8.13, 1.54 Hz), 7.52-7.68 (5H, m), 5.01-5.08 (1H, m), 4.35 (2H, d, J=5.49 Hz), 3.34-3.64 (3H, m), 2.97-3.14 (2H, m), 2.68-2.76 (1H, m), 1.83-2.09 (3H, m), 1.77 (2H, dq, J=15.27, 7.65 Hz), 1.37-1.71 (3H, m), 1.05 (3H, t, J=7.25 Hz). MS (m+1)=517. HPLC Peak RT=3.38 and 3.53 minutes are product (Analytical Method A). Purity=95%. LCMS shows a 1 to 9 ratio of diastereomers (with respect to above LC retention times).

Example 10

2-((2S)-1-(2-Hydroxy-2-(4-(5-(5-phenyl-4-propyl-isoxazol-3-yl)-1,2,4-oxadiazol-3-yl)phenyl)ethyl)pyrrolidin-2-yl)acetic acid (10)

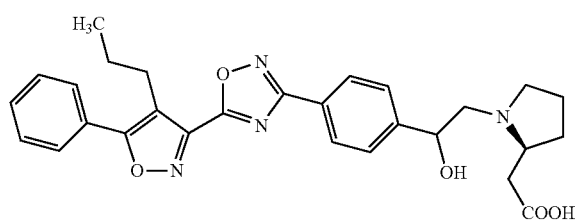

84

To a solution of (S)-2-(1-(tert-butoxycarbonyl)pyrrolidin-2-yl)acetic acid (45.4 mg, 0.198 mmol) in DCM was added TFA. The reaction mixture was stirred for 1 hour followed by the removal of solvents in vacuo and drying of the solid material. Next, DMSO (2 mL) was added followed by the addition of tetrabutylammonium hydroxide (0.198 mL, 0.198 mmol) and then 2-bromo-1-(4-(5-(5-phenyl-4-propylisoxazol-3-yl)-1,2,4-oxadiazol-3-yl)phenyl)ethanol, Preparation 1C (30 mg, 0.066 mmol). The reaction mixture was heated at 80° C. for 2 hours. The reaction mixture was filtered and purified by HPLC. HPLC conditions: PHENOMENEX® Luna C18 5 micron column (250×30mm); 30-100% $CH_3CN$/water (0.1% TFA); 25 minute gradient; 30 mL/min. Isolated fractions with correct mass were freeze-dried overnight to yield 9 mg of 2-((2S)-1-(2-hydroxy-2-(4-(5-(5-phenyl-4-propylisoxazol-3-yl)-1,2,4-oxadiazol-3-yl)phenyl)ethyl)pyrrolidin-2-yl)acetic acid as a TFA salt. $^1$H NMR (400 MHz, MeOH-$d_3$) δ ppm 8.18 (4H, d, J=8.35 Hz), 7.77-7.84 (2H, m), 7.54-7.67 (5H, m), 5.92-6.01 (1H, m), 5.00-5.09 (2H, m), 4.26-4.42 (1H, m), 3.76-3.94 (1H, m), 3.00-3.11 (2H, m), 2.75-2.98 (2H, m), 2.18-2.34 (1H, m), 1.90-2.14 (2H, m), 1.60-1.85 (3H, t, J=7.25 Hz). MS (m+1)=503. HPLC Peak RT=3.50 minutes (Analytical Method A). Purity=90%.

Example 11

4-(2-Hydroxy-2-(4-(5-(5-phenyl-4-propylisoxazol-3-yl)-1,2,4-oxadiazol-3-yl)phenyl)ethyl)morpholine-2-carboxylic acid (11)

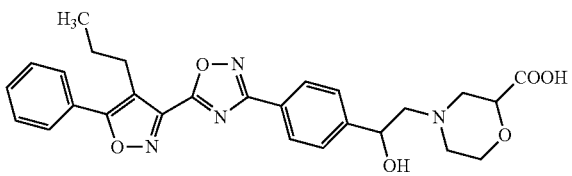

To a mixture of 2-bromo-1-(4-(5-(5-phenyl-4-propylisoxazol-3-yl)-1,2,4-oxadiazol-3-yl)phenyl)ethanol, Preparation 1C (30 mg, 0.066 mmol) in DMSO (2 mL) was added tetrabutylammonium hydroxide (0.264 mL, 0.264 mmol). After 5 minutes, 2-bromo-1-(4-(5-(5-phenyl-4-propylisoxazol-3-yl)-1,2,4-oxadiazol-3-yl)phenyl)ethanol (30 mg, 0.066 mmol) was added. The reaction mixture was heated at 80° C. for 2 hours. The reaction mixture was filtered and purified by HPLC. HPLC conditions: PHENOMENEX® Luna C18 5 micron column (250×30mm); 25-100% $CH_3CN$/water (0.1% TFA); 25 minute gradient; 20 mL/min. Isolated fractions with correct mass were freeze-dried overnight to yield 9 mg of 4-(2-hydroxy-2-(4-(5-(5-phenyl-4-propylisoxazol-3-yl)-1,2,4-oxadiazol-3-yl)phenyl)ethyl)morpholine-2-carboxylic acid as a TFA salt. $^1$H NMR (400 MHz, DMSO-$d_6$) δ ppm 8.16 (2H, d, J=6.15 Hz), 7.83 (1H, dd, J=7.91, 1.54 Hz), 7.59-7.72 (5H, m), 3.60-4.67 (4H, m), 3.06-3.06 (1H, m), 2.96-3.04 (2H, m), 2.66 (1H, t, J=1.98 Hz), 2.57 (1H, d, J=2.20 Hz), 2.44-2.47 (4H, m), 2.32 (1H, d, J=1.76 Hz), 1.63-1.78 (2H, m), 0.98 (3H, t, J=7.36 Hz). MS (m+1)=504. HPLC Peak RT=3.35 minutes (Analytical Method A). Purity=85%.

Example 12

2-((3 S)-1-(2-Hydroxy-2-(4-(5-(5-phenyl-4-propyl-isoxazol-3-yl)-1,2,4-oxadiazol-3-yl)phenyl)ethyl)piperidin-3-yl)acetic acid (12)

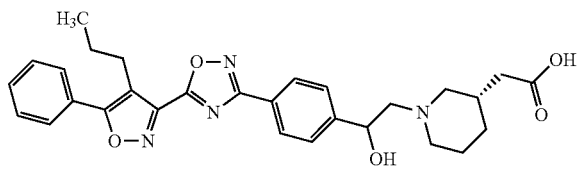

To (S)-tert-butyl 2-(piperidin-3-yl)acetate, HCl (31.1 mg, 0.132 mmol) was added 4M HCl/dioxane (3 mL) and the reaction mixture was stirred for 30 minutes. Next, the reaction mixture was concentrated in vacuo and dried. This crude material was dissolved in DMSO (2 mL) and tetrabutylammonium hydroxide (0.198 mL, 0.198 mmol) was added. The reaction mixture was stirred for 30 minutes, followed by the addition of 2-bromo-1-(4-(5-(5-phenyl-4-propylisoxazol-3-yl)-1,2,4-oxadiazol-3-yl)phenyl)ethanol, Preparation 1C (30 mg, 0.066 mmol). The reaction mixture was heated at 80° C. for 2 hours, and then filtered and purified by HPLC. HPLC conditions: PHENOMENEX® Luna C18 5 micron column (250×30mm); 25-100% CH$_3$CN/water (0.1% TFA); 25 minute gradient; 20 mL/min. Isolated fractions with correct mass were freeze-dried overnight to yield 5 mg of ((3S)-1-(2-hydroxy-2-(4-(5-(5-phenyl-4-propylisoxazol-3-yl)-1,2,4-oxadiazol-3-yl)phenyl)ethyl)piperidin-3-yl)acetic acid as a TFA salt. $^1$H NMR (400 MHz, MeOH-d$_3$) δ ppm 8.12 (2H, m, J=8.35 Hz), 7.69-7.75 (2H, m), 7.60 (2H, m, J=8.13 Hz), 7.43-7.55 (3H, m), 5.16 (1H, dd, J=9.34, 4.50 Hz), 3.71-3.89 (1H, m), 3.52-3.68 (3H, m), 3.23-3.28 (1H, m), 2.96 (2H, dd, J=8.90, 6.92 Hz), 2.84-2.92 (1H, m), 2.17-2.38 (3H, m), 1.76-1.93 (3H, m), 1.62-1.73 (2H, m), 1.21 (1H, dd, J=12.30, 4.17 Hz), 0.95 (3H, t, J=7.25 Hz). MS (m+1)=517. HPLC Peak RT=3.37 minutes. (Analytical Method A). Purity=94%.

Example 13

2-((3R)-1-(2-Hydroxy-2-(4-(5-(5-phenyl-4-propyl-isoxazol-3-yl)-1,2,4-oxadiazol-3-yl)phenyl)ethyl)piperidin-3-yl)acetic acid (13)

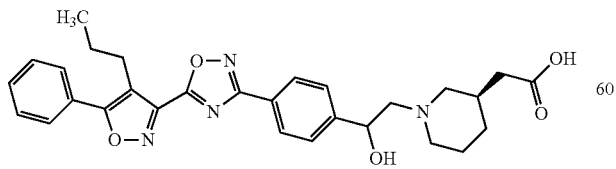

(R)-tert-Butyl 2-(piperidin-3-yl)acetate (66 mg, 0.331 mmol) was treated with 4N HCl/dioxane for 30 minutes. The reaction mixture was concentrated in vacuo and dried. The solid material was dissolved in DMSO (2 mL) and tetrabutylammonium hydroxide (0.352 mL, 0.352 mmol) was added. After stirring 15 minutes, 2-bromo-1-(4-(5-(5-phenyl-4-propylisoxazol-3-yl)-1,2,4-oxadiazol-3-yl)phenyl)ethanol, Preparation 1C (40 mg, 0.088 mmol) was added. The reaction mixture was heated at 80° C. for 2 hours, and then filtered and purified by HPLC. HPLC conditions: PHENOMENEX® Luna C18 5 micron column (250×30mm); 25-100% CH$_3$CN/water (0.1% TFA); 25 minute gradient; 20 mL/min. Isolated fractions with correct mass were freeze-dried overnight to yield 9 mg of 2-((3R)-1-(2-hydroxy-2-(4-(5-(5-phenyl-4-propylisoxazol-3-yl)-1,2,4-oxadiazol-3-yl)phenyl)ethyl)piperidin-3-yl)acetic acid as a TFA salt. $^1$H NMR (400 MHz, MeOH-d$_3$) δ ppm 8.11 (2H, m), 7.68-7.75 (2H, m), 7.59 (2H, m, J=8.35 Hz), 7.43-7.55 (3H, m), 5.16 (1H, dd, J=9.01, 4.61 Hz), 3.71-3.89 (1H, m), 3.50-3.67 (2H, m), 3.24 (1H, d, J=2.42 Hz), 2.96 (2H, dd, J=8.90, 6.92 Hz), 2.83-2.93 (1H, m), 2.72 (1H, td, J=11.86, 5.27 Hz), 2.16-2.39 (3H, m), 1.77-2.00 (3H, m), 1.59-1.75 (2H, m, J=7.61, 7.61, 7.61, 7.61, 7.36 Hz), 1.13-1.32 (1H, m), 0.95 (3H, t, J=7.25 Hz). MS (m+1)=517. HPLC Peak RT=3.32 minutes (Analytical Method A). Purity=95%.

Example 14

(S)-1-((S)-2-Hydroxy-2-(4-(5-(3-phenyl-4-(trifluoromethyl)isoxazol-5-yl)-1,2,4-oxadiazol-3-yl)phenyl)ethyl)piperidine-3-carboxylic acid (14)

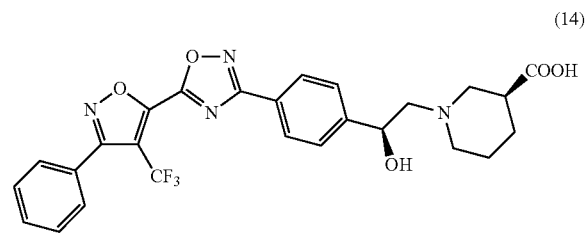

Preparation 14A: (3S)-Ethyl 1-(2-(4-cyanophenyl)-2-hydroxyethyl)piperidine-3-carboxylate (14A)-isomer A

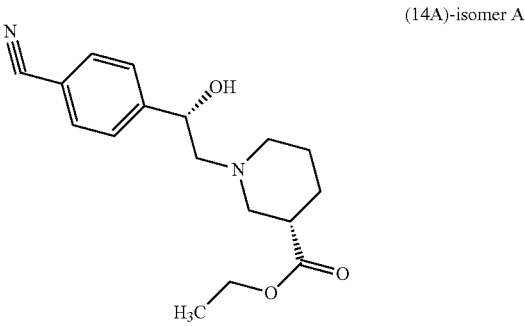

(14A)-isomer B

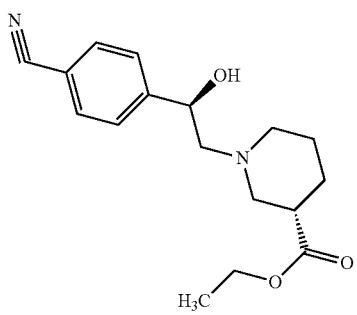

To a mixture of (S)-ethyl piperidine-3-carboxylate (1.3 g, 8.27 mmol) in toluene (50 mL) was added 4-(2-bromoacetyl)benzonitrile (2.4 g, 10.71 mmol). The reaction mixture was stirred overnight. LCMS indicated completion of reaction. MeOH (10 mL) was added to the mixture, followed by the portionwise addition of sodium borohydride (0.313 g, 8.27 mmol). After 1 hour, LCMS show complete reduction to the desired alcohol. The reaction was quenched with water. The reaction mixture was diluted with ethyl acetate and washed with saturated NaCl. The organic layer was dried with $MgSO_4$, filtered, concentrated, and purified on a silica gel cartridge using an EtOAc/hexanes gradient to yield 2.0 g of solid product. The product was separated by chiral HPLC (Berger SFC MGIII instrument equipped with a CHIRALCEL® OJ (25×3 cm, 5 μM). Temp: 30° C.; Flow rate: 130 mL/min; Mobile phase: $CO_2$/(MeOH+0.1% DEA) in 9:1 ratio isocratic:

Peak 1 (Isomer A): RT=2.9 min. for (S)-ethyl 1-((S)-2-(4-cyanophenyl)-2-hydroxyethyl)piperidine-3-carboxylate (>99% d.e.). The absolute and relative stereochemistry of compound 14A-isomer A was assigned (S,S) by X-ray crystal structure (see Alternative Route data). $^1$H NMR (400 MHz, $CDCl_3$) δ ppm 7.63 (2H, m, J=8.35 Hz), 7.49 (2H, m, J=8.35 Hz), 4.77 (1H, dd, J=10.55, 3.52 Hz), 4.17 (2H, q, J=7.03 Hz), 3.13 (1H, d, J=9.23 Hz), 2.53-2.67 (3H, m), 2.44 (2H, dd, J=18.68, 9.89 Hz), 2.35 (1H, dd, J=12.74, 10.55 Hz), 1.87-2.01 (1H, m), 1.71-1.82 (1H, m), 1.52-1.70 (2H, m), 1.28 (3H, t, J=7.03 Hz).

Peak 2 (Isomer B): RT=3.8 min for (S)-ethyl 1-((R)-2-(4-cyanophenyl)-2-hydroxyethyl)piperidine-3-carboxylate (>99% d.e.). The absolute and relative stereochemistry of 14A-isomer B was assigned (S,R) based on the crystal structure of 14A-isomer A. $^1$H NMR (400 MHz, $CDCl_3$) δ ppm 7.63 (2H, m, J=8.35 Hz), 7.49 (2H, m, J=8.35 Hz), 4.79 (1H, dd, J=10.55, 3.52 Hz), 4.16 (2H, q, J=7.03 Hz), 2.69-2.91 (3H, m), 2.60-2.68 (1H, m), 2.56 (1H, dd, J=12.30, 3.52 Hz), 2.36 (1H, dd, J=12.52, 10.77 Hz), 2.25 (1H, t, J=8.79 Hz), 1.65-1.90 (3H, m), 1.52-1.64 (1H, m, J=12.69, 8.49, 8.49, 4.17 Hz), 1.27 (3H, t, J=7.25 Hz).

(S)-Ethyl 1-((S)-2-(4-cyanophenyl)-2-hydroxyethyl)piperidine-3-carboxylate (14A-isomer A) was carried forward to make Example 14 and (S)-ethyl 1-((R)-2-(4-cyanophenyl)-2-hydroxyethyl)piperidine-3-carboxylate (14A-isomer B) was carried forward to make Example 15.

Preparation 14B: (S)-Ethyl 1-((S)-2-hydroxy-2-(4-((Z)-N'-hydroxycarbamimidoyl)phenyl)ethyl)piperidine-3-carboxylate

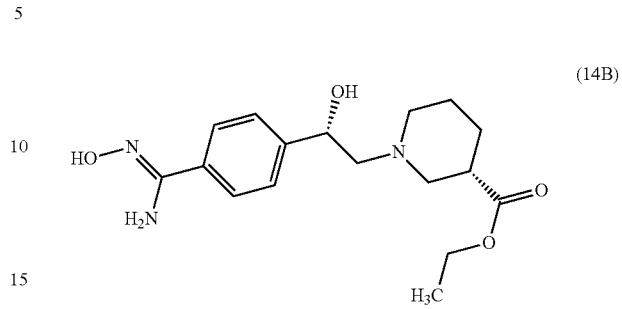

To a mixture of ((S)-ethyl 1-((S)-2-hydroxy-2-(4-((Z)-N'-hydroxycarbamimidoyl)phenyl)ethyl)piperidine-3-carboxylate (14A-Isomer A) (58 mg, 0.192 mmol) and hydroxylamine hydrochloride (26.7 mg, 0.384 mmol) in 2-propanol (10 mL) was added sodium bicarbonate (64.5 mg, 0.767 mmol). The reaction mixture was heated at 85° C. The reaction mixture was diluted with ethyl acetate and washed with sat NaCl. The organic layer was dried with $MgSO_4$, filtered, and concentrated to yield 56 mg. MS (M+1)=464. HPLC Peak RT=1.50 minutes.

Preparation 14C: (S)-Ethyl 1-((S)-2-hydroxy-2-(4-(5-(3-phenyl-4-(trifluoromethyl)isoxazol-5-yl)-1,2,4-oxadiazol-3-yl)phenyl)ethyl)piperidine-3-carboxylate

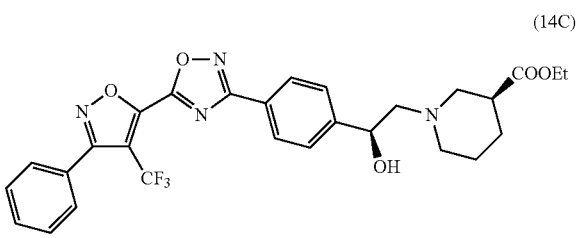

3-Phenyl-4-(trifluoromethyl)isoxazole-5-carbonyl fluoride, Int-I-G (214 mg, 0.78 mmol) was dissolved in acetonitrile (5.00 mL). DIEA (0.272 mL, 1.555 mmol) and (S)-ethyl-1-((S)-2-hydroxy-2-(4-((Z)-N'-hydroxycarbamimidoyl)phenyl)ethyl)-piperidine-3-carboxylate (261 mg, 0.778 mmol) were added. The reaction mixture was stirred for 2 hours, then 1M TBAF in THF (0.778 mL, 0.778 mmol) was added. The reaction mixture was stirred overnight at room temperature. The reaction mixture was filtered and purified by HPLC in three batches. HPLC conditions: PHENOMENEX® Luna C18 5 micron column (250×30mm); 25-100% $CH_3CN$/water (0.1% TFA); 25 minute gradient; 30 mL/min. Isolated fractions with correct mass were partitioned between EtOAc and saturated $NaHCO_3$ with back extracting aqueous layer once. The organic layer was dried with $MgSO_4$, filtered, and concentrated to give 155mg of (S)-ethyl 1-((S)-2-hydroxy-2-(4-(5-(3-phenyl-4-(trifluoromethyl)isoxazol-5-yl)-1,2,4-oxadiazol-3-yl)phenyl)ethyl)piperidine-3-carboxylate. $^1$H NMR (400 MHz, MeOH-$d_3$) δ ppm 8.04 (2H, d, J=8.13

Hz), 7.55-7.60 (2H, m), 7.41-7.54 (5H, m), 4.81 (1H, ddd, J=8.35, 4.06, 3.84 Hz), 3.96-4.10 (2H, m), 2.82-3.08 (1H, m), 2.67-2.82 (1H, m, 2.36-2.61 (3H, m), 2.08-2.33 (2H, m), 1.73-1.87 (1H, m, J=8.54, 8.54, 4.45, 4.17 Hz), 1.32-1.70 (3H, m), 1.09-1.19 (3H, m). MS (m+1)=557. HPLC Peak RT=3.36 minutes. Purity=99%.

Example 14

(S)-Ethyl 1-((S)-2-hydroxy-2-(4-(5-(3-phenyl-4-(trifluoromethyl)isoxazol-5-yl)-1,2,4-oxadiazol-3-yl)phenyl)ethyl)piperidine-3-carboxylate (89 mg, 0.16 mmol) was heated at 50° C. in 6N HCl (5 mL) in acetonitrile (5 mL). The reaction mixture was stirred overnight and then filtered and purified by HPLC. HPLC conditions: PHENOMENEX® Luna C18 5 micron column (250×30mm); 25-100% CH$_3$CN/water (0.1% TFA); 25 minute gradient; 30 mL/min. Isolated fractions with correct mass were freeze-dried overnight to yield 36 mg of (S)-1-((S)-2-hydroxy-2-(4-(5-(3-phenyl-4-(trifluoromethyl)isoxazol-5-yl)-1,2,4-oxadiazol-3-yl)phenyl)ethyl) piperidine-3-carboxylic acid as a TFA salt. $^1$H NMR (400 MHz, MeOH-d$_3$) δ ppm 8.23 (2H, d, J=8.35 Hz), 7.65-7.74 (4H, m), 7.54-7.65 (3H, m), 5.29 (1H, t, J=7.03 Hz), 4.00 (1H, br. s.), 3.43-3.75 (1H, m), 3.34-3.41 (2H, m), 2.82-3.24 (2H, m), 2.26 (1H, d, J=11.86 Hz), 1.84-2.14 (2H, m), 1.52-1.75 (1H, m). MS (m+1)=529. HPLC Peak RT=3.24 minutes. Purity=98%.

Example 14-Alternate Synthesis Route 1

Preparation 14D (Alternate Synthesis Route 1): (S)-4-(Oxiran-2-yl)benzonitrile

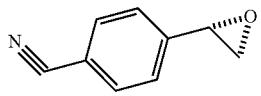

(14D)

To 800 mL of 0.2M, pH 6.0 sodium phosphate buffer in a 2 L flask equipped with an overhead stirrer was added D-glucose (38.6 g, 1.2 eq), β-nicotinamide adenine dinucleotide, free acid (1.6 g, mmol), glucose dehydrogenase (36 mg, 3.2 kU, CODEXIS® GDH-102, 90 U/mg), and enzyme KRED-NADH-110 (200 mg, CODEXIS®, 25 U/mg). The vessels containing the reagents above were rinsed with 200 mL of fresh sodium phosphate buffer and added to the reaction which was stirred to dissolution and then heated to 40° C. To this mixture was added a solution of 2-bromo-4'-cyanoacetophenone (40 g, 178.5 mmol) in 100 mL DMSO through an addition funnel in about 30 min. The container was rinsed with 20 mL DMSO and the rinse was added to the reactor. A pH of 5.5-6.0 was maintained by adding 1 M NaOH through a fresh addition funnel (total volume of 200 mL over 6 h) after which HPLC showed complete consumption of the starting material. The reaction mixture was extracted with 800 mL MTBE×2 and the combined extracts were washed with 300 mL of 25% brine. The crude alcohol was transferred to a 3 L 3-neck flask and treated with solid NaOtBu (34.3 g, 357 mmol) stirring for 1 h and then additional NaOtBu (6.9 g, 357 mmol) and stirring for 30 min. The reaction mixture was filtered and the solution was washed with 300 mL 0.2 M pH 6.0 sodium phosphate buffer, brine, and then the solvent was removed in vacuo and the resulting white solid was dried in a vacuum oven to give (S)-4-(oxiran-2-yl)benzonitrile (23 g, 90% yield, 100% e.e.). $^1$H NMR (400 MHz, CDCl$_3$) δ ppm 7.62 (2H, d), 7.35 (2H, d), 3.88 (1H, dd), 3.18 (1H, app t), 2.73 (1H, dd) Purity=99%.

Chiral HPLC was done on a CHIRALPAK® AD-RH 4.6× 150 mm (Daicel Chemical Industries Ltd.) column using gradient of solvent A (10 mM NH$_4$OAc in water/acetonitrile, 90:10) and solvent B (10 mM NH$_4$OAc in water/acetonitrile, 10:90) with 70% to 90% in 40 min at a flow rate of 0.5 ml/min at ambient temperature. The detection employed UV at 235 nm. The retention times are as follows:

Peak 1 (Isomer A): RT=16.7 min. for (S)-4-(oxiran-2-yl)benzonitrile

Peak 2 (Isomer B): RT=14.0 min. for (R)-4-(oxiran-2-yl)benzonitrile

Preparation of 14A-isomer A (Alternate Synthesis Route 1): (S)-Ethyl 1-((S)-2-(4-cyanophenyl)-2-hydroxyethyl)piperidine-3-carboxylate

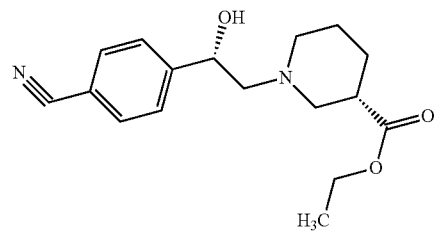

(14A)-isomer A (S)-4-(Oxiran-2-yl)benzonitrile (10.00 g, 68.9 mmol), (S)-ethyl piperidine-3-carboxylate (10.83 g, 68.9 mmol) and iPrOH (100 mL) was charged into a round bottom flask under N$_2$. After heating at 55° C. for 4 hours, 4-dimethylaminopyridine (1.683 g, 13.78 mmol) was then added. The reaction mixture was then heated to 50° C. for an additional 12 hours. At this time HPLC indicated the starting material was completely converted to the desired product. The reaction mixture was then cooled to room temperature. EtOAc (120 ml) was added, followed by 100 ml of water. The organic layer was separated, extracted with EtOAc (2×100 mL) and concentrated under vacuo to give a crude product. The crude product was recrystallized from EtOH/EtOAc/H$_2$O (3/2/2) (8 ml/1 g) to give a crystalline off-white solid 14A-alt (15 g, 72% yield, 99.6% e.e.). The absolute and relative stereochemistry was determined by single X-ray crystallography employing a wavelength of 1.54184 Å. The crystalline material had an orthorhombic crystal system and unit cell parameters approximately equal to the following:

| | |
|---|---|
| a = 5.57 Å | α = 90.0° |
| b = 9.71 Å | β = 90.0° |
| c = 30.04 Å | γ = 90.0° |
| Space group: P2$_1$2$_1$2$_1$ | |
| Molecules/asymmetric unit: 2 | |
| Volume/Number of molecules in the unit cell = 1625 Å$^3$ | |
| Density (calculated) = 1.236 g/cm$^3$ | |
| Temperature 298 K. | |

Preparation 14E (Alternate Route 1): (S)-Ethyl 1-((S)-2-(tert-butyldimethylsilyloxy)-2-(4-cyanophenyl)ethyl)piperidine-3-carboxylate

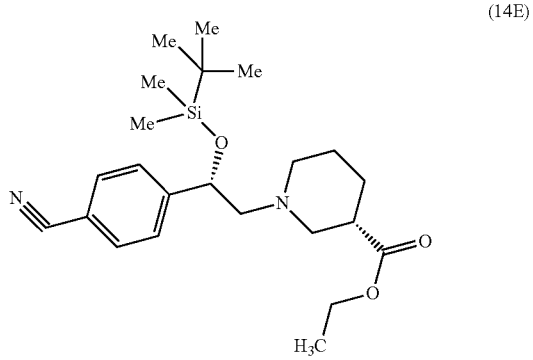 [SMILES: CCOC(=O)[C@H]1CCCN(C[C@@H](O[Si](C)(C)C(C)(C)C)c2ccc(C#N)cc2)C1]

(14E)

To a mixture of (S)-ethyl 1-((S)-2-(4-cyanophenyl)-2-hydroxyethyl)piperidine-3-carboxylate (17.0 g, 56.2 mmol) and DIPEA (17.68 ml, 101 mmol) in $CH_2Cl_2$ (187 mL) was added tert-butyldimethylsilyl trifluoromethanesulfonate (16 ml, 69.6 mmol) slowly. The reaction was monitored with HPLC. The reaction completed in 2 hours. The reaction mixture (a light brown solution) was quenched with water, the aqueous layer was extracted with DCM. The organic phase was combined and dried with $Na_2SO_4$. After concentration, the crude material was further purified on a silica gel cartridge (330 g silica, 10-30% EtOAc/hexanes gradient) to afford a purified product (S)-ethyl 1-((S)-2-(tert-butyldimethylsilyloxy)-2-(4-cyanophenyl)ethyl)piperidine-3-carboxylate (22.25 g, 53.4 mmol, 95% yield). $^1$H NMR (400 MHz, $CDCl_3$) δ ppm 7.61 (2H, d), 7.45 (2H, d), 4.79 (1H, m), 4.15 (2H, m), 2.88 (1H, m), 2.75 (1H, m), 2.60 (1H, dd), 2.48 (1H, m), 2.40 (1H, dd), 2.33 (1H, tt), 2.12 (1H, tt), 1.90 (1H, m), 1.68 (1H, dt), 1.52 (1H, m), 1.48 (1H, m), 1.27 (3H, t), 0.89 (9H, s), 0.08 (3H, s), −0.07 (3H, s).

Preparation 14F (Alternate Route 1): (S)-Ethyl 1-((S)-2-(tert-butyldimethylsilyloxy)-2-(4-((Z)-N'-hydroxycarbamimidoyl)phenyl)ethyl)piperidine-3-carboxylate

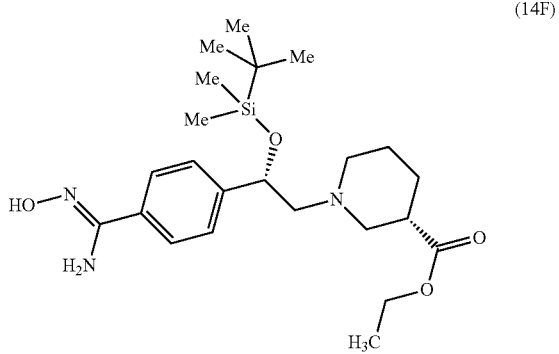 [SMILES: CCOC(=O)[C@H]1CCCN(C[C@@H](O[Si](C)(C)C(C)(C)C)c2ccc(/C(N)=N/O)cc2)C1]

(14F)

(S)-Ethyl-1-((S)-2-(tert-butyldimethylsilyloxy)-2-(4-cyanophenyl)ethyl)piperidine-3-carboxylate (31.0 g, 74.4 mmol) was dissolved in EtOH (248 mL). Hydroxylamine (50% aq) (6.84 ml, 112 mmol) was added and stirred at room temperature overnight. Then all volatiles were removed with ROTAVAPOR®. The residue was purified with on a silica gel cartridge (330 g silica, 0-50% EtOAc/hexanes gradient) to give (S)-ethyl 1-((S)-2-(tert-butyldimethylsilyloxy)-2-(4-((Z)-N'-hydroxycarbamimidoyl)phenyl)ethyl)piperidine-3-carboxylate (31 g, 68.9 mmol, 93% yield) as a white foam. $^1$H NMR (400 MHz, $CDCl_3$) δ ppm 8.38 (1H, br s), 7.58 (2H, d), 7.37 (2H, d), 4.88 (2H, br s), 4.81 (1H, m), 4.13 (2H, m), 2.96 (1H, m), 2.82 (1H, m), 2.61 (1H, dd), 2.51 (1H, m), 2.42 (1H, dd), 2.32 (1H, tt), 2.13 (1H, dt), 1.91 (1H, m), 1.66 (1H, dt), 1.58 (1H, m), 1.48 (1H, m), 1.27 (3H, t), 0.89 (9H, s), 0.08 (3H, s), −0.09 (3H, s).

Preparation 14G (Alternate Route 1): (S)-Ethyl 1-((S)-2-(tert-butyldimethylsilyloxy)-2-(4-(5-(3-phenyl-4-(trifluoromethyl)isoxazol-5-yl)-1,2,4-oxadiazol-3-yl)phenyl)ethyl)piperidine-3-carboxylate

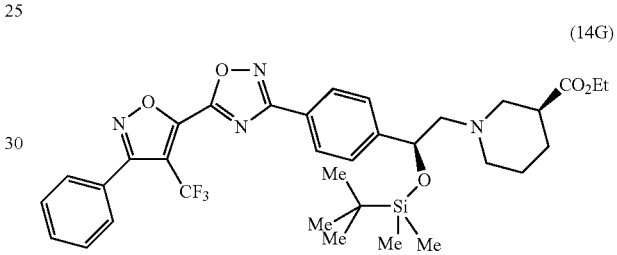

(14G)

(S)-Ethyl-1-((S)-2-(tert-butyldimethylsilyloxy)-2-(4-((Z)-N'-hydroxycarbamimidoyl)phenyl)ethyl)piperidine-3-carboxylate (32.6 g, 72 5 mmol) was dissolved in acetonitrile (145 ml) (anhydrous) and cooled to ~3° C. with ice-bath. 3-phenyl-4-(trifluoromethyl)isoxazole-5-carbonyl chloride (19.98 g, 72.5 mmol) was dissolved in 50 mL anhydrous acetonitrile and added dropwise. The internal temperature was kept below 10° C. during addition. After addition, the reaction mixture was allowed to warm to room temperature. At 30 minutes, HPLC showed completion of the first reaction step. The reaction mixture was re-cooled to below 10° C. DIEA (18.99 ml, 109 mmol) was added slowly. After the addition, the reaction mixture was heated up to 55° C. for 17 hrs. HPLC/LCMS showed completion of the reaction. The solvents were removed by ROTAVAPOR®. The residue was stirred in 250 mL 20% EtOAc/hexanes and the DIPEA HCl salt precipitated from solution and was removed via filtration. The filtrate was concentrated and purified using a silica gel cartridge (3×330 g silica, 0-50% EtOAc/hexanes gradient). (S)-ethyl 1-((S)-2-(tert-butyldimethylsilyloxy)-2-(4-(5-(3-phenyl-4-(trifluoromethyl)isoxazol-5-yl)-1,2,4-oxadiazol-3-yl)phenyl)ethyl)piperidine-3-carboxylate (43g, 64.1 mmol, 88% yield) was obtained a light yellow oil. $^1$H NMR (400 MHz, $CDCl_3$) δ ppm 8.16 (2H, d), 7.68 (2H, d), 7.57 (5H, m), 4.85 (1H, m), 4.14 (2H, m), 2.95 (1H, m), 2.82 (1H, m), 2.64 (1H, dd), 2.51 (1H, m), 2.49 (1H, dd), 2.35 (1H, tt), 2.14 (1H, dt), 1.91 (1H, m), 1.66 (1H, dt), 1.57 (1H, m), 1.48 (1H, m), 1.27 (3H, t), 0.92 (9H, s), 0.11 (3H, s), −0.05 (3H, s).

Example 14

(Alternate Route 1): (S)-1-((S)-2-Hydroxy-2-(4-(5-(3-phenyl-4-(trifluoromethyl)isoxazol-5-yl)-1,2,4-oxadiazol-3-yl)phenyl)ethyl)piperidine-3-carboxylic acid

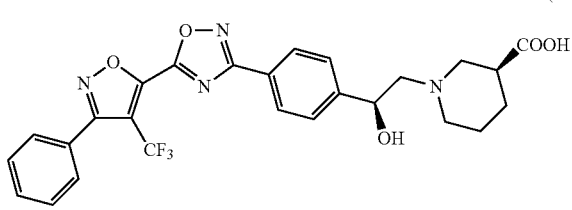

(14)

(S)-Ethyl 1-((S)-2-(tert-butyldimethylsilyloxy)-2-(4-(5-(3-phenyl-4-(trifluoromethyl)isoxazol-5-yl)-1,2,4-oxadiazol-3-yl)phenyl)ethyl)piperidine-3-carboxylate (42g, 62.6 mmol) was dissolved in dioxane (150 ml) and treated with 6M HCl (150 ml). The reaction mixture was heated to 65° C. for 6 hours (the reaction was monitored with HPLC, EtOH was distilled out to push the equilibrium forward). Dioxane was removed and the residue was redissolved in ACN/water and lyophilized separately to give crude (S)-1-((S)-2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid, HCl, (37 g crude foamy solid). The crude solid (36 g, 63.7 mmol) was suspended in acetonitrile (720 mL) and heated to 60° C. and water (14.4 mL) was added dropwise. A clear solution was obtained, which was cooled to room temperature and concentrated to a viscous oil, treated with ethyl acetate (1.44 L) with vigorously stirring, heated to 60° C., and cooled to room temperature. (S)-1-((S)-2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid, HCl (28 g, 49.3 mmol, 77% yield) was collected and vacuum dried. Characterization of product by $^1$H NMR and chiral HPLC matched Example 14 prepared in previous synthesis.

Preparation of Intermediate (14A)-isomer A-Alternate Route 2; 2-Steps: (S)-Ethyl 1-((S)-2-(4-cyanophenyl)-2-hydroxyethyl)piperidine-3-carboxylate

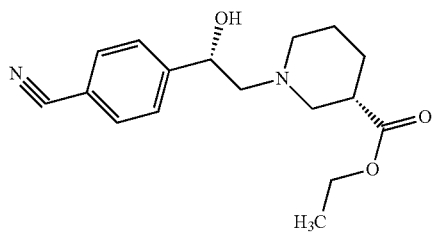

(14A)-isomer A

Step 1: Preparation (14D) (Alternate Route 2): (S)-Ethyl 1-(2-(4-cyanophenyl)-2-oxoethyl)piperidine-3-carboxylate hydrobromide

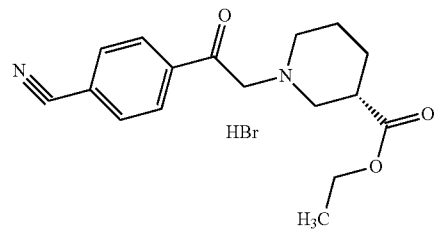

(14D)-isomer A

To a solution of commercially available (S)-ethyl piperidine-3-carboxylate (10 g, 63.6 mmol) in 200 mL toluene was added 4-(2-bromoacetyl)benzonitrile (17 g, 76 mmol). The reaction mixture was stirred overnight. The next day, the precipitated solid was collected by filtration and washed with ethyl acetate (×3) and dried under vacuum to give 15.2 g of (S)-ethyl 1-(2-(4-cyanophenyl)-2-oxoethyl)piperidine-3-carboxylate hydrobromide. MS (M+1)=301. HPLC Peak RT=1.51 minutes.

Step 2: Preparation of 14A-isomer A (Alternate Route 2): (S)-Ethyl 1-((S)-2-(4-cyanophenyl)-2-hydroxyethyl)piperidine-3-carboxylate Phosphate buffer (1100 mL, BF045, pH 7.0, 0.1M) was added into two liter jacketed glass reactor. The temperature of the reactor was adjusted to 20° C. with the help of a circulator and the reaction mixture was stirred with a magnetic stirrer. Dithiothretol (185.2 mg, 1 mM), magnesium sulfate (288.9 mg, 2 mM), and D-glucose (11.343 g, 62.95 m moles) were added into the reactor. (S)-Ethyl 1-(2-(4-cyanophenyl)-2-oxoethyl)piperidine-3-carboxylate HBr salt (12 g, 31.47 m moles dissolved in 60 mL DMSO) was added into the reactor slowly with continuous stirring. β-nicotinamide adenine dinucleotide phosphate sodium salt (NADP), 918.47 mg, glucose dehydrogenase, 240 mg (total 18360 U, 76.5 U/mg, ~15 U/mL, Amano Lot. GDHY1050601) and KRED-114, 1.2 g (CODEXIS® assay 7.8 U/mg of solid), were dissolved in 2.0 mL, 2.0 mL and 10 ml of the same buffer, respectively. Next, NADP, GDH and KRED-114 were added to the reactor in that order. The remaining 26 mL of same buffer was used to wash the NADP, GDH and KRED-114 containers and buffer was added into the same reactor. The starting pH of the reaction was 7.0 which decreased with the progress of the reaction and was maintained at pH 6.5 during the course of the reaction (used pH stat, maintained with 1M NaOH). The reaction was run for 4.5 hours and immediately stopped and extracted with ethyl acetate. The ethyl acetate solution was evaporated under reduced pressure and weight of the dark brown residue was 12.14 g. The product was precipitated with dichloromethane and heptane to give 9 g of crude product which was further purified by dissolving it in minimum amount of dichloromethane and re-precipitating by the addition of excess amount of heptane to give 5.22 g. The process was repeated to give an additional 2.82 g of highly pure product for a total of 8.02 g of de>99.5%.

Chiral HPLC was done on a CHIRALPAK® AD-RH 4.6× 150 mm (Daicel Chemical Industries Ltd.) column using gradient of solvent A (10 mM NH$_4$OAc in water/acetonitrile, 90:10) and solvent B (10 mM NH₄OAc in water/acetonitrile, 10:90) with 70% to 90% in 40 min at a flow rate of 0.5 ml/min at ambient temperature. The detection was done by UV at 235 nm. The retention times are as follows:

Peak 1 (14A-isomer A): RT=20.7 min. for (S)-ethyl 1-((S)-2-(4-cyanophenyl)-2-hydroxyethyl)piperidine-3-carboxylate.

Peak 2 (14B-isomer B): RT=30.4 min. for (S)-ethyl 1-((R)-2-(4-cyanophenyl)-2-hydroxyethyl)piperidine-3-carboxylate.

Compound 14A-isomer A prepared using this asymmetric method was unambiguously assigned since it was identical to the 14A-isomer A (by ¹H NMR and chiral HPLC retention time) that was prepared above and determined by X-ray crystallography. Synthesis of Example 14 from this material followed the same route as described above.

Example 15

(S)-1-((R)-2-Hydroxy-2-(4-(5-(3-phenyl-4-(trifluoromethyl)isoxazol-5-yl)-1,2,4-oxadiazol-3-yl)phenyl)ethyl)piperidine-3-carboxylic acid

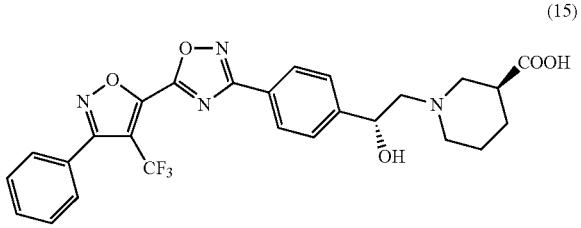 [SMILES: O=C(O)[C@H]1CCCN(C[C@H](O)c2ccc(-c3noc(-c4onc(-c5ccccc5)c4C(F)(F)F)n3)cc2)C1]

(15)

Example 15 was synthesized by the same route as used for Example 15 but using (S)-ethyl 1-((R)-2-(4-cyanophenyl)-2-hydroxyethyl)piperidine-3-carboxylate (15A-isomer B) to give (S)-1-((R)-2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid. ¹H NMR (400 MHz, MeOH-d₃) δ ppm 8.14 (2H, d, J=8.35 Hz), 7.57-7.66 (4H, m), 7.44-7.56 (3H, m), 5.17 (1H, dd, J=9.67, 4.39 Hz), 3.65-4.02 (2H, m), 3.25-3.46 (2H, m), 2.77-3.13 (3H, m), 1.98-2.29 (2H, m), 1.70-1.91 (2H, m), 1.42-1.64 (1H, m). MS (M+1)=529. HPLC Peak RT=3.27 minutes (Analytical Method A). Purity=99%.

Example 16

(3S)-1-(2-Hydroxy-2-(4-(5-(3-(pyridin-2-yl)-4-(trifluoromethyl)isoxazol-5-yl)-1,2,4-oxadiazol-3-yl)phenyl)ethyl)piperidine-3-carboxylic acid

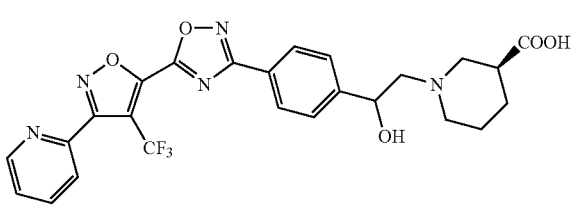

(16)

Preparation 16A: (3S)-Ethyl 1-(2-hydroxy-2-(4-(5-(3-(pyridin-2-yl)-4-(trifluoromethyl)isoxazol-5-yl)-1,2,4-oxadiazol-3-yl)phenyl)ethyl)piperidine-3-carboxylate To a mixture of 3-(pyridin-2-yl)-4-(trifluoromethyl)isoxazole-5-carboxylic acid, Int-IV (45 mg, 0.174 mmol), (3S)-ethyl 1-(2-hydroxy-2-(4-((E)-N'-hydroxycarbamimidoyl)phenyl)ethyl)piperidine-3-carboxylate (70 mg, 0.209 mmol), and BOP-Cl (53 mg, 0.208 mmol) in DMF (5 mL) was added TEA (0.073 mL, 0.523 mmol). The reaction mixture was stirred at room temperature for 2 hr then TBAF (0.174 mL, 0.174 mmol) was added. Next, the reaction mixture was stirred for 3 days. The reaction mixture was diluted with ethyl acetate and washed with saturated NaCl. The organic layer was dried with MgSO₄, filtered, and concentrated. The crude residue was purified by a silica gel cartridge using an EtOAc/hexanes gradient to yield 37 mg of (3S)-ethyl 1-(2-hydroxy-2-(4-(5-(3-(pyridin-2-yl)-4-(trifluoromethyl)isoxazol-5-yl)-1,2,4-oxadiazol-3-yl)phenyl)ethyl)piperidine-3-carboxylate.

Example 16

To a mixture of (3S)-ethyl 1-(2-hydroxy-2-(4-(5-(3-(pyridin-2-yl)-4-(trifluoromethyl)isoxazol-5-yl)-1,2,4-oxadiazol-3-yl)phenyl)ethyl)piperidine-3-carboxylate (37 mg, 0.066 mmol) in acetonitrile (1 ml) was added water (1 ml) and hydrochloric acid, 37% (1 ml). The reaction mixture was heated at 50° C. overnight, filtered, and purified by HPLC. HPLC conditions: PHENOMENEX® Luna C18 5 micron column (250×30 mm); 20-100% CH₃CN/water (0.1% TFA); 25 minute gradient; 30 mL/min. Isolated fractions with correct mass were freeze-dried overnight to yield 30 mg of (3S)-ethyl 1-(2-hydroxy-2-(4-(5-(3-(pyridin-2-yl)-4-(trifluoromethyl)isoxazol-5-yl)-1,2,4-oxadiazol-3-yl)phenyl)ethyl)piperidine-3-carboxylate as a TFA salt. ¹H NMR (400 MHz, MeOH-d₃) δ ppm 8.78 (1H, d, J=4.39 Hz), 8.23 (2H, d, J=8.35 Hz), 8.00-8.09 (1H, m), 7.95 (1H, d, J=7.91 Hz), 7.71 (2H, d, J=8.35 Hz), 7.57-7.65 (1H, m), 5.20-5.34 (1H, m), 3.80-4.08 (1H, m), 3.43-3.73 (1H, m), 3.34-3.43 (2H, m), 2.81-3.22 (3H, m), 1.83-2.37 (4H, m), 1.53-1.75 (1H, m). MS (m+1)=530. HPLC Peak RT=2.80 minutes (Analytical Method A). Purity=97%.

Example 17

(3S)-1-(2-Hydroxy-2-(4-(5-(3-phenyl-4-(trifluoromethyl)isoxazol-5-yl)-1,2,4-oxadiazol-3-yl)phenyl)propyl)piperidine-3-carboxylic acid

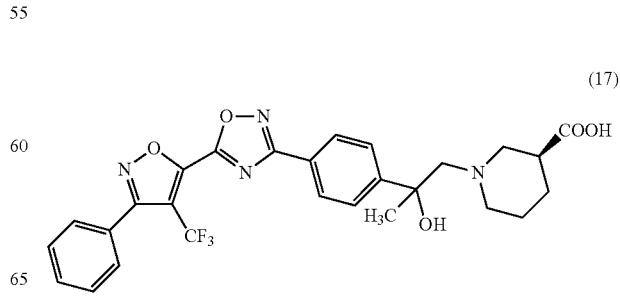

(17)

Preparation 17A: (S)-Ethyl 1-(2-(4-cyanophenyl)-2-oxoethyl)piperidine-3-carboxylate

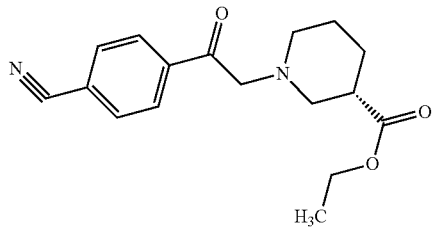

(17A)

To a mixture of (S)-ethyl piperidine-3-carboxylate (5 g, 31.8 mmol) in toluene (50 mL) was added 4-(2-bromoacetyl)benzonitrile (7.84 g, 35.0 mmol). The reaction mixture was stirred for 48 hours. The reaction mixture was concentrated in vacuo to yield 12 g of a yellow solid which was purified by triturating in EtOAc. The solid material was collected and washed with EtOAc then dried in vacuo to give 6 g of (S)-ethyl 1-(2-(4-cyanophenyl)-2-oxoethyl)piperidine-3-carboxylate, hydrobromide. MS (m+1)=301. HPLC Peak RT=1.57 minutes (Analytical Method B).

Preparation 17B: (3S)-Ethyl 1-(2-hydroxy-2-(4-((Z)-N'-hydroxycarbamimidoyl)phenyl)propyl)piperidine-3-carboxylate

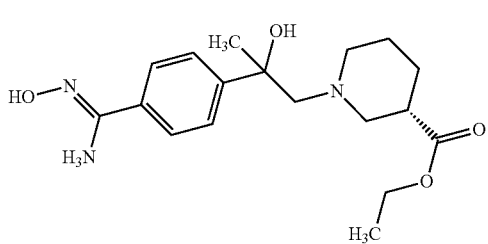

(17B)

To a mixture of (S)-ethyl 1-(2-(4-cyanophenyl)-2-oxoethyl)piperidine-3-carboxylate, hydrobromide (100 mg, 0.262 mmol) in THF (2 mL) was added methylmagnesium bromide (0.350 mL, 1.049 mmol). After 1 hour, the reaction was quenched with water. The reaction mixture was diluted with ethyl acetate and washed with saturated NaCl. The organic layer was dried with MgSO$_4$, filtered, and concentrated. The crude residue was dissolved in 2-propanol (10 mL). Sodium bicarbonate (88 mg, 1.049 mmol) and hydroxylamine hydrochloride (36.5 mg, 0.525 mmol) were added and the reaction was heated at 85° C. overnight. The reaction mixture was diluted with ethyl acetate and washed with saturated NaCl. The organic layer was dried with MgSO$_4$, filtered, and concentrated to yield 72 mg of (3S)-ethyl 1-(2-hydroxy-2-(4-((Z)-N'-hydroxycarbamimidoyl)phenyl)propyl)piperidine-3-carboxylate. MS (m+1)=350. HPLC Peak RT=0.11 minutes (Analytical Method B).

Example 17

(3S)-1-(2-Hydroxy-2-(4-(5-(3-phenyl-4-(trifluoromethyl)isoxazol-5-yl)-1,2,4-oxadiazol-3-yl)phenyl)propyl)piperidine-3-carboxylic acid To a mixture of (3S)-ethyl 1-(2-hydroxy-2-(4-((Z)-N'-hydroxycarbamimidoyl)phenyl)propyl)piperidine-3-carboxylate (72 mg, 0.206 mmol) and 3-phenyl-4-(trifluoromethyl)isoxazole-5-carbonyl fluoride (53.4 mg, 0.206 mmol) in acetonitrile (5 mL) was added DIEA (0.072 mL, 0.412 mmol). After 2 hr, TBAF in THF (0.206 mL, 0.206 mmol) was added and the reaction was stirred overnight at RT. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Isolated fractions with correct mass and concentrated in vacuo. The residue was treated with 6N HCl with MeCN as a co-solvent and heated at 50° C. for 4 days. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Isolated fractions with correct mass were freeze-dried overnight to yield 12 mg of (3S)-1-(2-hydroxy-2-(4-(5-(3-phenyl-4-(trifluoromethyl)isoxazol-5-yl)-1,2,4-oxadiazol-3-yl)phenyl)propyl)piperidine-3-carboxylic acid as a TFA salt. $^1$H NMR (400 MHz, MeOH-d$_3$) δ ppm 8.10-8.19 (2H, m), 7.68-7.80 (2H, m), 7.59 (2H, d, J=6.59 Hz), 7.44-7.56 (3H, m), 3.59-3.81 (2H, m), 3.31-3.53 (2H, m), 3.01-3.19 (1H, m), 2.73-3.00 (2H, m), 1.73-2.12 (2H, m), 1.60 (3H, d, J=15.82 Hz), 0.68-1.45 (3H, m). HPLC Peak RT=3.35 minutes (Analytical Method A). Purity=90%.

Example 18

2-((3R)-1-(2-Hydroxy-2-(4-(5-(3-phenyl-4-(trifluoromethyl)isoxazol-5-yl)-1,2,4-oxadiazol-3-yl)phenyl)ethyl)piperidin-3-yl)acetic acid

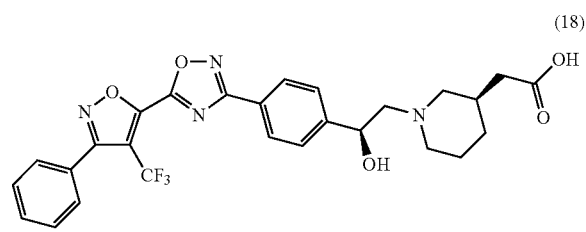 [SMILES: O=C(O)C[C@H]1CCCN(C[C@@H](O)c2ccc(-c3noc(-c4onc(-c5ccccc5)c4C(F)(F)F)n3)cc2)C1]

(18)

Preparation 18A: (R)-Ethyl 2-(piperidin-3-yl)acetate

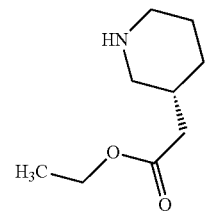

(18A)

To a mixture of (R)-2-(1-(tert-butoxycarbonyl)piperidin-3-yl)acetic acid (6 g, 24.66 mmol) in ethanol (20 mL) was bubbled HCl (g) for 10 minutes. The reaction mixture was stirred for 1 hr and then HCl was bubbled through the mixture for 5 minutes. After 1 hour, solvents were removed from the mixture in vacuo. The reaction mixture was diluted with ethyl acetate and washed with saturated NaHCO$_3$. The aqueous layer was backextracted 2 times with 10% IPA/chloroform.

The organic layers were combined, dried, and concentrated in vacuo to yield 4.05 g of (R)-ethyl 2-(piperidin-3-yl)acetate. MS (M+1)=172. HPLC Peak RT=0.96 minutes.

Preparation 18B: (R)-Ethyl 2-(1-(2-(4-cyanophenyl)-2-oxoethyl)piperidin-3-yl)acetate

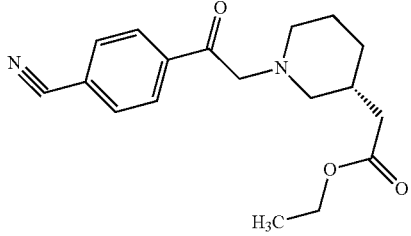

(18B)

To a mixture of 4-(2-bromoacetyl)benzonitrile (5.5g, 24.55 mmol) in toluene was added (R)-ethyl 2-(piperidin-3-yl)acetate (4 g, 23.36 mmol). The reaction mixture was stirred for 4 days at room temperature and then stirred from one day at 50° C. Solvents were removed in vacuo. The resulting solids were triturated with EtOAc. The solid material was filtered and washed with EtOAc. The solid material was collected and dried to yield 5 g of (R)-ethyl 2-(1-(2-(4-cyanophenyl)-2-oxoethyl)piperidin-3-yl)acetate. MS (M+1)=314. HPLC Peak RT=0.77 minutes.

Preparation 18C: Ethyl 2-((3R)-1-(2-(4-cyanophenyl)-2-hydroxyethyl)piperidin-3-yl)acetate

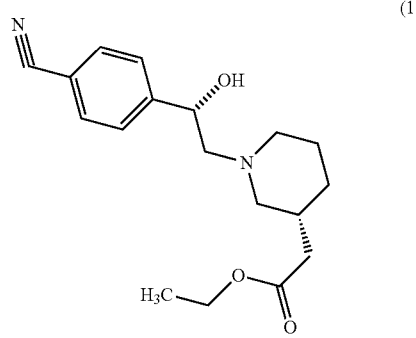

(18C)-isomer A (18C)-isomer B

To a mixture of (R)-ethyl 2-(1-(2-(4-cyanophenyl)-2-oxoethyl)piperidin-3-yl)acetate (1 g, 3.18 mmol) in MeOH was added sodium borohydride (0.120 g, 3.18 mmol). The reaction mixture was stirred for 1 hour. The reaction was quenched with water. The reaction mixture was diluted with ethyl acetate and washed with H₂O. The organic layer was dried with MgSO₄, filtered, and concentrated. The resulting solids were purified on a silica gel cartridge using an EtOAc/hexanes gradient to give 575 mg of ethyl 2-((3R)-1-(2-(4-cyanophenyl)-2-hydroxyethyl)piperidin-3-yl)acetate.

This diastereomeric mixture was separated by chiral HPLC (Thar preparative SFC instrument) equipped with a CHIRALPAK® AD-H (25×5 cm, 5 µM). Temp: 35° C.; Flow rate: 270 mL/min; Mobile phase: CO₂/(MeOH+0.1% DEA) in 3:1 ratio isocratic:

Peak 1 (Isomer A): Rt=5.5 min for ethyl 2-((R)-1-((S)-2-(4-cyanophenyl)-2-hydroxyethyl)-piperidin-3-yl)acetate (>99% d.e.). The hydroxyl stereochemistry of compound 18C-isomer A was assigned (R,S) because it matched (H NMR and chiral HPLC retention) 18C-isomer A that was prepared using a chiral reducing agent precedented to generate this stereoisomer (also see alternate synthesis of Example 18 below). ¹H NMR (400 MHz, CDCl₃) δ ppm 7.63 (2H, m), 7.48 (2H, m, J=8.14 Hz), 4.75 (1H, dd, J=10.67, 3.41 Hz), 4.15 (2H, q, J=7.19 Hz), 3.04 (1H, d, J=9.90 Hz), 2.65 (1H, d, J=11.22 Hz), 2.52 (1H, dd, J=12.54, 3.52 Hz), 2.18-2.43 (4H, m), 2.04-2.18 (1H, m, J=13.56, 6.81, 6.81, 3.63, 3.52 Hz), 1.88 (1H, t, J=10.34 Hz), 1.75-1.84 (1H, m), 1.59-1.74 (2H, m), 1.24-1.31 (3H, m), 1.00-1.15 (1H, m).

Peak 2 (Isomer B): Rt=7 0 min for ethyl 2-((R)-1-((R)-2-(4-cyanophenyl)-2-hydroxyethyl)-piperidin-3-yl)acetate (>99% d.e.). The hydroxyl stereochemistry of compound 18C-isomer B was assigned (R,R) because it matched (H NMR and chiral HPLC retention) 18C-isomer B prepared using a chiral reducing agent of known sense of chiral induction (see alternate synthesis of Example 18 below). ¹H NMR (400 MHz, CDCl₃) δ ppm 7.63 (2H, m), 7.48 (2H, m, J=7.92 Hz), 4.75 (1H, dd, J=10.56, 3.52 Hz), 4.14 (2H, q, J=7.04 Hz), 3.00 (1H, d, J=10.56 Hz), 2.72 (1H, d, J=7.92 Hz), 2.51 (1H, dd, J=12.32, 3.52 Hz), 2.32 (1H, dd, J=12.43, 10.67 Hz), 2.20-2.26 (2H, m), 2.01-2.20 (3H, m), 1.70-1.85 (2H, m), 1.52-1.68 (1H, m), 1.26 (3H, t, J=7.15 Hz), 1.00-1.13 (1H, m).

Ethyl 2-((R)-1-((S)-2-(4-cyanophenyl)-2-hydroxyethyl)-piperidin-3-yl)acetate (18C-isomer A) was carried forward to make Example 18 and ethyl 2-((R)-1-((R)-2-(4-cyanophenyl)-2-hydroxyethyl)-piperidin-3-yl)acetate (18C-isomer B) was carried forward to make Example 22.

Preparation 18D: Ethyl 2-((R)-1-((S)-2-hydroxy-2-(4-((Z)-N'-hydroxycarbamimidoyl)phenyl)ethyl)piperidin-3-yl)acetate

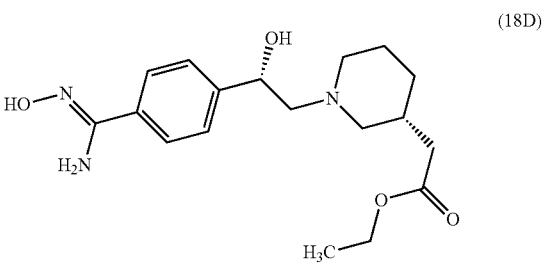 [SMILES: CCOC(=O)C[C@H]1CCCN(C[C@@H](O)c2ccc(/C(N)=N/O)cc2)C1]

(18D)

To a mixture of ethyl 2-((R)-1-((S)-2-hydroxy-2-(4-((Z)—N'-hydroxycarbamimidoyl)phenyl)ethyl)piperidin-3-yl)acetate (18C-Isomer A) and sodium bicarbonate (378 mg, 4.50 mmol) in 2-propanol (10 mL) was added hydroxylamine hydrochloride (156 mg, 2.250 mmol). The reaction mixture was heated at 85° C. overnight. The reaction mixture was diluted with ethyl acetate and washed with H₂O. The organic layer was dried with MgSO₄, filtered, and concentrated to yield 346 mg of ethyl 2-((3R)-1-(2-hydroxy-2-(4-((Z)—N'-hydroxycarbamimidoyl)phenyl)ethyl)piperidin-3-yl)acetate. MS (M+1)=336. HPLC Peak RT=0.12 minutes.

Example 18

2-((3R)-1-(2-Hydroxy-2-(4-(5-(3-phenyl-4-(trifluoromethyl)isoxazol-5-yl)-1,2,4-oxadiazol-3-yl)phenyl)ethyl)piperidin-3-yl)acetic acid To a mixture of ethyl 2-((R)-1-((S)-2-hydroxy-2-(4-((Z)—N'-hydroxycarbamimidoyl)phenyl)ethyl)piperidin-3-yl)acetate (198 mg, 0.567 mmol) and DIEA (0.198 mL, 1.133 mmol) in acetonitrile (10 mL) was added 3-phenyl-4-(trifluoromethyl)isoxazole-5-carbonyl fluoride, Int-I-G (147 mg, 0.567 mmol). The reaction mixture was stirred at room temperature. After 1 hr, TBAF in THF (0.567 mL, 0.567 mmol) was added and the reaction mixture was stirred overnight. The reaction mixture was diluted with ethyl acetate and washed with H₂O. The organic layer was dried with MgSO₄, filtered, and concentrated. The resulting solids were purified on a silica gel cartridge using an EtOAc/hexanes gradient. Isolated fractions with correct mass by LCMS were concentrated in vacuo. The product was then treated with 6N HCl/MeCN at 50° C. overnight. The reaction mixture was filtered and purified by HPLC. HPLC conditions: PHENOMENEX® Luna C18 5 micron column (250×30 mm); 25-100% CH₃CN/water (0.1% TFA); 25 minute gradient; 30 mL/min. Isolated fractions with correct mass were freeze-dried overnight to yield 107 mg of 2-((3R)-1-(2-hydroxy-2-(4-(5-(3-phenyl-4-(trifluoromethyl)isoxazol-5-yl)-1,2,4-oxadiazol-3-yl)phenyl)ethyl)piperidin-3-yl)acetic acid as a TFA salt. ¹H NMR (400 MHz, MeOH-d₃) δ ppm 8.13 (2H, d, J=8.35 Hz), 7.57-7.64 (4H, m), 7.44-7.55 (3H, m), 5.17 (1H, dd, J=9.23, 4.39 Hz), 3.81 (1H, d, J=11.86 Hz), 3.56 (1H, d, J=11.42 Hz), 3.24-3.31 (2H, m), 2.82-2.95(1H, m), 2.72 (1H, t, J=11.86 Hz), 2.16-2.40 (3H, m), 1.79-1.95 (3H, m), 1.10-1.34 (1H, m). MS (m+1)=543. HPLC Peak RT=3.26 minutes. Purity=98%.

Example 18

Alternate Route 1: 2-((3R)-1-(2-Hydroxy-2-(4-(5-(3-phenyl-4-(trifluoromethyl)isoxazol-5-yl)-1,2,4-oxadiazol-3-yl)phenyl)ethyl)piperidin-3-yl)acetic acid

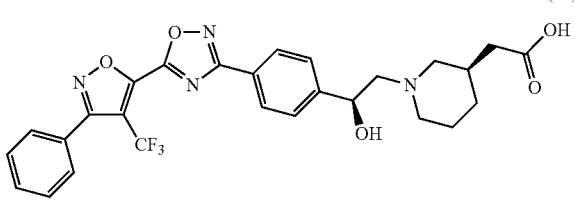

(18)

Preparation 18E (Alternate Route 1): (S)-4-(2-Bromo-1-hydroxyethyl)benzonitrile

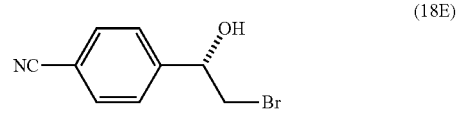 [SMILES: N#Cc1ccc([C@H](O)CBr)cc1]

(18E)

Following the procedure of Corey et al. (*Angew. Chem. Int. Ed.*, 37:1986-2012 (1998)), a solution of 4-(2-bromoacetyl)benzonitrile (10.00 g, 44.6 mmol) in THF (50 mL) was cooled to 0° C. and treated with (S)-methyl oxazaborolidine (1.0 M in toluene) (8.93 mL, 8.93 mmol) followed by borane-methyl sulfide complex (2.0 M in THF) (13.01 mL, 26.0 mmol) over 10 minutes. The reaction was stirred for 1.5 hours and then quenched by adding MeOH. The reaction was concentrated on a rotary evaporator and then extracted from 1 M HCl using DCM×3 followed by drying over MgSO₄, and filtering. The crude material was concentrated in vacuo and purified on a 220 g SiO₂ cartridge using 20-80% EtOAc/hexanes gradient over 10 column volumes. The product eluted in fractions 46-60 to afford 9.8 g of 4-(2-bromo-1-hydroxyethyl)-benzonitrile as a clear oil. Chiral HPLC conditions showed 80% e.e. favoring the (S) stereoisomer based on the Corey precedent. The minor (R) stereoisomer was removed by chiral HPLC using multiple runs on a Thar 350 Preparative SFC instrument equipped with a CHIRALPAK® AD-H (25×5 cm, 5 μM). Temp: 35° C.; Flow rate: 280 mL/min; Mobile phase: CO₂/iPrOH in 88:12 ratio; Runtime 7.7 min; Retention time=5.1 min to give (S)-4-(2-bromo-1-hydroxyethyl)-benzonitrile in 99.8% d.e. ¹H NMR (400 MHz, CDCl₃) δ ppm 7.76 (2H, d), 7.56 (2H, d), 5.02 (1H, dd), 3.68 (1H, dd), 3.55 (1H, dd), 3.53 (1H, s).

Preparation 18F (Alternate Route 1): (S)-4-(2-Bromo-1-(tert-butyldimethylsilyloxy)-ethyl)benzonitrile

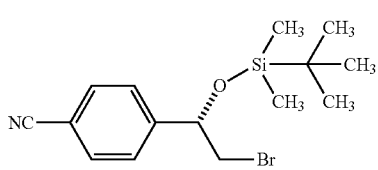

(18F)

To a mixture of (S)-4-(2-bromo-1-hydroxyethyl)benzonitrile (6.9 g, 30.5 mmol) and 2,6-dimethylpyridine (7.82 mL, 67.1 mmol) in DCM (20 mL) was added t-butyl-dimethylsilyltrifluoromethanesulfonate (14.02 mL, 61.0 mmol). The reaction mixture was stirred overnight at room temperature. The reaction mixture was diluted with ethyl acetate and washed with saturated NaCl. The organic layer was dried MgSO₄, filtered and concentrated. The crude material was purified on a 80 gram silica column and eluting with an EtOAc/Hex gradient to afford 12 g of (S)-4-(2-bromo-1-(tert-butyldimethylsilyloxy)ethyl)benzonitrile. MS (M+1)=340/342. HPLC Peak RT=2.16 minutes. ¹H NMR (400 MHz, CDCl₃) δ ppm 7.65 (2H, d), 7.45 (2H, d), 4.88 (1H, dd), 3.42 (1H, q), 3.39 (1H, dd), 0.85 (9H, s), 0.12 (3H, s), −0.09 (3H, s).

Preparation 18G (Alternate Route 1): Ethyl 2-((R)-1-((S)-2-(tert-butyldimethylsilyloxy)-2-(4-cyanophenyl)ethyl)piperidin-3-yl)acetate

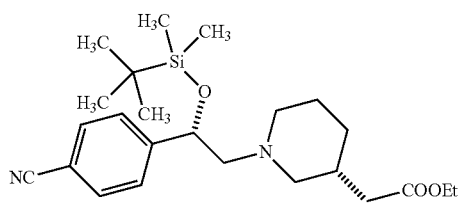

(18G)

To a mixture of (S)-4-(2-bromo-1-(tert-butyldimethylsilyloxy)ethyl)benzonitrile (7 g, 20.57 mmol) and sodium bicarbonate (2.073 g, 24.68 mmol) in THF (100 mL) was added (R)-ethyl 2-(piperidin-3-yl)acetate (3.52 g, 20.57 mmol). The reaction was heated at reflux for 5 days and then cooled, filtered, and concentrated in vacuo. The crude product was purified on a silica gel cartridge eluting with methanol/dichloromethane gradient (0% for 5 minutes then 0-100% over 20 minutes) to afford 5.5 g of ethyl 2-((R)-1-((S)-2-(tert-butyldimethylsilyloxy)-2-(4-cyanophenyl)ethyl)piperidin-3-yl)acetate. MS (M+1)=431; HPLC RT=1.90 minutes. ¹H NMR (400 MHz, CDCl₃) δ ppm 7.61 (2H, d), 7.45 (2H, d), 4.76 (1H, m), 4.12 (2H, q), 2.75 (1H, m), 2.69 (1H, m), 2.52 (1H, dd), 2.33 (1H, dd), 2.18 (2H, m), 2.10 (1H, dt), 2.00 (1H, m), 1.88 (1H, tt), 1.72 (1H, m), 1.59 (2H, m), 1.25 (3H, t), 1.0 (1H, m), 0.89 (9H, s), 0.08 (3H, s), −0.07 (3H, s).

Preparation 18H (Alternate Route 1): Ethyl 2-((R)-1-((S)-2-(tert-butyldimethylsilyloxy)-2-(4-((Z)—N'-hydroxycarbamimidoyl)phenyl)ethyl)piperidin-3-yl)acetate

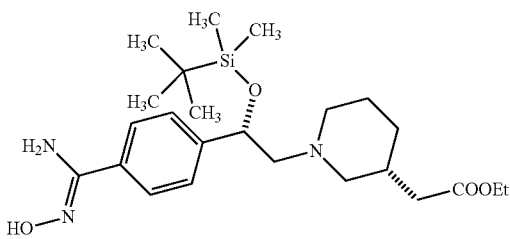

(18H)

To a mixture of ethyl 2-((R)-1-((S)-2-(tert-butyldimethylsilyloxy)-2-(4-cyanophenyl)ethyl)piperidin-3-yl)acetate (940 mg, 2.183 mmol) and sodium bicarbonate (733 mg, 8.73 mmol) in 2-propanol (50 mL) was added hydroxylamine hydrochloride (303 mg, 4.37 mmol). The reaction mixture was heated at 75° C. overnight. The reaction mixture was diluted with ethyl acetate and washed with saturated NaCl. The organic layer was dried MgSO₄, filtered, and concentrated to yield 920 mg of ethyl 2-((S)-1-((R)-2-hydroxy-2-(4-((Z)—N'-hydroxycarbamimidoyl)phenyl)ethyl)piperidin-3-yl)acetate. (M+H)=464; HPLC RT=1.57 minutes. ¹H NMR (400 MHz, CDCl₃) δ ppm 9.48 (1H, s), 7.55 (2H, d), 7.24 (2H, d), 5.68 (1H, s), 4.74 (1H, m), 4.00 (2H, q), 2.73 (1H, m), 2.65 (1H, m), 2.38 (1H, dd), 2.20 (1H, dd), 2.13 (2H, t), 2.00 (1H, m), 1.80 (3H, m), 1.58 (1H, m), 1.48 (1H, m), 1.38 (1H, m), 1.13 (3H, t), 1.0 (1H, m), 0.85 (9H, s), 0.00 (3H, s), −0.15 (3H, s).

Preparation 18I (Alternate Route 1): Ethyl 2-((R)-1-((S)-2-(tert-butyldimethylsilyloxy)-2-(4-(5-(3-phenyl-4-(trifluoromethyl)isoxazol-5-yl)-1,2,4-oxadiazol-3-yl)phenyl)ethyl)piperidin-3-yl)acetate

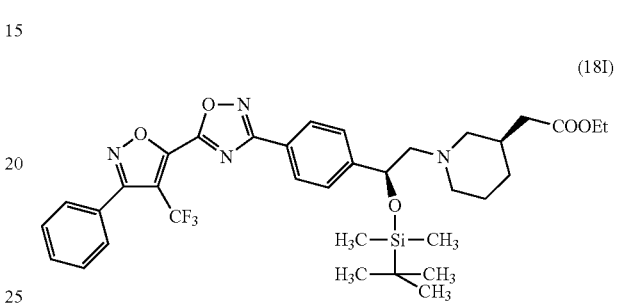

(18I)

To a mixture of 3-phenyl-4-(trifluoromethyl)isoxazole-5-carboxylic acid (620 mg, 2.411 mmol) and oxalyl chloride (0.6 mL, 6.85 mmol) in DCM (50 mL) was added DMF (3 drops) at 25° C. The reaction mixture was stirred at room temperature for 2 hours. The reaction mixture was concentrated in vacuo and dried. The residue was dissolved in acetonitrile (50.0 mL) then DIEA (0.6 mL, 3.44 mmol) and ethyl 2-((S)-1-((R)-2-hydroxy-2-(4-((Z)—N'-hydroxycarbamimidoyl)phenyl)ethyl)piperidin-3-yl)acetate (900 mg, 1.941 mmol) were added. The reaction mixture was stirred at 25° C. After 5 days, the reaction mixture was diluted with ethyl acetate and washed with saturated NaCl. The organic layer was dried MgSO₄, filtered, and concentrated. The product was purified on silica gel using an EtOAc/hexanes gradient to give 840 mg of ethyl 2-((R)-1-((S)-2-(tert-butyldimethylsilyloxy)-2-(4-(5-(3-phenyl-4-(trifluoromethyl)isoxazol-5-yl)-1,2,4-oxadiazol-3-yl)phenyl)ethyl)piperidin-3-yl)acetate. MS (M+1)=685; HPLC RT=2.37 min.

Preparation 18-Alternate Route 1: 2-((3R)-1-(2-Hydroxy-2-(4-(5-(3-phenyl-4-(trifluoromethyl)isoxazol-5-yl)-1,2,4-oxadiazol-3-yl)phenyl)ethyl)piperidin-3-yl)acetic acid

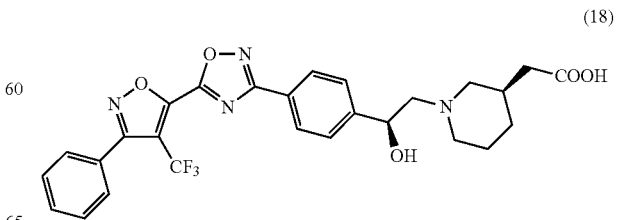

(18)

Ethyl 2-((R)-1-((S)-2-(tert-butyldimethylsilyloxy)-2-(4-(5-(3-phenyl-4-(trifluoromethyl)isoxazol-5-yl)-1,2,4-oxadiazol-3-yl)phenyl)ethyl)piperidin-3-yl)acetate (840 mg, 1.227 mmol) was heated in 1:1 6N HCl/dioxane at 50° C. overnight. The product was concentrated in vacuo and freeze dried from MeCN/water to yield 660 mg of 2-((3R)-1-(2-hydroxy-2-(4-(5-(3-phenyl-4-(trifluoromethyl)isoxazol-5-yl)-1,2,4-oxadiazol-3-yl)phenyl)ethyl)piperidin-3-yl)acetic acid. Characterization of product by $^1$H NMR and chiral HPLC matched Example 18 prepared in previous synthesis.

Preparation of Intermediate 18G (Alternate Route 2): Ethyl 2-((R)-1-((S)-2-(tert-butyldimethylsilyloxy)-2-(4-cyanophenyl)ethyl)piperidin-3-yl)acetate

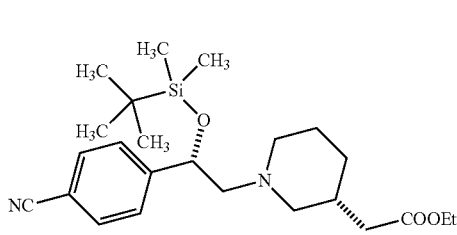

(18G)

Step 1: Preparation of (18C)-isomer A (Alternate Route 2): Ethyl 2-((R)-1-((S)-2-(4-cyanophenyl)-2-hydroxyethyl)piperidin-3-yl)acetate

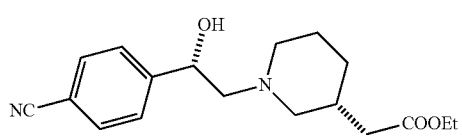

(18C)-isomer A (S)-Ethyl 2-(piperidin-3-yl)acetate, HCl (45.6 g, 220 mmol) was charged to a three-neck round bottom flask equipped with an overhead stirrer. Isopropanol (290 mL) was added under N$_2$. To this stirring slurry was added N,N-diisopropylethylamine (38.3 mL, 220 mmol) via an additional funnel. The inner temperature was maintained at 35° C. After stirred for 20 minutes at this temperature, a clear solution was obtained. The solution was then heated to 50° C. To this solution was added Intermediate 14E (S)-4-(oxiran-2-yl)benzonitrile (29.0 g, 200 mmol) portion-wise over a period of 1 hour. After stirring at this temperature for 5 hours, LC indicated ~50% conversion to the product. 4-dimethyl-aminopyridine (4.89 g, 40 mmol) was added and the reaction mixture was stirred at this temperature under N$_2$ for 12 hours. The reaction mixture was cooled to room temperature and the solvent was removed in vacuo to give ~100 mL of the mixture. Water (150 mL) was added and the product was extracted with DCM (2×150 mL). The organic solvent was removed in vacuo to give the product as a syrup which was passed through a silica pad eluting with EtOAc (100%). The fractions containing the desired product were pooled and concentrated in vacuo to give the desired product as a light yellow solid (56.9 g, 90%). This material was dissolved in 400 ml of aqueous ethanol EtOH/H$_2$O=1/1) at 90° C. under N$_2$. The solution was gradually cooled to room temperature over a period of 1.5 hr, left for 12 hr and then stirred in an ice-batch for additional 1.5 hr. The solid was collected by filtration, rinsed with cold aqueous EtOH (2×50 mL) and was dried under vacuo at 50° C. for 12 hours to give ethyl 2-((R)-1-((S)-2-(4-cyanophenyl)-2-hydroxyethyl)piperidin-3-yl)acetate as an off-white solid (48.3g, 76% yield). This material matched the 18C-isomer A prepared above by H NMR and chiral HPLC (99.5% e.e.). The absolute and relative stereochemistry was determined by single X-ray crystallography employing a wavelength of 1.54178 Å. The crystalline material had a monoclinic crystal system and unit cell parameters approximately equal to the following:

| | |
|---|---|
| a = 8.52 Å | α = 90.0° |
| b = 5.34 Å | β = 93.3° |
| c = 19.20 Å | γ = 90.0° |
| Space group: P2$_1$ | |
| Molecules/asymmetric unit: 2 | |
| Volume/Number of molecules in the unit cell = 872 Å$^3$ | |
| Density (calculated) = 1.205 g/cm$^3$ | |
| Temperature 203 K. | |

Step 2: Preparation of Intermediate 18G: (Alternate Route 2): Ethyl 2-((R)-1-((S)-2-(tert-butyldimethylsilyloxy)-2-(4-cyanophenyl)ethyl)piperidin-3-yl) acetate

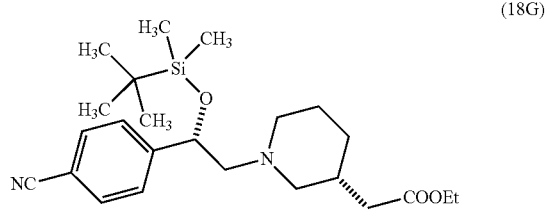 [SMILES: CCOC(=O)C[C@H]1CCCN(C[C@@H](O[Si](C)(C)C(C)(C)C)c2ccc(C#N)cc2)C1]

(18G)

To a mixture of (18C)-isomer A, ethyl 2-((R)-1-((S)-2-(4-cyanophenyl)-2-hydroxyethyl)piperidin-3-yl)acetate (6.00 g, 18.96 mmol) and DIPEA (5.96 ml, 34.1 mmol) in DCM (63 mL) was added tert-butyldimethylsilyl trifluoromethane-sulfonate (5.67 ml, 24.65 mmol) slowly. The reaction was monitored with HPLC and the reaction was complete in 2 hours. The reaction mixture (a light brown solution) was quenched with water, the aqueous layer was extracted twice with DCM. The organic phase was combined, dried with Na$_2$SO$_4$, filtered, and concentrated. The crude material was purified with on a silica gel cartridge (330 g silica, 10-30% EtOAc/hexanes gradient) to give ethyl 2-((R)-1-((S)-2-(tert-butyldimethylsilyloxy)-2-(4-cyanophenyl)ethyl)piperidin-3-yl)acetate (8 g, 18.58 mmol, 98% yield).

Example 19

2-((3R)-1-(2-Hydroxy-2-(4-(5-(3-phenyl-4-(trifluoromethyl)isoxazol-5-yl)-1,2,4-oxadiazol-3-yl)phenyl)ethyl)piperidin-3-yl)acetic acid (19)

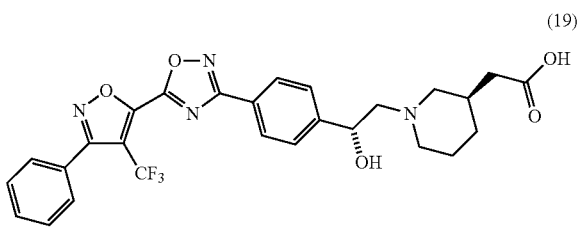 [SMILES: O=C(O)C[C@H]1CCCN(C[C@H](O)c2ccc(-c3noc(-c4onc(-c5ccccc5)c4C(F)(F)F)n3)cc2)C1]

Example 19 was synthesized by the same route as used for Example 18 but using ethyl 2-((R)-1-((R)-2-(4-cyanophenyl)-2-hydroxyethyl)-piperidin-3-yl)acetate (18C-isomer B) to give 2-((3R)-1-(2-hydroxy-2-(4-(5-(3-phenyl-4-(trifluoromethyl)isoxazol-5-yl)-1,2,4-oxadiazol-3-yl)phenyl)ethyl)piperidin-3-yl)acetic acid. $^1$H NMR (400 MHz, MeOH-d$_3$) δ ppm 8.14 (2H, d, J=8.35 Hz), 7.57-7.63 (4H, m), 7.45-7.56 (3H, m), 5.16 (1H, dd, J=8.79, 4.83 Hz), 3.54-3.81 (2H, m), 2.83-2.97 (1H, m), 2.66-2.78 (1H, m), 2.64-2.96 (2H, m), 2.14-2.46 (3H, m), 1.67-2.02 (3H, m), 1.11-1.42 (1H, m). MS (m+1)=543. HPLC Peak RT=3.26 minutes (Analytical Method A). Purity=98%.

Example 20

(3S)-1-(2-Hydroxy-2-(4-(5-(5-isobutyl-4-(trifluoromethyl)isoxazol-3-yl)-1,2,4-oxadiazol-3-yl)phenyl)ethyl)piperidine-3-carboxylic acid (20)

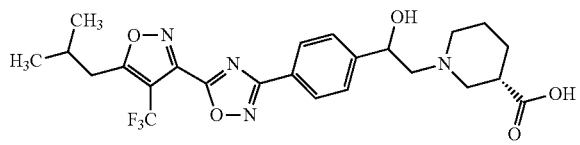

Preparation 20A: (3S)-Ethyl 1-(2-hydroxy-2-(4-(5-(5-isobutyl-4-(trifluoromethyl)isoxazol-3-yl)-1,2,4-oxadiazol-3-yl)phenyl)ethyl)piperidine-3-carboxylate (20A)

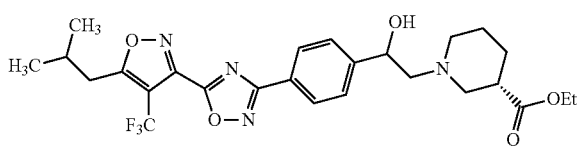

A mixture of 5-isobutyl-4-(trifluoromethyl)isoxazole-3-carbonyl fluoride; Int-V-D (0.045 g, 0.188 mmol), (3S)-ethyl 1-(2-hydroxy-2-(4-((Z)—N'-hydroxycarbamimidoyl)phenyl)ethyl)piperidine-3-carboxylate (0.063 g, 0.188 mmol), and DIEA (0.043 mL, 0.245 mmol) in acetonitrile (1 mL) was stirred at room temperature for 4 days. The reaction was complete by HPLC. The reaction mixture was diluted with dichloromethane, washed with a saturated aqueous solution of sodium bicarbonate, dried over anhydrous sodium sulfate, and concentrated. The crude reaction mixture was purified by flash silica gel chromatography using a 20% mixture of ethyl acetate in hexane to give (3S)-ethyl 1-(2-hydroxy-2-(4-(5-(5-isobutyl-4-(trifluoromethyl)isoxazol-3-yl)-1,2,4-oxadiazol-3-yl)phenyl)ethyl)piperidine-3-carboxylate (0.055 g, 0.103 mmol, 54.5% yield) as a clear, colorless oil. The product was >99% pure by HPLC with a ret. time=2.87 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=537.2.

Example 20

(3S)-1-(2-Hydroxy-2-(4-(5-(5-isobutyl-4-(trifluoromethyl)isoxazol-3-yl)-1,2,4-oxadiazol-3-yl)phenyl)ethyl)piperidine-3-carboxylic acid To a solution of (3S)-ethyl 1-(2-hydroxy-2-(4-(5-(5-isobutyl-4-(trifluoromethyl)isoxazol-3-yl)-1,2,4-oxadiazol-3-yl)phenyl)ethyl)piperidine-3-carboxylate (0.054 g, 0.101 mmol) in acetonitrile (1 mL) was added a solution of hydrochloric acid, 37% (0.5 mL) and water (0.5 mL). The reaction mixture was heated at 64° C. overnight. The homogeneous reaction mixture was concentrated to remove the acetonitrile. The aqueous residue was diluted with water and the pH was adjusted to ~4.5. The mixture was extracted with dichloromethane. The organic layer was collected, dried under reduced pressure, and concentrated to give 37 mg of the product as tan solid (~88% AP). The solid was suspended in MeOH and concentrated (2×), and after the third resuspension, the solid was collected by vacuum filtration to give (3S)-1-(2-hydroxy-2-(4-(5-(5-isobutyl-4-(trifluoromethyl)isoxazol-3-yl)-1,2,4-oxadiazol-3-yl)phenyl)ethyl)piperidine-3-carboxylic acid (0.007 g, 0.014 mmol, 13.54% yield) as a tan solid. The filtrate was concentrated under reduced pressure and dried to give (3S)-1-(2-hydroxy-2-(4-(5-(5-isobutyl-4-(trifluoromethyl)isoxazol-3-yl)-1,2,4-oxadiazol-3-yl)phenyl)ethyl)piperidine-3-carboxylic acid (0.024 g, 0.045 mmol, 44.6% yield) as a tan solid. The product was 97% pure by HPLC with a ret. time=2.76 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. $^1$H NMR (400 MHz, MeOD) δ ppm 8.19 (2H, d, J=8.36 Hz), 7.70 (2H, d, J=8.36 Hz), 5.26 (1H, dd, J=10.45, 2.97 Hz), 3.25-3.40 (6H, m), 3.02 (2H, dd, J=7.26, 1.10 Hz), 2.80-2.88 (1H, m), 2.14-2.26 (1H, m), 1.89-2.08 (4H, m), 1.05 (3H, s), 1.04 (3H, s).

Example 21

4-(2-Hydroxy-2-(4-(5-(5-phenyl-4-propylisoxazol-3-yl)-1,2,4-oxadiazol-3-yl)phenyl)ethyl)piperazine-2-carboxylic acid

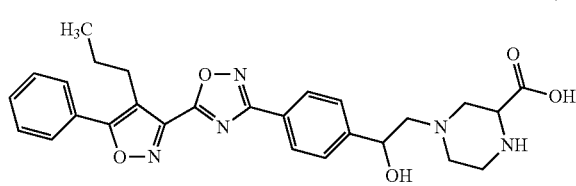

(21)

To a solution of 2-carboxypiperazine (47 mg, 0.36 mmol) in 0.5 mL dry DMSO was added tetrabutylammonium hydroxide (0.360 mL, 360 µmol, 1M in THF) and the reaction mixture was stirred at rt for 15 min. 2-bromo-1-(4-(5-(5-phenyl-4-propylisoxazol-3-yl)-1,2,4-oxadiazol-3-yl)phenyl)ethanol, Preparation 1C (30 mg, 0.066 mmol) was dissolved in 0.5 mL DMSO and added and the reaction was agitated at 400 rpm on an INNOVA® platform shaker at 80° C. for 1.5 hours. The reaction was diluted with 250 µL of MeOH and purified by HPLC (MeOH—H₂O-TFA) to give 4-(2-hydroxy-2-(4-(5-(5-phenyl-4-propylisoxazol-3-yl)-1,2,4-oxadiazol-3-yl)phenyl)ethyl)piperazine-2-carboxylic acid. MS (m+1)=504. HPLC RT=2.06 min Waters Masslynx instrument equipped with a 19×100 mm 5 uM C18 column and a method of 0-100% B solvent over 15 min at a flow rate of 20 mL/min. Solvent A is 5:95 acetonitrile/water; solvent B is 95:5 acetonitrile/water and both contain 0.5% TFA.

Example 22

2-(1-(2-Hydroxy-2-(4-(5-(5-phenyl-4-propylisoxazol-3-yl)-1,2,4-oxadiazol-3-yl)phenyl)ethyl)piperidin-3-yl)acetic acid

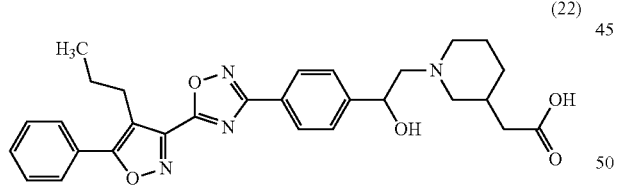

(22)

To a solution of 2-(piperidin-3-yl)acetic acid (51 mg, 0.36 mmol) in 0.5 mL dry DMSO was added tetrabutylammonium hydroxide (0.360 mL, 360 µmol, 1M in THF) and the reaction mixture was stirred at room temperature for 15 min. 2-bromo-1-(4-(5-(5-phenyl-4-propylisoxazol-3-yl)-1,2,4-oxadiazol-3-yl)phenyl)ethanol, Preparation 1C (30 mg, 0.066 mmol) was dissolved in 0.5 mL DMSO and added and the reaction mixture was agitated at 400 rpm on an INNOVA® platform shaker at 80° C. for 1.5 hours. The reaction was diluted with 250 µL of MeOH and purified by HPLC (MeOH—H₂O-TFA) to give 2-(1-(2-hydroxy-2-(4-(5-(5-phenyl-4-propylisoxazol-3-yl)-1,2,4-oxadiazol-3-yl)phenyl)ethyl)piperidin-3-yl)acetic acid. MS (m+1)=517. HPLC RT=2.08 min using a Waters Masslynx instrument equipped with a 19×100 mm 5 uM C18 column and a method of 0-100% B solvent over 15 min at a flow rate of 20 mL/min. Solvent A is 5:95 acetonitrile/water; solvent B is 95:5 acetonitrile/water and both contain 0.5% TFA.

Example 23

1-(2-Hydroxy-2-(4-(5-(5-phenyl-4-propylisoxazol-3-yl)-1,2,4-oxadiazol-3-yl)phenyl)ethyl)piperidin-3-ol

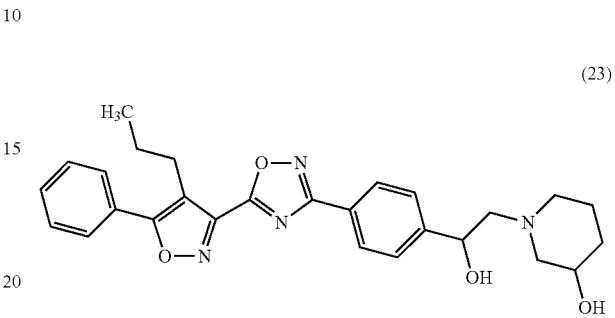

(23)

To a mixture of piperidin-3-ol (20.04 mg, 0.198 mmol) in DMSO (2 mL) was added tetrabutylammonium hydroxide (0.198 mL, 0.198 mmol). After 5 minutes, 2-bromo-1-(4-(5-(5-phenyl-4-propylisoxazol-3-yl)-1,2,4-oxadiazol-3-yl)phenyl)ethanol, Int-I-C (30 mg, 0.066 mmol) was added. The reaction mixture was heated at 80° C. for 2 hours. The reaction mixture was filtered and purified by HPLC. HPLC conditions: PHENOMENEX® Luna C18 5 micron column (250×30 mm); 25-100% CH₃CN/water (0.1% TFA); 25 minute gradient; 20 mL/min to yield 22 mg of 1-(2-hydroxy-2-(4-(5-(5-phenyl-4-propylisoxazol-3-yl)-1,2,4-oxadiazol-3-yl)phenyl)ethyl)piperidin-3-ol as the TFA salt. $^1$H NMR (400 MHz, DMSO-$d_6$) δ ppm 8.16 (2H, d, J=8.13 Hz), 7.83 (2H, dd, J=8.02, 1.65 Hz), 7.58-7.73 (5H, m), 5.17-5.28 (1H, m), 4.10 (1H, d, J=14.72 Hz), 3.06-3.91 (5H, m), 2.95-3.06 (2H, m), 2.59-2.95 (2H, m), 1.77-2.21 (2H, m), 1.64-1.76 (2H, m), 1.16-1.42 (1H, m), 0.98 (3H, t, J=7.36 Hz). MS (m+1)=475. HPLC Peak RT=3.32 minutes (Analytical Method A). Purity=98%.

Example 24

N,N-Diethyl-1-(2-hydroxy-2-(4-(5-(5-phenyl-4-propylisoxazol-3-yl)-1,2,4-oxadiazol-3-yl)phenyl)ethyl)piperidine-3-carboxamide

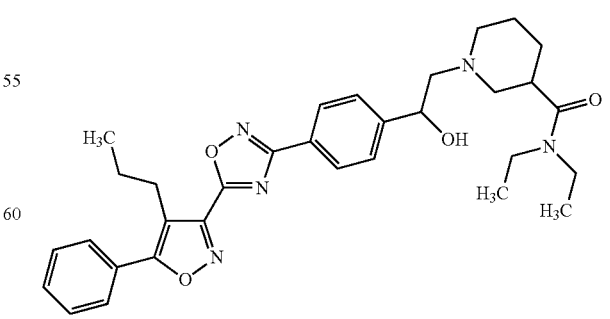

(24)

To a mixture of 2-bromo-1-(4-(5-(5-phenyl-4-propylisoxazol-3-yl)-1,2,4-oxadiazol-3-yl)phenyl)ethanol (30 mg, 0.066 mmol) in DMSO (2 mL) was added tetrabutylammonium hydroxide (0.132 mL, 0.132 mmol). After 5 minutes, 2-bromo-1-(4-(5-(5-phenyl-4-propylisoxazol-3-yl)-1,2,4-oxadiazol-3-yl)phenyl)ethanol (30 mg, 0.066 mmol) was added. The reaction mixture was heated at 80° C. for 2 hours. The reaction mixture was filtered and purified by HPLC. HPLC conditions: PHENOMENEX® Luna C18 5 micron column (250×30 mm); 25-100% CH₃CN/water (0.1% TFA); 25 minute gradient; 20 mL/min. Isolated fractions with correct mass were freeze-dried overnight to yield 5 mg of N,N-diethyl-1-(2-hydroxy-2-(4-(5-(5-phenyl-4-propylisoxazol-3-yl)-1,2,4-oxadiazol-3-yl)phenyl)ethyl)piperidine-3-carboxamide as a TFA salt. $^1$H NMR (400 MHz, DMSO-$d_6$) δ ppm 8.16 (2H, dt, J=8.35, 1.87 Hz), 7.83 (2H, dd, J=8.02, 1.65 Hz), 7.58-7.74 (5H, m), 5.15-5.31 (1H, m), 3.06-3.51 (10H, m), 2.95-3.06 (2H, m), 1.78-2.04 (2H, m), 1.63-1.77 (2H, m), 1.11-1.21 (2H, m), 0.94-1.10 (9H, m). MS (m+1)=558. HPLC Peak RT=3.46 minutes (Analytical Method A). Purity=95%.

Example 25

1-(2-Hydroxy-2-(4-(5-(3-phenyl-4-(trifluoromethyl)isoxazol-5-yl)-1,2,4-oxadiazol-3-yl)phenyl)ethyl)azetidine-3-carboxylic acid

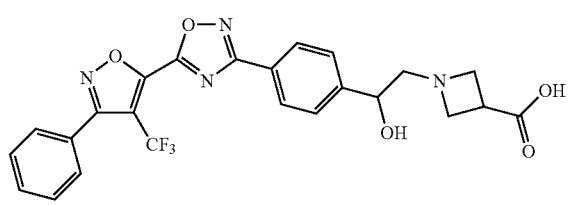

(25)

Preparation 25A:
1-(Benzyloxycarbonyl)azetidine-3-carboxylic acid

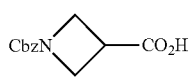

(25A)

To a solution of azetidine-3-carboxylic acid (88 g, 0.871 mol) and sodium bicarbonate (161 g, 1.92 mol) in water (1.75 L) at room temperature was added a solution of benzyl 2,5-dioxopyrrolidin-1-ylcarbonate (239 g, 0.959 mol) in tetrahydrofuran (3.5 L). The reaction mixture was stirred at room temperature overnight. The solvent was removed under reduced pressure, and the aqueous layer was washed with ethyl acetate (2×500 mL). The aqueous layer was acidified with a 1.0 N aqueous hydrochloric acid solution and was then extracted with ethyl acetate (3×750 mL). The organic layer was washed with water, followed by brine, and dried over anhydrous sodium sulfate. Concentration under reduced pressure afforded 1-(benzyloxycarbonyl)azetidine-3-carboxylic acid as colorless oil (202 g, 99% yield). The compound had an HPLC retention time=2.27 min.–Column: YMC COMBISCREEN® ODS-A 4.6×50 mm (4 min.); Solvent A=10% MeOH, 90% H₂O, 0.1% TFA; Solvent B=90% MeOH, 10% H₂O, 0.1% TFA. LC/MS M$^{+1}$=236.15. $^1$H NMR (400 MHz, CDCl₃) δ ppm 3.39-3.49 (m, 1H), 4.22 (d, J=7.28 Hz, 4H), 5.11 (s, 2H), and 7.29-7.39 (m, 5H).

Preparation 25B: 1-Benzyl 3-tert-butyl azetidine-1,3-dicarboxylate

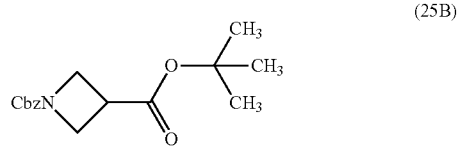 [SMILES: CC(C)(C)OC(=O)C1CN(C(=O)OCc2ccccc2)C1]

(25B)

To a solution of 1-(benzyloxycarbonyl)azetidine-3-carboxylic acid (200 g, 0.851 mol) in dichloromethane (6.0 L) at 0° C. was added t-butanol (158 g, 2.13 mol), DMAP (52.0 g, 0.425 mol), and EDCI (163 g, 0.853 mol). The reaction mixture was stirred at room temperature overnight. Next, the reaction mixture was concentrated and the residue was dissolved in ethyl acetate. The organic layer washed with 10% aqueous citric acid, 10% aqueous sodium bicarbonate solution, and brine. Drying over anhydrous sodium sulfate and concentration under reduced pressure afforded 1-benzyl-3-tert butyl-azetidine-1,3-dicarboxylate (200 g, 81% yield) as a colorless oil. The compound had an HPLC retention time=3.27 min.–Column: YMC COMBISCREEN® ODS-A 4.6×50 mm (4 min.); Solvent A=10% MeOH, 90% H₂O, 0.1% TFA; Solvent B=90% MeOH, 10% H₂O, 0.1% TFA. LC/MS M$^{+1}$=292.15. $^1$H NMR (400 MHz, CDCl₃) δ ppm 1.46 (s, 9H), 3.24-3.33 (m, 1H), 4.14 (d, J=7.53 Hz, 4H), 5.10 (s, 2H), and 7.30-7.39 (m, 5H).

Preparation 25C: tert-Butyl azetidine-3-carboxylate

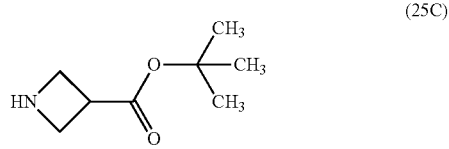

(25C)

A mixture of 1-benzyl-3-tert-butyl-azetidine-1,3-dicarboxylate (140 g, 0.480 mol) and 10% palladium on carbon (28.0 g) in ethyl acetate (1.40 L) was placed in an autoclave under 3.0 kg/cm² of hydrogen pressure overnight. The reaction mixture was filtered through CELITE®, and the CELITE® bed was washed with ethyl acetate. Acetic acid (28.9 g, 0.480 mol) was added to the filtrate and it was concentrated under reduced pressure maintaining the temperature below 50° C. to give tert-butyl azetidine-3-carboxylate acetic acid salt (96 g, 92% yield) as a colorless oil. $^1$H NMR (400 MHz, CDCl₃) δ ppm 1.47 (s, 9H), 2.02 (s, 3H), 3.52-3.63 (m, 1H), and 4.00-4.10 (m, 4H).

Preparation 25D: tert-Butyl 1-(2-(4-cyanophenyl)-2-oxoethyl)azetidine-3-carboxylate

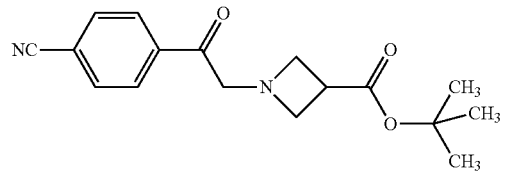
(25D)

To a mixture of 4-(2-bromoacetyl)benzonitrile (448 mg, 2 mmol) in toluene (10 mL) was added tert-butyl azetidine-3-carboxylate (346 mg, 2.2 mmol). The reaction mixture was stirred overnight and then, solvent was removed. The solids were triturated with EtOAC. The solids were collected and dried in vacuo to yield 170 mg of tert-butyl 1-(2-(4-cyanophenyl)-2-oxoethyl)azetidine-3-carboxylate as an off white solid. MS (m+1)=301. HPLC Peak RT=0.97 minutes (Analytical Method B).

Preparation 25E: tert-Butyl 1-(2-(4-cyanophenyl)-2-hydroxyethyl)azetidine-3-carboxylate

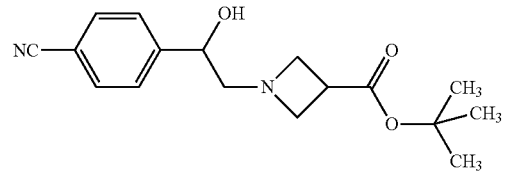
(25E)

To a mixture of tert-butyl 1-(2-(4-cyanophenyl)-2-oxoethyl)azetidine-3-carboxylate, hydrobromide (170 mg, 0.446 mmol) in MeOH (5 mL) was added sodium borohydride (25 mg, 0.661 mmol). The reaction mixture was stirred for 1 hour. The reaction was quenched with water. The reaction mixture was diluted with ethyl acetate and washed with $H_2O$. The organic layer was dried with $MgSO_4$, filtered, and concentrated to yield 100 mg of tert-butyl 1-(2-(4-cyanophenyl)-2-hydroxyethyl)azetidine-3-carboxylate. MS (m+1)=303. HPLC Peak RT=0.90 minutes (Analytical Method B).

Preparation 25F: tert-Butyl 1-(2-hydroxy-2-(4-(N'-hydroxycarbamimidoyl)phenyl)ethyl)azetidine-3-carboxylate

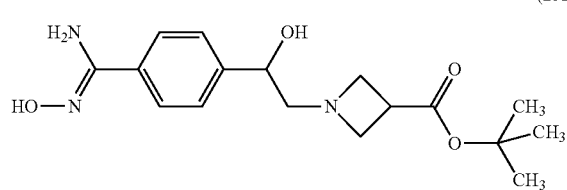
(25F)

To a mixture of tert-butyl 1-(2-(4-cyanophenyl)-2-hydroxyethyl)azetidine-3-carboxylate (100 mg, 0.331 mmol) and sodium bicarbonate (111 mg, 1.323 mmol) in 2-propanol was added hydroxylamine hydrochloride (22.98 mg, 0.331 mmol). The reaction mixture was heated at 85° C. overnight. The reaction mixture was diluted with ethyl acetate and washed with $H_2O$. The organic layer was dried with $MgSO_4$, filtered, and concentrated to yield 110 mg of tert-butyl 1-(2-hydroxy-2-(4-(N'-hydroxycarbamimidoyl)phenyl)ethyl)azetidine-3-carboxylate. MS (m+1)=336. HPLC Peak RT=0.91 minutes (Analytical Method B).

Example 25

1-(2-Hydroxy-2-(4-(5-(3-phenyl-4-(trifluoromethyl)isoxazol-5-yl)-1,2,4-oxadiazol-3-yl)phenyl)ethyl)azetidine-3-carboxylic acid To a mixture of tert-butyl 1-(2-hydroxy-2-(4-(N'-hydroxycarbamimidoyl)phenyl)ethyl)azetidine-3-carboxylate (111 mg, 0.33 mmol) and DIEA (0.115 mL, 0.660 mmol) in acetonitrile (10 mL) was added 3-phenyl-4-(trifluoromethyl)isoxazole-5-carbonyl fluoride, Int-I-G (86 mg, 0.33 mmol). After 1 hour, TBAF (0.330 mL, 0.330 mmol) was added and the reaction was stirred overnight. The reaction mixture was diluted with ethyl acetate and washed with $H_2O$. The organic layer was dried with $MgSO_4$, filtered, and concentrated. Crude residue was treated with TFA/DCM to remove t-butyl ester. The resulting material was concentrated in vacuo and purified by HPLC to yield 36 mg of 1-(2-hydroxy-2-(4-(5-(3-phenyl-4-(trifluoromethyl)isoxazol-5-yl)-1,2,4-oxadiazol-3-yl)phenyl)ethyl)azetidine-3-carboxylic acid as the tetrabutylammonium salt. $^1H$ NMR (400 MHz, MeOH-$d_3$) δ ppm 8.22 (2H, d, J=8.35 Hz), 7.68 (4H, d, J=8.35 Hz), 7.53-7.65 (3H, m), 5.04 (1H, dd, J=10.11, 3.08 Hz), 4.45 (4H, t, J=9.89 Hz), 3.73 (1H, br. s.), 3.36-3.62 (2H, m). MS (m+1)=501. HPLC Peak RT=3.23 minutes (Analytical Method A). Purity=98%.

Example 26

(3S)-1-(2-Hydroxy-2-(4-(5-(3-phenyl-4-(trifluoromethyl)isoxazol-5-yl)-1,2,4-oxadiazol-3-yl)-3-(trifluoromethyl)phenyl)ethyl)piperidine-3-carboxylic acid

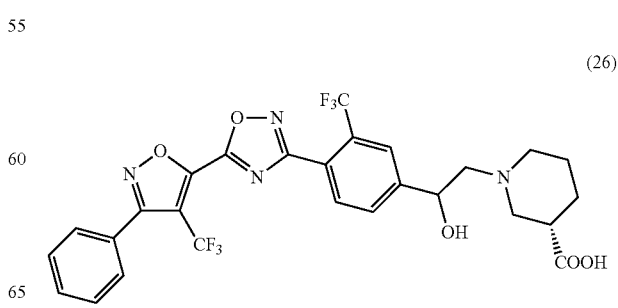
(26)

Preparation 26A: 2-(Trifluoromethyl)-4-vinylbenzonitrile

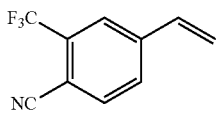

(26A)

To a mixture of 4-bromo-2-(trifluoromethyl)benzonitrile (500 mg, 2.000 mmol), cesium fluoride (668 mg, 4.40 mmol), tri-n-butylphosphine in hexane (0.347 mL, 0.120 mmol) and Pd$_2$(dba)$_3$ (36.6 mg, 0.040 mmol) in toluene (10 mL) was added tributyl(vinyl)stannane (0.587 mL, 2.000 mmol). The reaction mixture was heated at 80° C. overnight. Next, saturated KF solution was added and the resulting mixture was stirred 1 hour and then filtered. The filtrate was diluted with ethyl acetate and washed with H$_2$O. The organic layer was dried with MgSO$_4$, filtered, and concentrated. The solids were purified on a silica gel cartridge using an EtOAc/hexanes gradient to yield 450 mg of 2-(trifluoromethyl)-4-vinylbenzonitrile. $^1$H NMR (400 MHz, chloroform-d) δ ppm 7.79 (1H, s), 7.67 (1H, dd, J=7.91, 1.76 Hz), 7.40-7.45 (1H, m), 6.77 (1H, dd, J=17.58, 10.99 Hz), 5.97 (1H, d, J=17.58 Hz), 5.58 (1H, d, J=10.99 Hz)

Preparation 26B: N'-Hydroxy-2-(trifluoromethyl)-4-vinylbenzimidamide

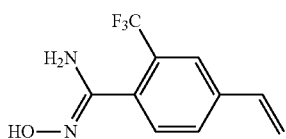

(26B)

To a mixture of 2-(trifluoromethyl)-4-vinylbenzonitrile (450 mg, 2.282 mmol) and sodium bicarbonate (767 mg, 9.13 mmol) in 2-propanol (10 mL) was added hydroxylamine hydrochloride (317 mg, 4.56 mmol). The reaction mixture was heated at 85° C. overnight. The reaction mixture was diluted with ethyl acetate and washed with H$_2$O. The organic layer was dried with MgSO$_4$, filtered, and concentrated to give 460 mg of N'-hydroxy-2-(trifluoromethyl)-4-vinylbenzimidamide. MS (m+1)=231. HPLC Peak RT=0.78 minutes (Analytical Method B).

Preparation 26C: 5-(3-Phenyl-4-(trifluoromethyl)isoxazol-5-yl)-3-(2-(trifluoromethyl)-4-vinylphenyl)-1,2,4-oxadiazole

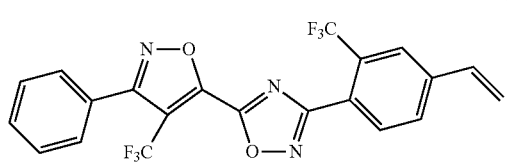

(26C)

To a mixture of N'-hydroxy-2-(trifluoromethyl)-4-vinylbenzimidamide (460 mg, 2 mmol), 3-phenyl-4-(trifluoromethyl)isoxazole-5-carboxylic acid, Int-I (350 mg, 1.361 mmol), and DIEA (0.475 mL, 2.72 mmol) in DMF (10 mL) was added BOP—Cl (346 mg, 1.361 mmol). The reaction mixture was stirred at room temperature for 2 hours and then 1M TBAF in THF (1.361 mL, 1.361 mmol) was added. The reaction was stirred overnight, diluted with ethyl acetate, and washed with H$_2$O. The organic layer was dried with MgSO$_2$, filtered, and concentrated. The resulting solids were purified on a silica gel cartridge using an EtOAc/hexanes gradient to yield 56 mg of 5-(3-phenyl-4-(trifluoromethyl)isoxazol-5-yl)-3-(2-(trifluoromethyl)-4-vinylphenyl)-1,2,4-oxadiazole. MS (m+1)=452. HPLC Peak RT=2.03 minutes (Analytical Method B).

Preparation 26D: 3-(4-(Oxiran-2-yl)-2-(trifluoromethyl)phenyl)-5-(3-phenyl-4-(trifluoromethyl)isoxazol-5-yl)-1,2,4-oxadiazole

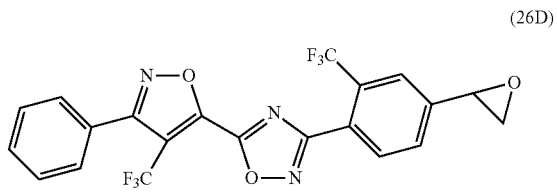 [SMILES: FC(F)(F)c1cc(C2CO2)ccc1-c1noc(-c2onc(-c3ccccc3)c2C(F)(F)F)n1]

(26D)

To a mixture of 5-(3-phenyl-4-(trifluoromethyl)isoxazol-5-yl)-3-(2-(trifluoromethyl)-4-vinylphenyl)-1,2,4-oxadiazole (56 mg, 0.124 mmol) in DCM (5 mL) was added mCPBA (64.2 mg, 0.372 mmol). The reaction mixture was stirred overnight. The reaction mixture was diluted with dichloromethane and washed with 1N NaOH. The organic layer was dried with MgSO$_4$, filtered, and concentrated to yield 50 mg of 3-(4-(oxiran-2-yl)-2-(trifluoromethyl)phenyl)-5-(3-phenyl-4-(trifluoromethyl)isoxazol-5-yl)-1,2,4-oxadiazole. MS (m+1)=468. HPLC Peak RT=2.12 minutes (Analytical Method B).

Example 26

(3S)-1-(2-Hydroxy-2-(4-(5-(3-phenyl-4-(trifluoromethyl)isoxazol-5-yl)-1,2,4-oxadiazol-3-yl)-3-(trifluoromethyl)phenyl)ethyl)piperidine-3-carboxylic acid To a mixture of 3-(4-(oxiran-2-yl)-2-(trifluoromethyl)phenyl)-5-(3-phenyl-4-(trifluoromethyl)isoxazol-5-yl)-1,2,4-oxadiazole (50 mg, 0.107 mmol) in EtOH (5 mL) was added (S)-ethyl piperidine-3-carboxylate (50.5 mg, 0.321 mmol). The reaction mixture was heated at 80° C. overnight and solvents were removed in vacuo. The mixture was treated with 6N HCl in MeCN at 50° C. for 24 h. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Isolated fractions with correct mass were freeze-dried overnight to yield 24 mg of (3S)-1-(2-hydroxy-2-(4-(5-(3-phenyl-4-(trifluoromethyl)isoxazol-5-yl)-1,2,4-oxadiazol-3-yl)-3-(trifluoromethyl)phenyl)ethyl)piperidine-3-carboxylic acid as a TFA salt. $^1$H NMR (400 MHz, MeOH-d$_3$) δ ppm 7.99-8.06 (1H, m), 7.91-7.96 (1H, m), 7.81-7.90 (1H, m), 7.59 (2H, d, J=6.59 Hz), 7.44-7.56 (3H, m), 3.69-4.04 (1H, m), 3.34-3.64 (3H, m), 3.26-3.35 (2H, m), 2.72-3.14

(2H, m), 2.00-2.22 (1H, m), 1.75-2.00 (2H, m), 1.56 (1H, t, J=12.81 Hz). MS (m+1)=597. HPLC Peak RT=3.4 minutes (Analytical Method A). Purity=92%.

Example 27

2-(1-(2-Hydroxy-2-(4-(5-(3-phenyl-4-(trifluoromethyl)isoxazol-5-yl)-1,2,4-oxadiazol-3-yl)phenyl)ethyl)azetidin-3-yl)acetic acid

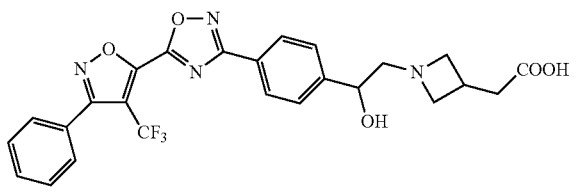

(27)

2-(1-(tert-Butoxycarbonyl)azetidin-3-yl)acetic acid (53.9 mg, 0.250 mmol) was treated with TFA/DCM for 1 hour. Solvents were removed in vacuo and the resulting material was dried. The solids were dissolved in 2-propanol (5 mL) and 3-(4-(oxiran-2-yl)phenyl)-5-(3-phenyl-4-(trifluoromethyl)isoxazol-5-yl)-1,2,4-oxadiazole (50 mg, 0.125 mmol) and cesium carbonate (245 mg, 0.751 mmol) were added. The reaction mixture was treated at 90° C. overnight. The reaction mixture was filtered and purified by HPLC. HPLC conditions: PHENOMENEX® Luna C18 5 micron column (250× 30 mm); 25-100% CH₃CN/water (0.1% TFA); 25 minute gradient; 30 mL/min. After concentration, the material was repurified by HPLC to yield 1 mg of 2-(1-(2-hydroxy-2-(4-(5-(3-phenyl-4-(trifluoromethyl)isoxazol-5-yl)-1,2,4-oxadiazol-3-yl)phenyl)ethyl)azetidin-3-yl)acetic acid as a TFA salt. MS (m+1)=515. HPLC Peak RT=3.24 minutes(Analytical Method A). Purity=95%.

Example 28

4-(2-Hydroxy-2-(4-(5-(3-phenyl-4-(trifluoromethyl)isoxazol-5-yl)-1,2,4-oxadiazol-3-yl)phenyl)ethyl)morpholine-2-carboxylic acid

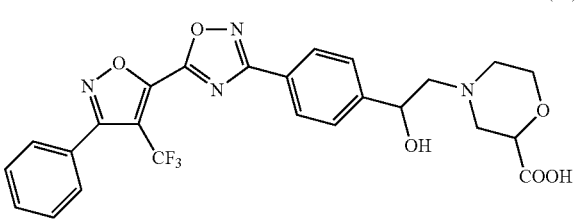

(28)

Preparation 28A: N'-Hydroxy-4-vinylbenzimidamide

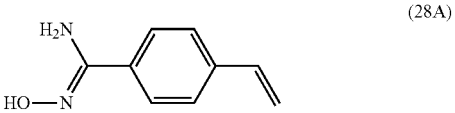

(28A)

To a mixture of 4-vinylbenzonitrile (4.36 g, 33.8 mmol) and hydroxylamine hydrochloride (4.69 g, 67.5 mmol) in 2-propanol (50 mL) was added sodium bicarbonate (11.34 g, 135 mmol). The reaction mixture was heated at 80° C. for 2 hours. The reaction mixture was diluted with ethyl acetate and washed with water. The organic layer was dried MgSO₄, filtered, and concentrated to yield 5.3 g of N'-hydroxy-4-vinylbenzimidamide. MS (m+1)=163. HPLC Peak RT=0.53 minutes (Analytical Method B).

Preparation 28B: 5-(3-Phenyl-4-(trifluoromethyl)isoxazol-5-yl)-3-(4-vinylphenyl)-1,2,4-oxadiazole

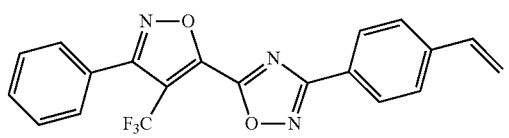

(28B)

To a mixture of (Z)—N'-hydroxy-4-vinylbenzimidamide (1.439 g, 8.87 mmol) and 3-phenyl-4-(trifluoromethyl)isoxazole-5-carbonyl fluoride (2.300 g, 8.87 mmol) in acetonitrile was added DIEA (1.860 mL, 10.65 mmol). The reaction mixture was heated to 62° C. After 3 hours, the reaction mixture was cooled and a white solid precipitate formed. The solid was filtered and washed with ethyl acetate, then dried to give about 2.1 g of 5-(3-phenyl-4-(trifluoromethyl)isoxazol-5-yl)-3-(4-vinylphenyl)-1,2,4-oxadiazole. MS (m+1)=384. HPLC Peak RT=1.24 minutes (Analytical Method B).

Preparation 28C: 3-(4-(Oxiran-2-yl)phenyl)-5-(3-phenyl-4-(trifluoromethyl)isoxazol-5-yl)-1,2,4-oxadiazole

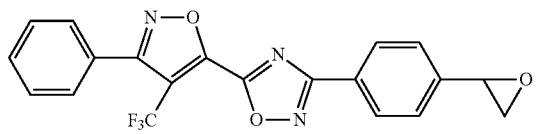

(28C)

To a mixture of 5-(3-phenyl-4-(trifluoromethyl)isoxazol-5-yl)-3-(4-vinylphenyl)-1,2,4-oxadiazole (1.200 g, 3.13 mmol) in DCM (50 mL) was added m-CPBA (1.754 g, 7.83 mmol) in portions. The mixtures were allowed to stir at room temperature overnight. The reaction mixture was diluted with 100 ml DCM and washed with 1N NaOH. The organic layer was then dried and concentrated to provide 1.22 g of product as white solid. MS (m+1)=400. HPLC Peak RT=2.13 minutes. The two enantiomers were separated using the conditions below: Berger SFC MGIII instrument equipped with a Whelk-O 1 (25×3 cm, 5 μm). Wavelength 250 nm; Temp 35° C.; Flow rate: 150 mL/min; Mobile phase: $CO_2$/(MeOH+ 0.1% DEA) in 4:1 ratio isocratic: RT=8.6 min for Peak 1 and 10.1 min for Peak 2. The absolution stereochemistry of the peak 1 (Isomer A) compound was unambiguously assigned as (S)-3-(4-(oxiran-2-yl)phenyl)-5-(3-phenyl-4-(trifluoromethyl)isoxazol-5-yl)-1,2,4-oxadiazole by treating it with (S)-ethyl piperidine-3-carboxylate using the procedure found in Example 26 followed by deprotection of the ester using the procedure found in Example 14 to provide Example 14. This product matched Example 14 by $^1$H NMR and chiral HPLC.

Example 28

4-(2-Hydroxy-2-(4-(5-(3-phenyl-4-(trifluoromethyl) isoxazol-5-yl)-1,2,4-oxadiazol-3-yl)phenyl)ethyl) morpholine-2-carboxylic acid 4-(tert-Butoxycarbonyl)morpholine-2-carboxylic acid (69.5 mg, 0.301 mmol) was treated with TFA/DCM for 1 hour. Solvents were removed in vacuo and the resulting material was dried. The solids were dissolved in 2-propanol (2 mL) and DMSO (1 mL). 3-(4-(oxiran-2-yl)phenyl)-5-(3-phenyl-4-(trifluoromethyl)isoxazol-5-yl)-1,2,4-oxadiazole (30 mg, 0.075 mmol) and cesium carbonate (98 mg, 0.301 mmol) were added. The reaction mixture was heated at 80° C. overnight. LCMS indicated almost complete conversion to desired product and no starting material. The reaction mixture was filtered and purified by HPLC. HPLC conditions: PHENOMENEX® Luna C18 5 micron column (250×30 mm); 25-100% $CH_3CN$/water (0.1% TFA); 25 minute gradient; 30 mL/min. Isolated fractions with correct mass were freeze-dried overnight to yield 21 mg of 4-(2-hydroxy-2-(4-(5-(3-phenyl-4-(trifluoromethyl)isoxazol-5-yl)-1,2,4-oxadiazol-3-yl)phenyl)ethyl)morpholine-2-carboxylic acid as a TFA salt. $^1$H NMR (400 MHz, MeOH-$d_3$) δ ppm 8.23 (2H, d, J=7.91 Hz), 7.69 (4H, dd, J=12.08, 7.69 Hz), 7.54-7.65 (3H, m), 5.29 (1H, td, J=6.81, 4.39 Hz), 4.41-4.65 (1H, m), 4.08-4.37 (1H, m), 3.92-4.05 (2H, m), 3.56-3.91 (1H, m), 3.44 (3H, t, J=6.81 Hz), 3.12-3.38 (1H, m). MS (m+1)=531. HPLC Peak RT=3.24 minutes (Analytical Method A). Purity=85%.

Example 29

2-(4-(2-Hydroxy-2-(4-(5-(3-phenyl-4-(trifluoromethyl)isoxazol-5-yl)-1,2,4-oxadiazol-3-yl)phenyl) ethyl)morpholin-3-yl)acetic acid

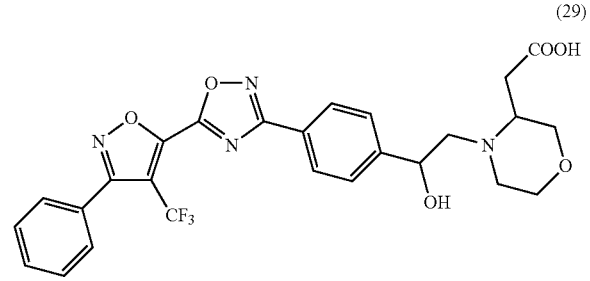 [SMILES: O=C(O)CC1COCCN1CC(O)c1ccc(-c2noc(-c3onc(-c4ccccc4)c3C(F)(F)F)n2)cc1]

(29)

To a mixture of 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol) in ethanol (2 mL) was added ethyl 2-(morpholin-3-yl)acetate (52.1 mg, 0.301 mmol). The resulting mixture was heated at 80° C. overnight. Solvent was removed in vacuo. The residue was treated with 6N HCl/MeCN at 50° C. overnight. The reaction mixture was filtered and purified by HPLC. HPLC conditions: PHENOMENEX® Luna C18 5 micron column (250×30 mm); 25-100% $CH_3CN$/water (0.1% TFA); 25 minute gradient; 30 mL/min. Isolated fractions with correct mass were freeze-dried overnight to yield 18 mg of 2-(4-(2-hydroxy-2-(4-(5-(3-phenyl-4-(trifluoromethyl)isoxazol-5-yl)-1,2,4-oxadiazol-3-yl)phenyl)ethyl) morpholin-3-yl)acetic acid as a TFA salt. $^1$H NMR (400 MHz, MeOH-$d_3$) δ ppm 8.23 (2H, d, J=7.91 Hz), 7.72 (2H, dd, J=8.35, 2.20 Hz), 7.68 (2H, d, J=7.03 Hz), 7.53-7.65 (3H, m), 5.22-5.30 (1H, m), 3.61-4.21 (7H, m), 3.35-3.55 (2H, m), 2.88-3.10 (2H, m). MS (m+1)=545. HPLC Peak RT=3.23 minutes (Analytical Method A). Purity=93%.

Example 30

2-(3-(Hydroxymethyl)piperidin-1-yl)-1-(4-(5-(3-phenyl-4-(trifluoromethyl)isoxazol-5-yl)-1,2,4-oxadiazol-3-yl)phenyl)ethanol

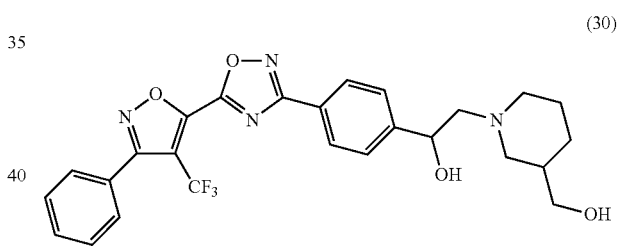

(30)

To a mixture of 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol) in 2-propanol (2 mL) was added piperidin-3-yl-methanol (17.31 mg, 0.150 mmol). The reaction mixture was heated to 80° C. DMSO (1 mL) was added to help solubilize. The reaction mixture was stirred overnight. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 MeOH:water with 10-mM ammonium acetate; Mobile Phase B: 95:5 MeOH:water with 10-mM ammonium acetate; Gradient: 45-100% B over 25 minutes, then a 5-minute hold at 100% B; Flow: 20 mL/min. Fractions containing the desired product were combined and dried via centrifugal evaporation. The yield of the Example 30 was 16.0 mg, and its purity was 100%. $^1$H NMR (400 MHz, MeOD) δ ppm 8.18 (2H, d, J=8.28 Hz), 7.49-7.75 (7H, m), 5.05 (1H, d, J=9.03 Hz), 3.36-3.56 (4H, m), 2.83 (2H, br. s.), 2.11-2.53 (2H, m), 1.62-2.02 (4H, m), 1.03-1.20 (1H, m). MS (m+1)=515.

Example 31

2-(3-(2-Hydroxyethyl)piperidin-1-yl)-1-(4-(5-(3-phenyl-4-(trifluoromethyl)isoxazol-5-yl)-1,2,4-oxadiazol-3-yl)phenyl)ethanol

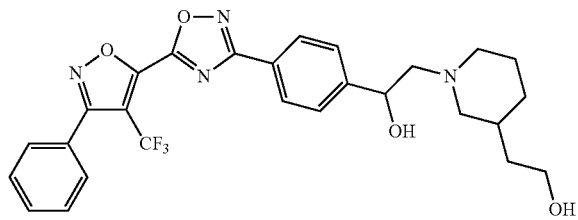

(31)

To a mixture of 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol) in 2-propanol (2 mL) was added 2-(piperidin-3-yl)ethanol (19.41 mg, 0.150 mmol). The reaction mixture was heated to 80° C. DMSO (1 mL) was added to help solubilize. The reaction mixture was stirred overnight. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 MeOH:water with 10-mM ammonium acetate; Mobile Phase B: 95:5 MeOH:water with 10-mM ammonium acetate; Gradient: 45-100% B over 25 minutes, then a 5-minute hold at 100% B; Flow: 20 mL/min. Fractions containing the desired product were combined and dried via centrifugal evaporation. The yield of the Example 31 was 13.0 mg, and its purity was 100%. $^1$H NMR (400 MHz, MeOD) δ ppm 8.18 (2H, d, J=8.03 Hz), 7.52-7.75 (7H, m), 5.01 (1H, ddd, J=8.60, 4.20, 4.02 Hz), 3.54-3.72 (2H, m), 3.13 (2H, br. s.), 2.73 (2H, br. s.), 2.32 (1H, br. s.), 2.11 (1H, br. s.), 1.61-1.92 (4H, m), 1.48 (2H, dd, J=13.68, 6.90 Hz), 1.04 (1H, br. s.). MS (m+1)=529.

Example 32

5-Hydroxy-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid

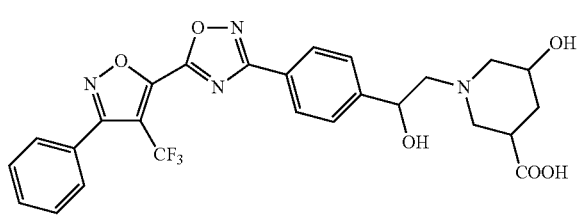

(32)

To a mixture of 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol) and 5-hydroxypiperidine-3-carboxylic acid (21.81 mg, 0.150 mmol) in 2-propanol (2 mL) and DMSO (2.000 mL) was added cesium carbonate (122 mg, 0.376 mmol). The reaction mixture was heated at 80° C. Next, 5-hydroxypiperidine-3-carboxylic acid (21.81 mg, 0.150 mmol) was added and the reaction was checked after 4 hr. Product peak was observed but starting material remained. The reaction mixture was heated overnight. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of the desired product was 5.6 mg, and its purity was 99%. $^1$H NMR (400 MHz, MeOD) δ ppm 8.21 (2H, d, J=7.78 Hz), 7.69 (4H, d, J=6.78 Hz), 7.53-7.65 (3H, m), 5.19 (1H, dt, J=10.10, 3.61 Hz), 4.16 (1H, br. s.), 3.08-3.26 (5H, m), 2.86-3.06 (2H, m), 1.87-2.06 (3H, m). MS (m+1)=545.

Example 33

2-(4-(2-Hydroxy-2-(4-(5-(3-phenyl-4-(trifluoromethyl)isoxazol-5-yl)-1,2,4-oxadiazol-3-yl)phenyl)ethyl)morpholin-2-yl)acetic acid

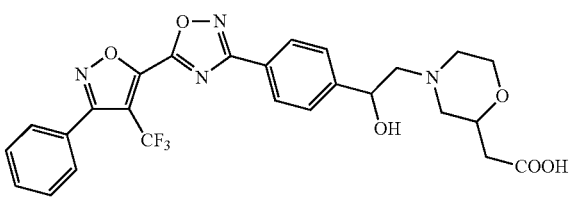

(33)

To a mixture of 3-(4-(oxiran-2-yl)phenyl)-5-(3-phenyl-4-(trifluoromethyl)isoxazol-5-yl)-1,2,4-oxadiazole, Preparation 28C (25 mg, 0.063 mmol) in 2-propanol (2 mL) and DMSO (1 mL) was added 2-(morpholin-2-yl)acetic acid (18.18 mg, 0.125 mmol). The reaction mixture was hated at 80° C. overnight. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of the desired product was 12.8 mg, and its purity was 99%. $^1$H NMR (400 MHz, MeOD) δ ppm 8.18 (2H, d, J=8.28 Hz), 7.38-7.86 (7H, m), 5.03 (1H, ddd, J=9.03, 4.39, 4.14 Hz), 3.97-4.11 (1H, m), 3.90 (1H, t, J=9.66 Hz), 3.69-3.84 (1H, m), 2.97-3.21 (2H, m), 2.69-2.93 (2H, m), 2.18-2.63 (4H, m). MS (m+1)=545.

Example 34

3-Fluoro-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (34)

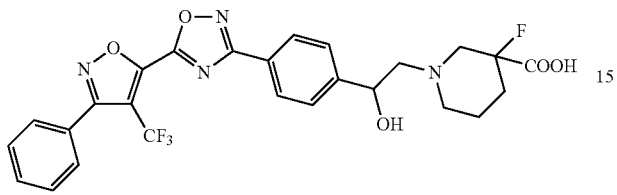

Preparation 34A: tert-Butyl 3-cyano-3-(trimethylsilyloxy)piperidine-1-carboxylate (34A)

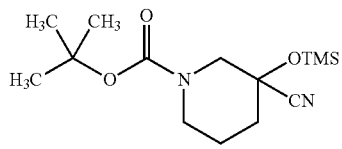

To tert-butyl 3-oxopiperidine-1-carboxylate (1.000 g, 5.02 mmol) in dry DCM (100 mL) was added trimethylsilyl cyanide (1.346 mL, 10.04 mmol) and tetrabutylammonium cyanide (0.135 g, 0.502 mmol). The reaction mixture began to turn deep brown and was stirred overnight. The reaction mixture was diluted with DCM and washed with H₂O. The organic layer was dried with MgSO₄, filtered, and concentrated to yield 1.5 g of tert-butyl 3-cyano-3-(trimethylsilyloxy)piperidine-1-carboxylate which was taken directly to the next step without further purification.

Preparation 34B: 3-Fluoropiperidine-3-carbonitrile (34B)

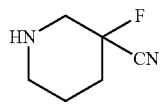

To a mixture of tert-butyl 3-cyano-3-(trimethylsilyloxy)piperidine-1-carboxylate (300 mg, 1.005 mmol) in DCM (10 mL) was added [bis(2-methoxyethyl)amino]sulfur trifluoride (0.222 mL, 1.206 mmol). The reaction mixture was stirred for 2 hours at room temperature. TLC (1:1 EtAOc/hexanes) shows a new higher Rf spot when stained with KMnO₄ and no starting material. The reaction mixture was diluted with DCM (10 mL) and washed with H₂O. The organic layer was dried with MgSO₄, filtered, and concentrated. Solids were purified on a silica gel cartridge using a 0-100% gradient of EtOAc/hexanes, concentrated, and then treated with TFA/DCM for 1 hour. Solvent was removed in vacuo and the solids were dried to give 201 mg of 3-fluoropiperidine-3-carbonitrile as a TFA salt. $^{1}$H NMR (400 MHz, chloroform-d) δ ppm 3.82-4.01 (1H, m), 3.68(1H, br. s.), 3.45-3.61 (1H, m), 3.37(1H, br. s.), 2.06-2.31 (2H, m), 1.79-1.94(1H, m), 1.63-1.76 (1H, m); $^{19}$F NMR (400 MHz, chloroform-d) δ ppm −157.4 (alpha-F); −156.5 (TFA).

Example 34

3-Fluoro-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid To a mixture of 3-fluoropiperidine-3-carbonitrile, TFA (55 mg, 0.227 mmol), and cesium carbonate (122 mg, 0.376 mmol) in 2-propanol (2 mL) and DMSO (0.5 mL) was added 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol). The reaction mixture was heated at 80° C. over a weekend. The reaction mixture was purified by HPLC. The purified product was lyophilized and then was dissolved in MeCN/6N HCl and heated at 50° C. overnight. The mixture was filtered and purified by HPLC. HPLC conditions: PHENOMENEX® Luna C18 5 micron column (250×30 mm); 25-100% CH₃CN/water (0.1% TFA); 25 minute gradient; 30 mL/min. Isolated fractions with correct mass were freeze-dried overnight to yield 6 mgs of 3-fluoro-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid as a TFA salt. $^{1}$H NMR (400 MHz, MeOH-d₃) δ ppm 8.14 (2H, d, J=7.91 Hz), 7.56-7.62 (4H, m), 7.44-7.56 (3H, m), 5.13-5.24 (1H, m), 3.86-4.28 (1H, m), 3.47-3.81 (2H, m), 3.25-3.41 (2H, m), 2.08-2.15 (3H, m), 1.87-2.02 (2H, m). MS (m+1)=547. HPLC Peak RT=3.32 minutes (Analytical Method A). Purity=98%.

Example 35

2-((3R)-1-(2-Hydroxy-2-(4-(5-(5-phenyl-4-(trifluoromethyl)isoxazol-3-yl)-1,2,4-oxadiazol-3-yl)phenyl)ethyl)piperidin-3-yl)acetic acid (35)

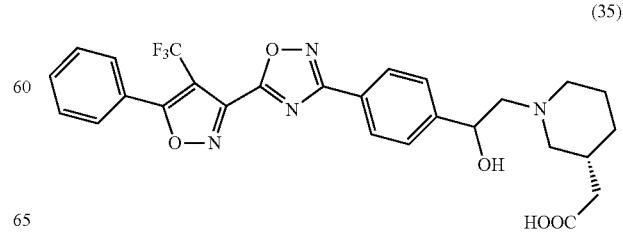

Preparation 35A: Ethyl 2-((3R)-1-(2-hydroxy-2-(4-(5-(5-phenyl-4-(trifluoromethyl)isoxazol-3-yl)-1,2,4-oxadiazol-3-yl)phenyl)ethyl)piperidin-3-yl)acetate

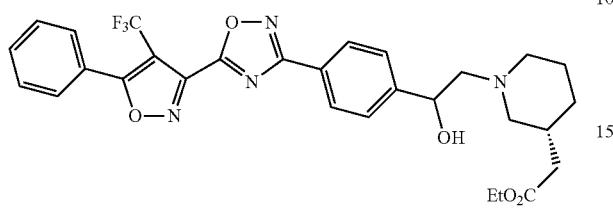

(35A)

5-Phenyl-4-(trifluoromethyl)isoxazole-3-carbonyl fluoride, Int-II-D (150 mg, 0.58 mmol) was dissolved in acetonitrile (10 mL) and DIEA (0.185 mL, 1.061 mmol) and ethyl 2-((3R)-1-(2-hydroxy-2-(4-((Z)—N'-hydroxycarbamimidoyl)phenyl)ethyl)piperidin-3-yl)acetate (185 mg, 0.530 mmol) were added. After one hr, TBAF in THF (0.530 mL, 0.530 mmol) was added and the reaction mixture was stirred overnight at room temperature. LCMS shows two new peaks. One is the desired mass and the other has a much higher mass which corresponds to double addition of acid fluoride. The reaction mixture was diluted with ethyl acetate and washed with saturated NaCl. The organic layer was dried with MgSO₄, filtered, and concentrated. Solids were purified by a silica gel cartridge using an EtOAc/hexanes gradient to yield 72 mgs of ethyl 2-((3R)-1-(2-hydroxy-2-(4-(5-(5-phenyl-4-(trifluoromethyl)isoxazol-3-yl)-1,2,4-oxadiazol-3-yl)phenyl)ethyl)piperidin-3-yl)acetate. MS (m+1)=571. HPLC Peak RT=3.39 minutes.

Example 35

2-((3R)-1-(2-Hydroxy-2-(4-(5-(5-phenyl-4-(trifluoromethyl)isoxazol-3-yl)-1,2,4-oxadiazol-3-yl)phenyl)ethyl)piperidin-3-yl)acetic acid To a mixture of ethyl 2-((3R)-1-(2-hydroxy-2-(4-(5-(5-phenyl-4-(trifluoromethyl)isoxazol-3-yl)-1,2,4-oxadiazol-3-yl)phenyl)ethyl)piperidin-3-yl)acetate (72 mg, 0.126 mmol) in acetonitrile (5 mL) was added 6N HCl (5 mL). The reaction mixture was stirred at room temperature for 3 days. The reaction mixture was filtered and purified by HPLC. HPLC conditions: PHENOMENEX® Luna C18 5 micron column (250×30 mm); 25-100% CH₃CN/water (0.1% TFA); 25 minute gradient; 30 mL/min. Isolated fractions with correct mass were freeze-dried overnight to yield 66 mg of 2-((3R)-1-(2-hydroxy-2-(4-(5-(5-phenyl-4-(trifluoromethyl)isoxazol-3-yl)-1,2,4-oxadiazol-3-yl)phenyl)ethyl)piperidin-3-yl)acetic acid as a TFA salt. $^1$H NMR (400 MHz, MeOH-d₃) δ ppm 8.12 (2H, d, J=8.35 Hz), 7.71 (2H, d, J=7.47 Hz), 7.49-7.66 (5H, m), 5.16 (1H, dd, J=9.67, 4.39 Hz), 3.81 (1H, d, J=11.86 Hz), 3.56 (1H, d, J=11.42 Hz), 3.14-3.33 (2H, m), 2.83-2.94 (1H, m), 2.72 (1H, t, J=11.86 Hz), 2.16-2.38(3H, m), 1.78-1.92 (3H, m), 1.10-1.33 (1H, m). MS (m+1)=543. HPLC Peak RT=3.24 minutes (Analytical Method A). Purity=98%.

Example 36

(3S)-1-(2-Hydroxy-2-(4-(5-(5-phenyl-4-(trifluoromethyl)isoxazol-3-yl)-1,2,4-oxadiazol-3-yl)phenyl)ethyl)piperidine-3-carboxylic acid

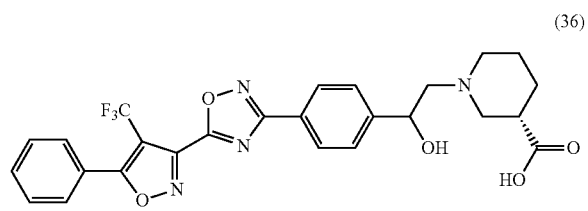 [SMILES: O=C(O)[C@H]1CCCN(CC(O)c2ccc(-c3noc(-c4noc(-c5ccccc5)c4C(F)(F)F)n3)cc2)C1]

(36)

Preparation 36A: (S)-Ethyl 1-((S)-2-hydroxy-2-(4-(5-(5-phenyl-4-(trifluoromethyl)isoxazol-3-yl)-1,2,4-oxadiazol-3-yl)phenyl)ethyl)piperidine-3-carboxylate 5-Phenyl-4-(trifluoromethyl)isoxazole-3-carbonyl fluoride, Int-II-D (78 mg, 0.3 mmol) was dissolved in acetonitrile (5 mL) and (S)-ethyl 1-((S)-2-hydroxy-2-(4-((Z)—N'-hydroxycarbamimidoyl)phenyl)ethyl)piperidine-3-carboxylate, Preparation 14B (100 mg, 0.298 mmol) was added. After 2 hours, 1M TBAF in THF (298 µL, 0.298 mmol) was added and the reaction mixture was stirred overnight. The reaction mixture was diluted with ethyl acetate and washed with H₂O. The organic layer was dried with MgSO₄, filtered, and concentrated. The resulting material was purified on a silica gel cartridge using an EtOAc/hexanes gradient to yield 67 mg of (S)-ethyl 1-((S)-2-hydroxy-2-(4-(5-(5-phenyl-4-(trifluoromethyl)isoxazol-3-yl)-1,2,4-oxadiazol-3-yl)phenyl)ethyl)piperidine-3-carboxylate. MS (m+1)=557. HPLC Peak RT=3.32 minutes (Analytical Method A).

Example 36

(3S)-1-(2-Hydroxy-2-(4-(5-(3-(6-methylpyridin-2-yl)-4-(trifluoromethyl)isoxazol-5-yl)-1,2,4-oxadiazol-3-yl)phenyl)ethyl)piperidine-3-carboxylic acid To a mixture of (S)-ethyl 1-((S)-2-hydroxy-2-(4-(5-(5-phenyl-4-(trifluoromethyl)isoxazol-3-yl)-1,2,4-oxadiazol-3-yl)phenyl)ethyl)piperidine-3-carboxylate (67 mg, 0.120 mmol) in acetonitrile (3 mL) was added 6N HCl (3 mL). The reaction mixture was stirred at 50° C. for 3 hours, then the heat was removed, and the reaction mixture was stirred over a weekend. The reaction mixture was filtered and purified by HPLC. HPLC conditions: PHENOMENEX® Luna C18 5 micron column (250×30 mm); 25-100% CH₃CN/water (0.1% TFA); 25 minute gradient; 30 mL/min to yield 55 mg of (3S)-1-(2-hydroxy-2-(4-(5-(3-(6-methylpyridin-2-yl)-4-(trifluoromethyl)isoxazol-5-yl)-1,2,4-oxadiazol-3-yl)phenyl) ethyl)piperidine-3-carboxylic acid as a TFA salt. $^1$H NMR (400 MHz, MeOD) δ ppm 8.13 (2H, d, J=8.36 Hz), 7.71 (2H, d, J=7.48 Hz), 7.58-7.65 (3H, m), 7.49-7.58 (2H, m), 5.19 (1H, t, J=6.93 Hz), 3.93 (1H, d, J=11.44 Hz), 3.57 (1H, d, J=12.54 Hz), 3.28 (2H, d, J=6.82 Hz), 3.07 (1H, t, J=12.21 Hz), 2.93 (1H, td, J=12.54, 3.52 Hz), 2.81 (1H, t, J=12.32 Hz), 2.17 (1H, d, J=12.10 Hz), 1.86-2.06 (2H, m), 1.45-1.64 (1H, m, J=13.09, 12.82, 12.82, 3.74 Hz). MS (m+1)=529. HPLC Peak RT=3.19 minutes (Analytical Method A). Purity =99%.

Example 37

(3S)-1-(2-Hydroxy-2-(4-(5-(3-(6-methylpyridin-2-yl)-4-(trifluoromethyl)isoxazol-5-yl)-1,2,4-oxadiazol-3-yl)phenyl)ethyl)piperidine-3-carboxylic acid

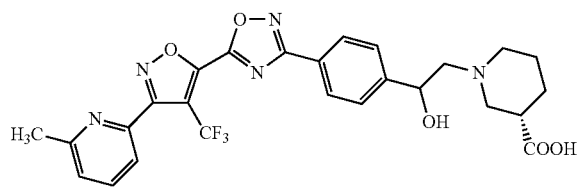

(37)

Preparation 37A:
(Z)—N-Hydroxy-6-methylpicolinimidoyl chloride

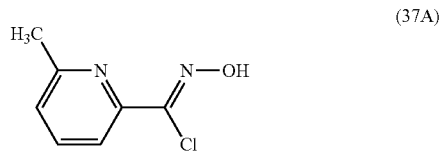

(37A)

To a mixture of commercially available (E)-6-methylpicolinaldehyde oxime (2 g, 14.69 mmol) in DMF (25 mL) was added 1-chloropyrrolidine-2,5-dione (2.158 g, 16.16 mmol). The reaction mixture was stirred overnight at room temperature. LCMS shows reaction was complete. The reaction mixture was diluted with ethyl acetate and washed with saturated NaCl (×3). The organic layer was dried with MgSO$_4$, filtered, and concentrated to yield 2.5 g of N-hydroxy-6-methylpicolinimidoyl chloride. MS (m+1)=171. HPLC Peak RT=0.79 minutes (Analytical Method B).

Preparation 37B: 3-(6-Methylpyridin-2-yl)-4-(trifluoromethyl)isoxazole-5-carboxylic acid

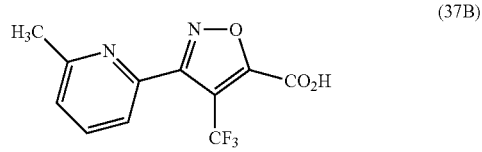 [SMILES: Cc1cccc(-c2noc(C(=O)O)c2C(F)(F)F)n1]

(37B)

To a mixture of N-hydroxy-6-methylpicolinimidoyl chloride (2.5 g, 14.65 mmol) and (Z)-ethyl 2-bromo-4,4,4-trifluorobut-2-enoate, Int-I-F (3 g, 12.15 mmol) in ethyl acetate (40 mL) was added indium(III) chloride (0.559 g, 2.53 mmol). After 1 hour, potassium hydrogen carbonate (2.022 g, 20.20 mmol) was added and the reaction mixture was stirred overnight. The reaction mixture was diluted with ethyl acetate (40 mL) and washed with H$_2$O. The organic layer was dried with MgSO$_4$, filtered, and concentrated. The resulting material was purified on a silica gel cartridge using an EtOAc/hexanes gradient. The fraction with desired mass was isolated and checked by NMR. The product was found to be contaminated with dimerization product of the starting bromoolefin. This material was hydrolyzed using 1N LiOH (2eq) in EtOH for 1 hour. The pH was adjusted to 6-7 with concentrated HCl. The resulting material was extract with EtOAc 4 times and then extracts were combined, dried, and concentrated to yield 360 mg of 3-(6-methylpyridin-2-yl)-4-(trifluoromethyl)isoxazole-5-carboxylic acid. MS (m+1)=273. HPLC Peak RT=1.66 minutes (Analytical Method B).

Example 37

(3S)-1-(2-Hydroxy-2-(4-(5-(3-(6-methylpyridin-2-yl)-4-(trifluoromethyl)isoxazol-5-yl)-1,2,4-oxadiazol-3-yl)phenyl)ethyl)piperidine-3-carboxylic acid To a mixture of 3-(6-methylpyridin-2-yl)-4-(trifluoromethyl)isoxazole-5-carboxylic acid (100 mg, 0.367 mmol) and DIEA (0.128 mL, 0.735 mmol) in DMF (3 mL) was added BOP—Cl (103 mg, 0.404 mmol). After 15 minutes, (3S)-ethyl 1-(2-hydroxy-2-(4-((Z)—N'-hydroxycarbamimidoyl)phenyl)ethyl)piperidine-3-carboxylate, (refer to Preparation 14B) (136 mg, 0.404 mmol) was added. The reaction mixture was stirred at room temperature. After 1 hour, 1M TBAF/THF (0.367 mL, 0.367 mmol) was added and the reaction mixture was stirred overnight. The reaction mixture was diluted with ethyl acetate and washed with saturated NaCl. The organic layer was dried with MgSO$_4$, filtered, and concentrated. The resulting material was purified by on a silica gel cartridge using an EtOAc/hexanes gradient. The peak with the desired mass was isolated by LCMS. This residue was dissolved in MeCN and treated with 6N HCl overnight. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Isolated fractions with correct mass were freeze-dried overnight to yield 6 mg of (3S)-1-(2-hydroxy-2-(4-(5-(3-(6-methylpyridin-2-yl)-4-(trifluoromethyl)isoxazol-5-yl)-1,2,4-oxadiazol-3-yl)phenyl)ethyl)piperidine-3-carboxylic acid as a TFA salt. $^1$H NMR (400 MHz, MeOH-d$_3$) δ ppm 8.14 (2H, d, J=8.35 Hz), 7.81 (1H, t, J=7.69 Hz), 7.63 (3H, t, J=7.25 Hz), 7.39 (1H, d, J=7.91 Hz), 5.12-5.24 (1H, m), 3.93 (1H, d, J=12.74 Hz), 3.70-3.86 (1H, m), 3.57 (1H, d, J=11.86 Hz), 3.32-3.44 (1H, m), 3.24-3.32 (2H, m), 2.73-3.12 (2H, m), 2.48-2.56 (3H, m), 1.74-2.32 (2H, m), 1.41-1.65 (1H, m). MS (m+1)=544. HPLC Peak RT=2.96 minutes (Analytical Method A). Purity=90%.

Example 38

1-(2-Hydroxy-2-(4-(5-(3-phenyl-4-(trifluoromethyl)isoxazol-5-yl)-1,2,4-oxadiazol-3-yl)phenyl)ethyl)-3-methylpiperidine-3-carboxylic acid (38)

To a mixture of ethyl 3-methylpiperidine-3-carboxylate, HCl (62.4 mg, 0.301 mmol), and cesium carbonate (98 mg, 0.301 mmol) in 2-propanol (2 mL) and DMSO (1 mL) was added 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol). The reaction mixture was heated at 80° C. overnight. The reaction mixture was filtered and purified by HPLC. HPLC conditions: PHENOMENEX® Luna 5 micron C18 column (30×100 mm); 10% MeOH/water (0.1% TFA)/90% MeOH/water (0.1% TFA); 10%-100% gradient over 15 minutes; 20 mL/min. Fraction with the correct mass were isolated and concentrated in vacuo. The residue was treated with 6N HCl/MeCN for 3 days and purified by HPLC. HPLC conditions: PHENOMENEX® Luna C18 5 micron column (250×30 mm); 25-100% CH$_3$CN/water (0.1% TFA); 25 minute gradient; 30 mL/min. Isolated fractions with correct mass were freeze-dried overnight to yield 1 mg of 1-(2-hydroxy-2-(4-(5-(3-phenyl-4-(trifluoromethyl)isoxazol-5-yl)-1,2,4-oxadiazol-3-yl)phenyl)ethyl)-3-methylpiperidine-3-carboxylic acid as a TFA salt. MS (m+1)=543. HPLC Peak RT=3.29 minutes (Analytical Method A). Purity=95%.

Example 39

3-Hydroxy-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (39)

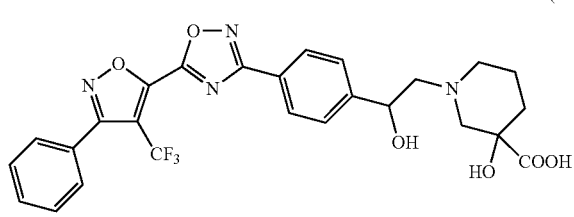

Preparation 39A: Methyl 3-(trimethylsilyloxy)piperidine-3-carboxylate tert-Butyl 3-cyano-3-(trimethylsilyloxy)piperidine-1-carboxylate, Preparation 34A (170 mg, 0.570 mmol) was treated with 6N HCl in MeOH (10 mL) at 80° C. for 12 hours. Solvents were removed in vacuo and the resulting material was dissolved in MeOH (10 mL). HCl (g) was bubbled through the mixture for 15 minutes. The solids were concentrated in vacuo. The residue was dissolved in DCM (10.00 mL) and cesium carbonate (928 mg, 2.85 mmol) was added. Next, TMS—Cl (0.146 mL, 1.139 mmol) was added and the mixture was stirred for 1 hour. The mixture was filtered and the solids were concentrated in vacuo and taken to the next step without further purification.

Example 39

3-Hydroxy-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid To a mixture of 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol) in MeOH (3 mL) was added methyl 3-(trimethylsilyloxy)piperidine-3-carboxylate (100 mg, 0.432 mmol). The reaction mixture was heated at 80° C. for 2 days. The reaction mixture was concentrated in vacuo. The residue was treated with 6N HCl/MeCN at 50° C. overnight. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Isolated fractions with correct mass were freeze-dried overnight to yield 14 mg of 3-hydroxy-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid as a TFA salt. $^1$H NMR (400 MHz, MeOH-d$_3$) δ ppm 8.23 (2H, d, J=7.91 Hz), 7.69 (4H, t, J=7.91 Hz), 7.54-7.65 (3H, m), 5.21-5.32 (1H, m), 3.69-4.01 (1H, m), 3.51 (2H, d, J=12.30 Hz), 3.33-3.43 (1H, m), 3.07-3.27 (2H, m), 2.32 (1H, br. s.), 1.78-2.08 (3H, m). MS (m+1)=545. HPLC Peak RT=3.24 minutes (Analytical Method A). Purity=95%.

Example 40

3-(1-(2-Hydroxy-2-(4-(5-(3-phenyl-4-(trifluoromethyl)isoxazol-5-yl)-1,2,4-oxadiazol-3-yl)phenyl)ethyl)piperidin-3-yl)propanoic acid (40)

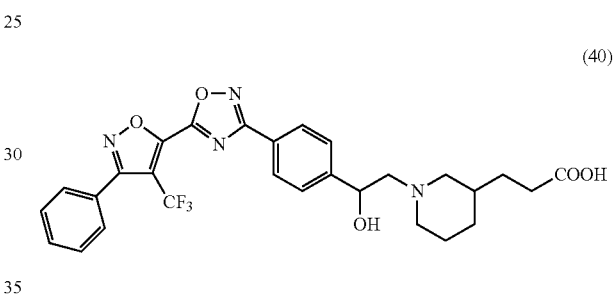

A two dram vial was charged with 3-(4-(oxiran-2-yl)phenyl)-5-(3-phenyl-4-(trifluoromethyl)isoxazol-5-yl)-1,2,4-oxadiazole, Preparation 28C (30 mg, 0.075 mmol), methyl 3-(piperidin-3-yl)propanoate, HCl (23.41 mg, 0.113 mmol), acetonitrile (1.5 mL), and DIEA (30 µL, 0.172 mmol). The vial was flushed with nitrogen, sealed, and placed on a Reactor Block heated to 80° C. overnight. The reaction mixture became homogeneous within a few minutes of heating to give a clear, yellow solution. The reaction mixture was cooled to room temperature and HCl (6N Aq) (500 µL, 3.00 mmol) was added. The vial was sealed and placed back on the reaction block overnight. The solution was filtered, concentrated, then re-constituted in DMF (2mL).

The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of the desired product was 12.6 mg, and its purity was 88%. $^1$H NMR (400 MHz, MeOD) δ ppm 8.12-8.33 (2H, m), 7.66-7.75 (4H, m), 7.54-7.66 (3H, m), 5.16-5.33 (1H, m), 4.01-4.16 (1H, m), 3.69 (1H, t, J=11.29 Hz), 3.46-3.61 (1H, m), 3.20-3.26 (1H, m), 2.94 (1H, br. s.), 2.56-2.79 (1H, m), 2.18-2.37 (2H, m), 1.76-2.08 (4H, m), 1.43-1.73 (2H, m), 1.22 (1H, br. s.). MS (m+1)=557. HPLC Peak RT=3.08 minutes. (Analytical Method C). Purity=88%.

Example 41

(2R)-1-(2-Hydroxy-2-(4-(5-(3-phenyl-4-(trifluoromethyl)isoxazol-5-yl)-1,2,4-oxadiazol-3-yl)phenyl)ethyl)piperidine-2-carboxylic acid

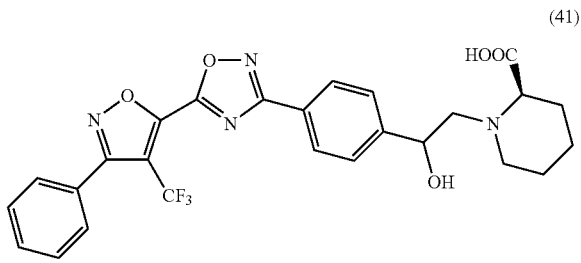 [SMILES: O=C(O)[C@H]1CCCCN1CC(O)c1ccc(-c2noc(-c3onc(-c4ccccc4)c3C(F)(F)F)n2)cc1]
(41)

An oven dried two dram vial containing a stir bar was charged with (R)-methyl piperidine-2-carboxylate, HCl (18.70 mg, 0.104 mmol), DMSO (1 mL), and tetrabutylammonium hydroxide (0.208 mL, 0.208 mmol). The clear, colorless solution was stirred at room temperature for 15 minutes. Next, 2-bromo-1-(4-(5-(3-phenyl-4-(trifluoromethyl)isoxazol-5-yl)-1,2,4-oxadiazol-3-yl)phenyl)ethanol (prepared from intermediate 28C using the same procedure as described to make 1C) (25 mg, 0.052 mmol) was added and dissolved with gentle heating and sonication to yield a clear, pale yellow solution. The vial was placed on a reactor block set to 80° C. for 1.5h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of Example 41 was 4.5 mg, and its purity was 96%. $^1$H NMR (400 MHz, MeOD) δ ppm 8.10-8.31 (2H, m), 7.67 (4H, t, J=8.53 Hz), 7.53-7.63 (3H, m), 5.23 (1H, d, J=13.80 Hz), 4.38-4.55 (1H, m), 3.52-3.93 (2H, m), 3.15 (1H, br. s.), 2.25 (1H, br. s.), 1.76-2.09 (4H, m), 1.64 (2H, br. s.). MS (m+1)=529. HPLC Peak RT=2.24 minutes (Analytical Method C). Purity=96%.

Example 42

1-(2-Hydroxy-2-(4-(5-(3-phenyl-4-(trifluoromethyl)isoxazol-5-yl)-1,2,4-oxadiazol-3-yl)phenyl)ethyl)-6-methylpiperidine-2-carboxylic acid

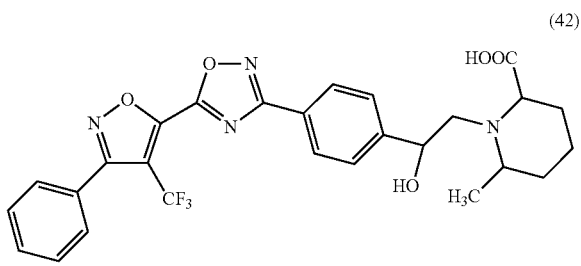 [SMILES: CC1CCCC(C(=O)O)N1CC(O)c1ccc(-c2noc(-c3onc(-c4ccccc4)c3C(F)(F)F)n2)cc1]
(42)

A two dram vial containing a stir bar was charged with 3-(4-(oxiran-2-yl)phenyl)-5-(3-phenyl-4-(trifluoromethyl)isoxazol-5-yl)-1,2,4-oxadiazole, Preparation 28C (21.84 mg, 0.055 mmol), butyl 6-methylpiperidine-2-carboxylate (10.9 mg, 0.055 mmol), acetonitrile (1.5 mL), and DIEA (0.029 mL, 0.164 mmol). The vial was flushed with nitrogen, sealed, and placed on a Reactor Block heated to 80° C. The reaction mixture was placed on a SPEED VAC® and evaporated to dryness. The reaction mixture was re-constituted in 2-propanol (3 mL) and cesium carbonate (82 mg, 0.251 mmol) was added. The solution was stirred for 30-45 minutes (with occasional sonication), then filtered to remove the inorganic solids. The solution was placed on a heated reactor block set to 80° C. The solvents were evaporated and the residue purified by preparative HPLC. The product containing fraction was evaporated and placed under high vacuum. 1-(2-hydroxy-2-(4-(5-(3-phenyl-4-(trifluoromethyl)isoxazol-5-yl)-1,2,4-oxadiazol-3-yl)phenyl)ethyl)-6-methylpiperidine-2-carboxylic acid, TFA (9 mg, 0.013 mmol, 23.06% yield). $^1$H NMR (500 MHz, MeOD) δ ppm 8.13 (2H, d, J=8.32 Hz), 7.56-7.63 (4H, m), 7.44-7.56 (3H, m), 5.18 (1H, dd, J=10.54, 2.22 Hz), 4.44 (1H, br. s.), 3.72-3.87 (1H, m), 3.54 (1H, dd, J=13.32, 2.77 Hz), 3.29-3.47 (2H, m), 2.23 (1H, d, J=14.43 Hz), 1.79-1.90 (2H, m), 1.65-1.79 (1H, m), 1.46-1.61 (1H, m), 0.98 (3H, d, J=6.10 Hz). MS (m+1)=543. HPLC Peak RT=1.15 minutes. Purity=92%.

Examples 43 to 53

The compounds of Examples 43 to 53 were prepared by the general coupling procedure described below:

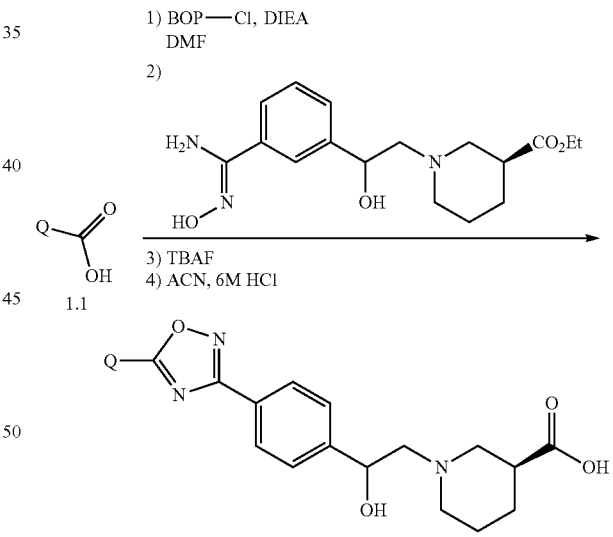

General Coupling Procedure

The commercially available carboxylic acid (1.1) (0.075 mmol) was weighed into 16×100 mm Wheaton tubes which were placed in a Bohdan MINIBLOCK® XT. 1 mL of a 0.08M solution of BOP—Cl in DMF (0.08 mmol) was added to each tube. The reactions were agitated at 400 rpm on an INNOVA® platform shaker at room temperature for 10 minutes. 1 mL of a 0.07 M DMF solution of (3S)-ethyl 1-(2-hydroxy-2-(4-((Z)—N'-hydroxycarbamimidoyl)phenyl)ethyl)piperidine-3-carboxylate, Preparation 14B (0.07 mmoles) was added to each vial and the reaction mixtures were agitated at 400 rpm on an INNOVA® platform shaker at room temperature. The Wheaton tubes were removed from the reactor, the reactions were analyzed by LCMS for the intermediate formation. To each vial was added TBAF in THF (0.075 mL, 0.075 mmol) and the reaction mixtures were agitated at 400 rpm on an INNOVA® platform shaker at 80° C. The samples were placed in a SPEEDVAC® to dry for 3 hours at 45° C. Each sample was dissolved in 1.0 mL of acetonitrile, followed by the addition of 6N HCl (1.0 mL) and the reaction mixtures were agitated at 400 rpm on an INNOVA® platform shaker at 50° C. and then diluted with 250 μL of MeOH for purified by preparative LCMS as described in Table 1. Products were collected and dried by Genevac (less than 45 C for 15 h).

TABLE 1

| Ex. | Q | Name | Observed MS Ion (M + H)+ | RT[a] [min] |
|---|---|---|---|---|
| 43 | 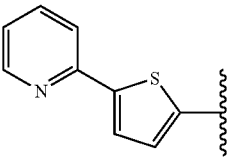 [SMILES: *c1ccc(-c2ccccn2)s1] | (3S)-1-(2-hydroxy-2-(4-(5-(5-(pyridin-2-yl)thiophen-2-yl)-1,2,4-oxadiazol-3-yl)phenyl)ethyl)piperidine-3-carboxylic acid | 477.2 | 3.93 |
| 44 | 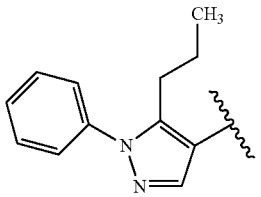 [SMILES: *c1cnn(-c2ccccc2)c1CCC] | (3S)-1-(2-hydroxy-2-(4-(5-(1-phenyl-5-propyl-1H-pyrazol-4-yl)-1,2,4-oxadiazol-3-yl)phenyl)ethyl)piperidine-3-carboxylic acid | 502.3 | 4.31 |
| 45 | 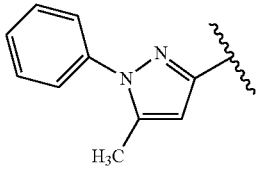 | (3S)-1-(2-hydroxy-2-(4-(5-(5-methyl-1-phenyl-1H-pyrazol-3-yl)-1,2,4-oxadiazol-3-yl)phenyl)ethyl)piperidine-3-carboxylic acid | 474.29 | 4.02 |
| 46 | 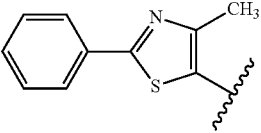 | (3S)-1-(2-hydroxy-2-(4-(5-(4-methyl-2-phenylthiazol-5-yl)-1,2,4-oxadiazol-3-yl)phenyl)ethyl)piperidine-3-carboxylic acid | 491.25 | 4.65 |
| 47 | 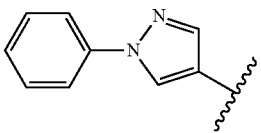 [SMILES: *c1cnn(-c2ccccc2)c1] | (3S)-1-(2-hydroxy-2-(4-(5-(1-phenyl-1H-pyrazol-4-yl)-1,2,4-oxadiazol-3-yl)phenyl)ethyl)piperidine-3-carboxylic acid | 460.26 | 4.0 |
| 48 | 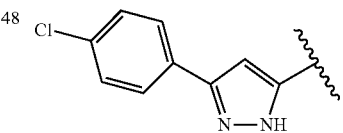 | (3S)-1-(2-(4-(5-(3-(4-chlorophenyl)-1H-pyrazol-5-yl)-1,2,4-oxadiazol-3-yl)phenyl)-2-hydroxyethyl)piperidine-3-carboxylic acid | 494.23 | 4.11 |
| 49 | 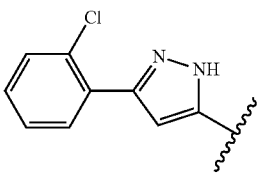 [SMILES: *c1cc(-c2ccccc2Cl)n[nH]1] | (3S)-1-(2-(4-(5-(3-(2-chlorophenyl)-1H-pyrazol-5-yl)-1,2,4-oxadiazol-3-yl)phenyl)-2-hydroxyethyl)piperidine-3-carboxylic acid | 494.19 | 3.86 |
| 50 | 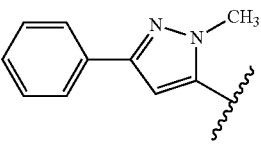 [SMILES: *c1cc(-c2ccccc2)nn1C] | (3S)-1-(2-hydroxy-2-(4-(5-(1-methyl-3-phenyl-1H-pyrazol-5-yl)-1,2,4-oxadiazol-3-yl)phenyl)ethyl)piperidine-3-carboxylic acid | 474.32 | 4.4 |

TABLE 1-continued

| Ex. | Q | Name | Observed MS Ion (M + H)+ | RT[a] [min] |
|---|---|---|---|---|
| 51 | (pyrazole with pyridin-2-yl and ethyl substituents) | (3S)-1-(2-(4-(5-(5-ethyl-1-(pyridin-2-yl)-1H-pyrazol-4-yl)-1,2,4-oxadiazol-3-yl)phenyl)-2-hydroxyethyl)piperidine-3-carboxylic acid | 489.29 | 3.97 |
| 52 | (pyrazole with phenyl and methyl substituents) | (3S)-1-(2-hydroxy-2-(4-(5-(5-methyl-1-phenyl-1H-pyrazol-4-yl)-1,2,4-oxadiazol-3-yl)phenyl)ethyl)piperidine-3-carboxylic acid | 474.17 | 1.7 |
| 53 | (isoxazole with 4-chlorophenyl substituent) | (3S)-1-(2-(4-(5-(5-(4-chlorophenyl)isoxazol-3-yl)-1,2,4-oxadiazol-3-yl)phenyl)-2-hydroxyethyl)piperidine-3-carboxylic acid | 495.04 | 2.13 |

[a] Analyzed on a Waters Masslynx instrument equipped with a 4.6x50 mm 2.7 μM MacMod Halo C18 column and using a method of 0-100% B solvent over 5.3 min at a flow rate of 3 mL/min. Solvent A is 5:95 acetonitrile/water; solvent B is 95:5 acetonitrile/water and both contain 10 mM ammonium acetate.

Example 54

2-((3R)-1-(2-Hydroxy-2-(4-(5-(3-(pyridin-2-yl)-4-(trifluoromethyl)isoxazol-5yl-1,2,4-oxadiazol-3-yl)phenyl)ethyl)piperidin-3-yl)acetic acid (54)

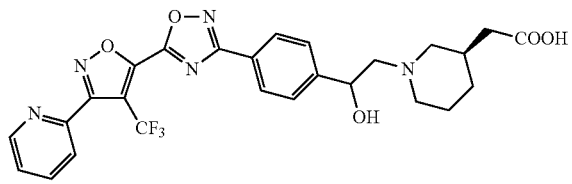

Under an argon atmosphere, 3-(pyridin-2-yl)-4-(trifluoromethyl)isoxazole-5-carboxylic acid, Int-IV (40 mg, 0.155 mmol) was suspended in dichloromethane (1.5 mL) with sonication and DMF (5 μl, 0.065 mmol) was added. Oxalyl chloride (54.3 μl, 0.620 mmol) was added dropwise over 1-2 minutes. The reaction vial was flushed with argon and sealed. After 3 h, the contents were concentrated in vacuo. The material was re-constituted in dichloromethane and a solution of ethyl 2-((3R)-1-(2-hydroxy-2-(4-((Z)—N'-hydroxycarbamimidoyl)phenyl)ethyl)piperidin-3-yl)acetate (54.1 mg, 0.155 mmol) in DCM (1-2 mL) was added. The reaction mixture was stirred for 3 days at room temperature and then purified by Prep HPLC to afford ethyl 2-((3R)-1-(2-hydroxy-2-(4-(5-(3-(pyridin-2-yl)-4-(trifluoromethyl)isoxazol-5-yl)-1,2,4-oxadiazol-3-yl)phenyl)ethyl)piperidin-3-yl)acetate which was suspended in dioxane (2-3 mL) and 3N aq HCl (1 mL) was added. The mixture was placed in a sand bath heated to 50° C. overnight. The solution was evaporated, re-evaporated from chloroform-d and then placed under high vacuum to give 2-((3R)-1-(2-hydroxy-2-(4-(5-(3-(pyridin-2-yl)-4-(trifluoromethyl)isoxazol-5-yl)-1,2,4-oxadiazol-3-yl)phenyl)ethyl)piperidin-3-yl)acetic acid as a clear colorless film. $^1$H NMR (500 MHz, MeOD) δ ppm 8.69 (1 H, d, J=4.72 Hz), 8.14 (2H, d, J=8.32 Hz), 7.95 (1H, td, J=7.70, 1.80 Hz), 7.86 (1H, d, J=7.77 Hz), 7.61 (2H, d, J=8.32 Hz), 7.49-7.56 (1H, m), 5.17 (1H, dd, J=9.71, 4.16 Hz), 3.80 (1H, br. s.), 3.52-3.67 (4H, m), 2.89 (1H, br. s.), 2.73 (1H, t, J=11.93 Hz), 2.18-2.39 (3H, m), 1.79-1.94 (3H, m). HPLC RT=0.77 min, MH+=544. Waters Masslynx instrument equipped with a BEH 2.1×50 mm 17 uM C18 column and a method of 2-98% B solvent over 1.6 min at a flow rate of 0.8 mL/min. Solvent A is water; solvent B is acetonitrile and both contain 0.5% TFA.

Example 55

(3S)-1-(1-Hydroxy-2-methyl-1-(4-(5-(3-phenyl-4-(trifluoromethyl)isoxazol-5-yl)-1,2,4-oxadiazol-3-yl)phenyl)propan-2-yl)piperidine-3-carboxylic acid, TFA (55)

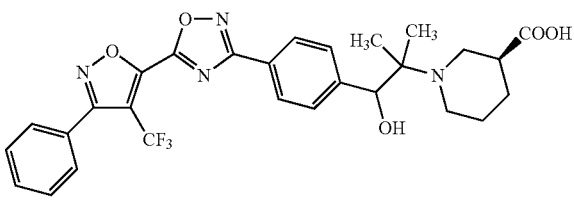

Preparation 55A: 4-Isobutyrylbenzonitrile (55A)

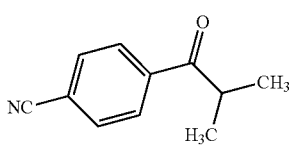

To 4-(1-hydroxy-2-methylpropyl)benzonitrile (2.500 g, 14.27 mmol) (Prepared according to the method of Keh et al., J. Amer. Chem. Soc., 125(14):4062-4063 (2003)) in dry DCM (200 mL) was added Dess-Martin Periodinane (7.26 g, 17.12 mmol The reaction mixture was stirred for 2 h. The reaction mixture was diluted with DCM and washed with 1N NaOH solution. The organic layer was dried with MgSO₄, filtered, and concentrated to yield 2.4 g of 4-isobutyrylbenzonitrile. MS (m+1)=174. HPLC Peak RT=1.60 minutes (Analytical Method B).

Preparation 55B:
4-(2-Bromo-2-methylpropanoyl)benzonitrile

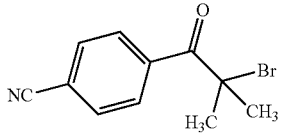

(55B)

To a mixture of 4-isobutyrylbenzonitrile (2.4 g, 13.86 mmol) in acetic acid (50 mL) was added bromine (0.8 mL, 15.53 mmol). The mixture was stirred for 3 days and then concentrated in vacuo. The reaction mixture was diluted with ethyl acetate and washed with sat NaHCO₃. The organic layer was dried MgSO₄, filtered, concentrated, and then purified on silica gel using an EtOAc/hexanes gradient to yield 2.5 g of 4-(2-bromo-2-methylpropanoyl)benzonitrile. ¹H NMR (400 MHz, chloroform-d) δ ppm 8.00-8.07 (2H, m), 7.76-7.79 (2H, m), 1.24 (3H, s), 1.22 (3H, s).

Preparation 55C: 4 (S)-Ethyl 1-(1-(4-cyanophenyl)-2-methyl-1-oxopropan-2-yl)piperidine-3-carboxylate

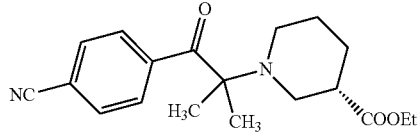

(55C)

To a mixture of (S)-ethyl piperidine-3-carboxylate (125 mg, 0.793 mmol), cesium carbonate (258 mg, 0.793 mmol), and sodium iodide (13 mg, 0.087 mmol) in DMSO (2 mL) was added 4-(2-bromo-2-methylpropanoyl)benzonitrile (200 mg, 0.793 mmol). The reaction mixture was heated at 90° C. overnight. The reaction mixture was diluted with ethyl acetate and washed with sat NaCl. The organic layer was dried MgSO₄, filtered, concentrated, and then purified on silica gel using an EtOAc/hexanes gradient to yield 90 mg of 4 (S)-ethyl 1-(1-(4-cyanophenyl)-2-methyl-1-oxopropan-2-yl)piperidine-3-carboxylate. MS (m+1)=329. HPLC Peak RT=1.22 minutes (Analytical Method B).

Preparation 55D: (3S)-Ethyl 1-(1-hydroxy-1-(4-((Z)—N'-hydroxycarbamimidoyl)phenyl)-2-methylpropan-2-yl)piperidine-3-carboxylate

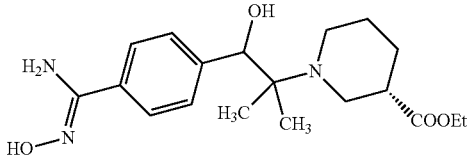

(55D)

To a mixture of (S)-ethyl 1-(1-(4-cyanophenyl)-2-methyl-1-oxopropan-2-yl)piperidine-3-carboxylate (90 mg, 0.274 mmol) in MeOH (5 mL) was added sodium borohydride (15 mg, 0.396 mmol). After 1 hr, the reaction was quenched with water. The reaction mixture was diluted with ethyl acetate and washed with sat NaCl. The organic layer was dried MgSO₄, filtered, and concentrated. To a mixture of hydroxylamine hydrochloride (38.1 mg, 0.548 mmol) and sodium bicarbonate (92 mg, 1.096 mmol) in 2-propanol (10 mL) was added the crude product from step one. The reaction mixture was heated at 75° C. overnight. The reaction mixture was diluted with ethyl acetate and washed with H₂O. The organic layer was dried MgSO₄, filtered, and concentrated to yield 100 mg of (3S)-ethyl 1-(1-hydroxy-1-(4-((Z)—N'-hydroxycarbamimidoyl)phenyl)-2-methylpropan-2-yl)piperidine-3-carboxylate. MS (m+1)=364. HPLC Peak RT=0.27 minutes (Analytical Method B).

Example 55

3-Fluoro-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid To a mixture of 3-phenyl-4-(trifluoromethyl)isoxazole-5-carboxylic acid (70.8 mg, 0.275 mmol) and oxalyl chloride (0.048 mL, 0.550 mmol) in DCM (5 mL) was added DMF (3 drops) at 25° C. The reaction mixture was stirred at room temperature for 2 hours. The reaction mixture was concentrated in vacuo and dried. The residue was dissolved in acetonitrile (5.00 mL). Next, DIEA (0.048 mL, 0.275 mmol) and (3S)-ethyl 1-(1-hydroxy-1-(4-((Z)—N'-hydroxycarbamimidoyl)phenyl)-2-methylpropan-2-yl)piperidine-3-carboxylate (100 mg, 0.275 mmol) were added. The reaction mixture was stirred at 25° C. After stirring overnight, the reaction mixture showed a significant amount of coupled but uncyclized material. Next, 1M TBAF in THF (0.275 mL, 0.275 mmol) was added and reaction mixture was stirred for another 48 hrs. The reaction mixture was filtered and purified by HPLC. HPLC conditions: PHENOMENEX® Luna C18 5 micron column (250×30 mm); 25-100% CH₃CN/water (0.1% TFA); 25 minute gradient; 30 mL/min. Fractions with correct mass were isolated and concentrated in vacuo. The residue was treated with 6N HCl/dioxane (1:1) at 50° C. overnight. The reaction mixture was filtered and purified by HPLC. HPLC conditions: PHENOMENEX® Luna C18 5 micron column (250×30 mm); 25-100% CH₃CN/water (0.1% TFA); 25 minute gradient; 30 mL/min. Isolated fractions with correct mass and freeze-dried overnight. Recovered 32 mg of (3S)-1-(1-hydroxy-2-methyl-1-(4-(5-(3-phenyl-4-(trifluoromethyl)isoxazol-5-yl)-1,2,4-oxadiazol-3-yl)phenyl)propan-2-yl)piperidine-3-carboxylic acid, TFA. MS (m+1)=547. HPLC Peak RT=1.90 minutes (Analytical Method B). Purity=92%.

Example 56

2-(1-((S)-2-Hydroxy-2-(4-(5-(3-phenyl-4-(trifluoromethyl)isoxazol-5-yl)-1,2,4-oxadiazol-3-yl)phenyl)ethyl)piperidin-3-yl)-2-methylpropanoic acid

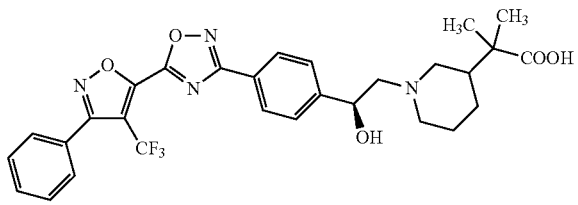
(56)

Preparation 56A: Ethyl 2-methyl-2-(pyridin-3-yl)propanoate

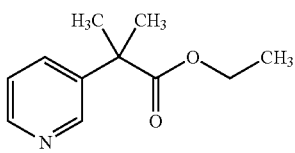
(56A)

To a mixture of ethyl 2-methyl-2-(pyridin-3-yl)propanoate (500 mg, 2.59 mmol) (prepared by the procedure of Ujjainwalla et al., *Tetrahedron Letters*, 42:6441-6446 (2001)) in acetic acid (10 mL) was added platinum(IV) oxide (100 mg, 0.440 mmol). The reaction mixture was charged with hydrogen at 50 psi and placed on a Parr shaker for 3 days. Solids were filtered and concentrated in vacuo to give the desired product as an AcOH salt.

Example 56

2-(1-(2-Hydroxy-2-(4-(5-(3-phenyl-4-(trifluoromethyl)isoxazol-5-yl)-1,2,4-oxadiazol-3-yl)phenyl)ethyl)piperidin-3-yl)-2-methylpropanoic acid To a mixture of (S)-3-(4-(oxiran-2-yl)phenyl)-5-(3-phenyl-4-(trifluoromethyl)isoxazol-5-yl)-1,2,4-oxadiazole, Preparation 28C-peak 1 (30 mg, 0.075 mmol) and ethyl 2-methyl-2-(piperidin-3-yl)propanoate (14.97 mg, 0.075 mmol) in EtOH (10 mL) was added cesium carbonate (147 mg, 0.451 mmol). The reaction mixture was heated at 80° C. overnight. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Fractions with correct mass were isolated and concentrated in vacuo. This residue was heated in 6N HCl/dioxane (1:1) at 60° C. for 3 days. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Fractions with correct mass were isolated and freeze-dried overnight. Obtained 6 mg of 2-(1-((S)-2-hydroxy-2-(4-(5-(3-phenyl-4-(trifluoromethyl)isoxazol-5-yl)-1,2,4-oxadiazol-3-yl)phenyl)ethyl)piperidin-3-yl)-2-methylpropanoic. $^1$H NMR (400 MHz, MeOD) δ ppm 8.14 (2H, d, J=8.36 Hz), 7.57-7.64 (4H, m), 7.44-7.55 (3H, m), 5.09-5.27 (1H, m), 3.70 (2H, d, J=10.34 Hz), 3.57 (1H, br. s.), 3.23-3.27 (2H, m), 2.79-2.97 (1H, m), 1.73-1.95 (2H, m), 1.24-1.42 (2H, m), 1.15 (3H, d, J=2.86 Hz), 1.11 (3H, s), 0.76 (1H, dd, J=11.44, 9.68 Hz). MS (m+1)=571 HPLC Peak RT=3.35 minutes (Analytical Method A). Purity=92%.

Example 57

(S)-1-((S)-2-Hydroxy-2-(4-(5-(1-phenyl-5-(trifluoromethyl)-1H-pyrazol-4-yl)-1,2,4-oxadiazol-3-yl)phenyl)ethyl)piperidine-3-carboxylic acid

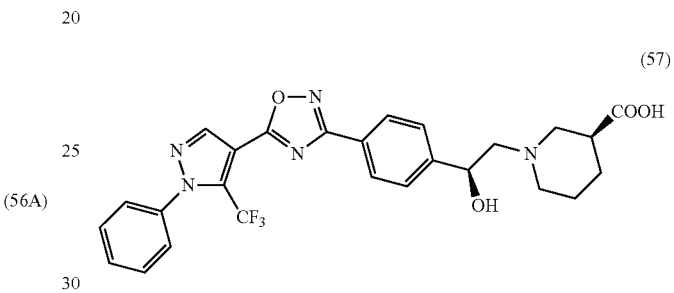
(57)

To a mixture of ((S)-ethyl 1-((S)-2-hydroxy-2-(4-((Z)—N'-hydroxycarbamimidoyl)phenyl)ethyl)piperidine-3-carboxylate, Preparation 14B (92 mg, 0.273 mmol) and DIEA (0.048 mL, 0.273 mmol) in acetonitrile (5 mL) was added the 1-phenyl-5-(trifluoromethyl)-1H-pyrazole-4-carbonyl chloride (75 mg, 0.273 mmol). After stirring 1 hour, 1M TBAF in THF (0.273 mL, 0.273 mmol) was added and the reaction mixture was stirred overnight at 60° C. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 30 mL/min. Isolated fractions with correct mass and concentrated in vacuo. This product was treated with 6N HCl/dioxane at 60° C. overnight. Solvents were removed in vacuo to give 52 mg of Example 57. $^1$H NMR (400 MHz, MeOD) δ ppm 8.38 (1H, s), 8.07 (2H, m), 7.60 (2H, m), 7.43-7.56 (5H, m), 5.10-5.28 (1H, m), 3.82-3.99 (1H, m), 3.51-3.69 (1H, m), 3.29 (2H, d, J=5.50 Hz), 2.78-3.17 (2H, m), 2.04-2.04 (1H, m), 1.94 (1H, br. s.), 1.46-1.67 (1H, m), 1.13-1.41 (1H, m), 0.93 (1H, t, J=6.82 Hz).

Examples 58 to 107

The pyrazole carboxylic acids Int-VI through Int-XXXVI found in Table 2, were prepared by the general procedure described below:

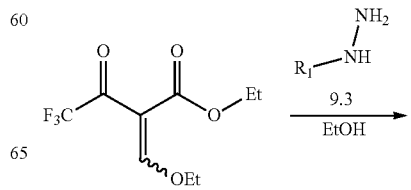

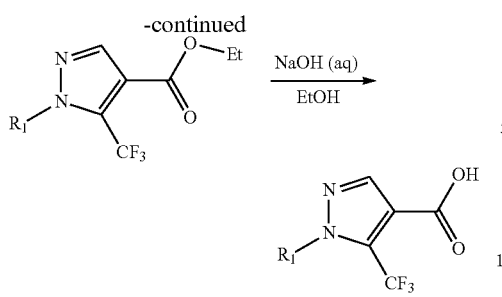

General Procedure

To a solution of the hydrazine (5.3) (10 mmol) in ethanol was added (E)-ethyl 2-(ethoxymethylene)-4,4,4-trifluoro-3-oxobutanoate (1.0 mmol). The reaction mixture was heated to 80° C. for 1 h. The reaction mixture was diluted with ethyl acetate and washed with saturated NaCl. The organic layer was dried with $MgSO_4$, filtered, and concentrated to give the desired pyrazole ester. The ester was then dissolved in ethanol and treated with 1N NaOH for 2 hours. The reaction mixture was diluted with ethyl acetate and washed with 1N HCl. The organic layer was dried with $MgSO_4$, filtered, and concentrated to give the desired pyrazole acid.

TABLE 2

| Int. | Q | Name | Obs. MS Ion (M + H)+ | RTa [min] |
|---|---|---|---|---|
| VI | | 1-cyclohexyl-5-(trifluoromethyl)-1H-pyrazole-4-carboxylic acid | 263 | 2.07 |
| VII | | 1-(3-chloropyridin-2-yl)-5-(trifluoromethyl)-1H-pyrazole-4-carboxylic acid | 292 | 1.31 |
| VIII | | 1-(6-chloropyridin-2-yl)-5-(trifluoromethyl)-1H-pyrazole-4-carboxylic acid | 292 | 1.76 |
| IX | | 5-(trifluoromethyl)-1-(5-(trifluoromethyl)pyridin-2-yl)-1H-pyrazole-4-carboxylic acid | 326 | 0.87 |
| X | | 1-(tetrahydro-2H-pyran-4-yl)-5-(trifluoromethyl)-1H-pyrazole-4-carboxylic acid | 265 | 1.43 |
| XI | | 1-(5-chloropyridin-2-yl)-5-(trifluoromethyl)-1H-pyrazole-4-carboxylic acid | 292 | 1.73 |
| XII | | 1-(2,2,2-trifluoroethyl)-5-(trifluoromethyl)-1H-pyrazole-4-carboxylic acid | — | 1.52 |

TABLE 2-continued

| Int. | Q | Name | Obs. MS Ion (M + H)+ | RTa [min] |
|---|---|---|---|---|
| XIII | (2-chlorophenyl, 5-CF3, pyrazole-4-COOH) | 1-(2-chlorophenyl)-5-(trifluoromethyl)-1H-pyrazole-4-carboxylic acid | 29 | 1.72 |
| XIV | (2,4-difluorophenyl, 5-CF3, pyrazole-4-COOH) | 1-(2,4-difluorophenyl)-5-(trifluoromethyl)-1H-pyrazole-4-carboxylic acid | 293 | 1.80 |
| XV | (2-(trifluoromethyl)phenyl, 5-CF3, pyrazole-4-COOH) | 5-(trifluoromethyl)-1-(2-(trifluoromethyl)phenyl)-1H-pyrazole-4-carboxylic acid | 325 | 1.81 |
| XVI | (3-(trifluoromethyl)phenyl, 5-CF3, pyrazole-4-COOH) | 5-(trifluoromethyl)-1-(3-(trifluoromethyl)phenyl)-1H-pyrazole-4-carboxylic acid | 325 | 1.97 |
| XVII | (4-(trifluoromethyl)phenyl, 5-CF3, pyrazole-4-COOH) | 5-(trifluoromethyl)-1-(4-(trifluoromethyl)phenyl)-1H-pyrazole-4-carboxylic acid | 325 | 1.99 |
| XVIII | (o-tolyl, 5-CF3, pyrazole-4-COOH) | 1-o-tolyl-5-(trifluoromethyl)-1H-pyrazole-4-carboxylic acid | 271 | 1.82 |
| XIX | (p-tolyl, 5-CF3, pyrazole-4-COOH) | 1-p-tolyl-5-(trifluoromethyl)-1H-pyrazole-4-carboxylic acid | 271 | 1.87 |
| XX | (4-isopropylphenyl, 5-CF3, pyrazole-4-COOH) | 1-(4-isopropylphenyl)-5-(trifluoromethyl)-1H-pyrazole-4-carboxylic acid | 299 | 2.08 |
| XXI | (4-methoxyphenyl, 5-CF3, pyrazole-4-COOH) | 1-(4-methoxyphenyl)-5-(trifluoromethyl)-1H-pyrazole-4-carboxylic acid | 287 | 1.76 |
| XXII | (isobutyl, 5-CF3, pyrazole-4-COOH) | 1-isobutyl-5-(trifluoromethyl)-1H-pyrazole-4-carboxylic acid | 237 | 0.85 |

TABLE 2-continued

| Int. | Q | Name | Obs. MS Ion (M + H)+ | RTa [min] |
|---|---|---|---|---|
| XXIII | (5-fluoropyridin-2-yl, 5-CF3, pyrazole-4-COOH) | 1-(5-fluoropyridin-2-yl)-5-(trifluoromethyl)-1H-pyrazole-4-carboxylic acid | 276 | 1.53 |
| XXIV | (5-chloro-3-fluoropyridin-2-yl, 5-CF3, pyrazole-4-COOH) | 1-(5-chloro-3-fluoropyridin-2-yl)-5-(trifluoromethyl)-1H-pyrazole-4-carboxylic acid | 310 | 0.83 |
| XXV | (5-ethoxy-3-fluoropyridin-2-yl, 5-CF3, pyrazole-4-COOH) | 1-(5-ethoxy-3-fluoropyridin-2-yl)-5-(trifluoromethyl)-1H-pyrazole-4-carboxylic acid | 320 | 0.84 |
| XXVI | (pyrimidin-2-yl, 5-CF3, pyrazole-4-COOH) | 1-(pyrimidin-2-yl)-5-(trifluoromethyl)-1H-pyrazole-4-carboxylic acid | 259 | 0.64 |
| XXVII | (pyridin-3-yl, 5-CF3, pyrazole-4-COOH) | 1-(pyridin-3-yl)-5-(trifluoromethyl)-1H-pyrazole-4-carboxylic acid | 258 | 1.25 |
| XXVIII | (3,5-dichloropyridin-2-yl, 5-CF3, pyrazole-4-COOH) | 1-(3,5-dichloropyridin-2-yl)-5-(trifluoromethyl)-1H-pyrazole-4-carboxylic acid | 326 | 0.87 |
| XXIX | (2,4-dichlorophenyl, 5-CF3, pyrazole-4-COOH) | 1-(2,4-dichlorophenyl)-5-(trifluoromethyl)-1H-pyrazole-4-carboxylic acid | 327 | 2.01 |
| XXX | (4-chloro-2-methylphenyl, 5-CF3, pyrazole-4-COOH) | 1-(4-chloro-2-methylphenyl)-5-(trifluoromethyl)-1H-pyrazole-4-carboxylic acid | 305 | 2.02 |
| XXXI | (4-chloro-3-methylphenyl, 5-CF3, pyrazole-4-COOH) | 1-(4-chloro-3-methylphenyl)-5-(trifluoromethyl)-1H-pyrazole-4-carboxylic acid | 305 | 2.07 |
| XXXII | (3,4-dichlorophenyl, 5-CF3, pyrazole-4-COOH) | 1-(3,4-dichlorophenyl)-5-(trifluoromethyl)-1H-pyrazole-4-carboxylic acid | 325 | 0.92 |

TABLE 2-continued

| Int. | Q | Name | Obs. MS Ion (M + H)+ | RTa [min] |
|---|---|---|---|---|
| XXXIII | (structure) | 1-(4-methylpyridin-2-yl)-5-(trifluoromethyl)-1H-pyrazole-4-carboxylic acid | 272 | 1.58 |
| XXXIV | (structure) | 1-(4-methylpyridin-2-yl)-5-(trifluoromethyl)-1H-pyrazole-4-carboxylic acid | 272 | 0.78 |
| XXXV | (structure) | 1-(5-chloro-3-(trifluoromethyl)pyridin-2-yl)-5-(trifluoromethyl)-1H-pyrazole-4-carboxylic acid | 360 | 0.89 |
| XXXVI | (structure) | 1-(6-methyl-4-(trifluoromethyl)pyridin-2-yl)-5-(trifluoromethyl)-1H-pyrazole-4-carboxylic acid | 340 | 0.94 |

The substituted hydrazines used to make the intermediates in Table 2 are either commercially available or prepared using well-established synthetic procedures. Hydrazine 5-fluoro-2-hydrazinylpyridine was prepared as follows:

To 2,5-difluoropyridine (3 g, 26.1 mmol) was added hydrazine (1.636 ml, 52.1 mmol) and the contents were heated in a microwave at 120° C. for 1 h. Upon cooling, a white solid formed. The solid was collected by filtration, washed with ether and dried in vacuo to give 1.74 g of 5-fluoro-2-hydrazinylpyridine, hydrofluoride that was used without further purification. $^1$H NMR (400 MHz, DMSO-d$_6$) δ ppm 7.96 (1H, d, J=2.86 Hz), 7.42 (1H, td, J=8.80, 2.86 Hz), 7.35 (1H, br. s.), 6.73 (1H, dd, J=9.02, 3.74 Hz), 4.12 (2H, br. s.).

Examples 58 to 107 in Table 3 were prepared by the general coupling procedure described below:

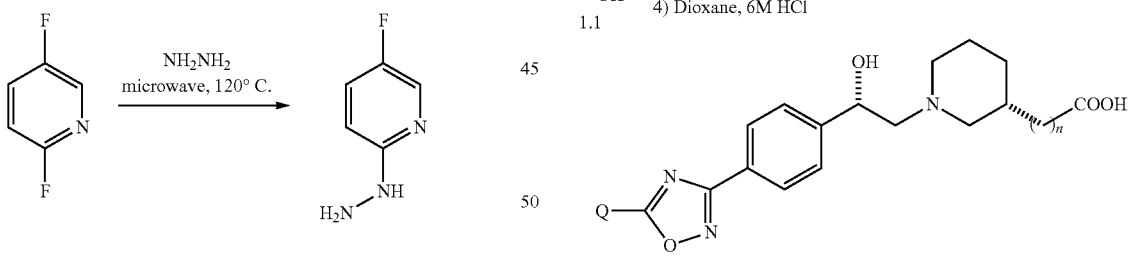

General Coupling Procedure

To a mixture of the carboxylic acid (1.1) (0.065 mmol) in DCM (1 mL) was added oxalyl chloride (0.011 mL, 0.129 mmol) and 1 drop of DMF. The reaction mixture was stirred for 30 minutes, then concentrated and reconstituted in THF (2 mL). Either ethyl 2-((R)-1-((S)-2-(tert-butyldimethylsilyloxy)-2-(4-((Z)—N'-hydroxycarbamimidoyl)phenyl)ethyl)piperidin-3-yl)acetate (0.129 mL, 0.065 mmol) and DIEA (0.011 mL, 0.065 mmol) were added. After 1 hour, potassium tert-butoxide (21.78 mg, 0.194 mmol) was added and the reaction mixture was heated at 60° C. overnight. Solvent was removed and residue was treated with 6N HCl/dioxane at 60° C. for 2 h. The reaction mixture was filtered and purified by HPLC. Products were collected and dried.

TABLE 3

| Ex. | Q | n | Name | Obs. MS Ion (M + H)+ | RT$^a$ [min] |
|---|---|---|---|---|---|
| 58 | phenyl | 1 | 2-((R)-1-((S)-2-hydroxy-2-(4-(5-(1-phenyl-5-(trifluoromethyl)-1H-pyrazol-4-yl)-1,2,4-oxadiazol-3-yl)phenyl)ethyl)piperidin-3-yl)acetic acid, HCl | 543 | 3.03 |
| 59 | cyclohexyl | 1 | 2-((R)-1-((S)-2-(4-(5-(1-cyclohexyl-5-(trifluoromethyl)-1H-pyrazol-4-yl)-1,2,4-oxadiazol-3-yl)phenyl)-2-hydroxyethyl)piperidin-3-yl)acetic acid, HCl | 548 | 3.46 |
| 60 | 3-chloropyridin-2-yl | 1 | 2-((3R)-1-((2S)-2-(4-(5-(1-(3-chloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, TFA | 577 | 2.83 |
| 61 | 6-chloropyridin-2-yl | 1 | 2-((R)-1-((S)-2-(4-(5-(1-(6-chloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl | 577 | 3.06 |
| 62 | 4-fluorophenyl | 1 | 2-((R)-1-((S)-2-(4-(5-(1-(4-fluorophenyl)-5-(trifluoromethyl)-1H-pyrazol-4-yl)-1,2,4-oxadiazol-3-yl)phenyl)-2-hydroxyethyl)piperidin-3-yl)acetic acid, HCl | 560 | 3.06 |
| 63 | 3-chlorophenyl | 1 | 2-((R)-1-((S)-2-(4-(5-(1-(3-chlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl | 576 | 3.26 |
| 64 | pyridin-2-yl | 1 | 2-((R)-1-((S)-2-hydroxy-2-(4-(5-(1-(pyridin-2-yl)-5-(trifluoromethyl)-1H-pyrazol-4-yl)-1,2,4-oxadiazol-3-yl)phenyl)ethyl)piperidin-3-yl)acetic acid, tetrabutylammonium salt | 543 | — |
| 65 | 4-chlorophenyl | 1 | 2-((R)-1-((S)-2-(4-(5-(1-(4-chlorophenyl)-5-(trifluoromethyl)-1H-pyrazol-4-yl)-1,2,4-oxadiazol-3-yl)phenyl)-2-hydroxyethyl)piperidin-3-yl)acetic acid | 576 | 2.16 |
| 66 | 4-bromophenyl | 1 | 2-((R)-1-((S)-2-(4-(5-(1-(4-bromophenyl)-5-(trifluoromethyl)-1H-pyrazol-4-yl)-1,2,4-oxadiazol-3-yl)phenyl)-2-hydroxyethyl)piperidin-3-yl)acetic acid | 620 | 2.12 |
| 67 | m-tolyl | 1 | 2-((R)-1-((S)-2-hydroxy-2-(4-(5-(1-m-tolyl-5-(trifluoromethyl)-1H-pyrazol-4-yl)-1,2,4-oxadiazol-3-yl)phenyl)ethyl)piperidin-3-yl)acetic acid, HCl | 556 | 3.22 |

TABLE 3-continued

| Ex. | Q | n | Name | Obs. MS Ion (M + H)+ | RT[a] [min] |
|---|---|---|---|---|---|
| 68 | 2-methoxyphenyl | 1 | 2-((3R)-1-((2S)-2-hydroxy-2-(4-(5-(1-(2-methoxyphenyl)-5-(trifluoromethyl)-1H-pyrazol-4-yl)-1,2,4-oxadiazol-3-yl)phenyl)ethyl)piperidin-3-yl)acetic acid | 572 | 1.77 |
| 69 | tetrahydro-2H-pyran-4-yl | 1 | 2-((R)-1-((S)-2-hydroxy-2-(4-(5-(1-(tetrahydro-2H-pyran-4-yl)-5-(trifluoromethyl)-1H-pyrazol-4-yl)-1,2,4-oxadiazol-3-yl)phenyl)ethyl)piperidin-3-yl)acetic acid | 550 | 0.75 |
| 70 | 5-chloropyridin-2-yl | 1 | 2-((R)-1-((S)-2-(4-(5-(1-(5-chloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl | 577 | 0.84 |
| 71 | 2,2,2-trifluoroethyl | 1 | 2-((R)-1-((S)-2-hydroxy-2-(4-(5-(1-(2,2,2-trifluoroethyl)-5-(trifluoromethyl)-1H-pyrazol-4-yl)-1,2,4-oxadiazol-3-yl)phenyl)ethyl)piperidin-3-yl)acetic acid, HCl | 548 | 2.86 |
| 72 | 2-chlorophenyl | 1 | 2-((3R)-1-((2S)-2-(4-(5-(1-(2-chlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl | 576 | 0.83 |
| 73 | 2,4-difluorophenyl | 1 | 2-((3R)-1-((2S)-2-(4-(5-(1-(2,4-difluorophenyl)-5-(trifluoromethyl)-1H-pyrazol-4-yl)-1,2,4-oxadiazol-3-yl)phenyl)-2-hydroxyethyl)piperidin-3-yl)acetic acid, HCl | 578 | 0.83 |
| 74 | 2-(trifluoromethyl)phenyl | 1 | 2-((3R)-1-((2S)-2-hydroxy-2-(4-(5-(5-(trifluoromethyl)-1-(2-(trifluoromethyl)phenyl)-1H-pyrazol-4-yl)-1,2,4-oxadiazol-3-yl)phenyl)ethyl)piperidin-3-yl)acetic acid, HCl | 610 | 0.84 |
| 75 | 3-(trifluoromethyl)phenyl | 1 | 2-((R)-1-((S)-2-hydroxy-2-(4-(5-(5-(trifluoromethyl)-1-(3-(trifluoromethyl)phenyl)-1H-pyrazol-4-yl)-1,2,4-oxadiazol-3-yl)phenyl)ethyl)piperidin-3-yl)acetic acid, HCl | 610 | 0.87 |
| 76 | 4-(trifluoromethyl)phenyl | 1 | 2-((R)-1-((S)-2-hydroxy-2-(4-(5-(5-(trifluoromethyl)-1-(4-(trifluoromethyl)phenyl)-1H-pyrazol-4-yl)-1,2,4-oxadiazol-3-yl)phenyl)ethyl)piperidin-3-yl)acetic acid | 610 | 1.68 |
| 77 | o-tolyl | 1 | 2-((3R)-1-((2S)-2-hydroxy-2-(4-(5-(1-o-tolyl-5-(trifluoromethyl)-1H-pyrazol-4-yl)-1,2,4-oxadiazol-3-yl)phenyl)ethyl)piperidin-3-yl)acetic acid | 556 | 1.5 |

TABLE 3-continued

| Ex. | Q | n | Name | Obs. MS Ion (M + H)+ | RT[a] [min] |
|---|---|---|---|---|---|
| 78 | H3C-C6H4- | 1 | 2-((R)-1-((S)-2-hydroxy-2-(4-(5-(1-p-tolyl-5-(trifluoromethyl)-1H-pyrazol-4-yl)-1,2,4-oxadiazol-3-yl)phenyl)ethyl)piperidin-3-yl)acetic acid | 556 | 1.56 |
| 79 | (H3C)2CH-C6H4- | 1 | 2-((R)-1-((S)-2-hydroxy-2-(4-(5-(1-(4-isopropylphenyl)-5-(trifluoromethyl)-1H-pyrazol-4-yl)-1,2,4-oxadiazol-3-yl)phenyl)ethyl)piperidin-3-yl)acetic acid | 584 | 1.89 |
| 80 | H3CO-C6H4- | 1 | 2-((R)-1-((S)-2-hydroxy-2-(4-(5-(1-(4-methoxyphenyl)-5-(trifluoromethyl)-1H-pyrazol-4-yl)-1,2,4-oxadiazol-3-yl)phenyl)ethyl)piperidin-3-yl)acetic acid | 572 | 1.42 |
| 81 | isobutyl | 1 | 2-((R)-1-((S)-2-hydroxy-2-(4-(5-(1-isobutyl-5-(trifluoromethyl)-1H-pyrazol-4-yl)-1,2,4-oxadiazol-3-yl)phenyl)ethyl)piperidin-3-yl)acetic acid, HCl | 522 | 3.12 |
| 82 | 5-fluoropyridin-2-yl | 1 | 2-((R)-1-((S)-2-(4-(5-(1-(5-fluoropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl | 560 | 1.82 |
| 83 | 5-chloro-3-fluoropyridin-2-yl | 1 | 2-((3R)-1-((2S)-2-(4-(5-(1-(5-chloro-3-fluoropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl | 595 | 3.07 |
| 84 | 5-methoxy-3-fluoropyridin-2-yl | 1 | 2-((3R)-1-((2S)-2-(4-(5-(1-(5-ethoxy-3-fluoropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl | 605 | 3.07 |
| 85 | pyrimidin-2-yl | 1 | 2-((R)-1-((S)-2-hydroxy-2-(4-(5-(1-(pyrimidin-2-yl)-5-(trifluoromethyl)-1H-pyrazol-4-yl)-1,2,4-oxadiazol-3-yl)phenyl)ethyl)piperidin-3-yl)acetic acid | 544 | 1.24 |
| 86 | pyridin-3-yl | 1 | 2-((R)-1-((S)-2-hydroxy-2-(4-(5-(1-(pyridin-3-yl)-5-(trifluoromethyl)-1H-pyrazol-4-yl)-1,2,4-oxadiazol-3-yl)phenyl)ethyl)piperidin-3-yl)acetic acid | 543 | 1.31 |
| 87 | 5-(trifluoromethyl)pyridin-2-yl | 1 | 2-((R)-1-((S)-2-hydroxy-2-(4-(5-(5-(trifluoromethyl)-1-(5-(trifluoromethyl)pyridin-2-yl)1H-pyrazol-4-yl)-1,2,4-oxadiazol-3-yl)phenyl)ethyl)piperidin-3-yl)acetic acid, HCl | 611 | 3.29 |
| 88 | 3,5-dichloropyridin-2-yl | 1 | 2-((3R)-1-((2S)-2-(4-(5-(1-(3,5-dichloropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl | 611 | 3.19 |

TABLE 3-continued

| Ex. | Q | n | Name | Obs. MS Ion (M + H)+ | RT$^a$ [min] |
|---|---|---|---|---|---|
| 89 | 2,4-dichlorophenyl | 1 | 2-((3R)-1-((2S)-2-(4-(5-(1-(2,4-dichlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl | 610 | 3.39 |
| 90 | 4-chloro-2-methylphenyl | 1 | 2-((3R)-1-((2S)-2-(4-(5-(1-(4-chloro-2-methylphenyl)-5-(trifluoromethyl)-1H-pyrazol-4-yl)-1,2,4-oxadiazol-3-yl)phenyl)-2-hydroxyethyl)piperidin-3-yl)acetic acid, HCl | 590 | 3.36 |
| 91 | 4-chloro-3-methylphenyl | 1 | 2-((R)-1-((S)-2-(4-(5-(1-(4-chloro-3-methylphenyl)-5-(trifluoromethyl)-1H-pyrazol-4-yl)-1,2,4-oxadiazol-3-yl)phenyl)-2-hydroxyethyl)piperidin-3-yl)acetic acid, HCl | 590 | 3.43 |
| 92 | 3,4-dichlorophenyl | 1 | 2-((R)-1-((S)-2-(4-(5-(1-(3,4-dichlorophenyl)-5-(trifluoromethyl)-1H-pyrazol-4-yl)-1,2,4-oxadiazol-3-yl)phenyl)-2-hydroxyethyl)piperidin-3-yl)acetic acid, HCl | 610 | 3.48 |
| 93 | 4-methylpyridin-2-yl | 1 | 2-((R)-1-((S)-2-hydroxy-2-(4-(5-(1-(4-methylpyridin-2-yl)-5-(trifluoromethyl)-1H-pyrazol-4-yl)-1,2,4-oxadiazol-3-yl)phenyl)ethyl)piperidin-3-yl)acetic acid, HCl | 557 | 2.91 |
| 94 | 5-methylpyridin-2-yl | 1 | 2-((R)-1-((S)-2-hydroxy-2-(4-(5-(1-(5-methylpyridin-2-yl)-5-(trifluoromethyl)-1H-pyrazol-4-yl)-1,2,4-oxadiazol-3-yl)phenyl)ethyl)piperidin-3-yl)acetic acid | 557 | 1.84 |
| 95 | 5-chloro-3-(trifluoromethyl)pyridin-2-yl | 1 | 2-((3R)-1-((2S)-2-(4-(5-(1-(5-chloro-3-(trifluoromethyl)pyridin-2-yl)-5-(trifluoromethyl)-1H-pyrazol-4-yl)-1,2,4-oxadiazol-3-yl)phenyl)-2-hydroxyethyl)piperidin-3-yl)acetic acid | 645 | 2.11 |
| 96 | 6-methyl-4-(trifluoromethyl)pyridin-2-yl | 1 | 2-((R)-1-((S)-2-hydroxy-2-(4-(5-(1-(6-methyl-4-(trifluoromethyl)pyridin-2-yl)-5-(trifluoromethyl)-1H-pyrazol-4-yl)-1,2,4-oxadiazol-3-yl)phenyl)ethyl)piperidin-3-yl)acetic acid, HCl | 625 | 3.37 |
| 97 | 4-chlorophenyl | 0 | (S)-1-((S)-2-(4-(5-(1-(4-chlorophenyl)-5-(trifluoromethyl)-1H-pyrazol-4-yl)-1,2,4-oxadiazol-3-yl)phenyl)-2-hydroxyethyl)piperidine-3-carboxylic acid, HCl | 562 | 2.12 |

TABLE 3-continued

| Ex. | Q | n | Name | Obs. MS Ion (M + H)+ | RT$^a$ [min] |
|---|---|---|---|---|---|
| 98 | 5-CF$_3$-pyridin-2-yl | 0 | (S)-1-((S)-2-hydroxy-2-(4-(5-(5-(trifluoromethyl)-1-(5-(trifluoromethyl)pyridin-2-yl)-1H-pyrazol-4-yl)-1,2,4-oxadiazol-3-yl)phenyl)ethyl)piperidine-3-carboxylic acid, HCl | 597 | 3.01 |
| 99 | 4-methoxyphenyl | 0 | (S)-1-((S)-2-hydroxy-2-(4-(5-(1-(4-methoxyphenyl)-5-(trifluoromethyl)-1H-pyrazol-4-yl)-1,2,4-oxadiazol-3-yl)phenyl)ethyl)piperidine-3-carboxylic acid, HCl | 558 | 1.95 |
| 100 | 3,5-dichloropyridin-2-yl | 0 | (S)-1-((S)-2-(4-(5-(1-(3,5-dichloropyridin-2-yl)-5-(trifluoromethyl)-1H-pyrazol-4-yl)-1,2,4-oxadiazol-3-yl)phenyl)-2-hydroxyethyl)piperidine-3-carboxylic acid, HCl | 597 | 2.83 |
| 101 | 5-fluoropyridin-2-yl | 0 | (S)-1-((S)-2-(4-(5-(1-(5-fluoropyridin-2-yl)-5-(trifluoromethyl)-1H-pyrazol-4-yl)-1,2,4-oxadiazol-3-yl)phenyl)-2-hydroxyethyl)piperidine-3-carboxylic acid, HCl | 547 | 1.83 |
| 102 | m-tolyl | 0 | (S)-1-((S)-2-hydroxy-2-(4-(5-(1-m-tolyl-5-(trifluoromethyl)-1H-pyrazol-4-yl)-1,2,4-oxadiazol-3-yl)phenyl)ethyl)piperidine-3-carboxylic acid | 542 | 2.12 |
| 103 | 5-methylpyridin-2-yl | 0 | (S)-1-((S)-2-hydroxy-2-(4-(5-(1-(5-methylpyridin-2-yl)-5-(trifluoromethyl)-1H-pyrazol-4-yl)-1,2,4-oxadiazol-3-yl)phenyl)ethyl)piperidine-3-carboxylic acid | 543 | 1.85 |
| 104 | pyridin-2-yl | 0 | (S)-1-((S)-2-hydroxy-2-(4-(5-(1-(pyridin-2-yl)-5-(trifluoromethyl)-1H-pyrazol-4-yl)-1,2,4-oxadiazol-3-yl)phenyl)ethyl)piperidine-3-carboxylic acid | 529 | 1.79 |
| 105 | 5-chloropyridin-2-yl | 0 | (S)-1-((S)-2-(4-(5-(1-(5-chloropyridin-2-yl])-5-(trifluoromethyl)-1H-pyrazol-4-yl)-1,2,4-oxadiazol-3-yl)phenyl)-2-hydroxyethyl)piperidine-3-carboxylic acid | 562 | 2.09 |
| 106 | cyclohexyl | 0 | (S)-1-((S)-2-(4-(5-(1-cyclohexyl-5-(trifluoromethyl)-1H-pyrazol-4-yl)-1,2,4-oxadiazol-3-yl)phenyl)-2-hydroxyethyl)piperidine-3-carboxylic acid | 534 | 2.27 |
| 107 | 2,4-difluorophenyl | 0 | (S)-1-((S)-2-(4-(5-(1-(2,4-difluorophenyl)-5-(trifluoromethyl)-1H-pyrazol-4-yl)-1,2,4-oxadiazol-3-yl)phenyl)-2-hydroxyethyl)piperidine-3-carboxylic acid, HCl | 564 | 2.78 |

Examples 108 to 115

The intermediate carboxylic acids found in Table 4 were prepared from commercially available starting materials using the same general procedure as used for the synthesis of Intermediate V (Int-V) except for Int-XL, Int-XLI, and Int-XLII, which were prepared as follows:

Intermediate XL (Int-XL)

5-Cyclohexyl-4-(trifluoromethyl)isoxazole-3-carboxylic acid

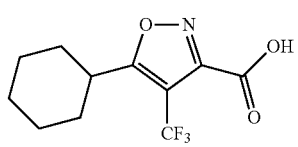

To a mixture of ethynylcyclohexane (0.425 mL, 3.30 mmol) and (Z)-ethyl 2-chloro-2-(hydroxyimino)acetate (500 mg, 3.30 mmol) in diethyl ether (10 mL) was added triethylamine (0.460 mL, 3.30 mmol). After 4 days, the reaction mixture was diluted with ethyl acetate and washed with water. The organic layer was dried MgSO₄, filtered, and concentrated. The crude material was purified on a silica gel cartridge (40 g) using an EtOAc/Hex gradient (0-50% EtOAc over 20 minutes). Recovered 78 mg of ethyl 5-cyclohexyl-isoxazole-3-carboxylate. The product had an HPLC ret. time =2.11 min.-Column: Waters Sunfire C18 2.5 um 2.1×30 mm (2 min); Solvent A=10% MeOH, 90% H₂O, 0.1% TFA; Solvent B=90% MeOH, 10% H₂O, 0.1% TFA. LC/MS M+1=224. This material was hydrolyzed as described for Int-V-C and used without further purification.

Intermediate XLI (Int-XLI)

5-(3-Chlorophenyl)-4-(trifluoromethyl)isoxazole-3-carboxylic acid

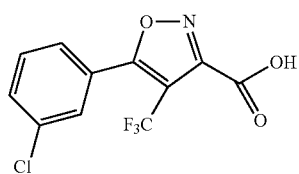

To a mixture of 1-chloro-3-ethynylbenzene (451 mg, 3.30 mmol) and (Z)-ethyl 2-chloro-2-(hydroxyimino)acetate (500 mg, 3.30 mmol) in diethyl ether (10 mL) was added triethylamine (0.460 mL, 3.30 mmol). The reaction mixture was stirred at 25° C. for 3 days. The reaction mixture was diluted with ethyl acetate and washed with water. The organic layer was dried MgSO₄, filtered and concentrated. The crude material was purified on a silica gel cartridge (40 g) using an EtOAc/Hex gradient (0-50% EtOAc over 20 minutes). Recovered 235 mg of ethyl 5-(3-chlorophenyl)isoxazole-3-carboxylate. The product had an HPLC ret. time=2.08 min.-Column: Waters Sunfire C18 2.5 um 2.1×30 mm (2 min); Solvent A=10% MeOH, 90% H₂O, 0.1% TFA; Solvent B=90% MeOH, 10% H₂O, 0.1% TFA. LC/MS M+1=252. This material was hydrolyzed as described for Int-V-C and used without further purification.

Intermediate XLII (Int-XLII)

3-Phenyl-4-(trifluoromethyl)isothiazole-5-carboxylic acid

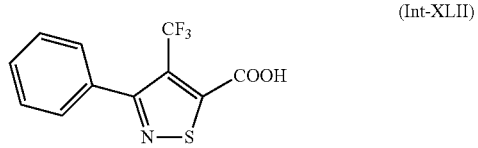 [SMILES: O=C(O)c1snc(-c2ccccc2)c1C(F)(F)F]

Preparation of Int-XLII-A:
(Z)—N-Hydroxybenzimidoyl cyanide

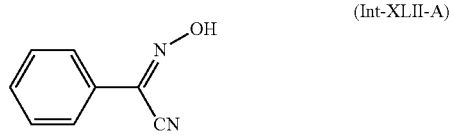 [SMILES: N#C/C(=N\O)c1ccccc1]

A solution of isopentyl nitrite (16.00 g, 137 mmol) in ethyl alcohol (30 mL) was added dropwise to a solution of 2-phenylacetonitrile (16 g, 137 mmol) and sodium hydroxide (5.46 g, 137 mmol) in ethyl alcohol (30 mL) at 0° C. Once the addition was complete, the mixture was allowed to warm to room temperature. After stirring for 2h, the reaction mixture was diluted with diethyl ether and the resultant solid was collected by filtration and washed with diethyl ether. The solid was vacuum dried to yield (Z)—N-hydroxybenzimidoyl cyanide (10 g, 68.9 mmol, 50.4% yield) as a light yellow solid.

Preparation of Int-XLII-B:
(Z)—N-(Tosyloxy)benzimidoyl cyanide

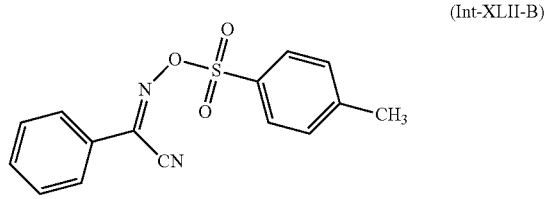 [SMILES: Cc1ccc(S(=O)(=O)O/N=C(\C#N)c2ccccc2)cc1]

A mixture of (Z)—N-hydroxybenzimidoyl cyanide (8 g, 55.1 mmol) and 4-methylbenzene-1-sulfonyl chloride (10.51 g, 55.1 mmol) in toluene (70 mL) was heated at reflux. After 2 h, the reaction was allowed to cool, diluted with ethyl acetate (100 mL) and washed with water (50 mL) and brine (50 mL). The organic layer was dried over anhydrous Na₂SO₄ and concentrated to yield (Z)—N-(tosyloxy)benzimidoyl cyanide (10 g, 33.3 mmol, 60.4% yield) as a light yellow solid.

Preparation of Int-XLII-C: Methyl 4-amino-3-phenylisothiazole-5-carboxylate

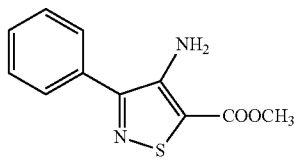
(Int-XLII-C)

Triethylamine (5.39 g, 53 3 mmol) was added dropwise to a stirring solution of (Z)—N-(tosyloxy)benzimidoyl cyanide (8 g, 26.6 mmol) and methyl 2-mercaptoacetate (2.86 mL, 32.0 mmol) in methanol (70 mL) at room temperature. After stirring for 3 h, the reaction was cooled and treated with 100 mL ice water. The resulting solid was removed by vacuum filtration and washed with water. The solid was vacuum dried to yield 6 g of a brown solid. Recrystallization from hexane/ethyl acetate yielded 3 g of methyl 4-amino-3-phenylisothiazole-5-carboxylate as beige colored needles.

Preparation of Int-XLII-D: Methyl 4-iodo-3-phenylisothiazole-5-carboxylate

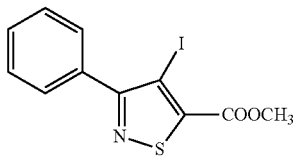
(Int-XLII-D)

To a solution of methyl 4-amino-3-phenylisothiazole-5-carboxylate (500 mg, 2.134 mmol) in chloroform (15 mL) was added iodine (287 mg, 11.31 mmol) and amyl nitrite (0.430 mL, 3.20 mmol). The resulting mixture was heated at reflux for 30 min., cooled to room temperature, washed with aqueous sodium thiosulfate and water. The organic layer was dried over $Na_2SO_4$. Removal of the solvent in vacuo and crystallization from ethanol yielded methyl 4-iodo-3-phenyl-isothiazole-5-carboxylate (300 mg, 0.869 mmol, 40.7% yield) as a pale yellow solid.

Preparation of Int-XLII-E: Methyl 3-phenyl-4-(trifluoromethyl)isothiazole-5-carboxylate

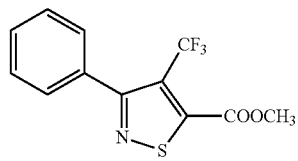
(Int-XLII-E)

Copper(I) iodide (1.104 g, 5.79 mmol), methyl 4-iodo-3-phenylisothiazole-5-carboxylate (1 g, 2.90 mmol) and methyl 2,2-difluoro-2-(fluorosulfonyl)acetate (0.742 mL, 5.79 mmol) were added to a sealed tube under a $N_2$ flow. The reaction mixture was heated at 85° C. overnight, cooled to room temperature, diluted with ethyl acetate (80 mL) and filtered through CELITE®. The organic layer was washed with water (3×20 mL) and brine (30 mL), dried over $Na_2SO_4$ and concentrated. The residue was subjected to silica gel chromatography eluting with an ethyl acetate/hexane to yield methyl 3-phenyl-4-(trifluoromethyl)isothiazole-5-carboxylate (580 mg, 2.019 mmol, 69.7% yield) as a clear oil. LC/MS M+1=288.25; $^1$H NMR (400 MHz, $CDCl_3$) δ ppm 7.43-7.56 (5H, m), 4.01 (3H, s).

Intermediate XLII

3-Phenyl-4-(trifluoromethyl)isothiazole-5-carboxylic acid

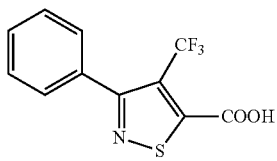
(Int-XLII)

To a solution of methyl 3-phenyl-4-(trifluoromethyl)isothiazole-5-carboxylate (50 mg, 0.174 mmol) in THF (0.5 mL) was added a 1M LiOH solution (0.2mL). The resulting mixture was stirred at room temperature overnight. The pH of the reaction mixture was made acidic using 1N HCl and the solid that separates out was collected by filtration and dried in vacuo to yield 3-phenyl-4-(trifluoromethyl)isothiazole-5-carboxylic acid (42 mg, 0.154 mmol, 88% yield) as a pale yellow solid. LC/MS M+1=274.

TABLE 4

| Int. | Q | Name | Obs. MS ion. (M + H)+ | RT$^a$ [min] |
|---|---|---|---|---|
| XXXVII | ![structure] | 5-isopropyl-4-(trifluoromethyl)isoxazole-3-carboxylic acid | 268 | 1.64 |
| XXXVIII | ![structure] | 5-tert-butyl-4-(trifluoromethyl)isoxazole-3-carboxylic acid | 292 | 1.31 |

TABLE 4-continued

| Int. | Q | Name | Obs. MS ion. (M + H)+ | RT$^a$ [min] |
|---|---|---|---|---|
| XXXIX | | 5-(2-chlorophenyl)-4-(trifluoromethyl)isoxazole-3-carboxylic acid | No MS obs | 2.08 |
| XL | | 5-cyclohexyl-4-(trifluoromethyl)isoxazole-3-carboxylic acid | No MS obs | 2.04 |
| XLI | | 5-(3-chlorophenyl)-4-(trifluoromethyl)isoxazole-3-carboxylic acid | No MS obs | 1.99 |
| XLII | | 3-phenyl-4-(trifluoromethyl)isothiazole-5-carboxylic acid | 274 | — |

Examples 108 to 115 in Tables 5-6 were prepared using the general coupling procedure described for the Examples in Table 2 and carboxylic acids Int-V and Int-XXXVII through Int-XLII found in Table 4.

TABLE 5

| Ex. | R$_a$ | n | Name | Obs. MS Ion (M + H)$^+$ | RT$^a$ [min] |
|---|---|---|---|---|---|
| 108 | | 1 | 2-((R)-1-((S)-2-hydroxy-2-(4-(5-(5-isobutyl-4-(trifluoromethyl)isoxazol-3-yl)-1,2,4-oxadiazol-3-yl)phenyl)ethyl)piperidin-3-yl)acetic acid, TFA | 523 | 3.28 |
| 109 | | 1 | 2-((R)-1-((S)-2-(4-(5-(5-tert-butyl-4-(trifluoromethyl)isoxazol-3-yl)-1,2,4-oxadiazol-3-yl)phenyl)-2-hydroxyethyl)piperidin-3-yl)acetic acid, TFA | 523 | 3.25 |

TABLE 5-continued

*[Structure: R_a-substituted isoxazole (with CF_3) connected to 1,2,4-oxadiazole, phenyl with CH(OH)CH_2-piperidine-(CH_2)_n-COOH]*

| Ex. | R_a | n | Name | Obs. MS Ion (M + H)+ | RT^a [min] |
|---|---|---|---|---|---|
| 110 | isopropyl (H_3C)_2CH- | 1 | 2-((R)-1-((S)-2-hydroxy-2-(4-(5-(5-isopropyl-4-(trifluoromethyl)isoxazol-3-yl)-1,2,4-oxadiazol-3-yl)phenyl)ethyl)piperidin-3-yl)acetic acid, HCl | 509 | 3.12 |
| 111 | cyclohexyl | 1 | 2-((R)-1-((S)-2-(4-(5-(5-cyclohexyl-4-(trifluoromethyl)isoxazol-3-yl)-1,2,4-oxadiazol-3-yl)phenyl)-2-hydroxyethyl)piperidin-3-yl)acetic acid, HCl | 549 | 3.20 |
| 112 | 3-chlorophenyl | 1 | 2-((R)-1-((S)-2-(4-(5-(5-(3-chlorophenyl)-4-(trifluoromethyl)isoxazol-3-yl)-1,2,4-oxadiazol-3-yl)phenyl)-2-hydroxyethyl)piperidin-3-yl)acetic acid | 577 | 2.27 |
| 113 | 2-chlorophenyl | 1 | 2-((3R)-1-((2S)-2-(4-(5-(5-(2-chlorophenyl)-4-(trifluoromethyl)isoxazol-3-yl)-1,2,4-oxadiazol-3-yl)phenyl)-2-hydroxyethyl)piperidin-3-yl)acetic acid, HCl | 577 | 3.28 |
| 114 | 3-phenyl-4-(trifluoromethyl)isothiazol-5-yl | 1 | (S)-1-((S)-2-hydroxy-2-(4-(5-(3-phenyl-4-(trifluoromethyl)isothiazol-5-yl)-1,2,4-oxadiazol-3-yl)phenyl)ethyl)piperidine-3-carboxylic acid, HCl | 576 | 3.26 |

TABLE 6

*[Structure: R_a-substituted isothiazole (with CF_3) connected to 1,2,4-oxadiazole, phenyl with CH(OH)CH_2-piperidine-(CH_2)_n-COOH]*

| Ex. | R_a | n | Name | Obs. MS Ion (M + H)+ | RT^a [min] |
|---|---|---|---|---|---|
| 115 | phenyl | 0 | (S)-1-((S)-2-hydroxy-2-(4-(5-(3-phenyl-4-(trifluoromethyl)isothiazol-5-yl)-1,2,4-oxadiazol-3-yl)phenyl)ethyl)piperidine-3-carboxylic acid, HCl | 544 | 2.16 |

Example 116

2-((R)-1-((S)-2-Hydroxy-2-(4-(5-(4-phenyl-5-(trifluoromethyl)thiophen-2-yl)-1,2,4-oxadiazol-3-yl)phenyl)ethyl)piperidin-3-yl)acetic acid

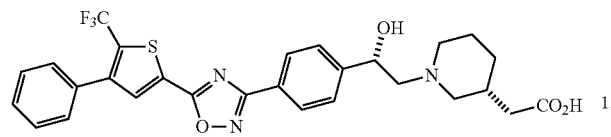

(116)

To a solution of commercially available 4-phenyl-5-(trifluoromethyl)thiophene-2-carboxylic acid (44.0 mg, 0.162 mmol) in DCM (4 mL) was added oxalyl chloride (45 µL, 0.514 mmol) followed by a drop of DMF. The solution bubbled. After 1 h, diisopropylethylamine (45 µL, 0.258 mmol) was added followed by ethyl 2-((R)-1-((S)-2-(tert-butyldimethylsilyloxy)-2-(4-((Z)—N'-hydroxycarbamimidoyl)phenyl)ethyl)piperidin-3-yl)acetate (50.0 mg, 0.108 mmol) in THF (2 mL). The reaction mixture was stirred overnight and the next day LCMS showed the product had formed so the reaction was treated with TBAF (216 µL, 0.216 mmol) and then heated to 60° C. overnight. The next day, the reaction was extracted from 1 M HCl using EtOAc×3 and the organics layers were combined and concentrated in vacuo. This residue was taken up in a 1:1 mixture of THF and 6 M HCl and heated for 2 h. LCMS after this time showed the desired product so the reaction was concentrated and then purified by HPLC to give 2-((R)-1-((S)-2-hydroxy-2-(4-(5-(4-phenyl-5-(trifluoromethyl)thiophen-2-yl)-1,2,4-oxadiazol-3-yl)phenyl)ethyl)piperidin-3-yl)acetic acid (42 mg, 98% yield). MS (M+1)=558.3; HPLC RT=2.11 minutes. $^1$H NMR (400 MHz, DMSO-$d_6$) δ ppm 12.27 (1H, br. s.), 9.72 (1H, br. s.), 8.14-8.26 (1H, m), 8.05 (2H, m, J=8.36 Hz), 7.61 (2H, m, J=8.14 Hz), 7.41-7.53 (5H, m), 6.35 (1H, br. s.), 5.18 (1H, br. s.), 3.42-3.71 (2H, m), 3.10-3.21 (1H, m), 2.63-2.94 (2H, m), 2.08-2.31 (3H, m), 1.66-1.91 (3H, m), 0.99-1.24 (1H, m).

Example 116

2-((R)-1-((S)-2-(4-(5-(1-(4-Fluorophenyl)-3-(trifluoromethyl)-1H-pyrazol-4-yl)-1,2,4-oxadiazol-3-yl)phenyl)-2-hydroxyethyl)piperidin-3-yl)acetic acid

Preparation 116A: Ethyl 1-(4-fluorophenyl)-3-(trifluoromethyl)-1H-pyrazole-4-carboxylate

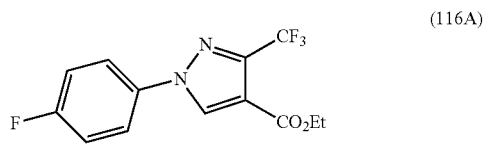 [SMILES: CCOC(=O)c1cn(-c2ccc(F)cc2)nc1C(F)(F)F]

(116A)

To a solution of ethyl 3-(trifluoromethyl)-1H-pyrazole-4-carboxylate (100 mg, 0.480 mmol) in toluene (0.5 mL) was added (1R,2R)-N1,N2-dimethylcyclohexane-1,2-diamine (13.67 mg, 0.096 mmol), 1-fluoro-4-iodobenzene (0.166 mL, 1.441 mmol), potassium carbonate (139 mg, 1.009 mmol), and copper(I) iodide (9.00 mg, 0.047 mmol). This reaction was heated to reflux overnight. The next day, the reaction was complete by HPLC so it was filtered through a frit with EtOAc and purified on a SiO$_2$ column using 25-100% EtOAc hexanes gradient to give white crystalline ethyl 1-(4-fluorophenyl)-3-(trifluoromethyl)-1H-pyrazole-4-carboxylate (140 mg, 0.463 mmol, 96% yield). The structure was assigned by small molecule X-ray crystallography. $^1$H NMR (400 MHz, CDCl$_3$) δ ppm 8.35 (1H, s), 7.62 (2H, m), 7.14 (2H, m), 4.25 (2H, q), 1.37 (3H, t).

Preparation 116B: 1-(4-Fluorophenyl)-3-(trifluoromethyl)-1H-pyrazole-4-carboxylic acid

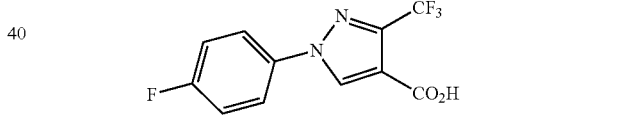

(116B)

To a solution of ethyl 1-(4-fluorophenyl)-3-(trifluoromethyl)-1H-pyrazole-4-carboxylate (140 mg, 0.463 mmol) in ethanol (4 mL) was added a solution of NaOH (4 mL, 4.00 mmol) in water (2 mL). The reaction mixture was stirred overnight. The next day, LCMS showed complete reaction so the reaction was concentrated in vacuo and then extracted using dilute HCl and EtOAc. Obtained 1-(4-fluorophenyl)-3-(trifluoromethyl)-1H-pyrazole-4-carboxylic acid (93 mg, 0.339 mmol, 73.2% yield) as a white powder. MS (M+1)=275; HPLC RT=0.82 minutes.

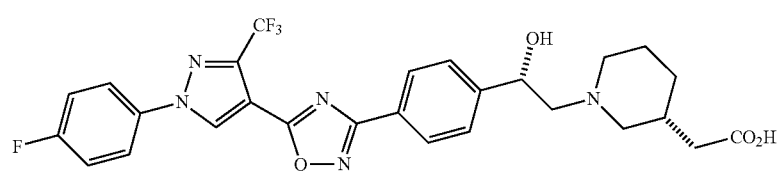

(116)

Example 116

2-((R)-1-((S)-2-(4-(5-(1-(4-Fluorophenyl)-3-(trifluoromethyl)-1H-pyrazol-4-yl)-1,2,4-oxadiazol-3-yl)phenyl)-2-hydroxyethyl)piperidin-3-yl)acetic acid To a solution of 1-(4-fluorophenyl)-3-(trifluoromethyl)-1H-pyrazole-4-carboxylic acid (40.0 mg, 0.146 mmol) in DCM (3 mL) was added oxalyl chloride (38.3 µL, 0.438 mmol). The reaction mixture was stirred at room temperature for 1 h, concentrated in vacuo and azeotroped with THF. To this reaction mixture was added ethyl 2-((R)-1-((S)-2-(tenbutyldimethylsilyloxy)-2-(4-((Z)—N'-hydroxycarbamimidoyl)phenyl)ethyl)piperidin-3-yl)acetate (67.6 mg, 0.146 mmol) in THF (1 mL) followed by DIEA (45 µL, 0.258 mmol). The reaction mixture was stirred overnight. The next day, THF (1 mL) was added followed by solid potassium tert-butoxide (32.7 mg, 0.292 mmol) and the reaction mixture was refluxed overnight. The next day, the solvents were removed by rotovap and the residue was taken up in dioxane (2 mL) and treated with 2 mL 6M HCl and heated to 80° C. overnight. LCMS of this reaction looked good so it was concentrated in vacuo, diluted with ACN, water, and some TFA and purified by HPLC to give 2-((R)-1-((S)-2-(4-(5-(1-(4-fluorophenyl)-3-(trifluoromethyl)-1H-pyrazol-4-yl)-1,2,4-oxadiazol-3-yl)phenyl)-2-hydroxyethyl)piperidin-3-yl) acetic acid (42 mg, 0.071 mmol, 48.9% yield). MS (M+1)=560.3; HPLC RT=1.22 minutes. $^1$H NMR (400 MHz, DMSO-$d_6$) δ ppm 9.65 (1H, s), 9.37 (1H, br. s.), 7.93-8.14 (4H, m), 7.56-7.70 (2H, m), 7.34-7.48 (2H, m), 6.39 (1H, d, J=3.52 Hz), 5.09-5.21 (1H, m), 3.63 (1H, d, J=11.00 Hz), 3.48 (1H, d, J=11.44 Hz), 3.12-3.28 (2H, m), 2.76-2.90 (1H, m), 2.63-2.76 (1H, m), 2.10-2.32 (3H, m), 1.63-1.92 (3H, m), 1.04-1.23 (1H, m).

Example 117

2-((R)-1-((S)-2-(4-(5-(1-(4-Chlorophenyl)-5-(trifluoromethyl)-1H-imidazol-4-yl)-1,2,4-oxadiazol-3-yl)phenyl)-2-hydroxyethyl)piperidin-3-yl)acetic acid

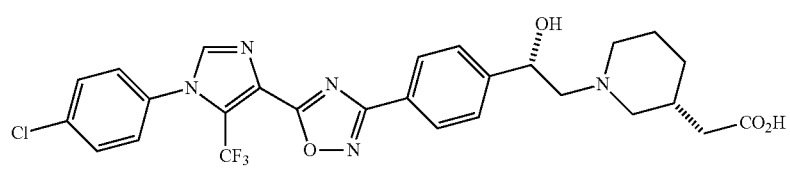

(117)

Preparation 117A: Ethyl 1-(4-chlorophenyl)-5-(trifluoromethyl)-1H-imidazole-4-carboxylate

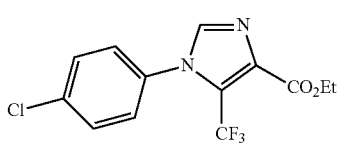

(117A)

The synthetic intermediate imine (Z)—N-(4-chlorophenyl)-2,2,2-trifluoroacetimidoyl chloride (a pale yellow oil) was prepared as described in Huang et al., *J. Fluorine Chem.*, 74:279-282 (1995) and used without distillation. To ethyl isocyanoacetate (0.467 g, 4.13 mmol) in dry THF (50 mL) was added NaH (170 mg, 4.13 mmol, 60% dispersed in oil) at 0° C. and after 5 minutes, (Z)—N-(4-chlorophenyl)-2,2,2-trifluoroacetimidoyl chloride (1.0 g, 4.13 mmol). The reaction mixture was allowed to warm to room temperature. The mixture was purified using an 80 g SiO$_2$ column and a 10-100% EtOAc/hexanes gradient. Obtained 900 mg (68% yield) of ethyl 1-(4-chlorophenyl)-5-(trifluoromethyl)-1H-imidazole-4-carboxylate as a pale yellow solid. This compound matched the $^1$H NMR found in the *J. Fluorine Chem.* reference.

Preparation 117B: Ethyl 1-(4-chlorophenyl)-5-(trifluoromethyl)-1H-imidazole-4-carboxylate

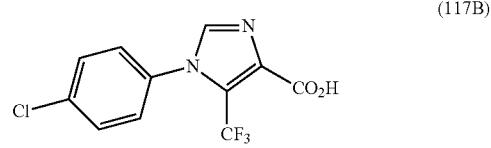 [SMILES: O=C(O)c1ncn(-c2ccc(Cl)cc2)c1C(F)(F)F]

(117B)

To a solution of ethyl 1-(4-chlorophenyl)-5-(trifluoromethyl)-1H-imidazole-4-carboxylate (800 mg, 2.51 mmol) in EtOH (20 mL) was added a predissolved solution of sodium hydroxide (1004 mg, 25.1 mmol) in Water (5.00 mL). The reaction was stirred overnight at room temperature. The next day, the reaction was concentrated in vacuo, acidified with dilute HCl and extracted 2×EtOAc. The organic layers were dried over MgSO$_4$, filtered, and concentrated to give 1-(4-chlorophenyl)-5-(trifluoromethyl)-1H-imidazole-4-carboxylic acid (400 mg, 1.376 mmol, 54.8% yield). $^1$H NMR (400 MHz, DMSO-$d_6$) δ ppm 13.3 (1H, br s), 8.19 (1H, dd), 7.68 (2H, d), 7.72 (2H, d).

Example 117

2-((R)-1-((S)-2-(4-(5-(1-(4-Chlorophenyl)-5-(trifluoromethyl)-1H-imidazol-4-yl)-1,2,4-oxadiazol-3-yl)phenyl)-2-hydroxyethyl)piperidin-3-yl)acetic acid This reaction was setup using the same procedure as used for Example 116. The final reaction was purified by HPLC to give 2-((R)-1-((S)-2-(4-(5-(1-(4-chlorophenyl)-5-(trifluoromethyl)-1H-imidazol-4-yl)-1,2,4-oxadiazol-3-yl)phenyl)-2-hydroxyethyl)piperidin-3-yl)acetic acid, HCl (30 mg, 0.030 mmol, 28.9% yield). MS (M+1)=576.2; HPLC RT=1.15 minutes. $^1$H NMR (400 MHz, DMSO-$d_6$) δ ppm 12.15 (1H, br. s.), 8.30 (1H, s), 7.92 (2H, d, J=8.36 Hz), 7.51-7.55 (4H, m), 7.48 (2H, d, J=8.14 Hz), 6.23 (1H, br. s.), 5.00 (1H, br. s.), 3.48 (1H, br. s.), 3.33 (1H, d, J=11.88 Hz), 2.94-3.07 (1H, m), 2.69 (1H, s), 2.50-2.62 (1H, m), 2.34-2.39 (1H, m), 1.96-2.15 (3H, m), 1.69 (1H, d, J=12.54 Hz), 1.60 (2H, d, J=12.54 Hz), 0.90-1.12 (1H, m).

Example 118

2-((R)-1-((S)-2-Hydroxy-2-(4-(5-(1-(pyridin-2-yl)-5-(trifluoromethyl)-1H-imidazol-4-yl)-1,2,4-oxadiazol-3-yl)phenyl)ethyl)piperidin-3-yl)acetic acid

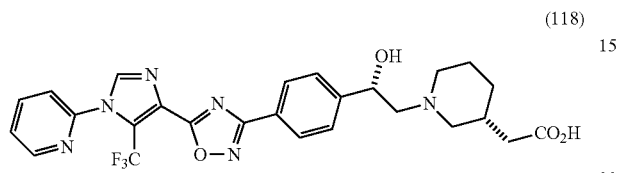
(118)

Preparation 118A: Ethyl 1-(pyridin-2-yl)-5-(trifluoromethyl)-1H-imidazole-4-carboxylate

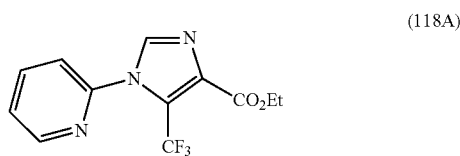 [SMILES: CCOC(=O)c1ncn(-c2ccccn2)c1C(F)(F)F]
(118A)

The synthetic intermediate imine (Z)-2,2,2-trifluoro-N-(pyridin-2-yl)acetimidoyl chloride was prepared as described in Huang et al., *J. Fluorine Chem.*, 74:279-282 (1995) and used without distillation. To ethyl isocyanoacetate (0.543 g, 4.8 mmol) in dry THF (50 mL) was added NaH (192 mg, 4 8 mmol, 60% dispersed in oil) at 0° C. and after 5 minutes, (Z)-2,2,2-trifluoro-N-(pyridin-2-yl)acetimidoyl chloride (1.0 g, 4.8 mmol) in 50 mL THF. The reaction mixture was allowed to warm to room temperature and then purified using an 80 g SiO₂ column and a 50-100% EtOAc/hexanes gradient. The product eluted to yield 1.23 g (90% yield) of ethyl 1-(pyridin-2-yl)-5-(trifluoromethyl)-1H-imidazole-4-carboxylate as a yellow oil. MS (M+1)=286.1; HPLC RT=1.08 minutes.

Preparation 118B: 1-(Pyridin-2-yl)-5-(trifluoromethyl)-1H-imidazole-4-carboxylate

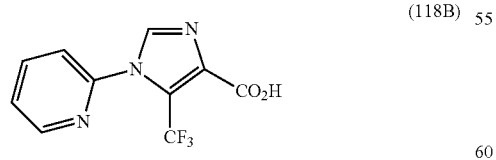
(118B)

To a solution of ethyl 1-(pyridin-2-yl)-5-(trifluoromethyl)-1H-imidazole-4-carboxylate (1.2 g, 4.21 mmol) in EtOH (20 mL) was added a predissolved solution of sodium hydroxide (1.00 g, 25.1 mmol) in water (5.00 mL). The reaction mixture was stirred overnight at room temperature. The next day, the reaction mixture was concentrated in vacuo, acidified with dilute HCl, and extracted from 1 M HCl with EtOAc. Some product did extract but the aqueous layer remained yellow with desired product as well. The aqueous layer was brought to pH 5 using ammonium hydroxide and NH₄Cl and extracted with EtOAc again which afforded additional product. The combined organic layers were dried over MgSO₄, filtered, concentrated to give 1-(pyridin-2-yl)-5-(trifluoromethyl)-1H-imidazole-4-carboxylic acid (140 mg, 0.544 mmol, 12.94% yield). ¹H NMR (400 MHz, DMSO-d₆) δ ppm 13.5 (1H, br s), 8.69 (1H, dd), 8.35 (s, 1H), 8.14 (1H, dt), 7.78 (1H, d), 7.67 (1H, dt).

Example 118

2-((R)-1-((S)-2-Hydroxy-2-(4-(5-(1-(pyridin-2-yl)-5-(trifluoromethyl)-1H-imidazol-4-yl)-1,2,4-oxadiazol-3-yl)phenyl)ethyl)piperidin-3-yl)acetic acid This reaction was setup using the same procedure as used for Example 118. The final reaction mixture was concentrated in vacuo and purified by HPLC to give 2-((R)-1-((S)-2-hydroxy-2-(4-(5-(1-(pyridin-2-yl)-5-(trifluoromethyl)-1H-imidazol-4-yl)-1,2,4-oxadiazol-3-yl)phenyl)ethyl)piperidin-3-yl)acetic acid, HCl (30 mg, 0.044 mmol, 37.8% yield). MS (M+1)=543.2; HPLC RT=0.94 minutes. ¹H NMR (400 MHz, MeOD) δ ppm 8.68 (1H, d, J=4.02 Hz), 8.27 (1H, s), 8.20 (2H, d, J=8.53 Hz), 8.11 (1H, td, J=7.78, 1.76 Hz), 7.58-7.70 (5H, m), 5.19 (1H, dd, J=8.78, 4.77 Hz), 3.70 (1H, d, J=11.80 Hz), 3.45 (1H, d, J=11.29 Hz), 3.14 (1H, s), 3.13 (1H, d, J=5.02 Hz), 2.80-2.93 (1H, m), 2.62 (1H, t, J=11.04 Hz), 2.25-2.41 (2H, m), 2.09-2.22 (1H, m), 1.86-1.99 (3H, m), 1.20-1.37 (1H, m).

Comparative Compound 119

(S)-1-(4-(5-(5-Phenyl-4-propylisoxazol-3-yl)-1,2,4-oxadiazol-3-yl)phenethyl)piperidine-3-carboxylic acid

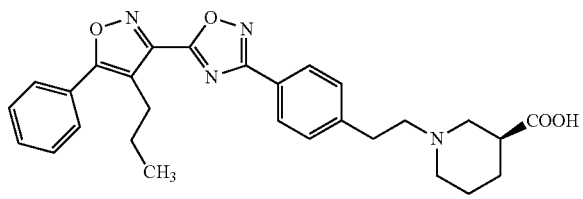
(119)

Preparation 119A: (Z)—N'-Hydroxy-4-(2-hydroxyethyl)benzimidamide

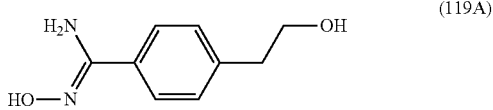
(119A)

To a mixture of 4-(2-hydroxyethyl)benzonitrile (500mg, 3.40 mmol) and sodium bicarbonate (1427 mg, 16.99 mmol) in 2-propanol (50 mL) was added hydroxylamine hydrochloride (472 mg, 6.79 mmol). The reaction mixture was heated at 80° C. overnight. The reaction mixture was diluted with ethyl acetate and washed with water. The organic layer was dried MgSO$_4$, filtered, and concentrated to yield 300 mg of (Z)—N'-hydroxy-4-(2-hydroxyethyl)benzimidamide. MS (m+1)=181. HPLC Peak RT=0.13 minutes. (Analytical Method B).

Preparation 119B: 2-(4-(5-(5-Phenyl-4-propylisoxazol-3-yl)-1,2,4-oxadiazol-3-yl)phenyl)ethanol

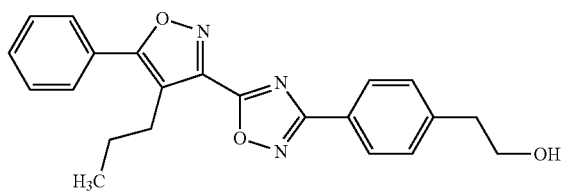

(119B)

To a mixture of 5-phenyl-4-propylisoxazole-3-carboxylic acid (385 mg, 1.665 mmol) and pyridine (0.135 mL, 1.665 mmol) in DCM (5 mL) was added cyanuric fluoride (0.141 mL, 1.665 mmol). The reaction mixture was stirred for 1 hour. The reaction mixture was diluted with dichloromethane and washed with 1M HCl. The organic layer was dried MgSO$_4$, filtered and concentrated. This crude residue was dissolved in acetonitrile (5.00 mL). (Z)—N'-hydroxy-4-(2-hydroxyethyl)benzimidamide (300 mg, 1.665 mmol) and DIEA (0.582 mL, 3.33 mmol) were added. The reaction mixture was heated at 75° C. overnight. The reaction mixture was diluted with ethyl acetate and washed with sat NaCl. The organic layer was dried MgSO$_4$, filtered, and concentrated to yield 800 mg of 2-(4-(5-(5-phenyl-4-propylisoxazol-3-yl)-1,2,4-oxadiazol-3-yl)phenyl)ethanol. MS (m+1)=376. HPLC Peak RT=2.09 minutes. (Analytical Method B).

Preparation 119C: 3-(4-(2-Bromoethyl)phenyl)-5-(5-phenyl-4-propylisoxazol-3-yl)-1,2,4-oxadiazole

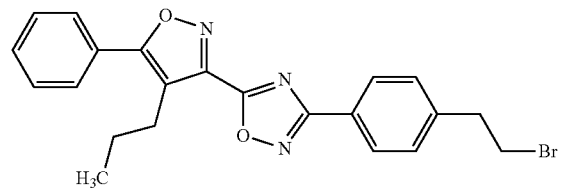

(119C)

To a mixture of 2-(4-(5-(5-phenyl-4-propylisoxazol-3-yl)-1,2,4-oxadiazol-3-yl)phenyl)ethanol (400 mg, 1.065 mmol) in DCE (20 mL) was added phosphorus tribromide in DCM (1.065 mL, 1.065 mmol). The reaction mixture was heated at 70° C. overnight. The reaction mixture was diluted with dichloromethane and washed with 1N NaOH. The organic layer was dried MgSO$_4$, filtered, and concentrated. The crude material was purified on a 40 gram silica column and eluting with EtOAc/Hex (0-50% gradient over 20 minutes) to afford 77 mg of 3-(4-(2-bromoethyl)phenyl)-5-(5-phenyl-4-propylisoxazol-3-yl)-1,2,4-oxadiazole. MS (m+1)=440. HPLC Peak RT=2.40 minutes. (Analytical Method B).

Comparative Compound 119: (S)-1-(4-(5-(5-Phenyl-4-propylisoxazol-3-yl)-1,2,4-oxadiazol-3-yl)phenethyl)piperidine-3-carboxylic acid To a mixture of (S)-piperidine-3-carboxylic acid, HCl (29.5 mg, 0.178 mmol) in NMP (2 mL) was added cesium carbonate (97 mg, 0.297 mmol). The reaction mixture was stirred for 30 minutes. Next, 3-(4-(2-bromoethyl)phenyl)-5-(5-phenyl-4-propylisoxazol-3-yl)-1,2,4-oxadiazole (26 mg, 0.059 mmol) and sodium iodide (2 mg, 0.013 mmol) were added. The reaction mixture was heated at 80° C. overnight. The reaction mixture was filtered and purified by HPLC. HPLC conditions: PHENOMENEX® Luna C18 5 micron column (250×30 mm); 25-100% CH$_3$CN/water (0.1% TFA); 25 minute gradient; 20 mL/min. The resulting material was 4mg of (S)-1-(4-(5-(5-phenyl-4-propylisoxazol-3-yl)-1,2,4-oxadiazol-3-yl)phenethyl)piperidine-3-carboxylic acid as a TFA salt. MS (m+1)=487. HPLC Peak RT=3.67 minutes (Analytical Method A). $^1$H NMR (400 MHz, MeOH-d$_3$) δ ppm 8.03 (2H, m), 7.71 (2H, dd, J=7.91, 1.54 Hz), 7.46-7.56 (3H, m), 7.39 (2H, m, J=8.57 Hz), 4.26-4.49 (2H, m), 3.27 (1H, dd, J=12.96, 3.95 Hz), 3.05-3.15 (3H, m), 2.86-3.04 (5H, m), 2.65-2.81 (1H, m), 1.89-2.03 (1H, m), 1.57-1.77 (5H, m), 0.95 (3H, t, J=7.36 Hz).

Biological Assays

S1P$_1$ Binding Assay

Membranes were prepared from CHO cells expressing human S1P$_1$. Cells were dissociated in buffer containing 20 mM HEPES, pH 7.5, 50 mM NaCl, 2 mM EDTA and Protease Inhibitor cocktail (Roche), and disrupted on ice using the Polytron homogenizer. The homogenate was centrifuged at 20,000 rpm (48,000 G) and the supernatant was discarded. The membrane pellets were resuspended in buffer containing 50 mM HEPES, pH 7.5, 100 mM NaCl, 1 mM MgCl$_2$, 2 mM EDTA and stored in aliquots at −80° C. after protein concentration determination.

Membranes (2 μg/well) and 0.03 nM final concentration of $^{33}$P-S1P ligand (1 mCi/ml, American Radiolabeled Chemicals) were added to the compound plates. Binding was performed for 45 minutes at room temperature, terminated by collecting the membranes onto GF/B filter plates, and radioactivity was measured by TOPCOUNT®. The competition data of the test compounds over a range of concentrations was plotted as percentage inhibition of radioligand specific binding. The IC$_{50}$ is defined as the concentration of competing ligand needed to reduce specific binding by 50%.

Table A below lists S1P$_1$ Binding IC$_{50}$ values from the following examples of this invention and Comparative Compound 119 measured in the S1P$_1$ binding assay described hereinabove. The results in Table A were rounded to two digits.

TABLE A

| Ex. | S1P1 binding IC$_{50}$ (nM) |
|---|---|
| 1 | 0.45 |
| 2 | 2.2 |
| 4 | 0.94 |
| 6 | 0.70 |
| 7 | 12 |
| 8 | 7.1 |
| 10 | 36 |
| 11 | 4.8 |
| 12 | 4.0 |

TABLE A-continued

| Ex. | S1P1 binding IC$_{50}$ (nM) |
|---|---|
| 13 | 0.21 |
| 14 | 0.72 |
| 15 | 3.1 |
| 16 | 2.6 |
| 17 | 28 |
| 18 | 3.4 |
| 19 | 4.2 |
| 24 | 43 |
| 26 | 14 |
| 27 | 14 |
| 28 | 31 |
| Comp. 119 | 420 |

Receptor [35S] GTPγS Binding Assays

Compounds were loaded in a 384 FALCON® v-bottom plate (0.5 μl/well in a 3-fold dilution). Membranes prepared from S1P$_1$/CHO cells or EDG3-Ga15-bla HEK293T cells were added to the compound plate (40 μl/well, final protein 3 μg/well) with MULTIDROP®. [$^{35}$S]GTP (1250 Ci/mmol, Perkin Elmer) was diluted in assay buffer: 20 mM HEPES, pH7.5, 10 mM MgCl$_2$, 150 mM NaCl, 1 mM EGTA, 1 mM DTT, 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to a 384 well FB filter plates via GPCR robot system. The filter plate was washed with water 4 times by using the modified manifold Embla plate washer and dried at 60° C. for 45 min. 30 μl of MicroScint 20 scintillation fluid was added to each well for counting at Packard TOP-COUNT®. EC$_{50}$ is defined as the agonist concentration that corresponds to 50% of the Ymax (maximal response) obtained for each individual compound tested.

TABLE B

| Ex. | S1P1 GTPγS EC$_{50}$ (nM) | S1P3 GTPγS EC$_{50}$ (nM) |
|---|---|---|
| 4 | 8.7 | 2000 |
| 8 | 110 | 1300 |
| 14 | 3.6 | 10200 |
| 17 | 320 | 1200 |
| 18 | 2.8 | 14600 |
| 21 | 95 | 20300 |
| 24 | 410 | 3500 |
| 35 | 3.9 | 4800 |
| 37 | 69 | 62000* |
| 41 | 5.4 | 7500 |
| 43 | 360 | 62000* |
| 46 | 630 | 8100 |
| 53 | 1900 | 31000* |
| 59 | 1.8 | 2080 |
| 70 | 1.2 | 10400 |
| 72 | 3.6 | 24800 |
| 73 | 2.1 | 2200 |
| 82 | 3.0 | 6090 |
| 94 | 8.6 | 6300 |
| 98 | 3.0 | 3300 |
| 100 | 6.8 | 31000* |
| 104 | 4.5 | 31000* |
| 106 | 1.0 | 2250 |
| 115 | 6.6 | 1640 |
| 117 | 26 | 62000* |
| Comp. 119 | 31000 | 62000* |

*Detection limit was either 31,000 nM or 62,000 nM in the GTPγS S1P$_3$ assay.

A smaller value for S1P$_1$ GTPγS EC$_{50}$ value indicated greater activity for the compound in the S1P$_1$ GTPγS binding assay. A larger value for the S1P$_3$ GTPγS EC$_{50}$ value indicated less activity in the S1P$_3$ GTPγS binding assay.

The compounds of the present invention, as exemplified by examples in Table B showed S1P$_1$ GTPγS EC$_{50}$ values of less than 5 μM, while in contrast, Comparative Compound 119 had a S1P$_1$ GTPγS EC$_{50}$ value of 31 μM.

The ratios of the S1P$_3$ GTPγS EC$_{50}$ values to the S1P$_1$ GTPγS EC$_{50}$ values, calculated from the data in Table B, are shown in Table C.

TABLE C

| Ex. | S1P3/S1P1 GTPγS |
|---|---|
| 4 | 232 |
| 8 | 12 |
| 14 | 2860 |
| 17 | 3.8 |
| 18 | 5200 |
| 21 | 210 |
| 24 | 8.6 |
| 35 | 1200 |
| 37 | 910* |
| 41 | 1400 |
| 43 | 170* |
| 46 | 13 |
| 53 | 16* |
| 59 | 1160 |
| 70 | 8800 |
| 72 | 6900 |
| 73 | 1030 |
| 82 | 2050 |
| 94 | 730 |
| 98 | 1100 |
| 100 | 4580* |
| 104 | 6900* |
| 106 | 2250 |
| 115 | 250 |
| 117 | 2400* |
| Comp. 119 | 2.3* |

*S1P3/S1P1 activity ratios may be greater than the reported value due to the 31,000 nM or 62,000 nM limits of the S1P$_3$ GTPγS assay.

In Table C, a larger value for the ratio of the S1P$_3$ GTPγS EC$_{50}$ value to the S1P$_1$ GTPγS EC$_{50}$ value indicates greater selectivity of S1P$_1$ activity over S1P$_3$ activity.

The compounds of the present invention, as exemplified by examples in Table C, show the surprising advantage as agonists of S1P$_1$ and are selective over S1P$_3$. For example, as compared to Comparative Compound 119, the exemplified compounds of the invention reported in Table C had selectivity ratios in the range of 3.8 to 8800, while in contrast, Comparative Compound 119 had a selectivity ratio of 2.3.

The compounds of the present invention possess activity as agonists of S1P$_1$ and are selective over S1P$_3$, and thus may be used in treating, preventing, or curing various S1P$_1$ receptor-related conditions while reducing or minimizing the side effects due to S1P$_3$ activity. The surprising selectivity of the compounds of the present invention indicate their potential use in treating, preventing, or curing autoimmune and inflammatory diseases such as multiple sclerosis, rheumatoid arthritis, inflammatory bowel disease, or psoriasis, while reducing or minimizing possible cardiovascular side effects such as bradycardia and hypertension. Other potential uses of the compounds of the present invention include minimizing or reducing rejection of transplanted organs, while reducing or minimizing side effects due to S1P$_3$ activity.

Blood Lymphocyte Reduction Assay (BLR) in Rodents

Lewis rats were dosed orally with test article (as a solution or suspension in the vehicle) or vehicle alone (polyethylene glycol 300, "PEG300"). Blood was drawn at 4 hr by retro-orbital bleeding. Blood lymphocyte counts were determined on an ADVIA® 120 Hematology Analyzer (Siemens Healthcare Diagnostics). The results were measured as a reduction in the percentage of circulating lymphocytes as compared to the vehicle treated group at the 4 hr measurement. The results represent the average results of all animals within each treatment group (n=3-4).

The following examples were tested in the Blood Lymphocyte Reduction assay (BLR) described hereinabove and the results are shown in Table D for rats.

TABLE D

| Example | Dose (mg/kg) | % Reduction in Lymphocytes at 4 hr. |
|---------|--------------|--------------------------------------|
| 4       | 3            | 71                                   |
| 14      | 3            | 83                                   |
| 18      | 1            | 82                                   |
| 35      | 2.4          | 82                                   |
| 40      | 5.5          | 80                                   |

What is claimed is:

1. A compound of Formula (I):

or a stereoisomer or a pharmaceutically acceptable salt thereof, wherein:
m is 1 or 2;
n is 1 or 2;
wherein:
W is $CH_2$ when (m +n) is 2 or 3; or
W is $CH_2$, O, or NH when (m +n) is 4;
$R_1$ is $—(CR_dR_d)_aOH$, $—(CR_dR_d)_aCOOH$, $—(CR_dR_d)_aC(O)NR_cR_c$, $—(CR_dR_d)_aC(O)NHS(O)_2(C_{1-3}alkyl)$, $—(CR_dR_d)_aC(O)NHS(O)_2(aryl)$, or $—(CR_dR_d)_a$tetrazolyl;
each $R_2$ is independently halo, $C_{1-4}$alkyl, $C_{1-2}$haloalkyl, $—OH$, $C_{1-3}$alkoxy, and/or $—NR_cR_c$;
$R_3$ and $R_4$ are independently H and/or $C_{1-6}$alkyl; or $R_3$ and $R_4$ together with the carbon atom to which they are attached, form a 3- to 6-membered ring containing zero or 1 heteroatom selected from O and N;
$R_5$ is H or $C_{1-4}$alkyl;
each $R_6$ is independently $C_{1-3}$alkyl, halo, $C_{1-3}$haloalkyl, $—CN$, $—OH$, $C_{1-3}$alkoxy, and/or $C_{1-3}$haloalkoxy;
A is Q is a 5-membered monocyclic heteroaryl group having 1 to 3 heteroatoms independently selected from N, O, and S, wherein said heteroaryl group is substituted with $R_a$ and zero or 1 $R_b$, provided that Q is not 2-furan-2-yl, 4-thiazolyl, 4-oxazolyl, or 1,2,3-triazolyl;
$R_a$ is $C_{2-6}$alkyl, $C_{2-4}$haloalkyl, $C_{3-6}$cycloalkyl, tetrahydropyranyl, or a cyclic group selected from phenyl, benzyl, and 5- to 6-membered monocyclic heteroaryl groups having 1 to 3 heteroatoms independently selected from N, O, and S, wherein said cyclic group is substituted with zero, 1, 2, or 3 substituents independently selected from halo, $—CN$, $—OH$, $C_{1-4}$alkyl, $C_{1-4}$alkoxy, $C_{1-3}$haloalkyl, and $C_{1-2}$haloalkoxy;
$R_b$ is $C_{1-3}$alkyl or $C_{1-3}$haloalkyl, provided that if $R_a$ is alkyl then $R_b$ is $C_{1-3}$haloalkyl;
each $R_c$ is independently H and/or $C_{1-4}$alkyl;
each $R_d$ is independently H, $—OH$, $C_{1-4}$alkyl, $C_{1-4}$haloalkyl, and/or $C_{1-4}$alkoxy;
a is zero, 1, 2, or 3;
t is zero, 1, 2, 3, or 4; and
x is zero, 1, or 2;
with the proviso that the following compounds are excluded:

2. The compound according to claim 1 or a stereoisomer or a pharmaceutically acceptable salt thereof, wherein:
$R_3$ and $R_4$ are independently H and/or $C_{1-4}$alkyl;
$R_a$ is $C_{2-4}$alkyl, $C_{2-3}$fluoroalkyl, $C_{4-6}$cycloalkyl, tetrahydropyranyl, or a cyclic group selected from phenyl, benzyl, and 5- to 6-membered monocyclic heteroaryl groups having 1 to 2 heteroatoms independently selected from N, O, and S, wherein said cyclic group is substituted with zero, 1, 2, or 3 substituents independently selected from halo, $—CN$, $C_{1-4}$alkyl, $C_{1-3}$alkoxy, $—CF_3$, and $—OCF_3$;
$R_b$ is $C_{1-3}$alkyl or $—CF_3$, provided that if $R_a$ is $C_{2-4}$alkyl then $R_b$ is $—CF_3$; and
each $R_d$ is independently H, $—OH$, and/or $—CH_3$.

3. The compound according to claim 1 or a stereoisomer or a pharmaceutically acceptable salt thereof, wherein:
$R_1$ is $—(CR_dR_d)_aOH$, $—(CR_dR_d)_aCOOH$, or $—C(O)NR_cR_c$;
each $R_2$ is independently F, Cl, $—OH$, and/or $C_{1-4}$alkyl;
each $R_6$ is independently $C_{1-2}$alkyl, F, Cl, $C_{1-2}$haloalkyl, $—CN$, $—OH$, $C_{1-2}$alkoxy, and/or $C_{1-2}$haloalkoxy;

R$_a$ is C$_{2-4}$alkyl, C$_{2-3}$fluoroalkyl, cyclohexyl, tetrahydropyranyl, or a cyclic group selected from phenyl, benzyl, and 5- to 6-membered monocyclic heteroaryl groups having 1 to 2 heteroatoms independently selected from N, O, and S, wherein said cyclic group is substituted with zero, 1, 2, or 3 substituents independently selected from halo, —CN, C$_{1-4}$alkyl, C$_{1-2}$alkoxy, —CF$_3$, and —OCF$_3$;

each R$_d$ is independently H, —OH, C$_{1-2}$alkyl, C$_{1-3}$fluoroalkyl, and/or C$_{1-2}$alkoxy; and t is zero, 1, 2, or 3.

4. The compound according to claim 1 or a stereoisomer or a pharmaceutically acceptable salt thereof, wherein: Q is a heteroaryl group selected from thiophenyl, pyrazolyl, isoxazolyl, 5-thiazolyl, imidazolyl, and isothiazolyl, wherein said heteroaryl group is substituted with R$_a$ and zero or 1 R$_b$.

5. The compound according to claim 1 having formula (Ie):

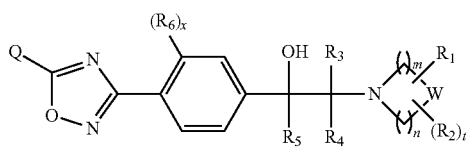

(Ie)

or a stereoisomer or a pharmaceutically acceptable salt thereof, wherein:

R$_1$ is —CH$_2$OH, —CH$_2$CH$_2$OH, —(CH$_2$)$_a$COOH, —C(CH$_3$)$_2$COOH, or —C(O)N(ethyl)$_2$;

R$_2$ is F, —OH, or —CH$_3$;

R$_3$ and R$_4$ are independently H and/or —CH$_3$;

R$_5$ is H or —CH$_3$

R$_6$ is —CF$_3$;

Q is a heteroaryl group selected from thiophenyl, pyrazolyl, isoxazolyl, 5-thiazolyl, imidazolyl, and isothiazolyl, wherein said heteroaryl group is substituted with R$_a$ and zero or 1 R$_b$;

R$_a$ is C$_{3-4}$alkyl, —CH$_2$CF$_3$, cyclohexyl, tetrahydropyranyl, or a cyclic group selected from phenyl, pyridinyl, and pyrimidinyl, wherein said cyclic group is substituted with zero to 2 substituents independently selected from F, Cl, Br, C$_{1-3}$alkyl, —CF$_3$,and —OCH$_3$;

R$_b$ is C$_{1-3}$alkyl or —CF$_3$, provided that if R$_a$ is C$_{3-4}$alkyl then R$_b$ is —CF$_3$;

a is zero, 1, or 2;

t is zero or 1; and x is zero or 1.

6. The compound according to claim 5 or a stereoisomer or a pharmaceutically acceptable salt thereof, wherein:

R$_1$ is —(CH$_2$)$_a$OH, —(CH$_2$)$_a$COOH, —C(CH$_3$)$_2$COOH, or —C(O)N(ethyl)$_2$;

R$_2$ is F, —OH, or —CH$_3$;

R$_3$ is H;

R$_4$ is H;

R$_5$ is H or —CH$_3$;

R$_6$ is —CF$_3$;

and t is zero or 1.

7. The compound according to claim 1 represented by formula (If):

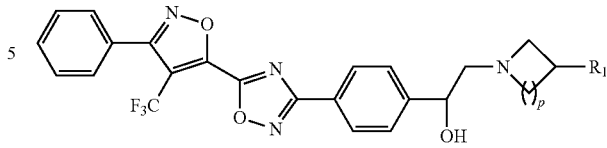

(If)

or a stereoisomer or a pharmaceutically acceptable salt thereof, wherein:

R$_1$ is —(CH$_2$)$_a$COOH; and p is 1, 2, or 3.

8. The compound according to claim 7 represented by formula (If):

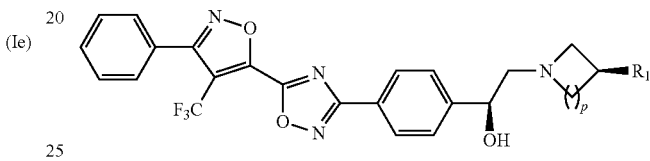

(If)

or a stereoisomer or a pharmaceutically acceptable salt thereof, wherein:

R$_1$ is —(CH$_2$)$_a$COOH; and p is 1, 2, or 3.

9. The compound according to claim 8 represented by formula (Ig):

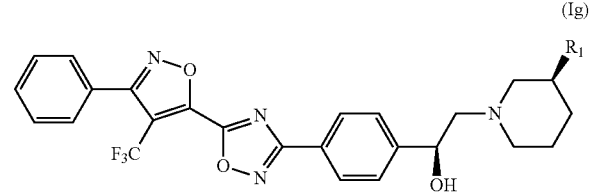

(Ig)

or a stereoisomer or a pharmaceutically acceptable salt thereof, wherein:

R$_1$ is —(CH$_2$)$_a$COOH; and a is zero, 1, or 2.

10. The compound of claim 1 or a salt thereof, wherein said compound is selected from:

1-(2-hydroxy-2-(4-(5-(5-phenyl-4-propylisoxazol-3-yl)-1,2,4-oxadiazol-3-yl) phenyl)ethyl)azetidine-3-carboxylic acid (1); 1-(2-hydroxy-2-(4-(5-(5-phenyl-4-propylisoxazol-3-yl)-1,2,4-oxadiazol-3-yl)phenyl) ethyl)piperidine-2-carboxylic acid (2); 1-(2-hydroxy-2-(4-(5-(5-phenyl-4-propylisoxazol-3-yl)-1,2,4-oxadiazol-3-yl) phenyl)ethyl)piperidine-3-carboxylic acid (3);

(3S)-1-(2-hydroxy-2-(4-(5-(5-phenyl-4-propylisoxazol-3-yl)-1,2,4-oxadiazol-3-yl)phenyl)ethyl)piperidine-3-carboxylic acid (4); (3R)-1-(2-hydroxy-2-(4-(5-(5-phenyl-4-propylisoxazol-3-yl)-1,2,4-oxadiazol-3-yl) phenyl)ethyl)piperidine-3-carboxylic acid (5); 1-(2-hydroxy-2-(4-(5-(5-phenyl-4-propylisoxazol-3-yl)-1,2,4-oxadiazol-3-yl)phenyl)ethyl)pyrrolidine-3-carboxylic acid (6); (2R)-1-(2-hydroxy-2-(4-(5-(5-phenyl-4-propylisoxazol-3-yl)-1,2,4-oxadiazol-3-yl) phenyl)ethyl)azetidine-2-carboxylic acid (7); 2-(1-(2- hydroxy-2-(4-(5-(5-phenyl-4-propylisoxazol-3-yl)-1,2,4-oxadiazol-3-yl)phenyl)ethyl)piperidin-2-yl)acetic acid (8 and 9); 2-((2S)-1-(2-hydroxy-2-(4-(5-(5-phenyl-4-propylisoxazol-3-yl)-1,2,4-oxadiazol-3-yl)phenyl)ethyl)pyrrolidin-2-yl)acetic acid (10); 4-(2-hydroxy-2-(4-(5-(5-phenyl-4-propylisoxazol-3-yl1)-1,2,4-oxadiazol-3-yl)phenyl)ethyl) morpholine-2-carboxylic acid (11); 2-((3S)-1-(2-hydroxy-2-(4-(5-(5-phenyl-4-propylisoxazol-3-yl)-1,2,4-oxadiazol-3-yl)phenyl)ethyl)piperidin-3-yl)acetic acid (12); 2-((3R)-1-(2-hydroxy-2-(4-(5-(5-phenyl-4-propylisoxazol-3-yl)-1,2,4-oxadiazol-3-yl)phenyl)ethyl)piperidin-3-yl)acetic acid (13); (S)-1-((S)-2-hydroxy-2-(4-(5-(3-phenyl-4-(trifluoromethyl)isoxazol-5-yl)-1,2,4-oxadiazol-3-yl)phenyl)ethyl) piperidine-3-carboxylic acid (14);

(S)-1-(R)-2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (15); (3S)-1-(2-hydroxy-2-(4-(5-(3-(pyridin-2-yl)-4-(trifluoromethyl)isoxazol-5-yl)-1,2,4-oxadiazol-3-yl)phenyl)ethyl)piperidine-3-carboxylic acid (16);

(3S)-1-(2-hydroxy-2-(4-(5-(3-phenyl-4-(trifluoromethyl)isoxazol-5-yl)-1,2,4-oxadiazol-3-yl)phenyl)propyl)piperidine-3-carboxylic acid (17); 2-((3R)-1-(2-hydroxy-2-(4-(5-(3-phenyl-4-(trifluoromethyl)isoxazol-5-yl)-1,2,4-oxadiazol-3-yl)phenyl)ethyl)piperidin-3-yl)acetic acid (18 and 19); (3S)-1-(2-hydroxy-2-(4-(5-(5-isobutyl-4-(trifluoromethyl)isoxazol-3-yl)-1,2,4-oxadiazol-3-yl)phenyl)ethyl) piperidine-3-carboxylic acid (20); 4-(2-hydroxy-2-(4-(5-(5-phenyl-4-propylisoxazol-3-yl)-1,2,4-oxadiazol-3-yl)phenyl)ethyl)piperazine-2-carboxylic acid (21); 2-(1-(2-hydroxy-2-(4-(5-(5-phenyl-4-propylisoxazol-3-yl)-1,2,4-oxadiazol-3-yl)phenyl)ethyl) piperidin-3-yl)acetic acid (22); 1-(2-hydroxy-2-(4-(5-(5-phenyl-4-propylisoxazol-3-yl)-1,2,4-oxadiazol-3-yl)phenyl)ethyl)piperidin-3-ol (23); N,N-diethyl-1-(2-hydroxy-2-(4-(5-(5-phenyl-4-propylisoxazol-3-yl)-1,2,4-oxadiazol-3-yl)phenyl)ethyl) piperidine-3-carboxamide (24); 1-(2-hydroxy-2-(4-(5-(3-phenyl-4-(trifluoromethyl) isoxazol-5-yl)-1,2,4-oxadiazol-3-yl)phenyl)ethyl)azetidine-3-carboxylic acid (25); (3S)-1-(2-hydroxy-2-(4-(5-(3-phenyl-4-(trifluoromethyl)isoxazol-5-yl)-1,2,4-oxadiazol-3-yl)-3-(trifluoromethyl)phenyl)ethyl)piperidine-3-carboxylic acid (26); 2-(1-(2-hydroxy-2-(4-(5-(3-phenyl-4-(trifluoromethyl)isoxazol-5-yl)-1,2,4-oxadiazol-3-yl)phenyl)ethyl)azetidin-3-yl)acetic acid (27); 4-(2-hydroxy-2-(4-(5-(3-phenyl-4-(trifluoromethyl)isoxazol-5-yl)-1,2,4-oxadiazol-3-yl)phenyl)ethyl)morpholine-2-carboxylic acid (28); 2-(4-(2-hydroxy-2-(4-(5-(3-phenyl-4-(trifluoromethyl)isoxazol-5-yl)-1,2,4-oxadiazol-3-yl)phenyl)ethyl)morpholin-3-yl)acetic acid (29);

2-(3-(hydroxymethyl)piperidin-1-yl)-1-(4-(5-(3-phenyl-4-(trifluoromethyl)isoxazol-5-yl)-1,2,4-oxadiazol-3-yl)phenyl)ethanol (30); 2-(3-(2-ydroxyethyl)piperidin-1-yl)-1-(4-(5-(3-phenyl-4-(trifluoromethyl)isoxazol-5-yl)-1,2,4-oxadiazol-3-yl)phenyl)ethanol (31); 5-hydroxy-1-(2-hydroxy -2-(4-(5-(3-phenyl-4-(trifluoromethyl)isoxazol-5-yl)-1,2,4-oxadiazol-3-yl)phenyl)ethyl)piperidine-3-carboxylic acid (32); 2-(4-(2-hydroxy-2-(4-(5-(3-phenyl-4-(trifluoromethyl)isoxazol-5-yl)-1,2,4-oxadiazol-3-yl)phenyl)ethyl)morpholin-2-yl)acetic acid (33); 3-fluoro-1-(2-hydroxy-2-(4-(5-(3-phenyl-4-(trifluoromethyl)isoxazol-5-yl)-1,2,4-oxadiazol-3-yl)phenyl)ethyl)piperidine-3-carboxylic acid (34); 2-((3R)-1-(2-hydroxy-2-(4-(5-(5-phenyl-4-(trifluoromethyl) isoxazol-3-yl)-1,2,4-oxadiazol-3-yl)phenyl)ethyl)piperidin-3-yl)acetic acid (35); (3S)-1-(2-hydroxy-2-(4-(5-(5-phenyl-4-(trifluoromethyl)isoxazol-3-yl)-1,2,4-oxadiazol-3-yl)phenyl)ethyl) piperidine-3-carboxylic acid (36);

(3S)-1-(2-hydroxy-2-(4-(5-(3-(6-methylpyridin-2-yl)-4-(trifluoromethyl)isoxazol-5-yl)-1,2,4-oxadiazol-3-yl)phenyl)ethyl)piperidine-3-carboxylic acid (37); 1-(2-hydroxy-2-(4-(5-(3-phenyl-4-(trifluoromethyl)isoxazol-5-yl)-1,2,4-oxadiazol-3-yl)phenyl)ethyl)-3-methylpiperidine-3-carboxylic acid (38); 3-hydroxy-1-(2-hydroxy-2-(4-(5-(3-phenyl-4-(trifluoromethyl)isoxazol-5-yl)-1,2,4-oxadiazol-3-yl)phenyl)ethyl) piperidine-3-carboxylic acid (39); 3-(1-(2-hydroxy-2-(4-(5-(3-phenyl-4-(trifluoromethyl)isoxazol-5-yl)-1,2,4-oxadiazol-3-yl)phenyl)ethyl)piperidin-3-yl) propanoic acid (40); (2R)-1-(2-hydroxy-2-(4-(5-(3-phenyl-4-(trifluoromethyl)isoxazol-5-yl)-1,2,4-oxadiazol-3-yl)phenyl)ethyl)piperidine-2-carboxylic acid (41); 1-(2-hydroxy-2-(4-(5-(3-phenyl-4-(trifluoromethyl)isoxazol-5-yl)-1,2,4-oxadiazol-3-yl)phenyl)ethyl)-6-methylpiperidine-2-carboxylic acid (42); (3S)-1-(2-hydroxy-2-(4-(5-(5-(pyridine-2-yl)thiophen-2-yl)-1,2,4-oxadiazol-3-yl)phenyl)ethyl)piperidine-3-carboxylic acid (43); (3S)-1-(2-hydroxy-2-(4-(5-(1-phenyl-5-propyl -1H-pyrazol-4-yl)-1,2,4-oxadiazol-3-yl)phenyl)ethyl)piperidine-3-carboxylic acid (44); (3S)-1-(2-hydroxy-2-(4-(5-(5-methyl-1-phenyl-1H-pyrazol-3-yl)-1,2,4-oxadiazol-3-yl)phenyl)ethyl) piperidine-3-carboxylic acid (45); (3S)-1-(2-hydroxy-2-(4-(5-(4-methyl-2-phenylthiazol-5-yl)-1,2,4-oxadiazol-3-yl)phenyl)ethyl)piperidine-3-carboxylic acid (46); (3S)-1-(2-hydroxy-2-(4-(5-(1-phenyl -1H-pyrazol-4-yl)-1,2,4-oxadiazol-3-yl) phenyl)ethyl)piperidine-3-carboxylic acid (47); (3S)-1-(2-(4-(5-(3-(4-chlorophenyl)-1H-pyrazol-5-yl)-1,2,4-oxadiazol-3-yl)phenyl)-2-hydroxyethyl)piperidine-3-carboxylic acid (48); (3S)-1-(2-(4-(5-(3-(2-chlorophenyl)-1H-pyrazol-5-yl)-1,2,4-oxadiazol-3-yl)phenyl)-2-hydroxyethyl)piperidine-3-carboxylic acid (49); (3S)-1-(2-hydroxy-2-(4-(5-(1-methyl -3-phenyl-1H-pyrazol-5-yl)-1,2,4-oxadiazol-3-yl)phenyl) ethyl)piperidine-3-carboxylic acid (50);

(3S)-1-(2-(4-(5-(5-ethyl-1-(pyridin-2-yl)-1H-pyrazol-4-yl)-1,2,4-oxadiazol-3-yl)phenyl)-2-hydroxyethyl)piperidine-3-carboxylic acid (51); (3S)-1-(2-hydroxy-2-(4-(5-(5-methyl-1-phenyl- 1H -pyrazol-4-yl)-1,2,4-oxadiazol-3-yl)phenyl)ethyl)piperidine-3-carboxylic acid (52); (3S)-1-(2-(4-(5-(5-(4-chlorophenyl)isoxazol-3-yl)-1,2,4-oxadiazol-3-yl)phenyl)-2-hydroxyethyl)piperidine-3-carboxylic acid (53); 2-((3R)-1-(2-hydroxy-2-(4-(5-(3-(pyridin-2-yl)-4-(trifluoromethyl)isoxazol-5y1)-1,2,4-oxadiazol-3-yl)phenyl)ethyl)piperidin-3-yl) acetic acid (54); (3S)-1-(1-hydroxy-2-methyl -1-(4-(5-(3-phenyl-4-(trifluoromethyl) isoxazol-5-yl)-1,2,4-oxadiazol-3-yl)phenyl)propan-2-yl)piperidine-3-carboxylic acid, TFA (55); 2-((3R)-1-(2-hydroxy-2-(4-(5-(3-(pyridin-2-yl)-4-(trifluoromethyl) isoxazol-5-yl)-1,2,4-oxadiazol-3-yl)phenyl)ethyl)piperidin-3-yl) acetic acid (56);

(S)-1-((S)-2-hydroxy-2-(4-(5-(1-phenyl-5-(trifluoromethyl)-1H-pyrazol-4-yl)-1,2,4-oxadiazol-3-yl)phenyl)ethyl)piperidine-3-carboxylic acid (57); 2-((R)-1-((S)-2-hydroxy-2-(4-(5-(1-phenyl-5-(trifluoromethyl)-1H-pyrazol-4-yl)-1,2,4-oxadiazol-3-yl)phenyl)ethyl)piperidin-3-yl)acetic acid, HCl (58); 2-((R)-1-((S)-2-(4-(5-(1-cyclohexyl-5-(trifluoromethyl)-1H-pyrazol-4-yl)-1,2,4-oxadiazol-3-yl)phenyl)-2-hydroxyethyl)

piperidin-3-yl)acetic acid, HCl(59); 2-((3R)-1-((2S)-2-(4-(5-(1-(3-chloropyridin-2-yl)-5-(trifluoromethyl)-1H-pyrazol-4-yl)-1,2,4-oxadiazol-3-yl) phenyl)-2-hydroxyethyl)piperidin-3-yl)acetic acid, TFA (60); 2-((R)-1-((S)-2-(4-(5-(1-(6-chloropyridin-2-yl) -5-(trifluoromethyl)-1H-pyrazol-4-yl)-1,2,4-oxadiazol-3-yl) phenyl)-2-hydroxyethyl)piperidin-3-yl)acetic acid, HCl(61); 2-((R)-1-((S)-2-(4-(5-(1-(4-fluorophenyl)-5-(trifluoromethyl)-1H-pyrazol-4-yl)-1,2,4-oxadiazol-3-yl)phenyl)-2-hydroxyethyl)piperidin-3-yl)acetic acid, HCl(62); 2-((R)-1-((S)-2-(4-(5-(1-(3-chlorophenyl)-5-(trifluoromethyl)-1H-pyrazol-4-yl)-1,2,4-oxadiazol-3-yl)phenyl) -2-hydroxyethyl)piperidin-3-yl)acetic acid, HCl(63); 2-((R)-1-((S)-2-hydroxy-2-(4-(5-(1-(pyridin-2-yl)-5-(trifluoromethyl)-1H-pyrazol-4-yl)-1,2,4-oxadiazol-3-yl)phenyl) ethyl)piperidin-3-yl)acetic acid, tetrabutylammonium salt (64); 2-((R)-1-((S)-2-(4-(5-(1-(4-chlorophenyl)-5-(trifluoromethyl) -1H-pyrazol-4-yl)-1,2,4-oxadiazol-3-yl) phenyl)-2-hydroxyethyl) piperidin-3-yl)acetic acid (65); 2-((R)-1-((S)-2-(4-(5-(1-(4-bromophenyl)-5-(trifluoromethyl)-1H-pyrazol-4-yl)-1,2,4-oxadiazol-3-yl)phenyl)-2-hydroxyethyl) piperidin-3-yl)acetic acid (66); 2-((R)-1-((S)-2-hydroxy-2-(4-(5-(1-m -tolyl-5-(trifluoromethyl)-1H-pyrazol-4-yl)-1,2,4-oxadiazol-3-yl)phenyl)ethyl) piperidin-3-yl)acetic acid, HCl(67); 2-((3R)-1-((2S)-2-hydroxy-2-(4-(5-(1-(2-methoxyphenyl)-5-(trifluoromethyl)-1H -pyrazol-4-yl)-1,2,4-oxadiazol-3-yl)phenyl) ethyl)piperidin-3-yl)acetic acid (68); 2-((R)-1-((S)-2-hydroxy-2-(4-(5-(1-(tetrahydro-2H-pyran-4-yl)-5-(trifluoromethyl)-1H-pyrazol-4-yl)-1,2,4-oxadiazol-3-yl)phenyl)ethyl)piperidin-3-yl)acetic acid (69); 2-((R)-1-((S)-2-(4-(5-(1-(5-chloropyridin-2-yl)-5-(trifluoromethyl)-1H-pyrazol-4-yl)-1,2,4-oxadiazol-3-yl)phenyl)-2-hydroxyethyl) piperidin-3-yl)acetic acid, HCl(70); 2-((R)-1-((S)-2-hydroxy-2-(4-(5-(1-(2,2,2-trifluoroethyl)-5-(trifluoromethyl)-1H-pyrazol-4-yl)-1,2,4-oxadiazol-3-yl)phenyl) ethyl)piperidin-3-yl)acetic acid, HCl(71); 2-((3R)-1-((2S)-2-(4-(5-(1-(2-chlorophenyl)-5-(trifluoromethyl)-1H -pyrazol-4-yl)-1,2,4-oxadiazol-3-yl)phenyl)-2-hydroxyethyl)piperidin-3-yl) acetic acid, HCl(72); 2-((3R)-1-((2S)-2-(4-(5-(1-(2,4-difluorophenyl)-5-(trifluoromethyl)-1H-pyrazol-4-yl)-1,2,4-oxadiazol -3-yl)phenyl)-2-hydroxyethyl) piperidin-3-yl)acetic acid, HCl(73); 2-((3R)-1-((2S)-2-hydroxy-2-(4-(5-(5-(trifluoromethyl)-1-(2-(trifluoromethyl)phenyl)-1H-pyrazol-4-yl)-1,2,4-oxadiazol-3-yl)phenyl)ethyl)piperidin-3-yl)acetic acid, HCl(74); 2-((R)-1-(S)-2-hydroxy-2-(4-(5-(5-(trifluoromethyl)-1-(3-(trifluoromethyl)phenyl)-1H-pyrazol-4-yl)-1,2,4-oxadiazol-3-yl)phenyl)ethyl)piperidin-3-yl)acetic acid, HCl(75); 2-((R)-1-(S)-2-hydroxy-2-(4-(5-(5-(trifluoromethyl)-1-(4-(trifluoromethyl)phenyl)-1H-pyrazol-4-yl)-1,2,4-oxadiazol-3-yl)phenyl)ethyl) piperidin-3-yl)acetic acid (76); 2-((3R)-1-((2S)-2-hydroxy-2-(4-(5-(1-o-tolyl-5-(trifluoromethyl)-1H-pyrazol-4-yl)-1,2,4-oxadiazol-3-yl)phenyl)ethyl) piperidin-3-yl)acetic acid (77);

2-((R)-1-((S)-2-hydroxy-2-(4-(5-(1-p-tolyl-5-(trifluoromethyl)-1H-pyrazol-4-yl)-1,2,4-oxadiazol-3-yl)phenyl) ethyl)piperidin-3-yl)acetic acid (78); 2-((R)-1-((S)-2-hydroxy-2-(4-(5-(1-(4-isopropylphenyl)-5-(trifluoromethyl)-1H-pyrazol-4-yl)-1,2,4-oxadiazol-3-yl) phenyl)ethyl)piperidin -3-yl)acetic acid (79); 2-((R)-1-((S)-2-hydroxy-2-(4-(5-(1-(4-methoxyphenyl)-5-(trifluoromethyl) -1H-pyrazol-4-yl)-1,2,4-oxadiazol-3-yl)phenyl) ethyl)piperidin-3-yl)acetic acid (80); 2-((R)-1-((S)-2-hydroxy-2-(4-(5-(1-isobutyl-5-(trifluoromethyl)-1H-pyrazol-4-yl)-1,2,4-oxadiazol-3-yl)phenyl) ethyl)piperidin-3-yl)acetic acid, HCl(81); 2-((R)-1-((S)-2-(4-(5-(1-(5-fluoropyridin-2-yl) -5-(trifluoromethyl)-1H-pyrazol-4-yl)-1,2,4-oxadiazol-3-yl)phenyl)-2-hydroxyethyl) piperidin-3-yl)acetic acid, HCl(82); 2-((3R)-1-((2S)-2-(4-(5-(1-(5-chloro-3-fluoropyridin-2-yl)-5-(trifluoromethyl)-1H-pyrazol-4-yl)-1,2,4-oxadiazol-3-yl) phenyl)-2-hydroxyethyl)piperidin-3-yl)acetic acid, HCl(83); 2-((3R)-1-((2S)-2-(4-(5-(1-(5-ethoxy-3-fluoropyridin-2-yl)-5-(trifluoromethyl)-1H-pyrazol-4-yl)-1,2,4-oxadiazol-3-yl)phenyl)-2-hydroxyethyl)piperidin-3-yl)acetic acid, HCl(84); 2-((R)-1-((S)-2-hydroxy-2-(4-(5-(1-(pyrimidin-2-yl)-5-(trifluoromethyl) -1H-pyrazol-4-yl)-1,2,4-oxadiazol-3-yl)phenyl)ethyl)piperidin-3-yl)acetic acid (85); 2-((R)-1-((S)-2-hydroxy-2-(4-(5-(1-(pyridin-3-yl)-5-(trifluoromethyl)-1H-pyrazol-4-yl)-1,2,4-oxadiazol-3-yl)phenyl)ethyl)piperidin-3-yl)acetic acid (86); 2-((R)-1-((S)-2-hydroxy-2-(4-(5-(5-(trifluoromethyl)-1-(5-(trifluoromethyl)pyridin-2-yl)-1H-pyrazol-4-yl)-1,2,4-oxadiazol-3-yl)phenyl)ethyl)piperidin-3-yl)acetic acid, HCl(87); 2-((3R)-1-((2S)-2-(4-(5-(1-(3,5-dichloropyridin-2-yl)-5-(trifluoromethyl)-1H-pyrazol-4-yl)-1,2,4-oxadiazol-3-yl)phenyl)-2-hydroxyethyl) piperidin-3-yl)acetic acid, HCl(88); 2-((3R)-1-((2S)-2-(4-(5-(1-(2,4-dichlorophenyl) -5-(trifluoromethyl)-1H-pyrazol-4-yl)-1,2,4-oxadiazol-3-yl)phenyl)-2-hydroxyethyl)piperidin-3-yl)acetic acid, HCl(89); 2-((3R)-1-((2S)-2-(4-(5-(1-(4-chloro-2-methylphenyl)-5-(trifluoromethyl) -1H-pyrazol-4-yl)-1,2,4-oxadiazol-3-yl)phenyl)-2-hydroxyethyl)piperidin-3-yl)acetic acid, HCl(90);

2-((R)-1-((S)-2-(4-(5-(1-(4-chloro-3-methylphenyl)-5-(trifluoromethyl)-1H-pyrazol-4-yl)-1,2,4-oxadiazol-3-yl)phenyl)-2-hydroxyethyl)piperidin-3-yl)acetic acid, HCl(91); 2-((R)-1-((S)-2-(4-(5-(1-(3,4-dichlorophenyl)-5-(trifluoromethyl)-1H-pyrazol-4-yl)-1,2,4-oxadiazol-3-yl)phenyl)-2-hydroxyethyl)piperidin-3-yl) acetic acid, HCl(92); 2-((R)-1-((S)-2-hydroxy-2-(4-(5-(1-(4-methylpyridin-2-yl)-5-(trifluoromethyl)-1H-pyrazol-4-yl)-1,2,4-oxadiazol-3-yl)phenyl)ethyl) piperidin-3-yl)acetic acid, HCl(93); 2-((R)-1-((S)-2-hydroxy-2-(4-(5-(1-(5-methylpyridin-2-yl)-5-(trifluoromethyl)-1H-pyrazol-4-yl)-1,2,4-oxadiazol-3-yl)phenyl)ethyl)piperidin-3-yl)acetic acid (94); 2-((3R)-1-((2S)-2-(4-(5-(1-(5-chloro-3-(trifluoromethyl)pyridin-2-yl)-5-(trifluoromethyl)-1H-pyrazol-4-yl)-1,2,4-oxadiazol-3-yl)phenyl)-2-hydroxyethyl)piperidin-3-yl)acetic acid (95); 2-((R)-1-((S)-2-hydroxy-2-(4-(5-(1-(6-methyl-4-(trifluoromethyl)pyridin-2-yl)-5-(trifluoromethyl)-1H-pyrazol-4-yl)-1,2,4-oxadiazol-3-yl )phenyl)ethyl)piperidin-3-yl)acetic acid, HCl(96); (S)-1-((S)-2-(4-(5-(1-(4-chlorophenyl)-5-(trifluoromethyl)-1H-pyrazol-4-yl)-1,2,4-oxadiazol-3-yl) phenyl)-2-hydroxyethyl)piperidine-3-carboxylic acid, HCl(97); (S)-1-((S)-2-hydroxy-2-(4-(5-(5-(trifluoromethyl)-1-(5-(trifluoromethyl)pyridin-2-yl)-1H-pyrazol-4-yl)-1,2,4-oxadiazol-3-yl)phenyl)ethyl)piperidine-3-carboxylic acid, HCl(98); (S)-1-((S)-2-hydroxy-2-(4-(5-(1-(4-methoxyphenyl)-5-(trifluoromethyl) -1H-pyrazol-4-yl)-1,2,4-oxadiazol-3-yl)phenyl)ethyl)piperidine-3-carboxylic acid, HCl(99); (S)-1-((S)-2-(4-(5-(1-(3,5-dichloropyridin-2-yl)-5-(trifluoromethyl)-1H-pyrazol-4-yl)-1,2,4-oxadiazol-3-yl)phenyl)-2-hydroxyethyl) piperidine-3-carboxylic acid, HCl(100); (S)-1-((S)-2-(4-(5-(1-(5-fluoropyridin-2-yl)-5-(trifluoromethyl)-

1H-pyrazol-4-yl)-1,2,4-oxadiazol-3-yl)phenyl)-2-hydroxyethyl)piperidine-3-carboxylic acid, HCl(101); (S)-1-((S)-2-hydroxy-2-(4-(5-(1-m-tolyl-5-(trifluoromethyl)-1H-pyrazol-4-yl)-1,2,4-oxadiazol-3-yl)phenyl) ethyl)piperidine-3-carboxylic acid (102); (S)-1-((S)-2-hydroxy-2-(4-(5-(1-(5-methylpyridin-2-yl)-5-(trifluoromethyl)-1H-pyrazol-4-yl) -1,2,4-oxadiazol-3-yl)phenyl)ethyl)piperidine-3-carboxylic acid (103); (S)-1-((S)-2-hydroxy-2-(4-(5-(1-(pyridin-2-yl)-5-(trifluoromethyl)-1H-pyrazol-4-yl)-1,2,4-oxadiazol-3-yl) phenyl)ethyl)piperidine -3-carboxylic acid (104); (S)-1-((S)-2-(4-(5-(1-(5-chloropyridin-2-yl)-5-(trifluoromethyl)-1H -pyrazol-4-yl)-1,2,4-oxadiazol-3-yl) phenyl)-2-hydroxyethyl)piperidine-3-carboxylic acid (105); (S)-1-((S)-2-(4-(5-(1-cyclohexyl-5-(trifluoromethyl)-1H-pyrazol-4-yl)-1,2,4-oxadiazol-3-yl)phenyl)-2-hydroxyethyl)piperidine-3-carboxylic acid (106); (S)-1-((S)-2-(4-(5-(1-(2,4-difluorophenyl)-5-(trifluoromethyl)-1H-pyrazol-4-yl)-1,2,4-oxadiazol-3-yl)phenyl)-2-hydroxyethyl)piperidine-3-carboxylic acid, HCl(107); 2-((R)-1-(S)-2-hydroxy-2-(4-(5-(5-isobutyl-4-(trifluoromethyl)isoxazol -3-yl)-1,2,4-oxadiazol-3-yl)phenyl)ethyl) piperidin-3-yl)acetic acid, TFA (108); 2-((R)-1-((S)-2-(4-(5-(5-tert-butyl-4-(trifluoromethyl)isoxazol-3-yl)-1,2,4-oxadiazol-3-yl)phenyl)-2-hydroxyethyl) piperidin-3-yl)acetic acid, TFA (109); 2-((R)-1-(S)-2-hydroxy-2-(4-(5-(5-isopropyl-4-(trifluoromethyl)isoxazol-3-yl)-1,2,4-oxadiazol-3-yl) phenyl)ethyl)piperidin-3-yl)acetic acid, HCl (110); 2-((R)-1-((S)-2-(4-(5-(5-cyclohexyl-4-(trifluoromethyl) isoxazol-3-yl)-1,2,4-oxadiazol-3-yl)phenyl)-2-hydroxyethyl)piperidin-3-yl)acetic acid, HCl(111); 2-((R)-1-((S)-2-(4-(5-(5-(3-chlorophenyl)-4-(trifluoromethyl)isoxazol-3-yl)-1,2,4-oxadiazol-3-yl)phenyl)-2-hydroxyethyl)piperidin-3-yl)acetic acid (112); 2-((3R)-1-((2S)-2-(4-(5-(5-(2-chlorophenyl)-4-(trifluoromethyl)isoxazol-3-yl)-1,2,4-oxadiazol-3-yl)phenyl)-2-hydroxyethyl)piperidin-3-yl)acetic acid, HCl (113); (S)-1(S)-2-hydroxy-2-(4-(5-(3-phenyl-4-(trifluoromethyl)isothiazol-5-yl)-1,2,4-oxadiazol-3-yl)phenyl) ethyl)piperidine-3-carboxylic acid, HCl (114); 2-((R)-1-(S)-2-hydroxy-2-(4-(5-(4-phenyl-5-(trifluoromethyl) thiophen-2-yl)-1,2,4-oxadiazol-3-yl)phenyl)ethyl) piperidin-3-yl)acetic acid (115); 2-((R)-1-((S)-2-(4-(5-(1-(4-fluorophenyl)-3-(trifluoromethyl)-1H-pyrazol-4-yl) -1,2,4-oxadiazol-3-yl)phenyl)-2-hydroxyethyl) piperidin-3-yl)acetic acid (116); 2-((R)-1-((S)-2-(4-(5-(1-(4-chlorophenyl)-5-(trifluoromethyl)-1H-imidazol-4-yl)-1,2,4-oxadiazol-3-yl)phenyl)-2-hydroxyethyl) piperidin-3-yl)acetic acid (117); and 2-((R)-1-(S)-2-hydroxy-2-(4-(5-(1-(pyridin-2-yl)-5-(trifluoromethyl)-1H-imidazol-4-yl)-1,2,4-oxadiazol-3-yl)phenyl) ethyl) piperidin-3-yl)acetic acid (118).

11. A pharmaceutical composition comprising a compound according to claim 1 or stereoisomers or pharmaceutically acceptable salts thereof, and a pharmaceutically acceptable carrier.

\* \* \* \* \*

UNITED STATES PATENT AND TRADEMARK OFFICE
CERTIFICATE OF CORRECTION

PATENT NO. : 8,399,451 B2
APPLICATION NO. : 12/850892
DATED : March 19, 2013
INVENTOR(S) : John Gilmore et al.

It is certified that error appears in the above-identified patent and that said Letters Patent is hereby corrected as shown below:

In the Claims:

In Claim 1, col. 177, delete " 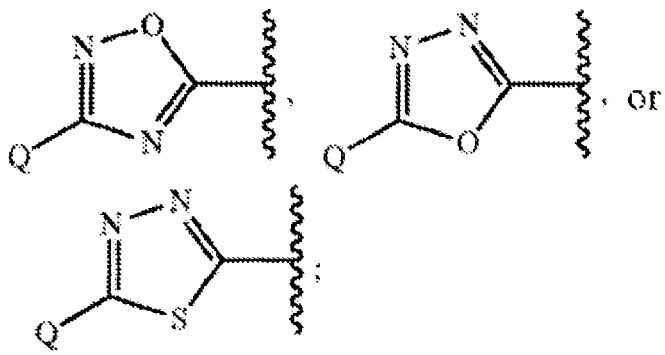 " and insert -- 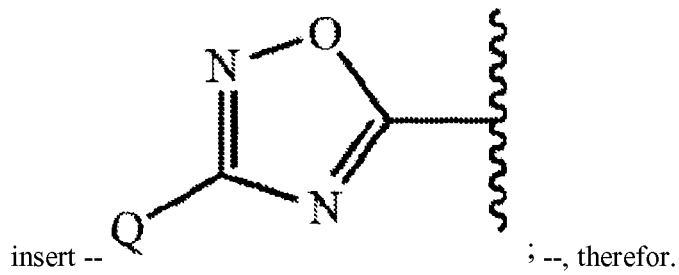 ; --, therefor.

In Claim 1, col. 178, line 3, delete "$R_a$is" and insert -- $R_a$ is --, therefor.
In Claim 3, col. 179, line 1, delete "$R_a$is" and insert -- $R_a$ is --, therefor.
In Claim 5, col. 179, line 42, delete "$R_a$is" and insert -- $R_a$ is --, therefor.
In Claim 5, col. 179, line 47, delete "—$CF_3$,and" and insert -- —$CF_3$, and --, therefor.

In the Claims:

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,399,451 B2

In Claim 10, col. 181, line 6, delete "yl1)" and insert -- yl) --, therefor.

In Claim 10, col. 181, line 13, delete "(S)" and insert -- ((S) --, therefor.

In Claim 10, col. 181, line 16, delete "(R)" and insert -- ((R) --, therefor.

In Claim 10, col. 181, line 56, delete "(2-ydroxyethyl)" and insert -- (2-hydroxyethyl) --, therefor.

In Claim 10, col. 181, line 59, delete "(2-hydroxy -2" and insert -- (2-hydroxy-2 --, therefor.

In Claim 10, col. 182, line 26, delete "propyl -1H" and insert -- propyl-1H --, therefor.

In Claim 10, col. 182, line 33, delete "phenyl -1H" and insert -- phenyl-1H --, therefor.

In Claim 10, col. 182, line 46, delete "phenyl- 1H -pyrazol" and insert -- phenyl-1H -pyrazol --, therefor.

In Claim 10, col. 182, line 52, delete "y1)" and insert -- yl) --, therefor.

In Claim 10, col. 183, line 5, delete "y1) -5-" and insert -- y1)-5- --, therefor.

In Claim 10, col. 183, line 18, delete "(trifluoromethyl) -1H" and insert -- (trifluoromethyl)-1H --, therefor.

In Claim 10, col. 183, line 24, delete "(1-m -tolyl" and insert -- (1-m-tolyl --, therefor.

In Claim 10, col. 183, line 44, delete "oxadiazol -3-yl)phenyl)" and insert -- oxadiazol-3-yl)phenyl)" --, therefor.

In Claim 10, col. 183, line 48, delete "y1)" and insert -- yl) --, therefor.

In Claim 10, col. 183, line 49, delete "(S)" and insert -- ((S) --, therefor.

In Claim 10, col. 183, line 52, delete "(S)" and insert -- ((S) --, therefor.

In Claim 10, col. 183, line 64, delete "piperidin -3-yl)" and insert -- piperidin-3-yl) --, therefor.

In Claim 10, col. 183, line 66, delete "(trifluoromethyl) -1H" and insert -- (trifluoromethyl)-1H --, therefor.

In Claim 10, col. 184, line 4-5, delete "(5-fluoropyridin-2-yl) -5-(trifluoromethyl)" and insert -- (5-fluoropyridin-2-yl)-5-(trifluoromethyl) --, therefor.

In Claim 10, col. 184, line 15, delete "(trifluoromethyl) -1H-pyrazol-4-yl)" and insert -- (trifluoromethyl)-1H-pyrazol-4-yl) --, therefor.

In Claim 10, col. 184, line 27, delete "dichlorophenyl) -5-" and insert -- dichlorophenyl)-5- --, therefor.

In Claim 10, col. 184, line 29, delete "y1)" and insert -- yl) --, therefor.

In Claim 10, col. 184, line 31, delete "(trifluoromethyl) -1H" and insert -- (trifluoromethyl)-1H --, therefor.

In Claim 10, col. 184, line 61, delete "(trifluoromethyl) -1H" and insert -- (trifluoromethyl)-1H --, therefor.

In the Claims:

CERTIFICATE OF CORRECTION (continued)
U.S. Pat. No. 8,399,451 B2

In Claim 10, col. 185, line 7, delete "1H-pyrazol-4-yl) -1,2,4" and insert -- 1H-pyrazol-4-yl)-1,2,4 --, therefor.

In Claim 10, col. 185, line 14, delete "1H -pyrazol-4-yl)" and insert -- 1H-pyrazol-4-yl) --, therefor.

In Claim 10, col. 185, line 22, delete "(S)" and insert -- ((S) --, therefor.

In Claim 10, col. 185, line 23, delete "isoxazol -3-yl)" and insert -- isoxazol-3-yl) --, therefor.

In Claim 10, col. 185, line 28, delete "(S)" and insert -- ((S) --, therefor.

In Claim 10, col. 186, line 10, delete "(S)" and insert -- ((S) --, therefor.

In Claim 10, col. 186, line 13, delete "(S)" and insert -- ((S) --, therefor.

In Claim 10, col. 186, line 17, delete "yl) -1,2,4" and insert -- yl)-1,2,4 --, therefor.

In Claim 10, col. 186, line 21, delete "(S)" and insert -- ((S) --, therefor.